(12) United States Patent
Silverstein et al.

(10) Patent No.: US 10,137,153 B2
(45) Date of Patent: Nov. 27, 2018

(54) METHODS FOR TREATING AN INFECTIOUS OR NEOPLASTIC DISEASE

(71) Applicant: THE TRUSTEES OF COLUMBIA UNIVERSITY IN THE CITY OF NEW YORK, New York, NY (US)

(72) Inventors: Samuel C. Silverstein, New York, NY (US); John D. Loike, Jamaica, NY (US); Sadna Budhu, Pelham, NY (US); Peter Lee, Menlo Park, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/345,144

(22) Filed: Nov. 7, 2016

(65) Prior Publication Data
US 2017/0106022 A1    Apr. 20, 2017

Related U.S. Application Data

(62) Division of application No. 13/509,405, filed as application No. PCT/US2010/056429 on Nov. 11, 2010, now Pat. No. 9,488,644.

(60) Provisional application No. 61/387,877, filed on Sep. 29, 2010, provisional application No. 61/260,249, filed on Nov. 11, 2009.

(51) Int. Cl.
| | |
|---|---|
| *G01N 33/50* | (2006.01) |
| *A61K 35/17* | (2015.01) |
| *A61K 38/20* | (2006.01) |
| *A61K 45/06* | (2006.01) |
| *A61K 35/12* | (2015.01) |

(52) U.S. Cl.
CPC .............. *A61K 35/17* (2013.01); *A61K 38/20* (2013.01); *A61K 38/208* (2013.01); *A61K 38/2013* (2013.01); *A61K 45/06* (2013.01); *G01N 33/5017* (2013.01); *G01N 33/5047* (2013.01); *A61K 2035/124* (2013.01); *C12N 2503/00* (2013.01)

(58) Field of Classification Search
None
See application file for complete search history.

(56) References Cited

U.S. PATENT DOCUMENTS

| | | |
|---|---|---|
| 2002/0119121 A1 | 8/2002 | Vitiello et al. |
| 2005/0118144 A1 | 6/2005 | Zhang |
| 2006/0073469 A1 | 4/2006 | Herlyn et al. |
| 2006/0240490 A1 | 10/2006 | Lee |

OTHER PUBLICATIONS

Moroz, A., et al. IL-21 enhances and sustains CD8+ T cell responses to achieve durable tumor immunity: comparative evaluation of IL-2, IL-15, and IL-21. J Immunol, 2004. 173(2): p. 900-9.

Nedergaard, B.S., et al. Low density of CD3+, CD4+ and CD8+ cells is associated with increased risk of relapse in squamous cell cervical cancer. Br J Cancer, 200T 97(8): p. 1135-8.

Newcomb, E.W., et al. Malignant mouse melanoma cells do not form tumors when mixed with cells of a non-malignant subclone: relationships between plasminogen activator expression by the tumor cells and the hosts immune response. J Cell Physiol, 1978. 95(2): p. 169-77.

Ochalek, T., et al. 1988. Correlation between cell deformability and metastatic potential in B16-F1 melanoma cell variants. Cancer Res. 48:5124-5128.

Petersen, C.C., et al. Accumulation in tumor tissue of adoptively transferred T cells: A comparison between intravenous and intraperitoneal injection. J Immunother, 2006. 29(3): p. 241-9.

Regoes, R.R., et al. 2007. Estimation of the rate of killing by cytotoxic T lymphocytes in vivo. Proc. Natl. Acad. Sci. USA. 104:1599-1603.

Rubio, V., et al. Ex vivo identification, isolation and analysis of tumor-cytolytic T cells. Nat Med, 2003. 9(11): p. 1377-82.

Snyder, C.A. and A.B. Bowers. A new inhalation exposure system for the determination of inhaled doses in laboratory rats. Arch Toxicol, 1987. 61(1): p. 3-6.

Snyder, J.E., et al. 2003. Measuring the frequency of mouse and human cytotoxic T cells by the Lysispot assay: independent regulation of cytokine secretion and short-term killing. Nat. Met 9:231-235.

Stephens, T.C., and J.H. Peacock 1978. Cell yield and cell survival following chemotherapy of the B16 melanoma. Br. J. Cancer. 38:591-598.

Stuge, T.B., et al., Diversity and recognition efficiency of T cell responses to cancer. PLoS Med, 2004. 1(2): p. e28.

Suciu-Foca, N. and R. Cortesini, Central role of ILT3 in the T suppressor cell cascade. Cell Immunol, 200T 248 (1): p. 59-67.

Sutherland, R.M., Cell and environment interactions in tumor microregions: the multicell spheroid model. Science, 1988. 240(4849): p. 177-84.

Svedman, C., et al. 2002. Plasma proteins in a standardised skin mini-erosion (I): permeability changes as a function of time. BMC Dermatol. 2: p. 1-7.

Takeda, Y., and A.Y. Chen. 1967. Studies of the metabolism and distribution of fibrinogen in patients with hemophilia A. J. Clin. Invest. 46:1979-1985.

Tomsova, M., et al., Prognostic significance of CD3+ tumor-infiltrating lymphocytes in ovarian carcinoma. Gynecol Oncol, 2008. 108(2): p. 415-20.

Virgin, H.W., et al. 2009. Redefining chronic viral infection. Cell. 138:30-50.

Wallace, A., et al., Transforming growth factor-beta receptor blockade augments the effectiveness of adoptive T-cell therapy of established solid cancers. Clin Cancer Res, 2008. 14(12): p. 3966-74.

(Continued)

*Primary Examiner* — Ralph J Gitomer

(74) *Attorney, Agent, or Firm* — Bryan Cave Leighton Paisner LLP

(57) ABSTRACT

A method is provided for treating a subject suffering from an infectious or neoplastic disease with immunotherapy. The method comprises determining the critical concentration of immune cells required to treat or eradicate an infectious or neoplastic disease in the subject using an in vitro assay of the present invention; and administering to the subject the critical concentration of immune cells determined in the assay.

8 Claims, 32 Drawing Sheets

(56) References Cited

OTHER PUBLICATIONS

White, L., et al., Differential effects of IL-21 and IL-15 on perforin expression, lysosomal degranulation, and proliferation in CD8 T cells of patients with human immunodeficiency virus-1 (HIV). Blood, 2007. 109(9): p. 3873-80.

Whiteside, T.L., et al. 1986. Separation of tumor-infiltrating lymphocytes from tumor cells in human solid tumors. A comparison between velocity sedimentation and discontinuous density gradients. J. Immunol. Methods. 90:221-233.

Agger, R., et al. T cell homing to tumors detected by 3D-coordinated positron emission tomography and magnetic resonance imaging. J Immunother, 2007. 30(1): p. 29-39.

Askenasy, N., et al. Mechanisms of T regulatory cell function. Autoimmun Rev, 2008. 7(5): p. 370-375.

Baramova, E.N., et al. Evaluation of matrix metalloproteinases and serine proteases activities in three B16 melanoma cell lines with distinct tumorigenic potential. Anticancer Res, 1994. 14(3A): p. 841-846.

Bathe, O.F., et al. Therapeutic limitations in tumor-specific CD8+ memory T cell engraftment. BMC Cancer, 2003. 3 (21): p. 1-9.

Blattman, J.N. and Greenberg, P.D. PD-1 blockade: rescue from a near-death experience. Nat. Immunol., 2006. 7(3): p. 227-228.

Bonifaz, L., et al. Efficient targeting of protein antigen to the dendritic cell receptor DEC-205 in the steady state leads to antigen presentation on major histocompatibility complex class I products and peripheral CD8+ T cell tolerance. J Exp Med., 2002. 196(12):1627-38.

Bonnefoix, T., et al. Quantitating effector and regulatory T lymphocytes in immune responses by limiting dilution analysis modeling. J Immunol, 2005. 174(6): p. 3421-31.

Boon, T. and Van Der Bruggen, P. Human tumor antigens recognized by T lymphocytelymphocytes. J Exp Med, 1996. 183 (3): p. 725-9.

Bronte, V. and Mocellin, S. Suppressive influences in the immune response to cancer. J. Immunother, 2009. 32 (1): p. 1-11.

Brunner, K.T., et al. Quantitative assay of the lytic action of immune lymphoid cells on 51-Cr-labelled allogeneic target cells in vitro; inhibition by isoantibody and by drugs. Immunology, 1968. 14: p. 181-196.

Buckanovich, R.J., et al. Endothelin B receptor mediates the endothelial barrier to T cell homing to tumors and disables immune therapy. Nat Med, 2008. 14(1): p. 28-36.

Budhu, S., et al. CD8+ T cell concentration determines their efficiency in killing cognate antigen-expressing syngeneic mammalian cells in vitro and in mouse tissues. J Exp Med, 2010.207:223-35.

Calvelli, T.A., et al. Leukocyte subpopulations elicited by a nontumorigenic variant of B16 melanoma: their role in direct rejection of the melanoma and in prevention of tumorigenesis in Winn assays. J Exp Med, 1982. 156(6): p. 1723-38.

Cerottini, J.C., et al. Generation of cytotoxic T lymphocytes in vitro. I. Response of normal and immune mouse spleen cells in mixed leukocyte cultures. J. Exp. Med, 1974. 140: p. 703-717.

Curiel, T.J. Tregs and rethinking cancer immunotherapy. J Clin Invest, 200T 117(5): p. 1167-74.

Curtsinger, J.M., et al. CD8+ memory T cells (CD44high, Ly-6C+) are more sensitive than naive cells (CD44low, Ly-6C-) to TCR/CD8 signaling in response to antigen. J Immunol, 1998. 160(7): p. 3236-43.

Daugherty, D.F., et al. Separation and characterization of the neoplastic and stromal elements of the R3230AC mammary adenocarcinoma. Cancer Res., 1981.41:5064-5069.

Dewever, J., et al. Caveolin-1 is critical for the maturation of tumor blood vessels through the regulation of both endothelial tube formation and mural cell recruitment. Am. J. Pathol., 200T 171(5):1619-1628.

Dobrzanski, M.J., et al. 2001. Immunopotentiating role of IFN-gamma in early and late stages of type 1 CD8 effector cell-mediated tumor rejection. Clin. Immunol. 98:70-84.

Dudley, M.E., and S.A. Rosenberg. 2003. Adoptive-cell-transfer therapy for the treatment of patients with cancer. Nat. Rev. Cancer. 3:666-675.

Dudley, M.E., et al., Adoptive cell therapy for patients with metastatic melanoma: evaluation of intensive myeloablative chemoradiation preparative regimens. J Clin Oncol, 2008.26(32): p. 5233-9.

Dudley, M.E., et al., Adoptive cell transfer therapy following non-myeloablative but lymphodepleting chemotherapy or the treatment of patients with refractory metastatic melanoma. J Clin Oncol, 2005.23(10): p. 2346-57.

Dudley, M.E., et al., Cancer regression and autoimmunity in patients after clonal repopulation with antitumor lymphocytes. Science, 2002. 298(5594): p. 850-4.

Dvorak, H.F., et al. 1992. Vascular permeability factor, fibrin, and the pathogenesis of tumor stroma formation. Ann. N. Y. Acad. Sci. 667:101-111.

Freedman, V.H., et al., Bacillus Calmette-Guerin-activated murine macrophages kill syngeneic melanoma cells under strict anaerobic conditions. J Exp Med, 1984. 160(1): p. 94-107.

Freedman, V.H., et al., Macrophages elicited with heat-killed Bacillus Calomette-Guerin protect C57BL/6J mice against a syngeneic melanoma. J Exp Med, 1980. 152(3): p. 657-73.

Grabowska, M. 1959. Collagen content of normal connective tissue, of tissue surrounding a tumour and of growing rat sarcoma. Nature. 183:1186-1187.

Helmich, B.K. and R.W. Dutton. The role of adoptively transferred CD8 T cells and host cells in the control of the growth of the EG7 thymoma: factors that determine the relative effectiveness and homing properties of Tc1 and Tc2 effectors. J Immunol, 2001. 166(11): p. 6500-8.

Hemstreet, G.P. III, et al. 1980. Tissue disaggregation of human renal cell carcinoma with further isopyknic and isokinetic gradient purification. Cancer Res. 40:1043-1049.

Hersh, E.M., et al., Mononuclear cell content of human solid tumors. Med Pediatr Oncol, 1976. 2(1): p. 1-9.

Hofmann, U.B., et al., Role of matrix metalloproteinases in melanoma cell invasion. Biochimie, 2005. 87(3-4): p. 307-314.

Hogquist, K.A., et al., T cell receptor antagonist peptides induce positive selection. Cell, 1994. 76(1): p. 17-27.

Hu, F. and P.F. Lesney, The Isolation and Cytology of Two Pigment Cell Strains from B16 Mouse Melanomas. Cancer Res, 1964.24: p. 1634-43.

Huang, S.-C., et al., Carnosol inhibits the invasion of B16/F10 mouse melanoma cells by suppressing metalloproteinase-9 through down-regulating nuclear factor-kappaB and c-Jun. Biochemical Pharmacology, 2005. 69 (2): p. 221-232.

Joseph-Pietras, D., et al. 2006. Anti-tumoural activity of peripheral blood mononuclear cells against melanoma cells: discrepant in-vitro and in-vivo effects. Melanoma Res 16:325-333.

Kataoka, T., et al. 1996. Concanamycin A, a powerful tool for characterization and estimation of contribution of perforin- and Fas-based lytic pathways in cell-mediated cytotoxicity. J. Immunol. 156:3678-3686.

Koehne, G., et al., Quantitation, selection, and functional characterization of Epstein-Barr virus-specific and alloreactive T cells detected by intracellular interferon-gamma production and growth of cytotoxic precursors. Blood, 2002. 99(5): p. 1730-40.

Kuwashima, Y., et al., Growth characteristics of murine B16 melanoma multicellular spheroids: a model for invasion and effects of doxorubicin treatments. Anticancer Res, 1993. 13(4): p. 1215-7.

Kyner, D., et al., Co-cultivation of tumorigenic mouse melanoma cells with cells of a non-tumorigenic subclone inhibits plasminogen activator expression by the melanoma cells. J Cell Physiol, 1978. 95(2): p. 159-67.

Le, D.T., et al. 1998. Hemostatic factors in rabbit limb lymph: relationship to mechanisms regulating extravascular coagulation. Am. J. Physiol. 274:H769-H776.

(56) References Cited

OTHER PUBLICATIONS

Li, X.H., et al. 1984. Growth response of B16 melanoma to in vivo treatment with 1-(2-chloroethyl)-3-cyclohexy-1-nitrosourea (CCNU) at the initial stage after tumor transplantation. Am. J. Pathol. 115:403-411.

Li, Y., et al. 2002. A critical concentration of neutrophils is required for effective bacterial killing in suspension. Proc. Natl. Acad. Sci. USA. 99:8289-8294.

Li, Y., et al. 2004. Determination of the critical concentration of neutrophils required to block bacterial growth in tissues. J. Exp. Med. 200:613-622.

Li, Y., et al. IL-21 influences the frequency, phenotype, and affinity of the antigen-specific CD8 T cell response. J Immunol, 2005. 175(4): p. 2261-9.

Liakou, Cl, et al., Focus on TILs: Prognostic significance of tumor infiltrating lymphocytes in human bladder cancer. Cancer Immun, 2007. 7: p. 10.

Lukacher, A.E., et al. 1999. Visualization of polyoma virus-specific CD8+ T cells in vivo during infection and tumor rejection. J. Immunol. 163:3369-3378.

Machlenkin, A., et al. Capture of tumor cell membranes by trogocytosis facilitates detection and isolation of tumor-specific functional CTLs. Cancer Res, 2008. 68(6): p. 2006-13.

Martz, E. Early steps in specific tumor cell lysis by sensitized mouse T lymphocytes. I. Resolution and characterization. J Immunol, 1975. 115(1): p. 261-7.

Moore, M.W., et al. Introduction of soluble protein into the class I pathway of antigen processing and presentation. Cell, 1988. 54(6): p. 777-85.

Morgan, R.A., et al. Cancer regression in patients after transfer of genetically engineered lymphocytes. Science, 2006. 314(5796): p. 126-9.

METHODS FOR TREATING AN INFECTIOUS OR NEOPLASTIC DISEASE

CROSS-REFERENCE TO RELATED APPLICATIONS

This application is a divisional application of U.S. application Ser. No. 13/509,405 filed Nov. 28, 2012, now U.S. Pat. No. 9,488,644, which is a National Stage Application of International Application No. PCT/US2010/056429, which was filed on Nov. 11, 2010, and which claims priority to U.S. Provisional Application No. 61/260,249 filed Nov. 11, 2009 and U.S. Provisional Application No. 61/387,877 filed Sep. 29, 2010. The entire contents of the above applications are incorporated by reference as if recited in full herein.

GOVERNMENT RIGHTS IN THE INVENTION

This invention was made with government support under Grant No. A120516 awarded by NIH-NIAID. The government has certain rights in the invention.

FIELD OF THE INVENTION

This invention is directed to, inter alia, in vitro assays and methods that are useful, for example, for determining the effect of an immune cell on a cell from an infectious disease or neoplastic disease and for improving the specific cytolytic activity (SCA) of an immune cell.

BACKGROUND OF THE INVENTION

Immunotherapy has great promise. To date, however, it has suffered a number of well publicized setbacks. Accordingly, an innovative model system is needed to, inter alia, quantitatively assess and proscribe the appropriate class of leukocytes to be elicited to fight specific cancers and other infectious disease. The present invention is directed, inter alia, to addressing these and other needs.

SUMMARY OF THE INVENTION

One embodiment of the present invention is in vitro assay for determining the effect of an immune cell on a cell from an infectious or neoplastic disease. This assay comprises: (a) providing a gel that comprises: (i) collagen and optionally fibrin, which gel is sufficient to support viability of an immune cell and growth of a cell from an infectious or neoplastic disease and (ii) an immune cell and a cell from an infectious or neoplastic disease disposed on a surface of or within the gel; (b) incubating the gel under conditions that support viability of the immune cell and growth of the cell from the infectious or neoplastic disease for a period of time sufficient to determine whether the immune cell has an effect on the cell from the infectious or neoplastic disease; and (c) determining the number of viable cells from the infectious or neoplastic disease, if any, that are present after step (b).

Another embodiment of the present invention is an in vitro assay for determining the effect of an activated $CD8^+$ T-cell on a sensitized melanoma cell. This embodiment comprises: (a) providing a gel comprising collagen type I and fibrin, which gel is sufficient to support viability of an activated $CD8^+$ T-cell and growth of a sensitized melanoma cell disposed on a surface of or within the gel; (b) incubating the gel under conditions that support viability of the $CD8^+$ T-cell and growth of the sensitized melanoma cell for a period of time sufficient to determine whether the activated $CD8^+$ T-cell has an effect on the sensitized melanoma cell; and (c) determining, by carrying out a clonogenic or fluorometric assay, the number of viable melanoma cells, if any, that survive after step (b).

Another embodiment of the present invention is an in vitro assay for determining the effect of an immune cell on a cell from an infectious or neoplastic disease. This assay comprises: (a) incubating a cell from an infectious or neoplastic disease and an immune cell in a suitable tissue culture apparatus under conditions that support viability of the immune cell and growth of the cell from an infectious or neoplastic disease for a period of time sufficient to determine whether the immune cell has an effect on the cell from the infectious or neoplastic disease; and (b) determining the number of viable cells from the infectious or neoplastic disease, if any, that are present after step (a).

Another embodiment of the present invention is an in vitro assay for determining the effect of an activated $CD8^+$ T-cell on a sensitized melanoma cell. This assay comprises: (a) incubating a sensitized melanoma cell and an activated $CD8^+$ T-cell in a suitable tissue culture apparatus under conditions that support viability of the activated $CD8^+$ T-cell and growth of the sensitized melanoma cell for a period of time sufficient to determine whether the activated $CD8^+$ T-cell has an effect on the melanoma cell; and (b) determining, by carrying out a clonogenic assay, the number of viable melanoma cells, if any, that survive after step (a).

Another embodiment of the present invention is a method for improving the specific cytolytic activity (SCA) of an immune cell. This method comprises contacting an immune cell with an antigen and an antigen-independent pro-inflammatory agent.

Another embodiment of the present invention is a method for ex vivo expansion of antigen-specific CD4+ or CD8+T-cells with enhanced specific cytolytic activity (SCA). This method comprises culturing the antigen-specific CD4+ or CD8+ T-cells in a suitable culture media comprising an amino acid or a tri-carboxylic acid.

Another embodiment of the present invention is a method of treating a subject suffering from an infectious or neoplastic disease with immuno therapy. This method comprises: (a) determining the critical concentration of total immune cells required to treat or eradicate an infectious or neoplastic disease in the subject using any of the assays of the present invention; and (b) administering to the subject the critical concentration of immune cells determined in step (a).

Another embodiment of the present invention is a substrate for use in an assay for determining the effect of an immune cell on a cell from an infectious or neoplastic disease. The substrate comprises: (a) at least one extracellular matrix polypeptide disposed in a configuration that is sufficient to support viability of an immune cell and growth of a cell from an infectious or neoplastic disease; and (b) an immune cell and a cell from an infectious or neoplastic disease disposed on a surface of or within the substrate.

A further embodiment of the present invention is a substrate for use in an assay for determining the effect of an activated CD8+T-cell on a sensitized melanoma cell. The substrate comprises: (a) a gel comprising collagen type I and optionally fibrin disposed in a configuration that is sufficient to support viability of an activated CD8+T-cell and growth of a sensitized melanoma cell; and (b) a sensitized melanoma cell and an activated CD8+T-cell disposed on a surface of or within the gel.

DETAILED DESCRIPTION OF THE INVENTION

Figure 1:
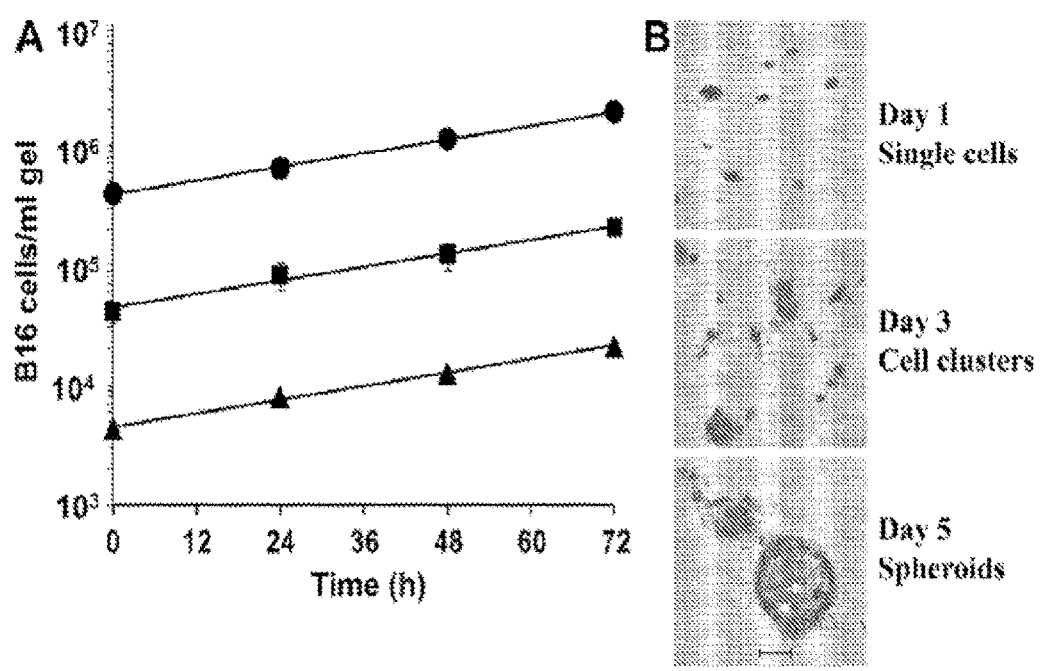
FIG. 1 Growth of B16 mouse melanoma cells in collagen-fibrin gels. (A) Collagen-fibrin gels containing $5 \times 10^4$ (▲), $5\times10^5$ (■), or $5\times10^6$ (●) B16 cells/ml and RPMI 1640 with 10% FBS and $5\times10^{-5}$ M β-ME were incubated at 37° C. for 3 d. Gels were harvested daily and their content of clonogenic B16 cells was assessed as described in the Examples. Data shown represent mean±SEM of n=3 experiments performed in duplicate. (B) Hematoxylin/eosin-stained frozen sections of B16 cells grown at 37° C. in collagen-fibrin gels for 1, 3, and 5 d. Bar, 50 μm.

One embodiment of the present invention is in vitro assay for determining the effect of an immune cell on a cell from an infectious or neoplastic disease. This assay comprises: (a) providing a gel that comprises: (i) collagen and optionally fibrin, which gel is sufficient to support viability of an immune cell and growth of a cell from an infectious or neoplastic disease and (ii) an immune cell and a cell from an infectious or neoplastic disease disposed on a surface of or within the gel; (b) incubating the gel under conditions that support viability of the immune cell and growth of the cell from the infectious or neoplastic disease for a period of time sufficient to determine whether the immune cell has an effect on the cell from the infectious or neoplastic disease; and (c) determining the number of viable cells from the infectious or neoplastic disease, if any, that are present after step (b).

In the present invention, the assays preferably are, or may be adapted to be, high throughput assays.

In the present invention, "gel" means a three dimensional matrix made up of one or more extracellular matrix ("ECM") proteins or polypeptides and may be made by conventional methods known in the art and described in the Examples below. The gel may be formed into any convenient shape, including, e.g., tubes and sheets, that is sufficient to support viability of an immune cell and growth of a cell from an infectious or neoplastic disease of the present invention. Representative, non-limiting examples of ECM proteins according to the present invention include proteoglycans, heparan sulfate, chondroitin sulfate, keratin sulfate, non-proteoglycan polysaccharides, including hyaluronic acid, collagen, including types I-XXIX, elastin, fibronectin, laminin, and fibrin. Sources of these ECM proteins include any mammal, such as for example rat, mouse, or human. Preferably, the gel is made from, e.g., rat tail collagen type I alone or in combination with fibrin. Methods for generating ECM, including collagen and collagen-fibrin, gels are known in the art and disclosed herein.

In the present invention, a gel is "sufficient to support viability of an immune cell and growth of a cell from an infectious or neoplastic disease" if the cell(s), when plated onto a surface of the gel and/or disposed within the gel, are able to grow, divide, and/or differentiate.

As used herein, "disposed on a surface of or within the gel" means that the immune cells and/or cells from an infectious or neoplastic disease are able to attach to and/or grow on a surface of and/or within the gel. Methods for achieving this are well known in the art and are disclosed herein and include mixing the immune cells alone or in combination with the cells from an infectious or neoplastic disease with the gel components prior to formation of the gel. Alternatively, by way of example, a first layer of gel may be formed followed by plating the immune cells alone or in combination with the cells from an infectious or neoplastic disease, which may be overlayed with a second gel layer.

The particular conditions required to incubate the gel under conditions that support viability of the immune cell and growth of the cell from the infectious or neoplastic disease will varying depending upon many well known factors, including the particular cells used, and the volume and structure of the gel used. The particular parameters, including culture media, humidity, and temperature are known in the art and disclosed in more detail in the Examples.

The particular period of time that is sufficient to determine whether an immune cell has an effect on the cell from the infectious or neoplastic disease may be determined empirically, as required, or by reference to the Examples disclosed herein.

In the present invention, determining the number of viable cells from the infectious or neoplastic disease, if any, that are present after incubation in the presence of the immune cells may be accomplished using any known technique, such as for example, the clonogenic or fluorometric assays disclosed in more detail in the Examples. Preferably, the selected technique is amenable to adaptation to a high throughput assay.

In the present invention, "a cell from an infectious disease" means that the cell is obtained from a sample from a subject, such as a human, who has an infectious disease or from an appropriate cell culture line. In the present invention, an "infectious disease" is any disease that may afflict a subject, such as a human, which disease may be treated by immuno therapy. For example, the cell from an infectious disease may be selected from the group consisting of a virus-infected cell, a transplant cell, and a cell infected with a eukaryotic cell parasite.

In the present invention, "a cell from a neoplastic disease" means a cell from a neoplasm, i.e., an abnormal tissue that grows by cellular proliferation more rapidly than normal tissue and continues to grow after the stimuli that initiated the new growth cease. Neoplastic diseases exhibit partial or complete lack of structural organization and functional coordination with the normal tissue, and usually form a distinct mass of tissue which may be benign (benign tumor) or malignant (carcinoma). The term "cancer" is used as a general term to describe any of various types of malignant neoplastic diseases, most of which invade surrounding tissues, may metastasize to several sites, and are likely to recur after attempted removal and to cause death of the patient unless adequately treated. As used herein, the term cancer is subsumed under the term neoplastic disease. In the present invention, non-limiting examples of neoplastic diseases include those include, which may be treated by immuno therapy and include a solid tumor, a blood-based tumor, or a nervous system tumor. Non-limiting examples of such neoplastic diseases also include leukemia and lymphoma.

In the present invention, the solid tumor may be selected from the group consisting of bladder cancer, colon cancer, breast cancer, lung cancer, melanoma, and sarcoma. Preferably, the cell from the solid tumor is a sensitized melanoma cell. A sensitized cell from an infectious or neoplastic disease, such as a sensitized melanoma cell, is one that has been treated in a manner so that it displays a marker or other agent that is targeted by an immune cell, such as a CD8+ T-cell. Thus, by way of example only, and as disclosed in more detail below, a B16 melanoma cell may be sensitized by exposure to the ovalbumin peptide BIINFEKL.

Non-limiting examples of the source of the cells from a neoplastic disease according to the present invention include blood, urine, cerebrospinal fluid, ascites fluid, tumor ascites, and combinations thereof. Thus, a population of cells from a neoplastic disease may be obtained by harvesting, e.g., cancer cells, from a cell culture using well know techniques.

In addition, a population of cancer cells may be obtained through the acquisition of a tumor sample from a cancer patient.

In the present invention, the immune cell is any cell of the immune system capable of targeting a cell from an infectious or neoplastic disease and, e.g., killing it. For example, the immune cell may be a lymphocyte. The lymphocyte may be selected from the group consisting of an activated CD4+T-cell, an activated CD8+T-cell, an activated NK cell, and combinations thereof. Preferably, the lymphocyte is an activated CD8+T-cell. In addition, the immune cell may also be an activated monocyte or an activated macrophage alone or in combination. As used herein, "activated", in reference to an immune cell, such as a CD8+T-cell, means that it is specific to a target antigen. Activation of such cells is known in the art and disclosed in more detail in the Examples. Thus, by way of example only, an OT-1 cell may be activated by incubation of OT-1 SIINFEKL-pulsed splenocytes in vitro for 5-7 days in the presence of IL-2.

The immune cell and the cell from an infectious or neoplastic disease are mammalian, such as for example, human or mouse. Thus, in one aspect of this embodiment, the cell from a neoplastic disease is a sensitized human melanoma cell and the immune cell is an activated human CD8+ cell.

As noted above, the determining step of this embodiment comprises carrying out a clonogenic or fluorometric assay to determine how many, if any, cells from the infectious or neoplastic disease are present.

Another embodiment of the present invention is an in vitro assay for determining the effect of an activated CD8+ T-cell on a sensitized melanoma cell. This embodiment comprises: (a) providing a gel comprising collagen type I and fibrin, which gel is sufficient to support viability of an activated CD8+T-cell and growth of a sensitized melanoma cell disposed on a surface of or within the gel; (b) incubating the gel under conditions that support viability of the CD8+ T-cell and growth of the sensitized melanoma cell for a period of time sufficient to determine whether the activated CD8+T-cell has an effect on the sensitized melanoma cell; and (c) determining, by carrying out a clonogenic or fluorometric assay, the number of viable melanoma cells, if any, that survive after step (b).

A further embodiment of the present invention is an in vitro assay for determining the effect of an immune cell on a cell from an infectious or neoplastic disease. This assay comprises: (a) incubating a cell from an infectious or neoplastic disease and an immune cell in a suitable tissue culture apparatus under conditions that support viability of the immune cell and growth of the cell from an infectious or neoplastic disease for a period of time sufficient to determine whether the immune cell has an effect on the cell from the infectious or neoplastic disease; and (b) determining the number of viable cells from the infectious or neoplastic disease, if any, that are present after step (a).

In one aspect of this embodiment, the cell from the infectious disease is selected from the group consisting of a virus-infected cell, a transplant cell, and a cell infected with a eukaryotic cell parasite. Preferably, the cell from the neoplastic disease is a cell from a cancer selected from a solid tumor, a leukemia, and a lymphoma. Non-limiting examples of solid tumors include bladder cancer, colon cancer, breast cancer, lung cancer, melanoma and sarcoma. More preferably, the solid tumor cell is a sensitized melanoma cell as previously defined.

In another aspect of this embodiment, the immune cell is a lymphocyte such as, e.g., an activated CD4+T-cell, an activated CD8+T-cell, an activated NK cell, and combinations thereof. In addition, the immune cell may be an activated monocyte or an activated macrophage.

In a further aspect of this embodiment, the cell from a neoplastic disease is a sensitized human melanoma cell and the immune cell is an activated human CD8+ cell as previously defined.

In a further aspect of this embodiment, the determining step comprises carrying out a clonogenic or fluorometric assay to determine how many, if any, human melanoma cells are present as previously defined.

Another embodiment of the present invention is an in vitro assay for determining the effect of an activated CD8+ T-cell on a sensitized melanoma cell. This assay comprises: (a) incubating a sensitized melanoma cell and an activated CD8+T-cell in a suitable tissue culture apparatus under conditions that support viability of the activated CD8+T-cell and growth of the sensitized melanoma cell for a period of time sufficient to determine whether the activated CD8+T-cell has an effect on the melanoma cell; and (b) determining, by carrying out a clonogenic or fluorometric assay, the number of viable melanoma cells, if any, that survive after step (a).

A further embodiment of the present invention is a method for improving the specific cytolytic activity (SCA) of an immune cell. This method comprises contacting an immune cell with an antigen and an antigen-independent pro-inflammatory agent.

In the present invention, "SCA" means the number of sensitized cells from an infectious or neoplastic disease killed/day/activated immune cell. The SCA may be obtained using any of the methods and assays of the present invention. For example, as disclosed in more detail below, the SCA may be obtained by determining the number of SIINFEKL-B16 cells killed in collagen-fibrin gels/d/OT-1 cyto cell.

In one aspect of this embodiment, the contacting step may include immunizing a subject, such as for example, by administering the antigen and antigen-independent pro-inflammatory agent to the subject. In this embodiment, the subject may be any suitable mammal, including a human, capable of generating an activated immune cell such as, e.g., a CD8+T-cell. Methods for carrying out such immunizations are known in the art and disclosed in more detail in the Examples.

In another aspect of this embodiment, the contacting step may include administering to immune cells in vitro the antigen and antigen-independent pro-inflammatory agent. Again, methods for carrying out such in vitro procedures are known in the art.

In the present invention, an "antigen-independent pro-inflammatory agent" is an substance that enhances the potency of the immune response that is independent of antigen. Such substances include certain antigen-independent adjuvants, such as for example synthetic peptides derived from tumor-associated Ags, including CpG oligodeoxynucleotides. Other such substances are disclosed in more detail below. Preferably, the antigen-independent pro-inflammatory agent is an adjuvant that activates dendritic cells.

In a further aspect of this embodiment, the SCA of an immune cell may be further improved by contacting the immune cell with a cytokine. This may be achieved in vivo, e.g., by co-administering to a subject a cytokine together with the antigen and antigen-independent pro-inflammatory agent. The cytokine may also be administered to the subject before or after administration of the antigen and antigen-independent pro-inflammatory agent. In addition, improved SCA may be achieved in vitro by concurrently adding a cytokine to immune cells in culture together with the antigen and antigen-independent pro-inflammatory agent. The cytokine may also be added to the culture before or after addition of the antigen and antigen-independent pro-inflammatory agent.

In the present invention, any cytokine that is capable of improving the SCA of an immune cell is contemplated. Preferably, the cytokine is selected from the group consisting of IL-2, IL-12, IL-21, and combinations thereof. More preferably, the cytokine is selected from the group consisting of IL-12, IL-21, and combinations thereof.

In another aspect of this embodiment, the immune cell is a lymphocyte, such as, e.g., an activated CD4+T-cell, an activated CD8+T-cell, an activated NK cell, and combinations thereof.

A further embodiment of the present invention is a method for ex vivo expansion of antigen-specific CD4+ or CD8+T-cells with enhanced specific cytolytic activity (SCA). This method comprises culturing the antigen-specific CD4+ or CD8+T-cells in a suitable culture media comprising an amino acid or a tri-carboxylic acid.

In one aspect of this embodiment, the amino acid or tri-carboxylic acid is any such agent capable of enhancing the SCA of antigen-specific CD4+ or CD8+T-cells in an ex vivo expansion culture. Preferably, the amino acid is selected from the group consisting of alanine, asparagine, aspartic acid, glycine, glutamic acid, proline, serine, and combinations thereof. Suitable culture media for use in the present invention are known and disclosed, e.g., herein.

A further embodiment of the present invention is a method of treating a subject suffering from an infectious or neoplastic disease with immuno therapy. This method comprises: (a) determining the critical concentration of total immune cells required to treat or eradicate an infectious or neoplastic disease in the subject using any of the assays of the present invention; and (b) administering to the subject the critical concentration of immune cells determined in step (a).

In the present invention, the critical concentration of total immune cells required to treat or eradicate an infectious or neoplastic disease in a subject, such as a human afflicted with such disease, is obtained by carrying out any of the assays or methods of the present invention. Methods for determining the critical concentration are exemplified in more detail below.

As used herein, "treat" includes ameliorating or decreasing the adverse affects associated with an infectious or neoplastic disease. In the present invention, "eradicate" means that the infectious or neoplastic disease has rendered below the level of detection.

In one aspect of this embodiment, the subject is a human.

In a further aspect of this embodiment, the neoplastic disease is a melanoma. In an additional aspect of this embodiment, the immune cell is a tumor antigen-specific CD4+ or CD8+T-cell.

In yet a further aspect of this embodiment, the critical concentration is at least $10^7$ tumor antigen-specific CD4+ or CD8+T-cells/ml tumor.

Additional agents may be administered concurrently or before or after the immune cells to further enhance the killing effect of the immune cells or otherwise aid in immuno therapy. For example, in step (b), a cytokine may be co-administered with the immune cells. In the present invention, the cytokine may be an interleukin, such as for example, IL-2, IL-12, IL-21, and combinations thereof.

Another embodiment of the present invention is a substrate for use in an assay for determining the effect of an immune cell on a cell from an infectious or neoplastic disease. The substrate comprises: (a) at least one extracellular matrix polypeptide disposed in a configuration that is sufficient to support viability of an immune cell and growth of a cell from an infectious or neoplastic disease; and (b) an immune cell and a cell from an infectious or neoplastic disease disposed on a surface of or within the substrate.

In one aspect of this embodiment, the at least one extracellular matrix polypeptide is as defined above. The substrate may comprise one extracellular matrix polypeptide, such as, e.g., collagen type I, including rat tail collagen type I. In another aspect of this embodiment, the substrate may comprise a mixture of extracellular matrix polypeptides, such as, e.g., collagen type I and fibrin.

The substrate may take any convenient form for carrying out the assays and methods of the present invention and may be combined with various tissue culture apparatus. For example, the substrate may be in the form of a gel.

In another aspect of this embodiment, the cell from an infectious or neoplastic disease and the immune cell are mammalian, such as, e.g., human. The cell from an infectious disease according to this aspect of this embodiment is selected from the group consisting of a virus-infected cell, a transplant cell, and a cell infected with a eukaryotic cell parasite. The cell from a neoplastic disease according to this aspect of this embodiment is a cell from a cancer selected from the group consisting of a solid tumor, a leukemia, and a lymphoma. The solid tumor may be selected from the group consisting of bladder cancer, colon cancer, breast cancer, lung cancer, melanoma and sarcoma. Preferably, the solid tumor is a sensitized melanoma and the immune cell is a lymphocyte. In this aspect of this embodiment, the lymphocyte is selected from the group consisting of an activated CD4+T-cell, an activated CD8+T-cell, an activated NK cell, and combinations thereof.

A further embodiment of the present invention is a substrate for use in an assay for determining the effect of an activated CD8+T-cell on a sensitized melanoma cell. The substrate comprises: (a) a gel comprising collagen type I and optionally fibrin disposed in a configuration that is sufficient to support viability of an activated CD8+T-cell and growth of a sensitized melanoma cell; and (b) a sensitized melanoma cell and an activated CD8+T-cell disposed on a surface of or within the gel. In this embodiment, the sensitized melanoma and activated CD8+T-cells are human.

The discoveries described herein encompass novel concepts, derived equations, and laboratory methods that enable investigators to prepare and to determine the quantity and quality of ex vivo expanded cytolytically active $CD8^+$ T cells required to control the growth of, and potentially to cure, metastatic melanoma involving antigen-bearing melanoma cells. These concepts, equations, and methods are also potentially applicable to cellular immunotherapy of other neoplastic diseases, and infectious diseases caused by viruses (e.g., influenza, HIV, EBV, CMV, Herpes), and facultative intracellular bacterial pathogens (e.g., *M. tuberculosis, Atypical mycobacteria, L. pneumophila, L. monocytogenes*).

We have discovered that the concentration of immune effector cells (e.g., neutrophils and $CD8^+$ T cells) is the key determinant of the rate and extent to which they are able to fulfill their effector functions. This concept is fundamental to understanding the behavior and effector functions of leukocytes and was discovered in studying the bactericidal activities of human neutrophils. They are described in two published papers (Li, Y., Karlin, A., Loike, J. D., Lu, E. and Silverstein, S. C. A Critical Concentration of Neutrophils is Required for Efficient Bacterial Killing in Suspension. Proc. Natl. Acad. Sci. U.S.A., 99(12):8289-8294, 2002, and Li, Y., Karlin, A., Loike, J., and Silverstein, S. C. A critical concentration of neutrophils is required to block growth of *Staphylococcus Epidermidis* in fibrin gels. J. Exp. Med. 200:613-622, 2004). The findings reported in the two Li et al. papers cited above led to the hypothesis that the concentration of antigen-specific $CD8^+$ T cells (often called "cytotoxic lymphocytes"), also governed their effector functions. In the case of antigen-specific $CD8^+$ T cells, the effector function of interest was their capacity to kill tumor cells expressing a cognate antigen. Hence, a study of killing of SIINFEKL peptide antigen-expressing B16 mouse melanoma cells by OT-1 $CD8^+$ T cells was undertaken. OT-1 $CD8^+$ T cells express a transgeneic T cell receptor that recognizes SIINFEKL-peptide in the context of MHC-1 kb. It was discovered that the fibrin gels Li et al. had used to study neutrophil bactericidal activity were degraded within a few days (2-3) by proteases produced and/or activated by B16 melanoma cells. Gels formed of rat tail collagen I and human fibrinogen were developed. These gels supported logarithmic growth of B16 melanoma cells for as long as 8-9 days without being lysed by B16 cell proteases. Having ascertained that collagen-fibrin gels supported B16 cell growth, in vitro activated and expanded OT-1 mouse spleen cells were co-incubated with SIINFEKL-B16 cells in them. The local concentration of antigen-specific $CD8^+$ T cells determines the efficiency with which these cells kill cognate antigen-expressing tumor cells. Only a small fraction (~2%) of tumor antigen-specific $CD8^+$ T cells are cytolytically active. The cytolytic activity of the cytolytically active fraction of $CD8^+$ T cells accounts for all of the tumoricidal activity of the entire $CD8^+$ T cell population. Tumor size will not increase so long as the intra-tumoral concentration of cytolytically active, antigen-specific $CD8^+$ T cells can be maintained at or above the critical cytolytic $CD8^+$ T cell concentration.

To kill all cancer cells in a tumor, the intra-tumoral concentration of cytolytically active, antigen-specific $CD8^+$ T cells must exceed the average critical cytolytic $CD8^+$ T cell concentration until all cancer cells have been killed. The equation $b_t = b_0 e^{-k \times p \times minutes + tumor\ cell\ growth\ rate/minute \times minutes} = 1$ (where $b_0$=the initial concentration of tumor cells, $b_t$=the concentration of tumor cells at any time t, K=the killing constant for cytolytically active cells ($K_{cytolytic}$), p is the intra-tumoral concentration of cytolytically active antigen-specific $CD8^+$ T cells, $p_{cytolytic}$=the intra-tumoral concentration of cytolytically active, antigen-specific $CD8^+$ T cells, g=the growth rate of the tumor cells, and t=time), accurately describes killing of cognate antigen-expressing tumor cells by antigen-specific $CD8^+$ T cells. Three other equations, $CT_{total}C=g/K_{total}$, $CT_{antigen-specific}C=g/K_{antigen-specific}$, and $CT_{cytolytic}C=g/K_{cytolytic}$, enable one to calculate the critical $CD8^+$ T cell concentration for all $CD8^+$ T cells in a population=$CT_{total}C$, for the tumor antigen-specific $CD8^+$ T cells in the population=$CT_{antigen-specific}C$, and for the cytolytically active fraction of antigen-specific $CD8^+$ T cells in the population=$CT_{cytolytic}C$. The intra-tumoral concentration of cytolytically active leukocytes required to eradicate all cancer cells in a tumor=the concentration of cancer cells/ml of tumor×e−K×p×minutes+tumor growth rate/minute×minutes, where K=the killing constant for cytolytically active cells ($K_{cytolytic}$) and p is the intra-tumoral concentration of cytolytically active leukocytes ($p_{cytolytic}$).

Two corollary rules flow from these findings. In general, it will not be possible to eradicate all tumor antigen-expressing cancer cells by immunization of tumor bearing hosts, or by adoptive transfer of ex vivo expanded cytolytically active cognate tumor antigen receptor-bearing $CD4^+$ or $CD8^+$ T cells without neutralization of the immuno-suppressive effects of the intra-tumoral environment. In general, it will be possible to eradicate all tumor antigen-expressing cancer cells by immunization of tumor bearing hosts, or by adoptive transfer of ex vivo expanded cytolytically active cognate tumor antigen receptor-bearing $CD4^+$ or $CD8^+$ T cells without neutralization of the immuno-suppressive effects of the intra-tumoral environment if the cognate tumor antigen receptor-bearing $CD4^+$ or $CD8^+$ T cells elicited by immunization or produced by ex vivo expansion contains >10% cytolytically active cognate tumor antigen receptor-bearing $CD4^+$ or $CD8^+$ T cells.

In addition, our studies have established the following: K is a measure of the efficiency of killing of antigen-expressing tumor cells by cytolytically active, tumor antigen-specific $CD8^+$ T cells. It is the first and most sensitive measure yet identified to compare the efficacy of different preparations of $CD8^+$ T cells in killing tumor cells. Using K as a measure of killing efficiency we have shown that killing of cognate antigen-expressing tumor cells by total, and by the cytolytically active fraction of, cognate antigen-specific $CD8^+$ T cells in collagen-fibrin gels precisely mimics killing in un-inflamed mouse spleen in vivo. In other words, this in vitro assay can be used to predict the in vivo situation.

The collagen-fibrin gel assay, combined with the clonogenic assay described herein is 5,000-fold more sensitive than currently employed assays for assessing the cytolytic activity of $CD8^+$ T cells. The value of k declines by 0.7 log 10 for every ten-fold increase in $CD8^{+\ T\ cell}$ concentration. The value of k increases logarithmically as the fraction of cytolytically active, antigen-specific $CD8^+$ T cells increases from <0.1% to ~2%. The value of k increases arithmetically as the fraction of cytolytically active, antigen-specific $CD8^+$ T cells increases from ~2%-100%.

Immunization with antigen alone increases the number of cytolytically active, antigen-specific $CD8^+$ T cells in a population. Immunization with antigen plus an adjuvant (e.g., anti-CD40 IgG) that activates dendritic cells increases both the number and the Specific Cytolytic Activity of antigen-specific $CD8^+$ T cells. (In this context, the Specific Cytolytic Activity of $CD8^+$ T cells is the number of antigen-expressing target cells killed by each cytolytically active, antigen-specific $CD8^+$ T cell per unit time.) This is the first evidence that the efficacy of cytolytic T cells bearing a given T cell antigen receptor (TCR) in killing antigen-expressing target cells can be increased. We have shown that two cytokines, IL-12 and IL-21, have the capacity to produce increases in SCA in $CD8^+$ T cells, and have described methods for measuring both the quantity and quality of $CD8^+$ T cells.

Addition of pyruvate and of non-essential amino acids to tissue culture medium in which antigen-specific $CD8^+$ T cells are activated and grown increases significantly the fraction of these cells that is cytolytically active. The concentrations of pyruvate required are above those found in mouse or human plasma. Thus it is likely that the efficacy of cellular immunotherapy in humans could be enhanced by infusion of pyruvate and non-essential amino acids together with $CD8^+$ T cells. Investigators and clinicians will be able to determine the efficacy of ex vivo expanded antigen-specific $CD4^+$ and $CD8^+$ T cells for treating viral and neoplastic diseases prior to infusing these cells into patients.

Cellular immunotherapy may thus become a more quantitative and predictable science. Blood banks and commercial enterprises may make ex vivo expanded $CD4^+$ and $CD8^+$ T cells for therapy of viral and neoplastic diseases. The findings described provide a quantitative, experimentally verified, conceptual and methodological framework for cellular immuno-pharmacology.

Collagen-fibrin gels in combination with clonogenic assays provide the most sensitive methods yet identified to assess the tumoricidal activity of tumor antigen-specific $CD4^+$ and $CD8^+$ T cells. They mimic the in vivo environment and are likely to prove useful in assessing quantitatively the immuno-suppressive activity of tumor cells and regulatory leukocytes (e.g., T-regulatory cells, alternatively activated macrophages). They enable in vitro testing of the efficacy of tumor antigen-specific $CD4^+$ and $CD8^+$ T cells vs. cognate antigen-expressing tumor cells prior to infusion of these $CD4^+$ and $CD8^+$ T cells into patients. They enable one to determine k in vitro and thereby calculate the likely activity of $CD4^+$ and $CD8^+$ T cells in vivo. They describe methods and technologies for assessing the quantity and quality of immune cells to be used therapeutically in humans.

In Budhu, S., et al., "$CD8^+$ T cell concentration determines their efficiency in killing cognate antigen-expressing syngeneic mammalian cells in vitro and in mouse tissues", 207 J. Exper. Med. 223-235 (2010), we describe a quantitative model for assessing the cytolytic activity of antigen-specific $CD8^+$ T cells in vitro and in vivo in which the concentration of antigen-specific $CD8^+$ T cells determines the efficiency with which these cells kill cognate antigen-expressing melanoma cells in packed cell pellets, in three-dimensional collagen-fibrin gels in vitro, and in established melanomas in vivo. In combination with a clonogenic assay for melanoma cells, collagen-fibrin gels are 4,500-5,500-fold more sensitive than the packed cell pellet-type assays generally used to measure $CD8^+$ T cell cytolytic activity. An equation previously used to describe neutrophil bactericidal activity in vitro and in vivo also describes antigen-specific $CD8^+$ T cell-mediated cytolysis of cognate antigen-expressing melanoma cells in collagen-fibrin gels in vitro and in transplanted tumors in vivo. This equation was used to calculate the critical concentration of antigen-specific $CD8^+$ T cells, which is the concentration of these cells required to hold constant the concentration of a growing population of cognate antigen-expressing melanoma cells. It is $\sim 3.5 \times 10^5$/ml collagen-fibrin gel in vitro and $\sim 3 \times 10^6$/ml or /g melanoma for previously published studies of ex vivo-activated adoptively transferred tumor antigen-specific $CD8^+$ T cell killing of cognate antigen-expressing melanoma cells in established tumors in vivo. The antigen-specific $CD8^+$ T cell concentration required to kill 100% of $2 \times 10^7$/ml cognate antigen-expressing melanoma cells in collagen fibrin gels is $\geq 10^7$/ml of gel.

Li et al. (2002, 2004) reported that the bactericidal activity of neutrophils depends on the absolute neutrophil concentration in fibrin gels, a condition which mimics tissue environments, and in rabbit dermis in vivo. The findings that the critical neutrophil concentration (CNC) for controlling bacterial growth in fibrin gels ($1-4 \times 10^6$ neutrophils/ml of gel) is similar to the CNC in rabbit dermis in vivo ($4-8 \times 10^6$ neutrophils/ml or /g dermis) showed that such gels are useful for studying neutrophil effector functions in tissue-like environments in vitro. We hypothesized that the critical concentration concept might be applicable to describing effector functions of other leukocytes, for example, the cytolytic activity of $CD8^+$ T cells. Therefore, we examined $CD8^+$ T cell-mediated killing of target cells expressing a cognate antigen.

We selected activated $CD8^+$ OT-1 cells as effector cells and SIINFEKL peptide-pulsed B16 melanoma cells as target cells for these studies because both cell types and their interactions had been well characterized in vitro (Moore et al., 1988; Ochalek et al., 1988; Snyder et al., 2003; Regoes et al., 2007) and in vivo (Dobrzanski et al., 2001; Regoes et al., 2007). To quantitatively assess OT-1 cell-mediated cytolysis of SIINFEKL peptide-pulsed B16 cells, we used a newly designed three-dimensional collagen-I-fibrin gel system and a previously described clonogenic assay for B16 mouse melanoma cells (Freedman et al., 1984). We report that in every situation examined (i.e., individual SIINFEKL-B16 cells and SIINFEKL-B16 cells in spheroids [Sutherland, 1988] in collagen-fibrin gels and SIINFEKL-B16 cells in centrifugally packed cell pellets), OT-1 T cell-mediated killing of SIINFEKL-B16 cells was strictly dependent on OT-1 cell concentration. Moreover, we determined that a concentration of $\geq 10^7$ OT-1 cells/ml of gel is required for them to produce sterilizing immunity versus SIINFEKL-B16 cells in vitro and that activated OT-1 cells kill SIIN-FEKL-B16 cells ~10-fold more efficiently in collagen-fibrin gels in vitro than ovalbumin peptide-expressing B16 cells in tumors in vivo (Petersen et al., 2006).

Growth of B16 Melanoma Cells in Collagen-fibrin Gels.

B16 melanoma cells embedded in collagen-I-fibrin gels at concentrations of 104-106/ml grow at an exponential rate and have a doubling time of µ58 h (FIG. 1 A), which is ~66-83% of their doubling time in vivo (Li et al., 1984). Microscopic observations of B16 cells maintained in these gels for 24 h showed mostly single B16 cells with lamellipods protruding in all directions (FIG. 1 B). By 72 h, many B16 cells aggregated into small clusters. By 96-120 h, these clusters developed into spheroids (Sutherland, 1988), varying from 50 to 100 µm in diameter. Each spheroid contained ~100 B16 cells. Hematoxylin/eosin-stained frozen sections of gels containing single B16 cells and B16 cell spheroids revealed considerable matrix remodeling by these cells during culture (FIG. 1 B). Gels containing B16 cells at an initial concentration of >106 B16 cells/ml in the absence of OT-1 cells remained intact for slightly >120 h. After this time, the gels began to dissolve and the growth rate of B16 cells slowed. B16 cells, like many other mouse and human tumor cells, secrete proteases which are likely responsible for gel dissolution (Baramova et al., 1994; Hofmann et al., 2005; Huang et al., 2005).

The Concentration of SIINFEKL Peptide Required for Optimal Killing of B16 Cells by OT-1 Cells.

Figure 9:
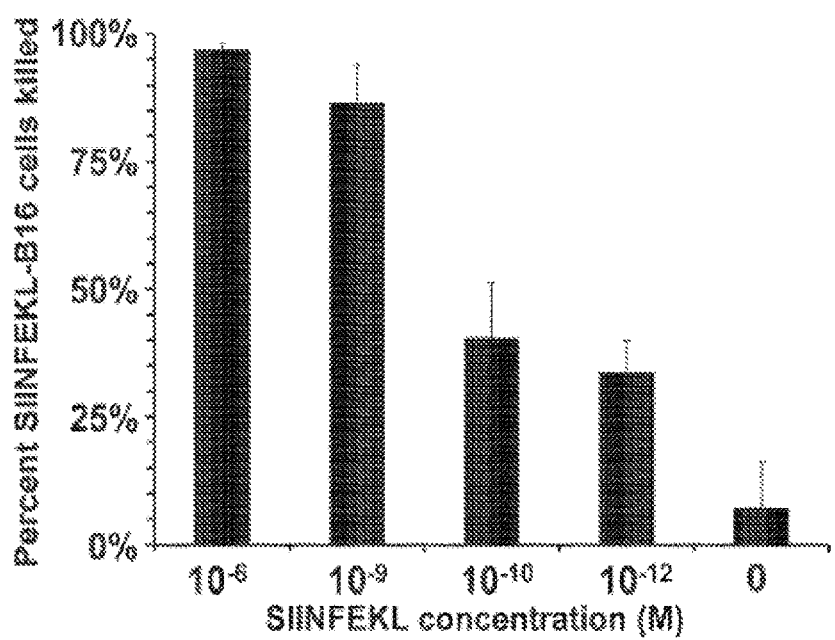
FIG. 9. SIINFEKL peptide concentration required for optimal killing of B16 cells in collagen-fibrin gels. B16 cells were pulsed with the indicated concentrations of SIINFEKL peptide and coincubated at a concentration of $10^5$/ml collagen-fibrin gel without or with $10^7$ OT-1 cells/ml of gel at 37° C. for 24 h. The gels were lysed and assayed for viable B16 cells. Data shown represent mean±SEM of n=3 experiments performed in duplicate.

Display of the ovalbumin peptide SIINFEKL (ova residues 257-264) in the context of B16 MHC I (H-2 kb) targets B16 cells for killing by activated OT-1 cells (Curtsinger et al., 1998; Moore et al., 1988). 96% of B16 cells incubated with 10-6 M SIINFEKL peptide for 2 h at 37° C. were killed by 107 OT-1 cells/ml of gel in 24 h, whereas 85, 40, and 32% of B16 cells treated with SIINFEKL at 10-9, 10-10, and 10-12 M, respectively, were killed by these cells in the same time period (FIG. 9). In contrast, coincubation of 107 OT-1 cells/ml of gel with unpulsed B16 cells at 105/ml of gel reduced recovery of clonogenic B16 cells by ≤10%, indicating a low level of nonspecific killing of unpulsed B16 cells by activated OT-1 cells. We used B16 cells pulsed with 10-6 M SIINFEKL peptide in all subsequent experiments.

OT-1 Cell Concentration Determines their Efficiency in Killing Growing and Nongrowing SIINFEKL-B16 Cells in Collagen-fibrin Gels.

Figure 2:
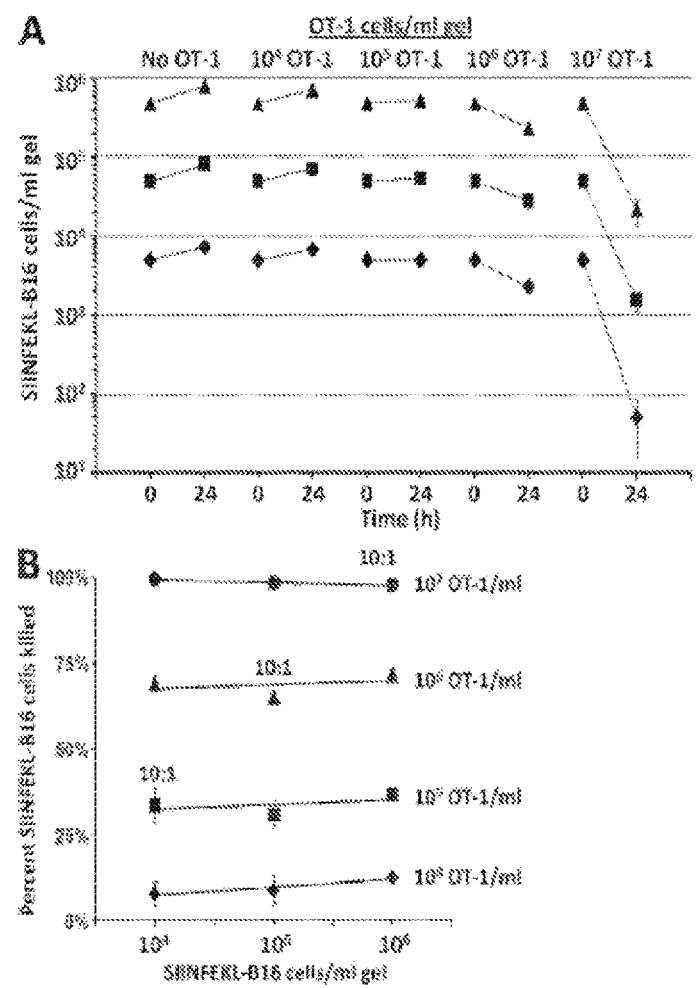
FIG. 2. (A) Collagen-fibrin gels containing $5\times10^4$ (♦), $5\times10^5$ (■), or $5\times10^6$ (▲) SIINFEKL-B16 cells/ml of gel, with or without $10^4$, $10^5$, $10^6$, or $10^7$ OT-1 cells/ml of gel, were overlaid with 0.5 ml RPMI 1640 with 10% FBS and $5\times10^{-5}$ M β-ME and incubated at 37° C. Shown is the number of clonogenic B16 cells recovered from gels at time 0 and after a 24-h incubation at 37° C. with the indicated concentration of OT-1 cells. Data shown represent mean±SEM of n=3 experiments performed in duplicate. (B) Relationship between OT-1 cell concentration, initial SIINFEKL-B16 cell concentration, and percentage of B16 cells killed.

To test whether the efficiency of OT-1 cell killing of SIINFEKL-B16 cells depends on OT-1 cell concentration, we examined the killing of 5×103-105/ml SIINFEKL-B16 cells by 104-107/ml of activated OT-1 cells in collagen-fibrin gels. Killing of SIINFEKL-B16 cells depended on OT-1 cell concentration and was unrelated to the effector/target cell ratio (FIG. 2, A and B). For example, 107 OT-1 cells/ml of gel killed ~98% of SIINFEKL-B16 cells in 24 h, regardless of whether the initial B16 cell concentration was 106/ml of gel, which is a 10:1 ratio of OT-1/B16 cells, or 104 B16 cells/ml of gel, which is a 1,000:1 ratio of OT-1/B16 cells (FIG. 2 B). At OT-1 cell concentrations of 105/ml or less, more clonogenic B16 cells were recovered after 24 h than were present in the inoculum (at time 0), even when the inoculum contained only 104 B16 cells/ml of gel (FIG. 2 A), indicating that at OT-1 cell concentrations ≤105/ml, the rate of B16 growth exceeded the rate of OT-1 cell killing.

Addition of β-ME to the culture medium improved survival and effector activity of OT-1 cells (Cerottini et al., 1974). It also improved B16 cell growth in the first 24 h after their placement into collagen-fibrin gels. In the absence of β-ME, B16 cells showed a small (~20%) decline in number during their first 24 h in these gels (not depicted and Table 1). We used this observation to compare the efficiency of OT-1 cell killing of nongrowing (without β-ME) versus growing (with β-ME) B16 cells in collagen-fibrin gels. OT-1 cells killed approximately the same percentage of nongrowing SIINFEKLB16 cells as growing SIINFEKL-B16 cells (FIG. 2 B and Table 1). However, with nonproliferating B16 cells (without n-ME in the medium), we observed a net reduction in B16 cells at every OT-1 cell concentration. OT-1 cell concentration also determined the efficiency with which these cells killed SIINFEKL-B16 cells in two-dimensional cultures (unpublished data). Thus, in both two- and three-dimensional cultures, OT-1 cell concentration was the critical determinant of killing of SIINFEKL-B16 cells.

The OT-1 Critical T Cell Concentration (CTC).

As noted, the CNC is the concentration of neutrophils required to hold constant the concentration of growing bacteria. We hypothesized that the critical concentration concept also applies to OT-1 cell killing of SIINFEKLB16 cells. Indeed, inspection of FIG. 2 A shows that the CTC for killing SIINFEKL-B16 cells lies between 105 and 106 OT-1 cells/ml collagen-fibrin gel. 105 OT-1 cells/ml of gel killed SIINFEKL-B16 cells at a slightly slower rate than the rate of B16 cell growth, whereas 106 OT-1 cells/ml killed SIINFEKL-B16 cells at a substantially higher rate than B16 cell growth (FIG. 2 A). Additional experiments (unpublished data) showed that 3-4×105 OT-1 cells/ml of gel were required to hold SIINFEKL-B16 melanoma cell concentration constant. Therefore, the experimentally determined CTC for OT-1 cell killing of SIINFEKL-B16 cells is ~3.5× 105 OT-1 cells/ml of gel.

Naive T Cells from Wild-Type C57BL/6 Mouse Spleen Had No Effect on the Efficiency with which OT-1 Cells Killed SIINFEKL Peptide-pulsed B16 Cells.

It was possible that nutrient deprivation by high concentrations (i.e., ≥$10^7$ cells/ml) of OT-1 cells was responsible for B16 cell killing. To test this possibility, we incubated $10^6$ SIINFEKL-B16 cells/ml of gel with $10^4$-$10^6$ OT-1 cells/ml of gel without and with sufficient naive or mitogen-activated C57BL/6 lymphocytes to bring the total number of lymphocytes to $10^7$/ml of gel. The presence of $10^7$ naive or mitogenactivated lymphocytes had no effect on viability or growth of $10^6$ SIINFEKL-B16 cells/ml of gel, and a 9-900-fold excess of naive or mitogen-activated lymphocytes in combination with activated OT-1 cells had no effect on the efficiency of OT-1 cell killing of $10^6$ SIINFEKL-pulsed B16 cells/ml of gel (Table 2). Thus, killing of SIINFEKL-B16 cells cocultivated with high concentrations of OT-1 cells was not the result of nutrient depletion by the OT-1 cells.

The Concentration of Activated OT-1 Cells Remains Constant for at Least 72 h of Co-Culture with SIINFEKL Peptide-pulsed B16 Cells in Collagen-fibrin Gels.

Figure 3:
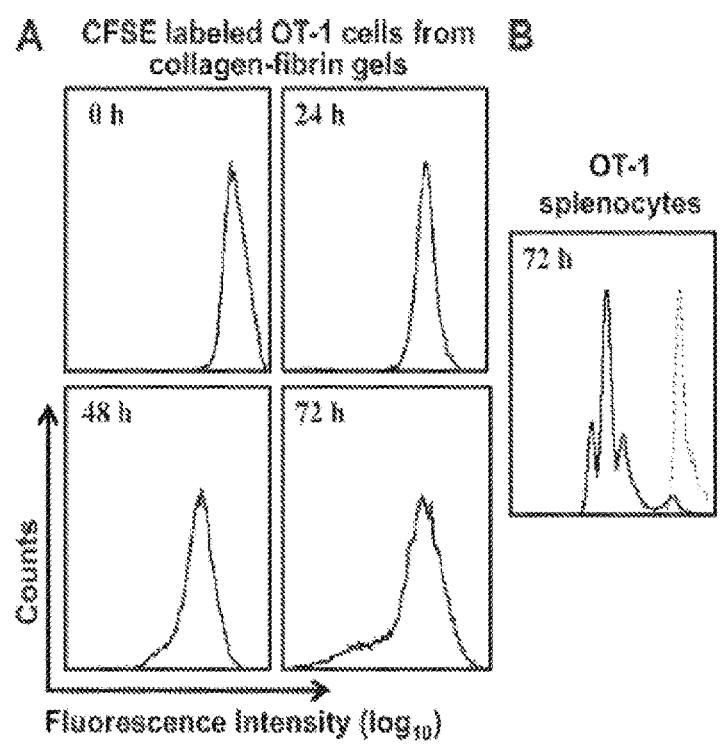
FIG. 3. CFSE-labeled OT-1 cells remain viable but do not divide when coincubated with SIINFEKL-B16 cells in collagen-fibrin gels. (A) $10^6$ SIINFEKL-B16 cells/ml were coincubated with $10^7$/ml CFSE-labeled OT-1 cells in collagen-fibrin gels in the presence or absence of 100 U/ml IL-2. Gels were lysed as described at 24, 48, and 72 h. The released cells were incubated in propidium iodide and analyzed by FACS. (B) CFSE-labeled naive OT-1 splenocytes were incubated with 0.75 μg/ml SIINFEKL peptide at 37° C. for 72 h, after which the cells were isolated and analyzed by FACS. Shown is a representative experiment of n=3 experiments performed in duplicate.

To determine whether the concentration of activated OT-1 cells changed during their incubation with SIINFEKL-B16 cells, we coincubated CFSE-labeled or unlabeled OT-1 cells with SIINFEKL-B16 cells in collagen-fibrin gels for 24-72 h, lysed the gels, and assayed the number of B16 cells and CFSE-labeled OT-1 cells by clonogenic assay and FACS, respectively. CFSE-labeled OT-1 cells killed SIINFEKL-B16 cells with the same efficiency as unlabeled OT-1 cells (unpublished data). FACS analysis of the CFSE-labeled cells showed that >90% of the OT-1 cells remained viable at 24-72 h and that their exposure to SIINFEKL-B16 cells in the presence or absence of IL-2 did not stimulate a significant number of them to divide (FIG. 3 A and not depicted). Control experiments in which CFSE-labeled naive OT-1 splenocytes were incubated with SIINFEKL peptide showed dilution of the CFSE label (FIG. 3 B), confirming that proliferation of the CFSE-labeled cells could be detected by this assay, had it occurred.

Mechanism of OT-1 Cell Killing of Peptide-pulsed B16 Cells.

Figure 10:
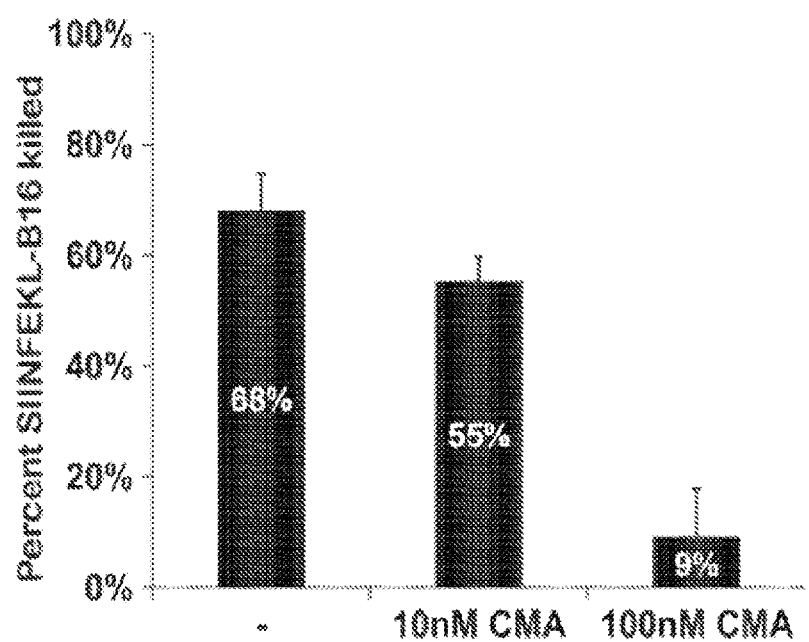
FIG. 10. CMA inhibits OT-1 cell killing of SIINFEKL-B16 cells. Collagen-fibrin gels containing $10^5$ SIINFEKL-B16 cells and $10^6$ OT-1 cells/ml of gel were overlaid with 0.5 ml RPMI 1640 containing 10% FBS, $5\times10^{-5}$ M β-ME, and the indicated concentration of CMA and incubated at 37° C. for 24 h. The gels then were lysed and assayed for viable B16 cells as described in Materials and methods. Data shown represent mean±SEM of n=3 experiments performed in duplicate FIG. 11. OT-1 cell killing of SIINFEKL-B16 cells in spheroids versus single SIINFEKL-B16 cells dissociated from these spheroids. Collagenfibrin gels containing $10^6$ OT-1 cells and 103 SIINFEKL peptide-pulsed B16 spheroids or 105 SIINFEKL-B16 cells dissociated from SIINFEKL peptide-pulsed spheroids were incubated in OT-1 growth medium at 37° C. At 24 and 48 h, gels were lysed and surviving B16 cells were assessed by colony formation as described in FIG. 1. Shown is the mean percentage of B16 cells killed±SEM for three experiments, each performed in duplicate.

Snyder et al. (2003) reported that activated OT-1 cell killing of SIINFEKL-sensitized targets is perforin dependent. Indeed, coincubation of 106 OT-1 cells and 105 SIINFEKL-B16 cells/ml collagen-fibrin gel in medium containing 10 or 100 nM concanamycin A (CMA), an inhibitor of vacuolar-type H+-ATPases (Kataoka et al., 1996) and of perforin-mediated killing, inhibited killing of the B16 cells by 19 and 87%, respectively (FIG. 10). CMA at >100 nM was toxic to B16 cells after 24 h (as measured by the clonogenic assay; unpublished data).

OT-1 Cell Concentration Determines the Efficiency of Killing of SIINFEKL Peptide-pulsed B16 Cells in Packed Cell Pellet-type Assays.

Release of 51Cr from 51Cr-labeled target cells coincubated with activated CD8+T lymphocytes in packed pellets is a standard technique for assessing CD8+T lymphocyte cytolytic activity (Brunner et al., 1968; Martz, 1975). Target cell killing in these packed cell pellet-type assays is generally reported as a function of effector/target cell ratio. Maximal target cell killing often plateaus at <100% in these assays, even when the effector/target cell ratio is very high (e.g., 100:1). This plateau effect is inconsistent with the concept that the extent of target cell killing is dependent on effector/target cell ratio. It is consistent, however, with a determinative role for effector cell concentration in target cell killing. This occurs because as effector cell concentration rises, it reaches close to the maximum effector cell concentration that can be attained in a packed pellet of effector cells alone. For example, the maximum concentration of activated OT-1 cells in a centrifugally packed pellet is 5.9×109 OT-1 cells/ml, whereas the maximum concentration of OT-1 cells in a packed pellet containing OT-1 cells and 104 B16 cells is ~5×109 OT-1 cells/ml. To test whether activated OT-1 cell-mediated killing of SIINFEKL-B16 cells in a packed cell pellet-type assay depends on OT-1 cell concentration, we cosedimented varying numbers of activated OT-1 cells with 104 SIINFEKL-pulsed or nonpulsed B16 cells in wells of a 96-well plate, incubated them for 4 h at 37° C., and assayed the number of clonogenic B16 cells remaining. Virtually no unpulsed B16 cells were killed (FIG.

4 A). In contrast, at OT-1/B16 cell ratios between 0.1:1 and 5:1, corresponding to OT-1 cell concentrations of $4\times10^7$ and $1.5\times10^9$/ml, SIINFEKL-B16 cell killing increased in proportion to both OT-1 cells/SIINFEKL-B16 ratio and OT-1 cell concentration. However, at OT-1/B16 cell ratios of ≥5:1 there was no proportionality between the OT-1/B16 ratio and OT-1 cell-mediated killing of B16 cells. At these high effector/target cell ratios, a 10-fold increase in the OT-1/B16 cell ratio (FIG. 4 A) produced an insignificant increase in B16 cytolysis (i.e., 58% killing at 5:1 and 62% killing at 50:1 [FIG. 4 A]) and only a 3.1-fold increase in OT-1 cell concentration.

Figure 4:
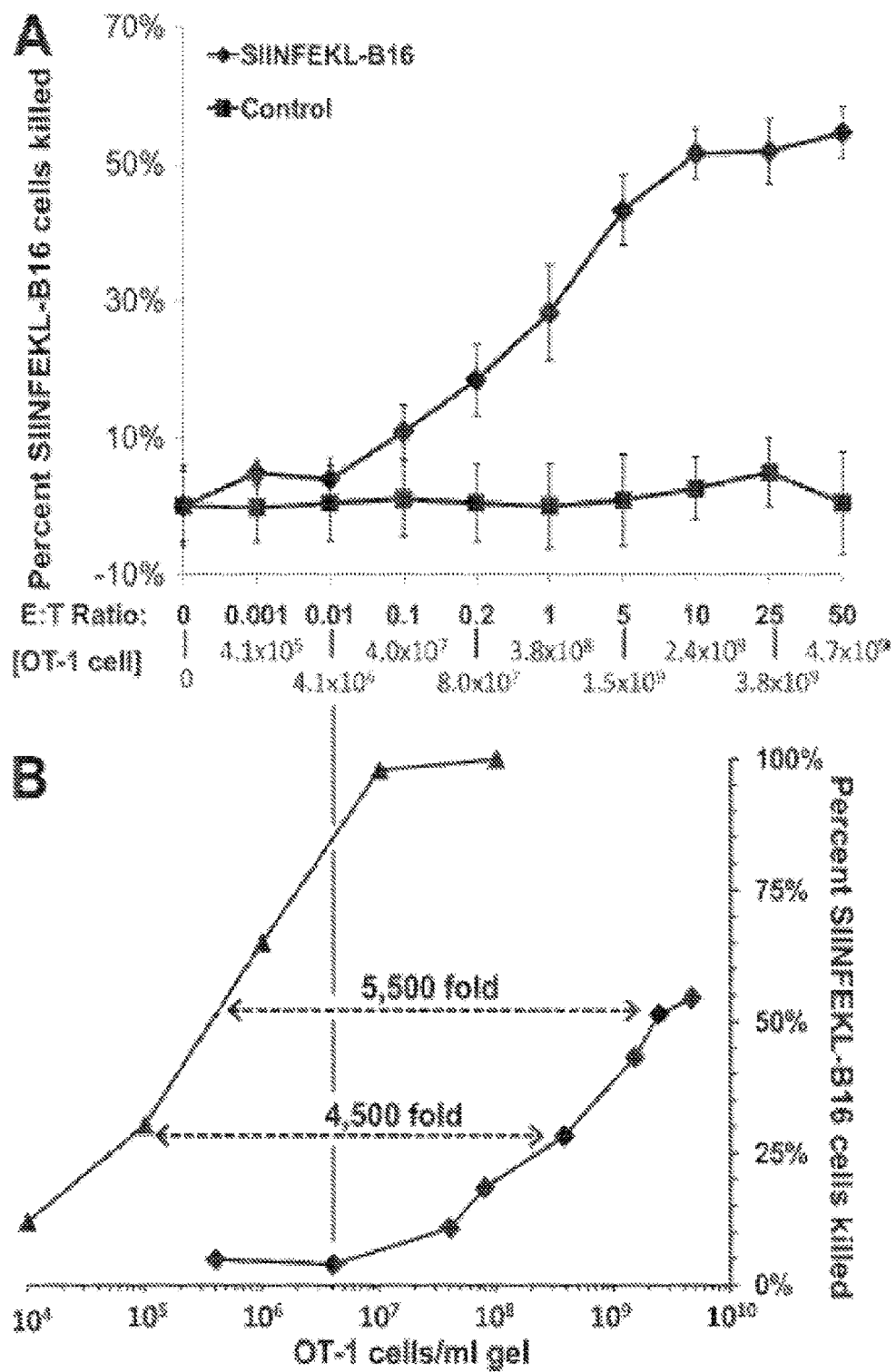
FIG. 4. OT-1 cell concentration determines the efficiency of killing of SIINFEKL peptide-pulsed B16 cells in packed cell pellet-type assays. (A) $10^4$ SIINFEKL-pulsed (♦) or nonpulsed (■) B16 cells were mixed with $10-5\times10^5$ activated OT-1 cells in 200 μl OT-1 medium in round-bottom wells of a 96-well plate. Plates were centrifuged at 50 g for 5 min to pellet the cells and incubated at 37° C. for 4 h. Cells in each well were dissociated with trypsin-EDTA, and their viability was measured by clonogenic assay. Data shown represent mean±SEM of n=3 experiments performed in duplicate. (B) Efficiency of OT-1 cell killing of SIINFEKL-B16 cells in collagen-fibrin gels (▲) versus packed pellet-type assays (♦). Data for collagen-fibrin gels were obtained from Table 1. Data for packed pellet-type assays were obtained from A.

It was possible that differences in density and deformability of B16 cells versus OT-1 cells could result in an inhomogeneous distribution of these cells in a cell pellet and contribute to the plateau effect observed in FIG. 4 A. To test this possibility, we cosedimented activated OT-1 and SIINFEKL-B16 cells at 10:1, 50:1, and 100:1 ratios of OT-1/B16 cells, fixed the pellets with formalin, bisected them parallel to the axis of sedimentation, sectioned them, stained the sections with hematoxylin/eosin, and observed the distribution of OT-1 and B16 cells in the pellet by light microscopy. Under all conditions tested, the OT-1 and B16 cells were randomly and uniformly distributed throughout the pellet (unpublished data). Thus, the observed plateau in killing is not a result of inhomogeneous distribution of the two cell types.

It was also possible that at very high OT-1 cell concentrations these cells saturate the B16 cells' MHC-I-SIINFEKL binding sites for OT-1 T cell receptors or cluster around the B16 cells and sterically hinder contact with them. Although we cannot formally exclude the former explanation, we examined the latter. Given diameters of 7 and 17.4 μm for OT-1 cells and B16 cells (Ochalek et al., 1988), respectively, and hexagonal packing of the OT-1 cells on the surfaces of B16 cells, we calculated that ~48 OT-1 cells could bind simultaneously to each SIINFEKL-B16 cell. This is approximately ninefold in excess of the 5:1 ratio of OT-1/B16 cells that produces near maximal killing of SIINFEKL-B16 cells in packed cell pellets (FIG. 4 A). Therefore, it is unlikely that at very high OT-1 cell concentrations, such as those which occur in packed cell pellet-type assays, access to each target cell's surface limits effector cell cytolytic activity.

These experiments reveal two major differences between OT-1 cell killing of target cells in packed cell pellet-type assays (FIG. 4) and in collagen-fibrin gels (FIG. 2 and Table 1). First, in packed cell pellet-type assays (FIG. 4) there was no detectable killing of SIINFEKL-B16 cells at OT-1 cell concentrations ≤$4\times10^6$/ml. In contrast, OT-1 cells at $10^6$ and $10^7$/ml killed ~62 and 98%, respectively, of nongrowing (Table 1) or growing (FIG. 2) SIINFEKL-B16 cells in 24 h in collagen-fibrin gels. Thus, packed cell pellet-type assays may underestimate the cytocidal activity of CD8+T cell populations by 70-90%. Second, packed cell pellet-type assays are 4,500-5,500-fold less sensitive than collagen-fibrin gel assays (FIG. 4 B).

To further examine the relationship between OT-1 cell concentration and B16 cell killing, we cosedimented a mixture containing $2\times10^4$, $4\times10^4$, or $10^5$ SIINFEKL-B16 cells, $10^5$ activated OT-1 cells, and sufficient naive wild-type C57BL/6 splenocytes to bring the total volume of cell pellets to ~263 nl (Table 3). Under these conditions, the ratio of OT-1/SIINFEKL-B16 cells rose from 1:1 to 5:1 but the OT-1 cell concentration remained constant at ~$3.8\times10^8$ OT-1 cells/ml. At all three ratios, the percentage of SIINFEKL-B16 cells killed was 18%. This result is consistent with those reported in FIG. 2 and Table 1 and confirms that OT-1 cell concentration determines the efficiency of OT-1 cell killing of SIINFEKL-B16 cells in packed cell pellet-type assays.

OT-1 Cells Kill SIINFEKL-B16 Cells in Spheroids as Efficiently as Single SIINFEKL-B16 Cells.

Figure 11:
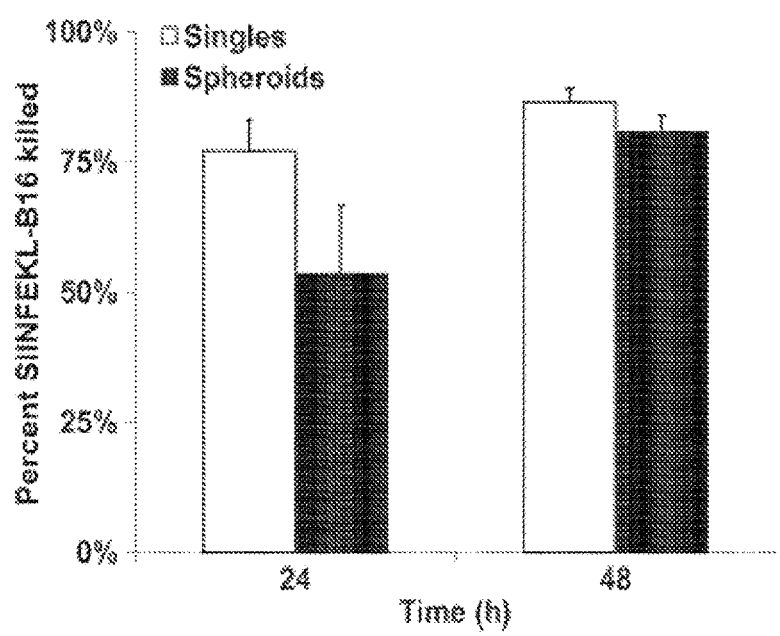

Melanoma cells, like many other tumor cells, grow in nests or clusters in vivo. B16 cells spontaneously form spheroids when cultured in suspension (Sutherland, 1988; Kuwashima et al., 1993) or in collagen-fibrin gels for more than 3 d (FIG. 1 B). To assess whether the multilayering of B16 cells that occurs in spheroids, or in the matrix proteins which the B16 cells produce (Dewever et al., 2007), affects the sensitivity of these cells to OT-1 cell-mediated killing, we pulsed intact spheroids (~100 B16 cells/spheroid) with SIINFEKL peptide, coincubated ~$10^3$ SIINFEKL-spheroids or ~$10^5$ SIINFEKL-B16 cells dissociated from these spheroids with $10^6$ activated OT-1 cells for 24 and 48 h in collagen-fibrin gels, and measured the number of clonogenic B16 cells remaining. OT-1 cells killed ~24% more (not significant) spheroid-derived single SIINFEKL-B16 cells than SIINFEKL-B16 cells in spheroids at 24 h (FIG. 11). At 48 h, OT-1 cells killed roughly equal percentages of B16 cells dissociated from spheroids (85%) and B16 cells in spheroids (80%). Light microscopy of sections of gels containing similar concentrations of OT-1 cells and SIINFEKL-B16 spheroids showed OT-1 cells clustered around and invading spheroids. Similarly, Joseph-Pietras et al. (2006) noted human monocyte invasion of B16 cell spheroids when the two cell types were co-cultured for 38-62 h. Thus, there was no evidence that multilayering of B16 cells in spheroids, or the matrix proteins associated with them (Dewever et al., 2007), affected OT-1 cell penetration of spheroids or their capacity to kill SIINFEKL-B16 cells in spheroids.

OT-1 Cells Kill SIINFEKL-B16 Cells at a Constant Exponential Rate and Produce Sterilizing Immunity in Collagen-fibrin Gels.

Figure 5:
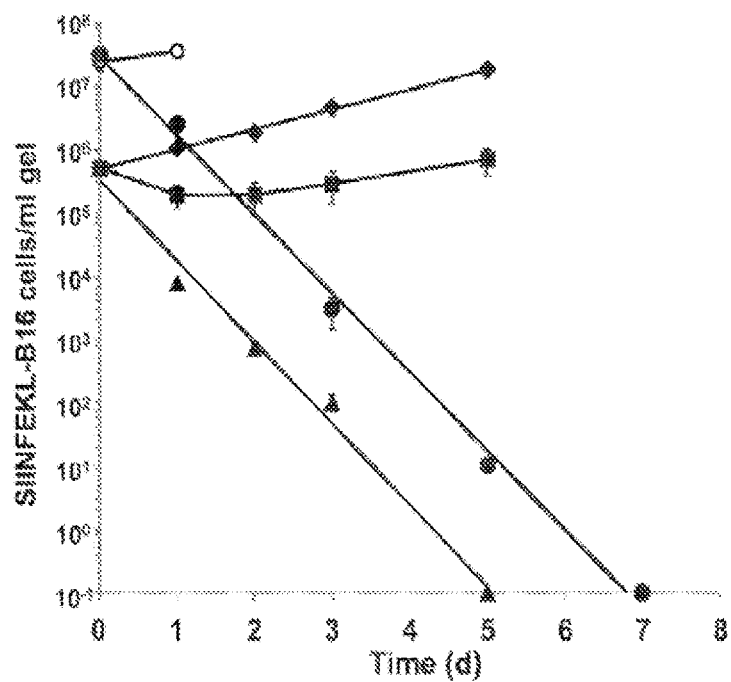
FIG. 5. OT-1 cells affect sterilizing immunity versus SIINFEKLB16 cells in collagen-fibrin gels. Collagen-fibrin gels containing $5\times10^5$ SIINFEKL-B16 cells/ml of gel alone (♦) or with $10^6$ (■) or $10^7$ (▲)/ml OT-1 cells were incubated at 37° C. for up to 5 d. Gels were lysed on the day indicated and assayed for viable B16 cells as described in the Examples. Data shown represent mean±SEM of n=3 experiments performed in duplicate. Collagen-fibrin gels containing $2\times10^7$ SIINFEKL-B16 cells/ml of gel in medium containing 20 U IL-2/ml of gel alone (○) or with $10^7$ (●)/ml OT-1 cells were incubated at 37° C. for up to 7 d, lysed, and assayed for viable B16 cells as described in the Examples. Shown are the results of a representative experiment performed in duplicate.

The most stringent test of the efficacy of cellular immunotherapy of tumors is eradication of all tumor cells. Therefore, we examined whether OT-1 cells generate sterilizing immunity in vitro. Co-incubation of $10^6$/ml activated OT-1 cells with $5\times10^5$/ml SIINFEKL-B16 cells in collagen-fibrin gels for 3 d resulted in recovery of 92% fewer B16 cells than gels containing B16 cells alone (FIG. 5). The B16 cells resumed growth thereafter, surpassing the initial inoculum of $5\times10^5$ B16 cells/ml of gel by day 5. In contrast, $10^7$ activated OT-1 cells/ml coincubated with $5\times10^5$ SIINFEKL-B16 cells/ml in collagen-fibrin gels killed the B16 cells at a constant exponential rate (~99.9%/d) for 5 d, killing 100% of the B16 inoculum over this period (FIG. 5). Under these conditions, 100% of B16 cells were killed. Gels harvested on days 6 and 7 also yielded no viable B16 cells (unpublished data).

Human and mouse melanomas are reported to contain $10^7$-$10^8$ tumor cells/ml or /g of tumor (Stephens and Peacock, 1978; Hemstreet et al., 1980; Daugherty et al., 1981; Whiteside et al., 1986). To determine whether activated OT-1 cells are capable of eradicating SIINFEKL-B16 cells growing in collagenfibrin gels at concentrations in this range, we coincubated $2\times10^7$ SIINFEKL-B16 cells/ml and $10^7$ OT-1 cells/ml collagen-fibrin gel for 7 d. (B16 cells at >$2\times10^7$/ml lysed the collagen-fibrin gels and could not be tested.) To assure that the OT-1 cells remained viable and active throughout this period, we supplemented the medium with IL-2. No viable B16 cells were recovered on day 7 (FIG. 5).

We draw three conclusions from these experiments. First, the finding that OT-1 cells kill SIINFEKL-B16 cells at a constant exponential rate (~99.3-99.9%/d) for 5-7 d (FIG. 5) provides independent confirmation that killing of SIINFEKLB16 cells depends strictly on OT-1 cell concentration (FIG. 5). Were this not so, the killing rate would change as the target cell concentration declined. Second, it indicates that the concentration of cytolytically active effector cells remained constant for 5 d in the absence of added IL-2 and for 7 d in its presence. Were this not so, the rate of target cell killing would change as the concentration of effector cells declined. Third, it demonstrates that $10^7$ OT-1 cells/ml produce sterilizing immunity versus $2\times10^7$ SIINFEKL-B16 cells/ml, a concentration of melanoma cells within the range found in human melanomas in vivo (Stephens and Peacock, 1978; Hemstreet et al., 1980; Daugherty et al., 1981; Whiteside et al., 1986).

Figure 6:
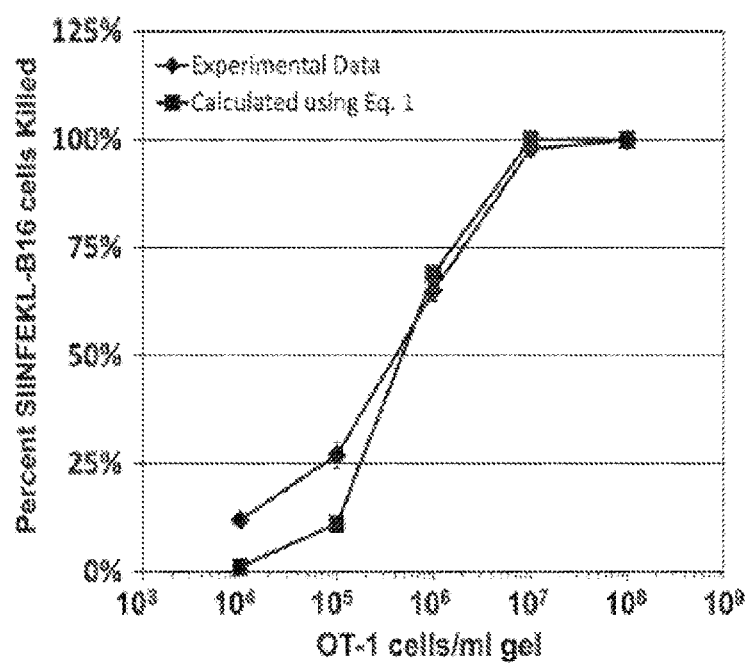
FIG. 6. Comparison of experimentally derived versus calculated values for OT-1 cell killing of SIINFEKL-B16 cells in collagen-fibrin gels. Experimental data±SEM are from FIG. 2 and Table 1. Calculated values were determined using Eq. 1 (Li et al., 2004), and k=$8.1\times10^{-10}$·ml/OT-1 cell/min. Pearson's correlation between experimental and calculated values=0.994 (P=0.00048).

Does $Bt/b0=e-Kpt+Gt$ (Eq. 1) describe OT-1 cell killing of SIINFEKL-B16 cells in collagen-fibrin gels? The experiments reported in FIG. 2, and in experiments which were not depicted, indicate that the CTC required to control growth of SIINFEKL-B16 cells in collagen-fibrin gels is $3-4\times10^5$ OT-1 cells/ml of gel. By definition (Li et al., 2002, 2004), the CTC=g/k (Eq. 2). We calculate that g, the growth rate of SIINFEKL-B16 cells in collagen-fibrin gels (FIGS. 1 and 2), is $2.84\times10^{-4}$ per min. Using this value of g and the experimentally determined value for the critical OT-1 cell concentration in collagen-fibrin gels of $3.5\times10^5$ OT-1 cells/ml, we solved Eq. 2, for k, the rate constant for effector cell killing of target cells, and obtained a value of $8.1\times10^{-10}$ ml/OT-1 cell/min. We also calculated k using Eq. 1 (Li et al., 2004 and Examples) and values of bt, b0, g, and t from experiments described in FIGS. 2 and 6, and obtained a mean value for k of $8.19\times10^{-10}$ ml/OT-1 cell/min. Substituting $k=8.1\times10^{-10}$ ml/OT-1 cell/min into Eq. 1, we compared the experimentally determined and calculated values for OT-1 cell killing of SIINFEKL-B16 cells in collagen-fibrin gels (FIG. 6). The Pearson correlation coefficient for the curves described by these datasets (FIG. 6) is 0.994 ($P=0.000483$; $R2=0.989$), which indicates that Eq. 1 accurately describes OT-1 cell killing of SIINFEKL-B16 cells in collagen-fibrin gels.

Does Eq. 1 describe CD8+T cell cytolytic activity in vivo? Regoes et al. (2007) derived an equation similar to Eq. 1 to model killing of lymphocytic choriomeningitis virus (LCMV)-infected splenocytes by LCMV-specific CD8+T cells in mouse spleen in vivo. Using Eq. 1 and the findings of Regoes et al. (2007) that LCMV-immune mouse spleen contains $\sim5\times10^6$ LCMV-specific CD8+T cells and that these T cells kill 99.994% of LCMV peptide-pulsed target cells in 240 min, we calculated k for LCMV-specific CD8+T cell killing. It is $6.4\times10^{-10}$ ml/LCMV-specific CD8+T cell/min, a value very similar to that observed for OT-1 cell killing of SIINFEKL-B16 cells in collagen-fibrin gels. Note that Regoes et al. (2007) used nongrowing splenocytes as target cells in their experiments. Therefore, g=0. For this reason, we could not calculate a CTC for LCMV-specific CD8+T cell-mediated killing of LCMV peptide-pulsed splenocytes. Thus, Eq. 1 describes CD8+T cell killing of cognate antigen-expressing target cells in vitro and in vivo.

Comparison of the Rates at which OT-1 Cells Kill SIINFEKLBI6 Cells in Collagen-Fibrin Gels In vitro and Ova Peptide-expressing B16 Cells in Tumors In vivo.

Figure 7:
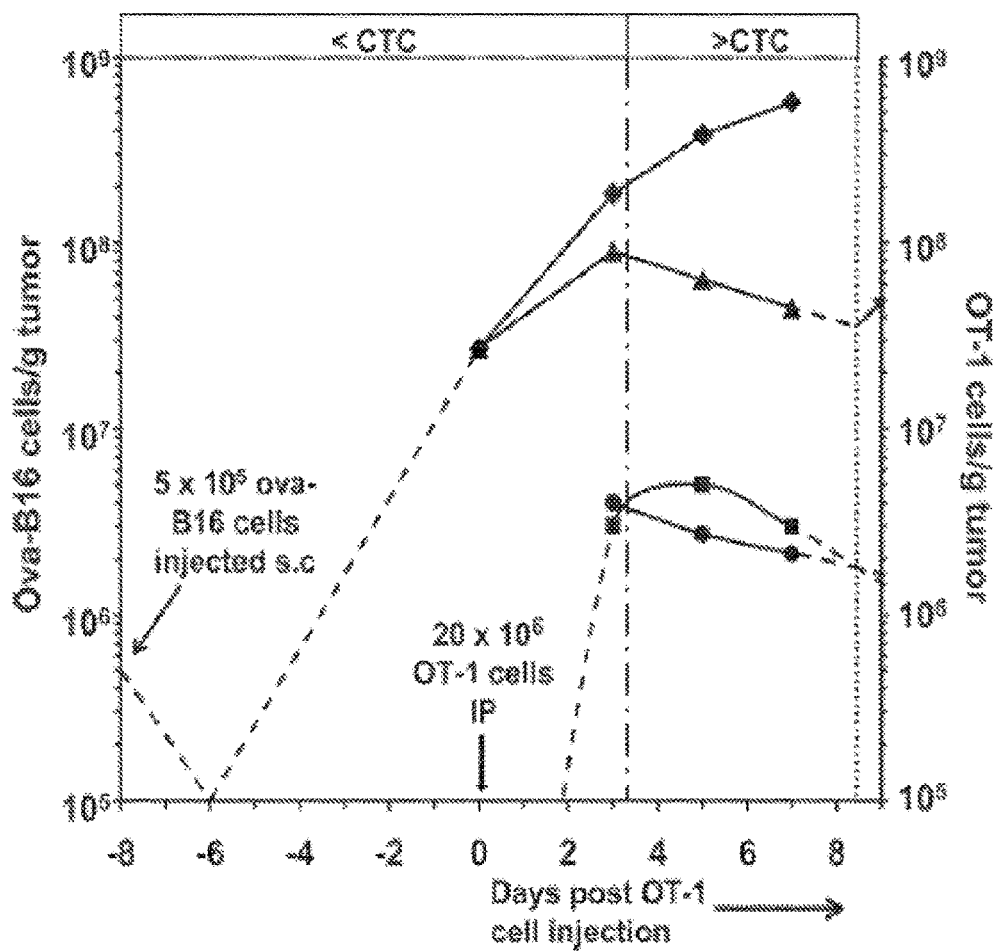
FIG. 7. Relationship between ova-B16 tumor growth/regression and intratumoral OT-1 cell concentration in OT-1 cell-treated ova-B16 tumor-bearing mice. Data are obtained from FIGS. 2 and 4 in Petersen et al. (2006) and were calculated as described in Table 4. C57BL/6 mice were inoculated with $5\times10^5$ ova-B16 cells subcutaneously on day −8, and with $20\times10^6$ in vitro-activated OT-1 cells i.p. on day 0. Intratumoral concentration is shown of OT-1 cells (■) from FIG. 2 (Petersen et al., 2006). Also shown are the number of ova-B16 cells in tumors of control mice (♦) and in tumors of mice that received 20×106 in vitro-activated OT-1 cells on day 0 (▲) calculated from FIG. 4 of Petersen et al. (2006) as described in (Table 4). CTC (●) was calculated as described in Li et al. (2004) and in the Materials and methods (Table 4). Dashed lines represent extrapolated trends based on findings reported in Petersen et al. (2006) and Stephens and Peacock (1978). The vertical dashed-dotted line indicates the point in time at which the intratumoral OT-1 concentration exceeds the CTC. The vertical dotted line indicates the estimated point in time at which the intratumoral OT-1 concentration falls below the CTC, thereby permitting resumption of tumor growth (arrow).

Petersen et al. (2006) studied the effect of i.p. administration of in vitro-activated OT-1 cells on growth/regression of established (8 d old, 90.5 mm3 mean vol) ova-B16 cell tumors. They reported the mean volume of these ova-B16 tumors in control (untreated) and in OT-1 cell-treated mice on days 3, 5, and 7 after OT-1 cell administration (FIG. 7). B16 tumors contain $\sim3\times10^5$ B16 cells/mm3 (Stephens and Peacock, 1978). We used this value to calculate the number of ova-B16 cells in tumors of control and OT-1 cell-treated mice (FIG. 7 and Table 4). Petersen et al. (2006) also reported the intratumoral concentration of OT-1 cells/g of tumor on days 3, 5, and 7. We have used these values, and those for ova-B16 tumor growth and regression, to calculate k and CTC (FIG. 7 and Table 4).

The growth rate of ova-B16 cell tumors slowed between the day of OT-1 cell administration (day 0) and day 3 (FIG. 7). However, tumor regression, as measured by a reduction in tumor volume and, therefore, in the total number of ova-B16 cells in these tumors, did not begin until day 3. It then proceeded at a constant rate through day 7. Note that the intratumoral OT-1 cell concentration averaged $1.5\times10^6$/g of tumor between days 0 and 3, was $3\times10^6$/g of tumor on day 3, peaked at $5\times10^6$/g of tumor on day 5, and declined to $3\times10^6$/g by day 7. Inspection of FIG. 7 shows that the CTC, the OT-1 concentration at which the rate of killing of ova-B16 cells exactly matched the rate of ova-B16 cell growth, was $\sim3\times10^6$ OT-1 cells/g of tumor and that so long as the intratumoral OT-1 concentration remained above the CTC (i.e., $3\times10^6$ OT-1 cells/g of tumor), tumors regressed. FIG. 7 also shows that when the intratumoral OT-1 cell concentration declines to less than the CTC (i.e., on days 8 or 9), tumor growth will resume. Indeed, this is consistent with the observations of Petersen et al. (2006).

To determine whether the CTC calculated using values of g and k obtained using Eq. 1 fits the findings of Petersen et al. (2006; FIG. 7), we used their data (Table 4) for g, t, and intratumoral OT-1 cell concentration for each of the three time intervals (days 0-3, 3-5, and 5-7) described in the previous paragraph to calculate the CTC. We obtained mean values for g and k of $2.7\times10^{-4}$/min and $8.9\times10^{-11}$ ml/OT-1 cell/min, respectively, for the three time intervals, yielding a mean CTC (g/k) of $2.93\times10^6$ OT-1 cells/g ova-B16 tumor. The values of g for ova-B16 cell growth in control mice (Table 4) were within the range of values we obtained for growth of B16 cells in collagen-fibrin gels in vitro (FIG. 1) and those reported by Li et al. (1984) for B16 cell growth in tumors in vivo. In contrast, the values of k and CTC for OT-1 cell killing of ova-B16 cells in vivo were approximately ninefold smaller and eightfold larger, respectively, than comparable values for OT-1 cell killing of SIINFEKL-B16 cells in collagenfibrin gels in vitro, indicating that OT-1 cells kill ova-B16 cells less efficiently in tumors in vivo than in collagen-fibrin gels in vitro.

Figure 8:
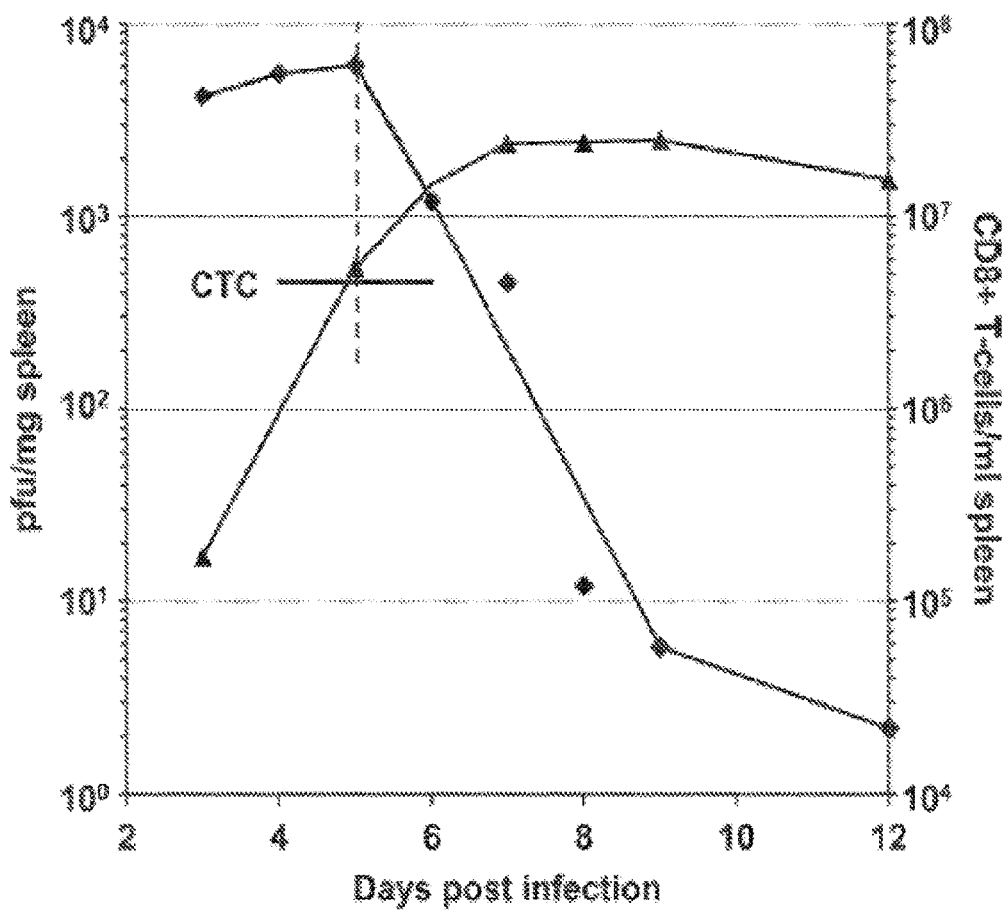
FIG. 8. Effect of polyoma antigen-specific CD8+T cells on polyoma virus growth in splenocytes from mice inoculated subcutaneously on day 0 with $2\times10^6$ PFU of virus. Data are obtained from FIG. 2 and Table I in Lukacher et al. (1999). Polyoma virus concentration (♦, PFU/mg of spleen). Intrasplenic concentration of polyoma antigen-specific CD8+T cells/ml of spleen (▲) was calculated as reported in Table 5. k and CTC were calculated using Eqs. 1 and 2 (Li et al., 2004), respectively, as described in Table 5 and in Materials and methods.

We made similar calculations using data from the study by Lukacher et al. (1999) of polyoma virus antigen-specific CD8+T cell-mediated killing of polyoma virus-infected splenocytes in spleens of immunocompetent mice. We found mean values of k and CTC of $5.7\times10^{-11}$ ml/polyoma virus antigen-specific CD8+T cell/min and $4.8\times10^6$ polyoma virus antigen-specific CD8+T cells/ml, respectively (FIG. 8 and Table 5). The value of k for polyoma virus antigen-specific CD8+T cell-mediated killing of polyoma virus-infected splenocytes is ~14-fold smaller than that calculated for OT-1 cell killing of ova-B16 cells in collagen-fibrin gels in vitro and for LCMV antigen-specific CD8+T cell killing of LCMV peptide-pulsed splenocytes in spleen (Regoes et al., 2007).

As observed for OT-1 cell killing of ova-B16 cells in vivo, elimination of polyoma virus-infected cells did not begin until the concentration of polyoma antigen-specific CD8+T cells was at or above the critical concentration of $4.8\times10^6$ polyoma virus antigen-specific CD8+T cells/ml or /g of spleen (FIG. 7 and Table 5). Moreover, in contrast to the situation described after administration of OT-1 cells to ova-B16 cell tumor-bearing mice (FIG. 7), the concentration of polyoma virus antigen-specific CD8+T cells/ml or /g of spleen remained well above the CTC for many days after the concentration of polyoma virus had fallen to undetectable levels. Lukacher et al. (1999) reported that the persistence of polyoma virus antigen-specific CD8+T cells above CTC resulted in sterilizing immunity versus polyoma virus.

We draw five conclusions from these findings. First, Eq. 1 accurately models killing of antigen-expressing tumor cells and virus-infected splenocytes by cognate antigen-specific CD8+T cells. Second, the critical concentration concept is applicable to CD8+T cell-mediated control of tumor cell growth and viral infection in vivo (FIG. 7 and FIG. 8) Third, by use of Eq. 1 it is possible to calculate and compare the efficiency (k) with which antigen-specific CD8+T cells kill cognate antigen-expressing target cells in vitro and in various tissue compartments in vivo. Fourth, by use of Eq. 2 it is possible to calculate the critical concentration of antigen-specific CD8+T cells under all conditions examined in vivo and in vitro. Fifth, by determining the rate of tumor regression, or the rate of clearance of virus-infected cells, and the time period during which the intratumoral or intralesional concentration of tumor or viral antigen-specific CD8+T cells remains above the CTC, it is possible to predict whether the tumor or virus infection will be eradicated or recrudesce.

These results enable us to define three principles that, in combination with Eqs. 1 and 2, provide a quantitative framework for describing CD8+T cell-mediated host defense versus viral and intracellular bacterial pathogens and for cellular immunotherapy. First, the concentration of activated antigenspecific CD8+T cells determines the efficiency with which these cells kill cognate antigen-expressing target cells under all conditions examined. Second, Eq. 1 (Li et al., 2004) describes CD8+T cell killing of cognate antigen-expressing target cells in vitro and in vivo. Third, a critical concentration of antigenspecific CD8+T cells is required to control growth of cognate antigen-expressing transformed cells in collagen gels in vitro and in mouse subcutaneous tissue in vivo, and of polyoma virus in mouse splenocytes in vivo.

Collagen-fibrin Gels

Melanomas originate in the epidermis but invade and grow in the dermis before spreading to other organs. The concentrations of collagen I and fibrinogen used to form the gels used in these experiments are in the range of those prevailing in carcinomas in rodent dermis and in normal human dermis (Grabowska, 1959; Dvorak et al., 1992; Dewever et al., 2007). The concentration of serum proteins in the medium bathing these gels is ~20% of that found in extracellular fluids from human skin (Takeda and Chen, 1967; Le et al., 1998; Svedman et al., 2002). Thus, the gels in which activated OT-1 and SIINFEKL-B16 cells were co-cultured contain similar concentrations of collagen and fibrin, but lower concentrations of serum proteins, than those found in tumors, in rodent dermis, and in human dermis in vivo.

Clonogenic Assay.

In combination with the collagen-fibrin gel system described in this paper, the clonogenic assay used to measure the number of viable B16 melanoma cells is 4,500-5,500-fold more sensitive than the packed cell pellet-type assays generally used to measure CD8+T cell cytocidal activity in vitro (FIG. 4 B). These methods enable us to distinguish 99.99 versus 99.9999% tumor cell killing and sterilizing immunity. Using this system, we demonstrate that at a concentration of $\geq 10^7$/ml of gel, OT-1 cells produce sterilizing immunity versus $2 \times 10^7$/ml SIINFEKL-B16 melanoma cells in 7 d (FIG. 5), a concentration of B16 cells which is at the lower range of tumor cells in human melanomas in vivo (Whiteside et al., 1986). We are certain that all clonogenic B16 cells were killed because the clonogenic assay used is capable of detecting a single clonogenic B16 cell, and because cultures harvested on subsequent days (FIG. 5) yielded no viable B16 cells. To our knowledge, this is the first identification of the concentration of antigenspecific CD8+T cells required to kill 100% of tumor cells growing at a concentration similar to that found in tumors. As Blattman and Greenberg (2006) note, in cancer therapy, the difference between mostly dead and all dead is a life and death distinction.

Relationship between antigen-specific CD8+T cell killing of target cells expressing a cognate antigen in collagenfibrin gels in vitro and in melanomas in vivo. The value of k for OT-1 cell killing of SIINFEKL-B16 cells in collagen-fibrin gels ($8.1 \times 10$-10 ml/OT-1 cell/min) is very similar to that for LCMV antigen-specific CD8+T cell killing of LCMV peptide-pulsed splenocytes in mouse spleen in vivo ($6.4 \times 10$-10 ml/LCMV antigen-specific CD8+T cell/min). In contrast, the values of k for OT-1 cell killing of ova-B16 cells in melanomas in vivo (~$8.9 \times 10$-11 ml/OT-1 cell/min) and for polyoma virus antigen-specific CD8+T cell killing of polyoma virus-infected splenocytes in spleen in vivo (~$5.7 \times 10$-11 ml/polyoma virus-specific CD8+T cell/min) are ~9- and 14-fold smaller than those for OT-1 cell killing of SIINFEKL-B16 cells in collagen-fibrin gels. In the case of OT-1 cells, these differences are particularly striking because D in both the in vitro (FIG. 2) and in vivo (FIG. 7 and Table 4) situations, the OT-1 cells were activated in vitro under similar conditions. This ~9- to 14-fold difference in k values also is matched by a ~10-fold difference in CTC. What accounts for these large differences in k and CTC in collagen-fibrin gels versus in tumors and in polyoma virus-infected spleen in vivo?

In the case of OT-1 cell killing of ova-B16 cells in tumors and of polyoma antigen-specific CD8+T cell killing of polyoma virus-infected splenocytes in spleen, immunomodulatory activities elicited by the tumor and by viral infection may have altered the tissue environment, thereby reducing the killing efficiency of the antigen-specific CD8+T cells. In the case of tumors (Whiteside et al., 1986; Bronte and Mocellin, 2009) and of chronic viral infections (Virgin et al., 2009), such immunomodulatory activities are well known. To our knowledge, there is no corresponding information about the extent to which the intrasplenic environment is modified by acute viral infection (e.g., polyoma virus [FIG. 8]). Nonetheless, it is likely that immunomodulatory factors (e.g., T cell suppressive factors) account for the ~9- to 14-fold difference in CTC observed in collagen-fibrin gels in vitro versus tumors and acute intrasplenic viral infections in vivo, respectively.

Spleen and tumors contain macrophages, dendritic cells, regulatory and effector T cells, fibroblasts, and endothelial cells, most of which have the capacity to produce proinflammatory (e.g., TNF and IL-12) and antiinflammatory (e.g., TGF-β and IL-10) substances and extracellular matrix components. In contrast, collagen-fibrin gels lack these stromal cells and their soluble and insoluble (e.g., matrix proteins) secretory products. This is a positive attribute of these gels in the sense that it enables investigators to compare the cytolytic activity of antigen-specific CD8+T cells versus cognate antigen-expressing target cells in a three-dimensional matrix devoid of stromal cells and stromal cell secretory products with the cytolytic activity of the same CD8+T cells versus the same target cells expressing the same antigens in tissues containing stromal cells and their secretory products. Investigators also can form gels containing antigen-specific CD8+T cells, peptidepulsed target cells, and one or more of these stromal cells and/or secretory products and assess their effects, individually and collectively, on the cytolytic activity of CD8+T cells. By these means, it may be possible to replicate in vitro the proand antiinflammatory environments of infected, inflamed, and tumor-bearing tissues. Thus, what might at first be perceived as a negative attribute of collagen-fibrin gels could be one of their greatest assets.

Implications of these Findings for Cellular Immunotherapy of Cancer.

The findings reported here have obvious relevance for cellular immunotherapy of melanoma and perhaps other tumors. Cellular immunotherapy produces objective melanoma regression in >50% of patients yet cures a very small percentage of them (Dudley et al., 2002; Dudley and Rosenberg, 2003). This paper suggests at least one reason for this disconnect between response and cure: it is the failure to deliver and maintain a sufficient intratumoral concentration of tumor antigen-specific CD8+T cells/ml of tumor for a sufficient time period to kill 100% of clonogenic tumor cells (FIGS. 5 and 7). The studies reported in this paper provide quantitative information regarding these parameters. They show that a concentration of $\geq 10^7$ activated OT-1 cells/ml is required to kill 100% of SIINFEKL-B16 cells/ml collagen-fibrin gel in 7 d (FIG. 5). In these gels, target cell cytolysis depends only on the CD8+T cell concentration (FIGS. 2, 5, and 7). Accordingly, assuming melanomas contain 3×10$^8$ melanoma cells/ml or /g of tumor (Stephens and Peacock, 1978), and that melanoma antigen-specific CD8+T cells kill melanoma cells in vivo at the same rate as the OT-1 cells used in the experiments shown in FIG. 5, delivery and maintenance of $\geq 10^7$ melanoma antigenspecific CD8+T cells/g melanoma for $\geq 8$ d should result in eradication of the melanoma. However, our analysis of the findings of Petersen et al. (2006; FIG. 7 and Table 4) shows that OT-1 cells kill ova-B16 cells at an approximately ninefold lower rate (k) and have an approximately eightfold higher CTC in tumors in vivo than in collagen-fibrin gels. Under these circumstances, delivery and maintenance of $\geq 10^8$ melanoma antigen-specific CD8+T cells/ml or /g melanoma for $\geq 8$ d would be required to effect tumor eradication. This is a very high threshold and one that does not bode well for success in cellular immunotherapy of cancer. Nonetheless, in a small number of cases cellular immunotherapy has been demonstrated to be curative (Dudley et al., 2002), suggesting that in vivo there are other factors that, under certain circumstances, contribute to the efficacy of antigen-specific CD8+T cells. We describe four of these factors in the subsequent paragraph.

First, our calculations regarding the concentration of tumor antigen-specific CD8+T cells that must accumulate in a tumor bed to effect tumor eradication assumes that these CD8+T cells are the sole cytolytic effectors. However, the presence of activated tumor antigen-specific CD8+T cells within the tumor bed may promote accumulation and tumor cell killing by other cytolytic effector cells (e.g., NK cells and activated macrophages). Under these conditions, CD8+T cells may be only one of several cytolytically active effector cells at work within the tumor. Therefore, our calculations may underestimate the total cytocidal activity of all effector leukocytes that assemble in a tumor in response to signals initiated by tumor antigen-specific CD8+T cells and or tumor cell cytolysis. Second, our calculations assume that tumor cell killing by clones of CD8+T cells whose TCRs recognize different tumor antigens is merely additive. It is possible it is multiplicative. If so, the intratumoral presence of 3×10$^6$ CD8+T cells versus putative tumor antigen A, 3×10$^6$ CD8+T cells versus putative tumor antigen B, and 3×10$^6$ CD8+T cells versus putative tumor antigen C could result in a 27-fold increase in tumor cell killing. Third, our calculations assume that all CD8+T cells kill with the same efficiency as OT-1 cells. CD8+T cells vary widely in their killing efficiencies (Stuge, et al., 2004). Accordingly, it may be possible to produce CD8+T cell populations that kill at a higher rate than that observed for OT-1 cells. Indeed, we have identified OT-1 cell activation protocols that more than double their efficiency in killing SIINFEKLB16 cells in collagen-fibrin gels (unpublished data). Fourth, we have assumed that the tumor vasculature of all melanomas is equally efficient in delivering CD8+T cells to the tumor parenchyma. Buckanovich et al. (2008) have shown that the efficiency of this process can be increased by >10-fold. For all of the reasons stated here, it is important to determine the efficiency of entry of ex vivo-expanded CD8+T cells into tumor beds, their residence time in the tumor bed, and their cytolytic activity under both ideal (e.g., collagen-fibrin gels) and in vivo conditions.

The studies reported in this paper identify three parameters that appear to be especially important for understanding the therapeutic potential of cellular immunotherapy. The first is the concentration of all cytolytic effector cells delivered to, and active within, tumors. The second is the killing efficiencies (k) of all effector cells, singly and in combination, within the tumor bed. The third is the length of time each of these effector cells remains cytolytically active within the tumor bed. Information about these parameters will enable investigators to assess whether the high frequency of objective tumor regression, but low frequency of cure, observed in melanoma patients treated with ex vivo-activated CD8+T cells is a consequence of delivery of an insufficient number of tumor antigen-specific CD8+T cells to tumors to raise the intratumoral concentration to 30-fold above the CTC (FIG. 5), or of deleterious effects of the tumor environment on the viability and/or effector functions of CD8+T cells. Studies in progress show that the collagen-fibrin gel system described in this paper is also useful for assessing killing by cloned tumor antigen-specific human CD8+T cells of human melanoma cells expressing a cognate antigen (unpublished data).

Other Applications of Eq. 1

Our findings with respect to CD8+T cell killing of non-growing B16 cells (Table 1) may be relevant to studying and understanding host defense versus viruses and intracellular bacterial pathogens and rejection of organ transplants. With respect to microbial pathogens, it will be useful to determine the CTC for antigen-specific CD8+T cells to control infection in various tissues. Assuming OT-1 cells are representative of the majority of antigen-specific CD8+T cells, the results reported in this paper and by Snyder et al. (2003) that only 2-4% of these cells are cytolytically active suggest that viral and bacterial antigen-specific CD8+T cells control infections largely by secreting IFN- and TNF and that CD8+T cells use their cytolytic effector activity more sparingly than previously assumed. With respect to the effects of host CD8+T cells on allogeneic transplants, we suggest that such transplants remain functional so long as they contain sufficient stem cells to replace differentiated cells at a rate equal to the rate of differentiated cell killing by CD8+T cells. However, if CD8+T cells kill the organ's differentiated cells at a faster rate than can be replaced by the organ's stem cells, or if CD8+T cells attack the organ's stem cells themselves, the organ is likely to fail.

The collagen-fibrin gel system described here may be useful for investigating these possibilities in vitro.

A Critical Intra-tumoral Concentration of Cytologically Active CD8+ T-cells is Required to Control Tumor Cell Growth We reported previously that the concentration of antigen-specific CD8+OT-1 cells determines their efficiency in killing cognate antigen-expressing B16 melanoma cells in vitro and in vivo. We report here that only 2% of in vitro-activated OT-1 cells are cytolytically active, that the cytolytically active fraction of OT-1 cells accounts for the cytocidal activity of the entire OT-1 cell population in vitro and in vivo; and that the killing constant k used to calculate the rate at which OT-1 cells kill SIINFEKL-peptide-pulsed-B16 cells decreases by 0.5 $\log_{10}$ for every $\log_{10}$ increase in the concentrations of total and cytolytically active OT-1 cells. By substituting values of k corrected for this 0.5 $\log_{10}$ decrease in k into the equation $b_t=b_0 e^{-kpt+gt}$, we show that this equation more precisely ($R^2=0.997$) models the rate at which OT-1 cells kill SIINFEKL-B16 cells in vitro in collagen-fibrin gels and ova-B16 cells in tumors in vivo than previously reported ($R^2=0.987$). Further analyses show that adoptive transfer of a $20\times10^6$ 2% cytolytically active MHC-Ik$^b$-SIINFEKL-specific CD8+T-cells reduces the size of, but cannot kill 100% of ovalbumin-expressing B16 melanoma cells in 8-day-established B16 melanomas in C57Bl/6 mice in vivo.

The concentration of antigen-specific CD8+T-cells determines the rate at which these cells kill cognate antigen-expressing target cells in vitro and in vivo (Budhu et al., 2010). An equation (Eq. 1: $bt=b_0 e^{-kpt+gt}$, in which $b_t$=the concentration of antigen-expressing target cells at any time t, $b_0$=the concentration of antigen-expressing target cells at t=0, k=an experimentally derived constant that defines the rate of killing of antigen-expressing target cells in ml/cognate antigen-specific CD8+T-cell/min, p=the concentration of cognate antigen-specific CD8+T-cells, and g=the growth rate of antigen-expressing target cells) (Budhu et al., 2010), originally derived to describe neutrophil bactericidal activity in vitro and in vivo (Li et al., 2002; Li et al., 2004), also describes CD8+T-cell killing of antigen-expressing B16 melanoma cells in vitro in collagen-fibrin gels and in B16 melanomas in vivo (Budhu et al., 2010).

In a previous report (Budhu et al., 2010), we described OT-1 cell-mediated killing of SIINFEKL peptide-pulsed B16 cells in three-dimensional collagen-fibrin gels in vitro, and in ova-expressing B16 melanomas in vivo as a function of the concentration of all OT-1 cells in the population. We report here that only 2% of OT-1 cells are cytolytically active, and that their efficiency in killing B16 melanoma cells decreases 0.5 $\log_{10}$ for every ten-fold increase in their concentration. Substitution of the concentration of the 2% of OT-1 cells that is cytolytically active ($p_{cytolytic}$), and the corrected value of k for these cells ($k_{cyto}$) into Eq 1 improves the precision with which Eq. 1 models ($R^2=0.997$ vs. 0.989 [Budhu et al. 2010, FIG. 17]), OT-1 cell-mediated killing of SIINFEKL-B16 cells in three dimensional collagen-fibrin gels, and in ova-B16 melanomas in vivo. We show that 2% of in vitro-activated OT-1 cells are cytolytically active, and that these cytolytically active OT-1 cells account for all cytocidal activity of the entire population of OT-1 cells. Further, we calculate that adoptive transfer of as many as $200\times10^6$ 2% cytolytically active OT-1 cells will kill 99.9995% of ova-B16 cells in 8-d-established ova-B16 melanomas, they cannot eradicate all of them.

The results indicate that two percent of in vitro activated CD8+OT-1 T-cells are cytolytically active. We employed limiting dilution assays (Bonnefoix et al., 2005; Koehne et al., 2002) to determine the fraction of cytolytically active ($f_c$) OT-1 100 cells in our in vitro-activated OT-1 cell preparations. We co-incubated 0, 25, 50, or 100 in vitro-activated OT-1 cells with 100 SIINFEKL-B16 cells in replicate wells of Terasaki plates at 37° C. for 24 h, harvested the B16 cells in each well, and assessed the number of viable B16 cells remaining in each well by clonogenic assay (Budhu et al., 2010). We used these results to determine the percentage of wells containing 25-100 OT-1 cells in which there was no killing of SIINFEKL-B16 cells, and used this percentage and the Poisson distribution to calculate the $f_c$ OT-1 cells in each OT-1 cell preparation.

Figure 12:
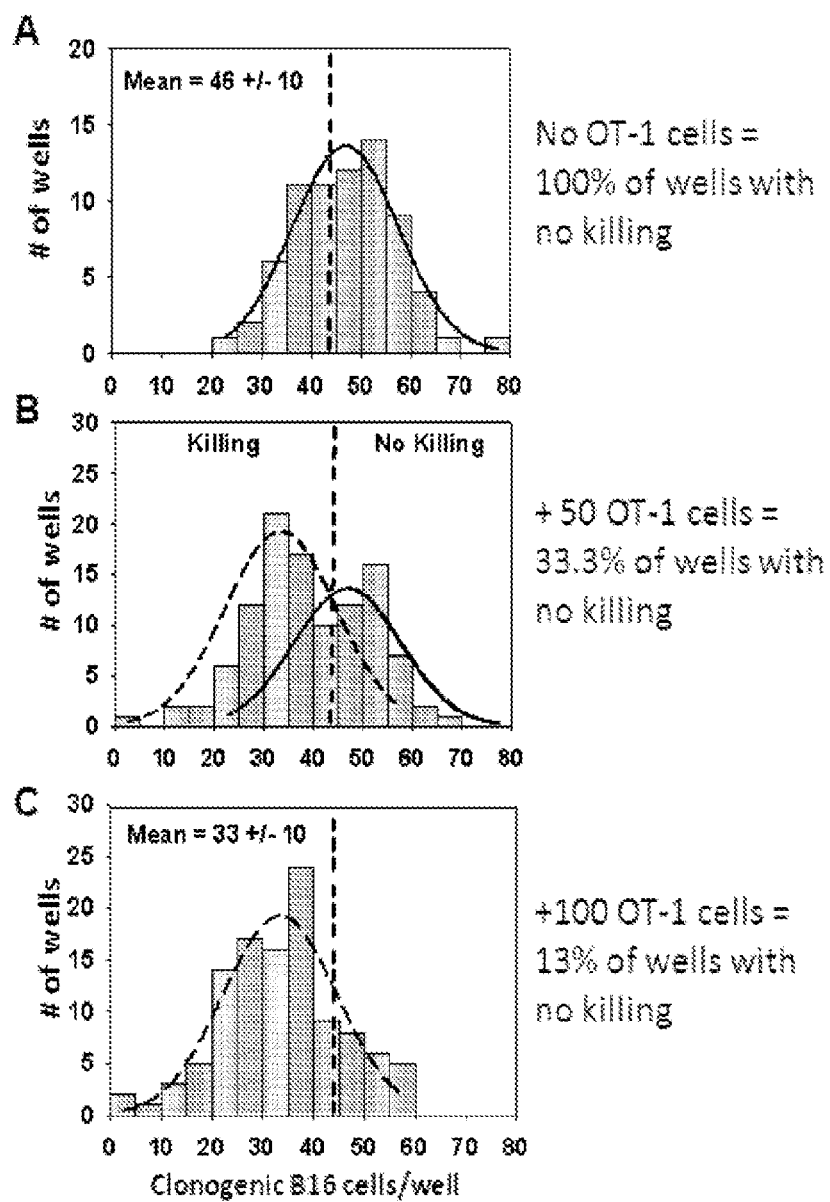
FIG. 12. Representative experiment of N=11 experiments performed showing the distribution of clonogenic B16 cells in Terasaki wells after 24 h co-incubation with 0(A), 50(B) or 100(C) OT-1 cells. Reported is the percent of wells containing 0-5, 6-10, 11-15 etc. CFU B16 cells per well. Student T-test revealed that differences in the number of B16 cells recovered in each of the three conditions are statistically significant at p<0.001.
Figure 13:
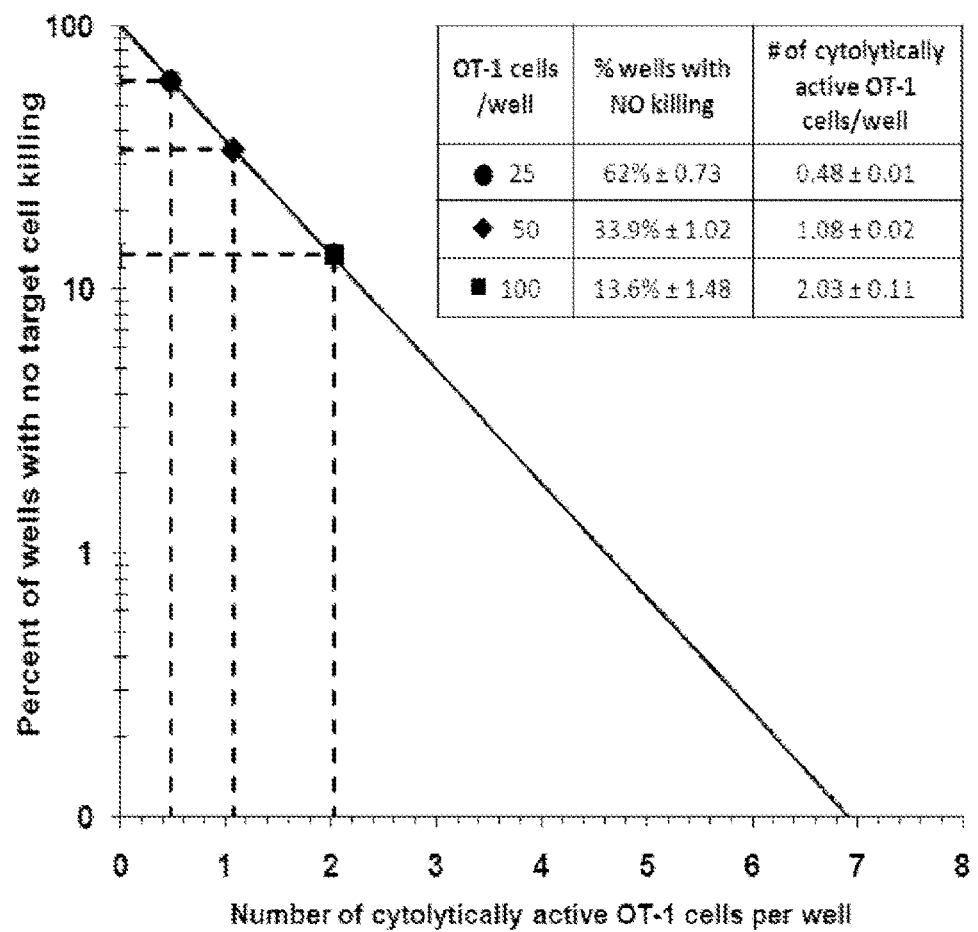
FIG. 13. Two percent of OT-1 T-cells are cytolytically active. ~100 SIINFEKL-pulsed B16 cells with or without 25 (●), 50 (♦), or 100 (■) OT-1 cells were added to each of 108 replicate wells of a Terasaki plate in 20 μl of OT-1 medium. The cells were incubated at 37° C. incubator for 24 h and the surviving B16 cells were detached and assayed as described in Methods. Solid line represents Poisson predictions of the fraction of wells with no killing at varying numbers of cytolytic OT-1 cells per well. Data shown represent the average percent of wells with no killing±SEM of 11 independent experiments.

The small volume (20 µL) and number (~100) of SIINFEKL-B16 cells added to each Terasaki plate well resulted in significant variation from experiment to experiment in the number of clonogenic B16 cells recovered from each well. To assure statistical significance, each condition utilized ≥100 replicate wells and each experiment was internally controlled and repeated at least three times. An example of the distribution of SIINFEKL-B16 cells recovered from each well in a single experiment is shown in FIG. 12A-C where the number of clonogenic B16 cells recovered/well averaged 46±10 cells/well. Accordingly, in this experiment "No killing of SIINFEKL-B16 cells" was defined as wells in which the number of B16 cells recovered was ≥46 cells/well (FIG. 12A). Co-incubation of 25, 50 or 100 OT-1 cells with 100 SIINFEKL-B16 cells resulted in 62±0.73% (FIG. 13), 34.5±1.02% (FIG. 12B & 2) and 14.3±1.48% (FIG. 12C & 2) of wells, respectively, in which no B16 cells were killed. Applying these results to the Poisson distribution (FIG. 13), revealed that 2.03% of the OT-1 cells used in the experiment described in FIG. 12 were cytolytically active. The combined data from 11 such experiments showed that on average 2±0.11% of in vitro activated OT-1 cells were cytolytically active (FIG. 13). We designate total and cytolytically active OT-1 cell populations OT-$1_{total}$ (OT-$1_{tot}$) and OT-$1_{cytocidal}$ (OT-$1_{cyto}$), respectively. Control experiments showed that co-incubation of 100 unpulsed B16 cells with 50 or 100 OT-1 cells produced no killing of B16 cells (not shown), indicating that there was no antigen-independent killing of B16 cells under these conditions.

To ensure that we accurately estimated the percentage of cytolytically active OT-1 cells in each population, we used a two-Gaussian mixture model Lynn, 2001, Murphy, 1979, Melnykov and Maitra, 2010), to determine the percentage of wells in which there was no killing. In this model, there are two components or Gaussian distributions; one where there was no killing of SIINFEKL-B16 cells (FIG. 12A) and one where there was killing (FIGS. 12B & C). Under conditions where there was no killing of SIINFEKL-B16 cells, or where there was killing of SIINFEKL-B16 cells in >85% of wells, the distribution of B16 cells recovered/well showed a single Gaussian distribution (FIGS. 12A and C). Under conditions where there was killing of B16 cells in only a fraction of the wells, there was a two Gaussian distribution (FIG. 12B).

To assess the statistical significance of conditions in which we observed a two Gaussian distribution of recovered B16 cells, we performed a bootstrap analysis (Politis and Romano, 1994, Taib, 2004, Sorensen, 2009). It confirmed the validity of the Gaussian models and showed that the differences observed were significant at p<0.05. We used these methods to calculate the $f_c$ OT-1 cells for all conditions reported.

Synder et al. (2003) developed an Elispot-type assay to measure the number of antigen-specific cytotoxic T-cells in a population. Using this assay they found that 2% of in vitro-activated OT-1 cells are cytolytic, a value consistent with the results reported here.

Figure 14:
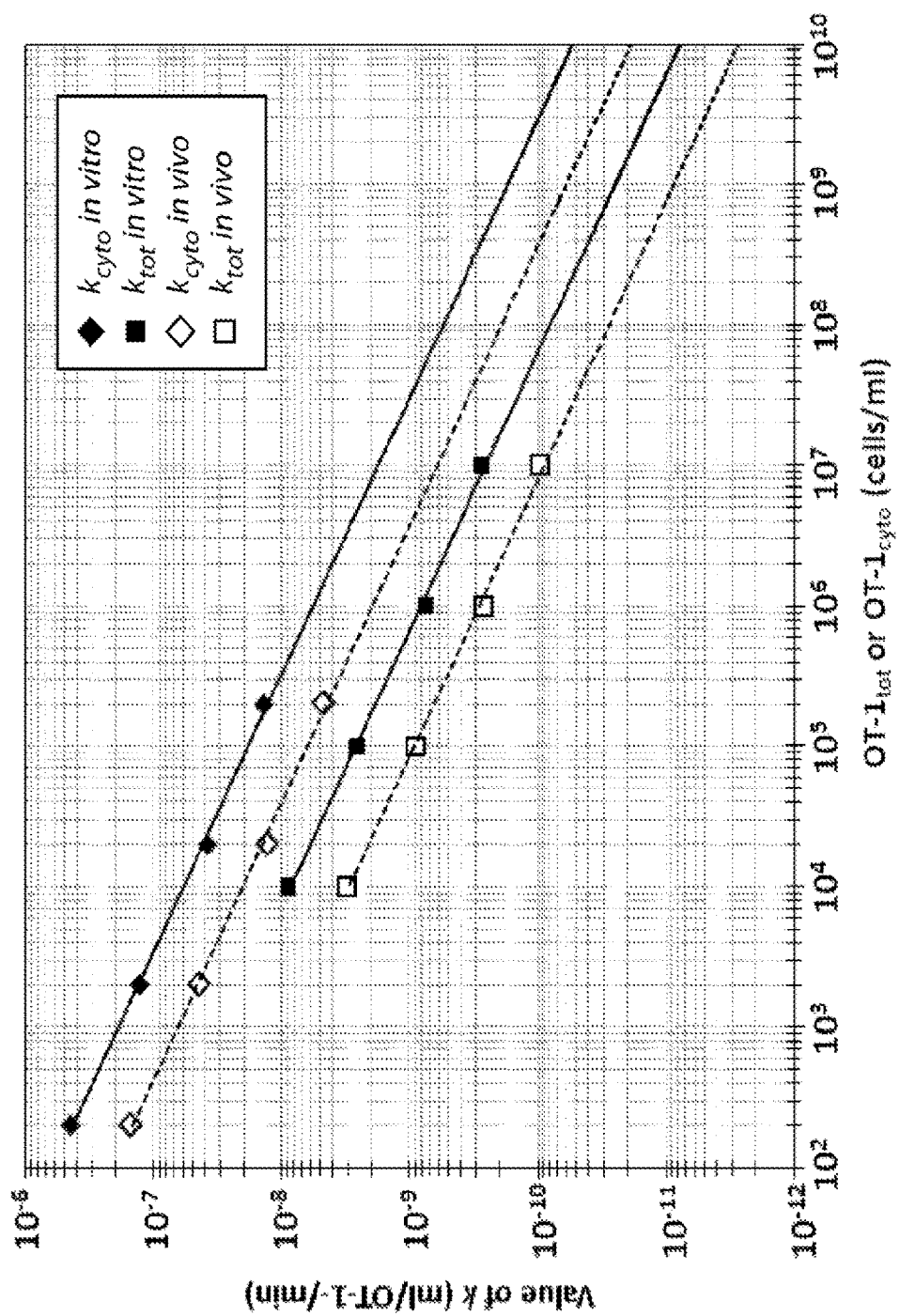
FIG. 14. $k_{tot}$ and $k_{cyto}$ are a function of OT-1 cell concentration. The value of $k_{tot}$ and $k_{cyto}$ declined ~0.7 $\log_{10}$ for every $\log_{10}$ increase in OT-$1_{cyto}$ or OT-$1_{tot}$ cell concentration. Shown are the calculated values of $k_{tot}$ (■) and $k_{cyto}$ (♦) for mouse OT-1 cells killing SIINFEKL-B16 cells in collagen-fibrin gels and for $k_{tot}$ (□) and $k_{cyto}$ (◇) for ova-B16 melanomas in vivo. Data represent the average value for $k_{tot}$ and $k_{cyto}$ of N=3 experiments performed in duplicate.

The experimentally determined killing constants $k_{tot}$ and $k_{cyto}$ decline by ~0.5 $\log_{10}$ for each $\log_{10}$ increase in OT-$1_{tot}$ and OT-$1_{cyto}$ cell concentration in collagen-fibrin gels and in tumors in vivo. The finding that only ~2% of OT-1 cells are cytolytically active led us to re-examine our calculations vis a vis OT-1 killing of SIINFEKL-B16 cells. We discovered that the values of the experimentally determined killing constants $k_{total}$ ($k_{tot}$), for all antigen-specific CD8+T-cells in a population, and $k_{cytolytic}$ ($k_{cyto}$) for the $f_c$ antigen-specific OT-1 cells in the population, decrease monotonically by ~0.5 $\log_{10}$ for every $\log_{10}$ increase in OT-$1_{tot}$ or OT-$1_{cyto}$ cell concentration (FIG. 14). For example, for a population containing $10^5$ OT-1 cells/ml, 2% of which are cytolytically active, $k_{tot}$ and $k_{cyto}$ for OT-1 cells killing SIINFEKL-B16 cells in collagen-fibrin gels are $2.8\times10^{-9}$ ml/OT-$1_{tot}$ cell/min and $1.4\times10^{-7}$ ml/OT-$1_{cyto}$ cell/min, respectively. For a population containing $10^6$ OT-1 cells/ml, 2% of which are cytolytically active, $k_{tot}$ and $k_{cyto}$ for killing SIINFEKL-B16 cells in collagen-fibrin gels are ~$8.7\times10^{-10}$ ml/OT-$1_{tot}$ cell/min and $4.35\times10^{-8}$ ml/OT-$1_{cyto}$ cell/min, respectively (FIG. 14).

Values of $k_{cyto}$, $p_{cyto}$, and $CT_{cyto}C$ for cytolytically active OT-1 cells. The values of k, p, and CTC for OT-1 cells killing SIINFEKL-B16 cells in collagen-fibrin reported by Budhu et al. (2010) were for the total population of OT-1 cells (OT-$1_{tot}$). Accordingly, the finding that ~2%±0.11% of OT-1 cells were cytolytically active indicated the concentration of OT-1 cells used previously by Budhu et al. (2010) to calculate k was ~50-fold higher than the concentration of OT-$1_{cyto}$ cells in these preparations. Therefore, the values reported previously for p (OT-1 cell concentration), k and CTC (Critical T-cell Concentration) were for $p_{tot}$, $k_{tot}$, and $CT_{tot}C$, not for $p_{cyto}$, $k_{cyto}$, and $CT_{cyto}C$. The values of $k_{cyto}$ and $CT_{cyto}C$ for 2% cytolytically active, in vitro activated, OT-1 cells killing SIINFEKL-B16 cells in collagen-fibrin gels are as follows: $CT_{cyto}C=f_c$ OT-$1_{tot}$ cells $(0.02)\times CT_{tot}C$ ($3.5\times10^5$/ml [Budhu et al. 2010])=$7\times10^3$ OT-$1_{cyto}$ cells/ml collagen-fibrin gel (Table 6). We substituted this last value and the value of g (the growth rate of B16 cells in collagen-fibrin gels=$2.84\times10^{-4}$/min) into Eq. 2 ($CT_{cyto}C$=g/$k_{cyto}$) and found $k_{cyto}$=$4.1\times10^{-8}$ ml/OT-$1_{cyto}$ cell/min for OT-$1_{cyto}$ cells killing SIINFEKL-B16 cells in collagen-fibrin gels (Table 6). In summary, $k_{cyto}$=$k_{tot}/f_c$, $CT_{cyto}C$=g/$k_{cyto}$, and $p_{cyto}$ (the concentration of cytolytically active OT-1 cells)=$p_{tot}\times f_c$.

Figure 15:
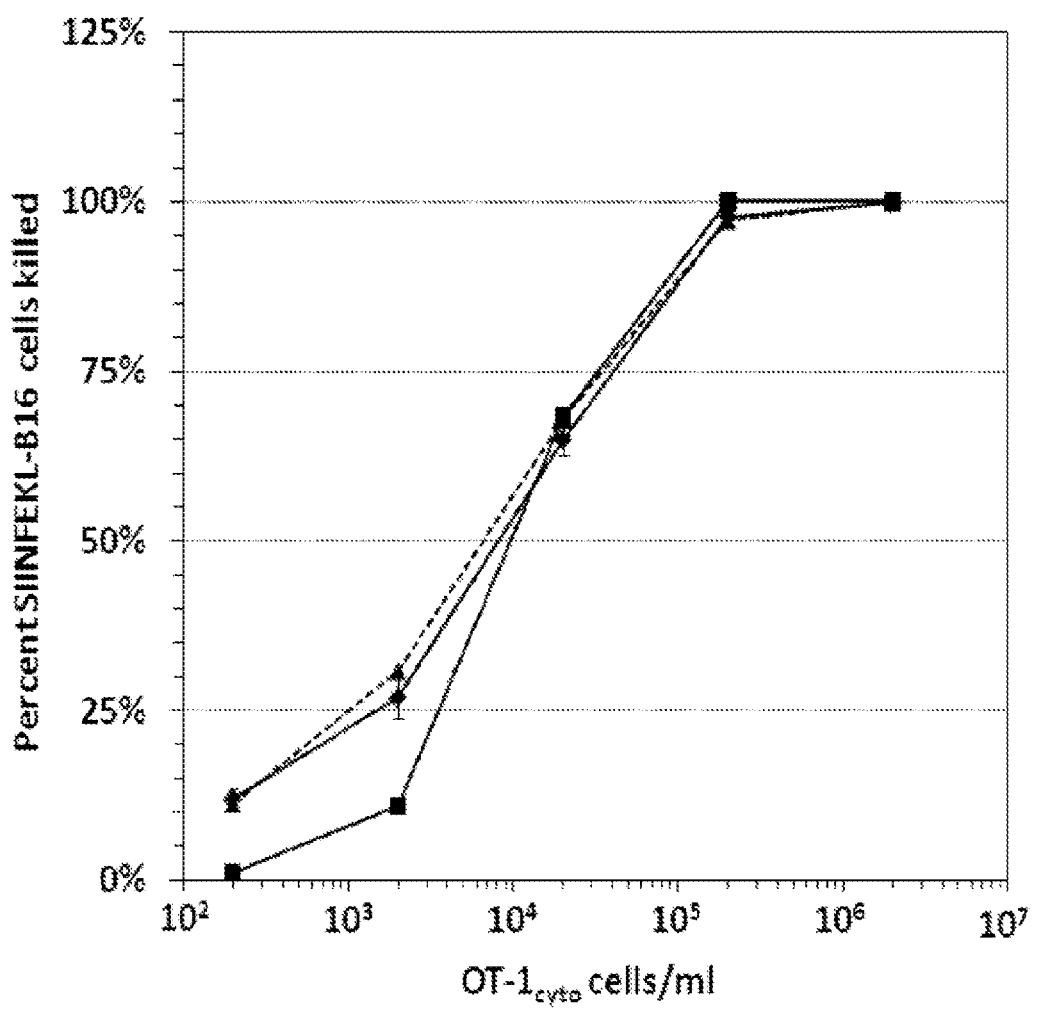
FIG. 15. Pearson plot of calculated and experimentally determined killing of SIINFEKL-B16 cells by OT-1 cells (2% cytolytically active) in collagen-fibrin gels. Relationships between calculated (▲,■) and experimentally determined (♦) values for B16 cells killed by the indicated concentrations of cytolytically active OT-1 cells in collagen-fibrin gels in 24 h. Data re-calculated from (Budhu et al. 2010, FIG. 17). Pearson correlation coefficients for the curves described by these two data sets were 0.994 ($R^2$=0.990) for the values predicted by Eq. 1 using $k_{cyto}$ average (4.1×10$^{-8}$ ml/OT-1 cell/min) (■), and 0.999 ($R^2$=0.997) for the values predicted by Eq. 1 using $k_{cyto}$ from FIG. 14 for the indicated OT-$1_{cyto}$ concentration (▲).

Eq. 1 describes OT-1 cell killing of SIINFEKL-B16 cells in collagen-fibrin gels more precisely when $k_{cyto}$ is corrected for the concentration of OT-$1_{cyto}$ cells ($p_{cyto}$). Budhu et al (2010) used Eq. 1 to calculate killing of SIINFEKL-B16 cells by OT-$1_{total}$ cells in collagen-fibrin gels. We used $f_c$=0.02 to calculate the concentration of OT-$1_{cyto}$ cells in each OT-1 cell preparation (>90% MHC-I$K^b$-SIINFEKL-tetramer+), and substituted this value together with the value of $k_{cyto}$ ($4.1\times10^{-8}$ ml/OT-$1_{cyto}$ cell/min) at the $CT_{cyto}C$ ($7\times10^3$ OT-$1_{cyto}$ cells/ml), and g ($2.84\times10^{-4}$/min), into Eq. 1 and calculated the percent of SIINFEKL-B16 cells killed in collagen-fibrin gels/24 h. Since $k_{cyto}$ decreases by 0.7 $\log_{10}$ for every $\log_{10}$ increase in OT-$1_{cyto}$ cell concentration (FIG. 14), we performed a second set of calculations in which we substituted the corrected value of $k_{cyto}$ at each OT-$1_{cyto}$ cell concentration from $2\times10^2$-$2\times10^5$ OT-$1_{cyto}$ cells/ml into Eq. 1, and used it to calculate the percent of SIINFEKL-B16 cells killed in collagen-fibrin gels/24 h. We then compared the two sets of calculated values with those determined experimentally (FIG. 15). The Pearson correlation coefficient for the curves described by Eq. 1 using $k_{cyto}$ ($4.1\times10^{-8}$ ml/OT-$1_{cyto}$ cell/min) at the $CT_{cyto}C$ ($7\times10^3$ OT-$1_{cyto}$ cells/ml vs. experimentally determined values was 0.994 ($R^2$=0.990). In contrast, the Pearson correlation coefficient for the curves described by Eq. 1 using the corrected values of $k_{cyto}$ at OT-$1_{cyto}$ cell concentrations of $2\times10^2$-$2\times10^5$ OT-$1_{cyto}$ cells/ml vs. experimentally determined values was 0.999 ($R^2$=0.997). In both cases, values calculated using Eq. 1 were in excellent agreement with experimentally derived results, but those using values of $k_{cyto}$ corrected for the OT-$1_{cyto}$ cell concentration correlated better with the experimentally determined values than those calculated using $k_{cyto}$ at the $CT_{cyto}C$ (FIG. 15). We draw three conclusions from these findings. First, Eq. 1 precisely describes killing of SIINFEKL-B16 cells in collagen-fibrin gels by OT-$1_{cyto}$ cells. Second, the $f_c$ OT-$1_{cyto}$ cells accounts for all of the cytolytic effector activity of OT-$1_{tot}$ cells. Third, for leukocyte populations in which every leukocyte executes the effector function of interest (e.g., neutrophil killing of bacteria (Li et al., 2002; Li et al., 2004), the value of k calculated using the total leukocyte concentration accurately represents the rate at which each leukocyte in the population carries out this effector function and $k_{tot}$=$k_{cyto}$. However, for leukocyte populations in which only a sub-population of the leukocytes executes the effector function of interest (e.g., OT-1 cell-mediated cytolysis of SIINFEKL-B16 cells), the value of $k_{cyto}$=$k_{tot}\times f_c$.

Figure 16:
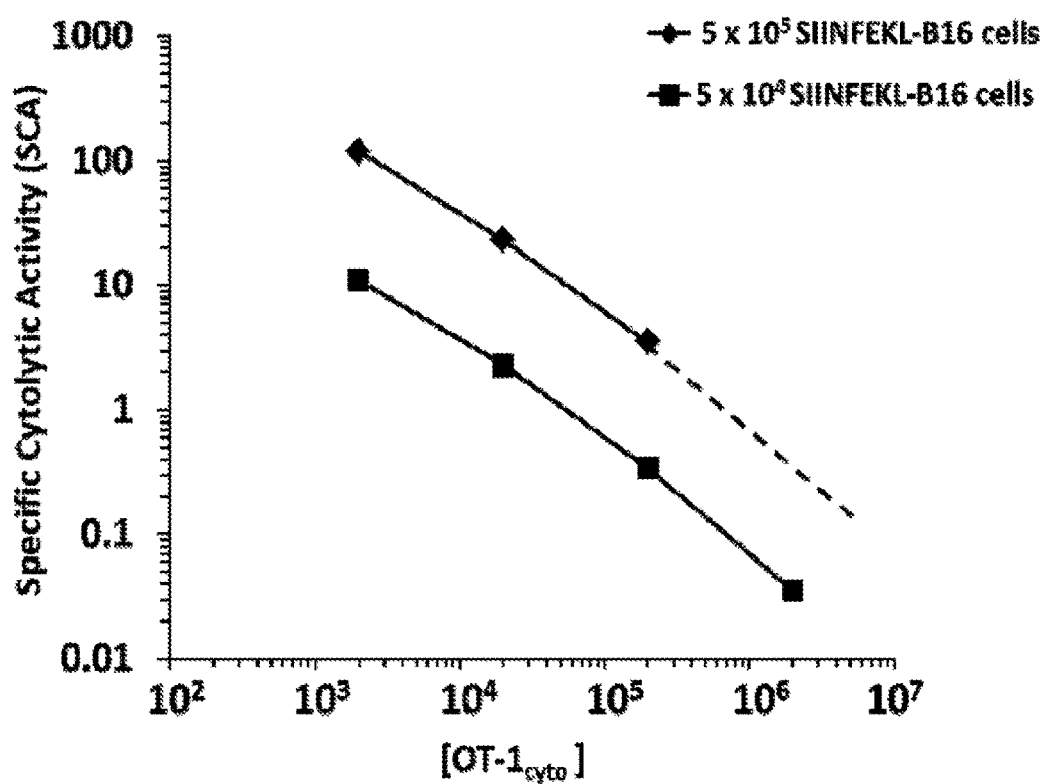
FIG. 16. Log-log plot describing the inverse relationship between the concentration of cytolytically active OT-1 cells and their specific cytolytic activity. Data from Table 7. Note that in contrast to the relationship between OT-1 cell concentration and percent of SIINFEKL-B16 cells killed, in which the percent of B16 cells killed depends only on OT-1 cell concentration (Budhu et al. 2010), the specific cytolytic activity of OT-$1_{cyto}$ cells at each OT-1 cell concentration rises as the B16 cell concentration rises. (Dashed line=projected result.)

The specific cytolytic activity (SCA) (i.e., the number of SIINFEKL-B16 cells killed/ml collagen-fibrin gel or per ml or g tumor/cytolytically active OT-1 cell/unit time) varies with both OT-1 cell and SIINFEKL-B16 cell concentration. Co-culture of $2\times10^5$ OT-$1_{cyto}$ cells/ml collagen-fibrin gel ($10^7$ 2% cytolytically active OT-$1_{tot}$ cells/ml gel) with $5\times10^4$ or $5\times10^5$ SIINFEKL-B16 cells/ml gel killed 98-99% of the B16 cells in these gels in 24 h (Budhu et al. [2010] FIG. 13). However, the SCA of $2\times10^5$ OT-$1_{cyto}$ cells co-incubated with an initial concentration of $5\times10^5$ SIINFEKL-B16 cells/ml was 3.48 SIINFEKL-B16 cells killed/OT-$1_{cyto}$ cell/ml collagen-fibrin gel/24 h, while the SCA of the same concentration of OT-$1_{cyto}$ cells co-incubated with $5\times10^4$ SIINFEKL-B16 cells/ml gel was 0.34 SIINFEKL-B16 cells killed/OT-$1_{cyto}$ cell/ml collagen-fibrin gel/24 h (Table 7). Similarly, the SCAs of $2\times10^4$ and $2\times10^3$ OT-$1_{cyto}$ cells/ml collagen-fibrin gel co-incubated with initial concentrations of $5\times10^5$ and $5\times10^4$ SIINFEKL-B16 cells/ml gel were 23.2 and 2.29 and 119 and 10.9 SIINFEKL-B16 cells killed/OT-$1_{cyto}$ cell/ml collagen-fibrin gel/24 h, respectively (Table 7). A log-log plot of these data (FIG. 16) shows SCA decreases ~5-fold for every 10-fold increase in OT-$1_{cyto}$ cell concentration up to the highest concentration tested ($10^8$ OT-$1_{tot}$ cells/ml collagen-fibrin gel=$2\times10^6$ OT-$1_{cyto}$ cells/ml gel). Accordingly, $10^5$ 2% cytolytically active OT-$1_{tot}$ cells/ml kill only ~4-fold fewer SIINFEKL-B16 cells/24 h as $10^8$ 2% cytolytically active OT-$1_{tot}$ cells/ml/24 h.

The intra-tumoral concentration of cytolytically active OT-1 cells determines killing of ova-B16 cells in melanomas in vivo. Petersen et al. (2006) described the effects of intra-peritoneal administration of $20\times10^6$ in vitro-activated OT-1 cells to C57Bl/6 mice bearing eight-d-established (90.5 mm$^3$) ova-B16 cell tumors on d 0-3, 3-5, 5-7, and thereafter. Budhu et al. (2010) substituted Petersen et al.'s data for $b_0$, $b_t$, g, t and intra-tumoral $p_{tot}$ into Eq. 1 to calculate $k_{tot}$, and substituted the values of g and $k_{tot}$ into Eq. 2 to calculate $CT_{tot}C$. Ova-B16 cell g and $k_{tot}$ averaged $2.7 \times 10^{-4}$/min and $8.9 \times 10^{-11}$ ml/OT-1 cell/min, respectively, for the three time intervals, yielding an average $CT_{tot}C$ of $2.9 \times 10^6$ OT-$1_{tot}$ cells/g ova-B16 tumor (Budhu et al., 2010).

Figure 17:
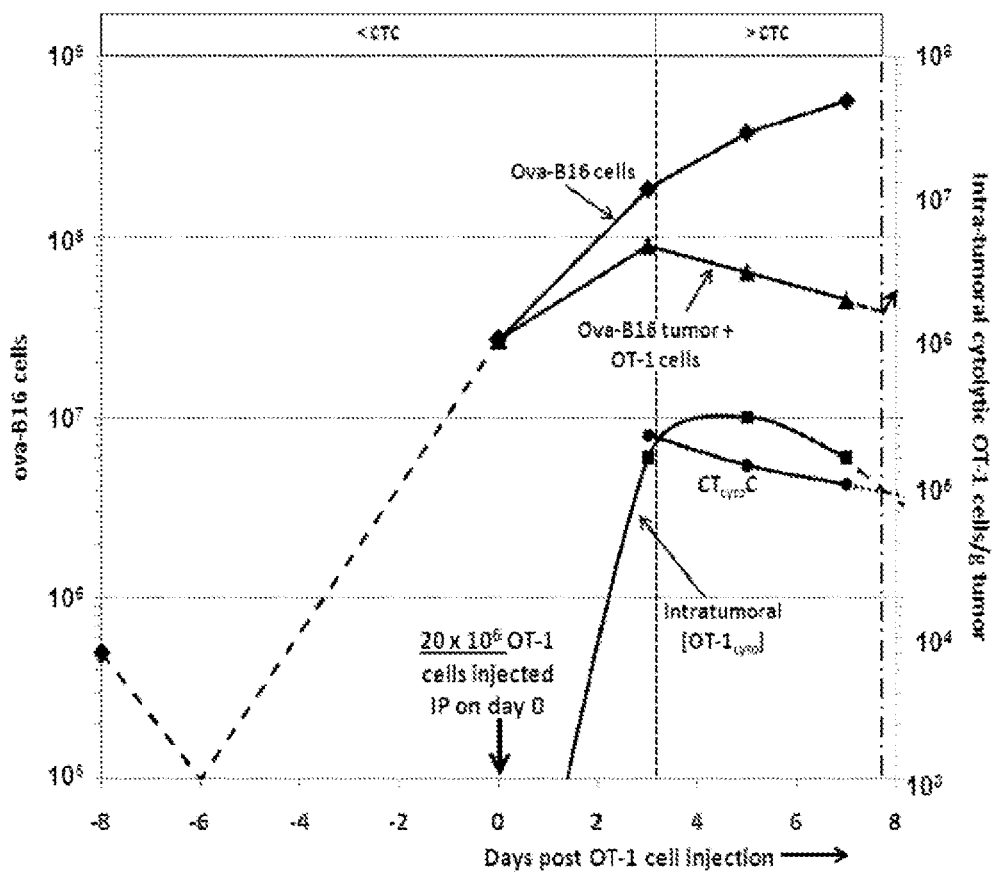
FIG. 17. Relationship between ova-B16 tumor growth/regression and intra-tumoral cytolytic OT-1 cell concentration in ova-B16 tumor-bearing mice. Data from Petersen et al. (2006), and calculated as described in Budhu et al (2010). C57Bl/6 mice were inoculated with 5×10$^5$ ova-B16 cells subcutaneously on d−8, and with 20×10$^6$ in vitro activated OT-1 cells intra-peritoneally on d 0. Intra-tumoral concentration of cytolytic OT-1 cells (■) was calculated assuming $f_c$=0.02 using data from Petersen et al. (2006) [FIG. 2]. The number of ova-B16 cells in tumors of control mice (♦), and in tumors of mice that received 20×10$^6$ in vitro activated OT-1 cells on day 0 (▲) calculated from FIG. 4 of Petersen, et al. (2006) as described in (Budhu et al., 2010). The $CT_{cyto}C$ (●) calculated as described in (Li, et al., 2004) and in Methods. Dashed lines represent extrapolated trends based on findings reported in (Petersen, et al., 2006) and (Stephens, et al., 1978). The vertical dashed line indicates the point in time at which the intra-tumoral cytolytic OT-1 concentration exceeds the $CT_{cyto}C$. The vertical dashed-dotted indicates the estimated point in time at which the intra-tumoral cytolytic OT-1 concentration falls below the $CT_{cyto}C$, thereby permitting resumption of tumor growth (arrow).

The OT-1 cells used in Petersen et al.'s experiments were prepared by in vitro activation and expansion of OT-1 spleen cells using a protocol nearly identical to the one we have employed (Budhu et al., 2010). Accordingly, we assumed 2% of the OT-1 cells used in Petersen et al.'s (2006) experiments were cytolytically active. We substituted experimentally determined values for $b_t$, $b_0$, and $p_{tot}$, and the calculated value of $p_{cyto}$ ($p_{tot} \times f_c$ [0.02]=$p_{cyto}$), into Eq. 1 to calculate $k_{tot}$ at each $P_{tot}$ and $k_{cyto}$ at each $p_{cyto}$; and thereby calculated OT-$1_{cyto}$ cell killing of ova-B16 cells in vivo at the average OT-$1_{cyto}$ cell concentration for each time interval (i.e., 0-3 d, 3-5 d, and 5-7 d) (FIG. 17). In re-assessing these calculations we modified our previous protocol in three respects. We used g=$4.4 \times 10^{-4}$/min throughout because we believe it more accurately describes ova-B16 cell growth rate under the conditions of Petersen et al.'s experiment. We used the intra-tumoral concentration of OT-$1_{cyto}$ cells and data in FIG. 14 to obtain the in vivo $k_{cyto}$ for each of the three time intervals; and we used g ($4.4 \times 10^{-4}$/min)/$k_{cyto}$ for each time interval to calculate the average $CT_{cyto}C$ for all three time intervals (Table 8). We found $k_{cyto}$ and $CT_{cyto}C$ for OT-$1_{cyto}$ cells killing ova-B16 cells in melanomas in vivo were ~6-fold smaller and ~10-fold larger, respectively, than $k_{cyto}$ and $CT_{cyto}C$ reported above for OT-$1_{cyto}$ cells killing SIINFEKL-B16 cells in collagen-fibrin gels (Table 6 vs. Table 8). Given the recognized immunosuppressive activity of the intra-tumoral environment (Curran et al., 2010) these differences in the values of k and CTC in collagen-fibrin gels vs. in melanomas in vivo are not surprising. However, they provide a much-needed quantitative measure of the magnitude of the immuno-suppressive effect of the intra-tumoral environment. It lowers $k_{tot}$ and $k_{cyto}$ by ~3-fold (FIG. 14), and, depending on g ($2.7$-$4.4 \times 10^{-4}$ for B16 cells in vitro and in vivo), increases $CT_{tot}C$ and $CT_{cyto}C$ by ~10-fold.

Substituting into Eq. 1 the average value of $k_{cyto}$ corrected for OT-$1_{cyto}$ cell concentration (Table 6) and the relevant intra-tumoral $p_{cyto}$ (calculated as above using values of $p_{tot}$ from Petersen et al. [2006] and $f_c$ OT-1 cells=2%), improved the accuracy with which Eq. 1 described the effects of administration of $20 \times 10^6$ in vitro activated, 2% cytolytically active, OT-$1_{tot}$ cells ($4 \times 10^5$ OT-$1_{cyto}$ cells), on 8-d-established 90.5 mm$^3$ ova-B16 tumors (FIG. 17). Note that the intra-tumoral OT-$1_{cyto}$ cell concentration determined the extent to which ova-B16 cell growth was inhibited, and/or the extent of killing of ova-B16 cells. For example, as OT-$1_{cyto}$ cell concentration increased from 0 at the time of OT-1 cell administration to $6 \times 10^4$ OT-$1_{cyto}$ cells/ml tumor on d 3, ova-B16 cell growth slowed (FIG. 17, d 0-3). When the intra-tumoral OT-$1_{cyto}$ cell concentration exceeded the $CT_{cyto}C$ ($6.9 \times 10^4$ OT-$1_{cyto}$ cells/ml tumor) on d 3, the number of ova-B16 cells began to decrease and continued doing so until d 9 (FIG. 17, d 3-9). When the intra-tumoral OT-$1_{cyto}$ cell concentration fell below the $CT_{cyto}C$ ($6.9 \times 10^4$ OT-$1_{cyto}$ cells/ml tumor) on d 9 and thereafter, ova-B16 cell growth resumed (FIG. 17).

Figure 18:
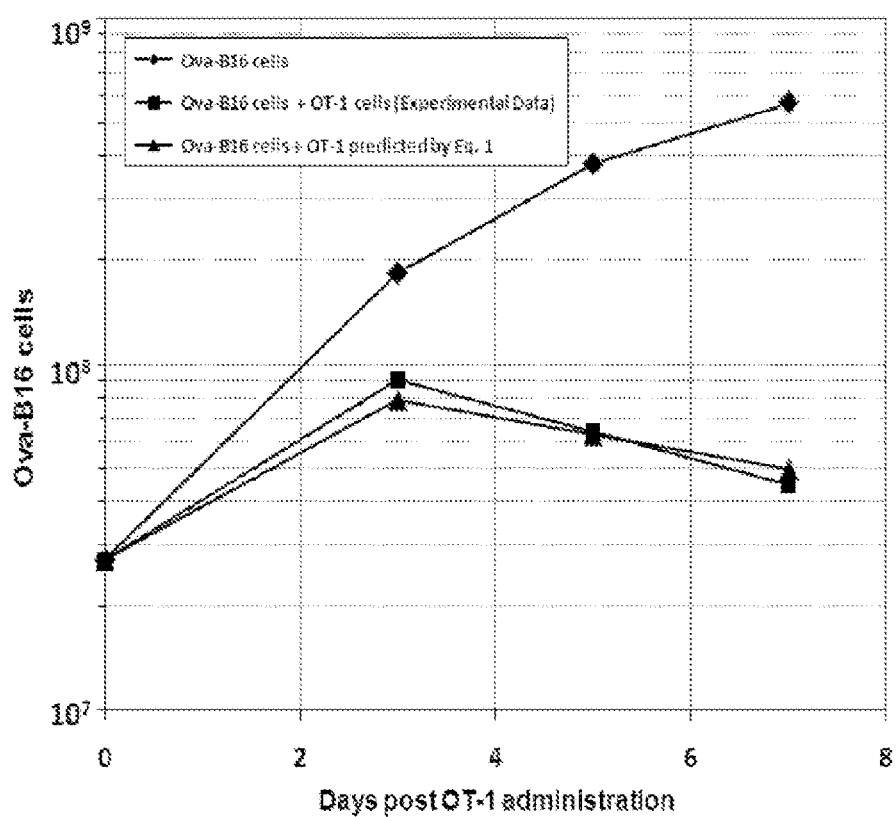
FIG. 18. Calculated vs. experimental values for OT-1 cell killing in vivo of ova-B16 cells (assuming 2% cytolytically active). Experimental data are from Petersen et al. (2006), re-calculated by Budhu et al. (2010) (FIG. 17). Eq. 1 predicted results calculated using $k_{cyto}$ for intra-tumoral concentrations of 3×10$^4$ OT-$1_{cyto}$ cell/g melanoma on d 0-3, and 8×10$^4$ OT-$1_{cyto}$ cell/g melanoma on d 3-7. Pearson correlation coefficient for the curves described by the observed and calculated data sets was 0.983 ($R^2$=0.967).

Correlation between calculated and experimentally determined values for OT-$1_{cyto}$ cell killing of ova-B16 cells in melanomas in vivo. Substitution of experimentally determined values of $b_0$, $p_{cyto}$, and g ($4.4 \times 10^{-4}$/min), and the values of $k_{cyto}$ at each $p_{cyto}$ (FIG. 14) for the time periods 0-3, 3-5, and 5-7 d (FIG. 17), we calculated the percent of ova-B16 cells killed by the indicated concentration of OT-$1_{cyto}$ cells in melanomas in vivo, and compared these calculated values to experimentally determined values. As in collagen-fibrin gels, we found excellent correspondence (Pearson correlation coefficient=0.98, $R^2$=0.97) between calculated and experimentally determined values (FIG. 18). We draw four conclusions from these results. First, Eq. 1 precisely describes the efficiency with which OT-$1_{cyto}$ cells kill ova-B16 cells in vivo (FIGS. 17, 18) when $k_{cyto}$ is corrected for the intra-tumoral concentration of OT-1 cells (FIG. 14). Second, the 2% of cytolytically active OT-1 cells accounts for all cytolytic activity of the entire OT-1 cell population. This conclusion is buttressed by the finding that the number of ova-B16 cells (Budhu et al., 2010), FIGS. 17, 18) did not decrease until the intra-tumoral concentration of OT-$1_{cyto}$ cells exceeded the $CT_{cyto}C$. Third, once the values of g and $k_{cyto}$ are known, Eq. 2 ($CT_{cyto}C=g/k_{cyto}$) can be used to calculate $CT_{cyto}C$ for OT-1 cells killing ova-B16 cells in tumors in vivo. Fourth, to eradicate all antigen-expressing cells in a tumor, the intra-tumoral concentration of cytolytically active antigen-specific CD8+T-cells must remain above the $CT_{cyto}C$ until all cognate antigen-expressing target cells have been killed (FIG. 17).

The findings reported here introduce three previously unrecognized aspects of CD8+T-cell physiology. First, they demonstrate that the intra-lesional concentration of the cytolytically active fraction of antigen-specific CD8+T-cells accounts for all cytocidal activity in vitro (FIG. 15) and in vivo (FIGS. 17, 18) vs. cognate antigen-expressing target cells of all CD8+T-cells whose TCRs recognize the cognate antigen. Second, they show that the cytolytic activity of antigen-specific CD8+T-cells declines by ~0.5 $\log_{in}$ for every 10-fold increase in the intra-lesional concentration of these cells (FIG. 14). Third, they demonstrate that the SCA of antigen-specific CD8+T-cells varies with both the intra-lesional concentration of these cells and the intra-lesional concentration of cognate antigen-expressing target cells (Table 6). These findings have profound implications for cellular immunotherapy of infectious and neoplastic diseases.

The inverse relationship between OT-1 cell concentration and the value of k (FIG. 14). Both mouse (FIG. 14) and human (Budhu et al., manuscript in preparation) antigen-specific CD8+T-cells exhibit a similar inverse relationship between CD8+T-cell concentration and $k_{cyto}$. We do not know the mechanism(s) responsible for it. One possibility was that it resulted from blockade of access of the 2% of cytolytically active OT-1 cells to cognate antigen-expressing target cells by the 98% of cytolytically inactive OT-1 cells. We have excluded this possibility by incubating SIINFEKL-B16 cells at concentrations varying from $5 \times 10^3$-$5 \times 10^5$/ml collagen-fibrin gel with a single concentration of OT-1 cells (e.g., $10^6$ OT-1 cells/ml gel) (Budhu et al. 2010, FIG. 13). Since the OT-1 cell concentration determines the fraction of SIINFEKL-B16 cells killed if the cytolytically inactive OT-1 cells interfere with access of OT-$1_{cyto}$ cells to SIINFEKL-B16 cells, then the percent of SIINFEKL-B16 cells killed should have increased as the concentration of B16 cells rose from $5 \times 10^3$-$5 \times 10^5$/ml gel. It did not, indicating that steric hindrance does not account for the inverse relationship between OT-1 cell concentration and k. This conclusion is further buttressed by calculations showing that each B16 cell can accommodate ~48 hexagonally packed OT-1 cells on its surface.

A second possibility was that secretory products of antigen-activated OT-1 cells, such as Interferon-γ (IFNγ) and Tumor Necrosis Factor-α (TNFα) that have been shown to block/slow leukocyte migration (Loike et al., 1999), were responsible for this inverse relationship. We used anti-mouse IFNγ IgG, and anti-mouse IFNγ receptor IgGs to inhibit IFNγ's potential effects on OT-1 cell killing of SIINFEKL-B16 cells in collagen-fibrin gels, but observed no change in OT-1 cell killing of SIINFEKL-B16 cells. We have not yet tested IgGs vs. TNFα or its receptor. We conclude that IFNγ secretion by activated OT-1 cells does not account for the inverse relationship between k and OT-1 concentration.

Finally, antigen-specific CD8+T-cells are reported to trogocytose cognate antigen-MHC-I complexes from the surfaces of antigen presenting cells (Hudrisier et al. 2001). We suggest a similar phenomenon occurs when cytolytically active and inactive OT-1 cells interact with cognate antigen-MHC-I expressing target cells. If so, as the concentration of OT-1 cells rises, the 98% of cytolytically inactive OT-1 cells in each OT-1 cell preparation will remove a larger and larger fraction of MHC-Ik$^b$-ova from the surfaces of the B16 cells. At the very low concentration of antigen-specific OT-1 cells used in limiting dilution assays ($5 \times 10^3$-$5 \times 10^4$ OT-1 cells/ml), however, the concentration of OT-$1_{cyto}$ cells is unlikely to be sufficient to have a significant effect on target cell cytolysis. We are presently testing these hypotheses.

Whatever the explanation for the inverse relationship between k and OT-1 cell concentration, it introduces yet another mechanism for regulation of CD8+T-cell effector function. It also raises the intriguing possibility that similar antigen-specific mechanisms affect the activities of CD4+ T-helper and CD8+T-regulatory cells.

Figure 19:
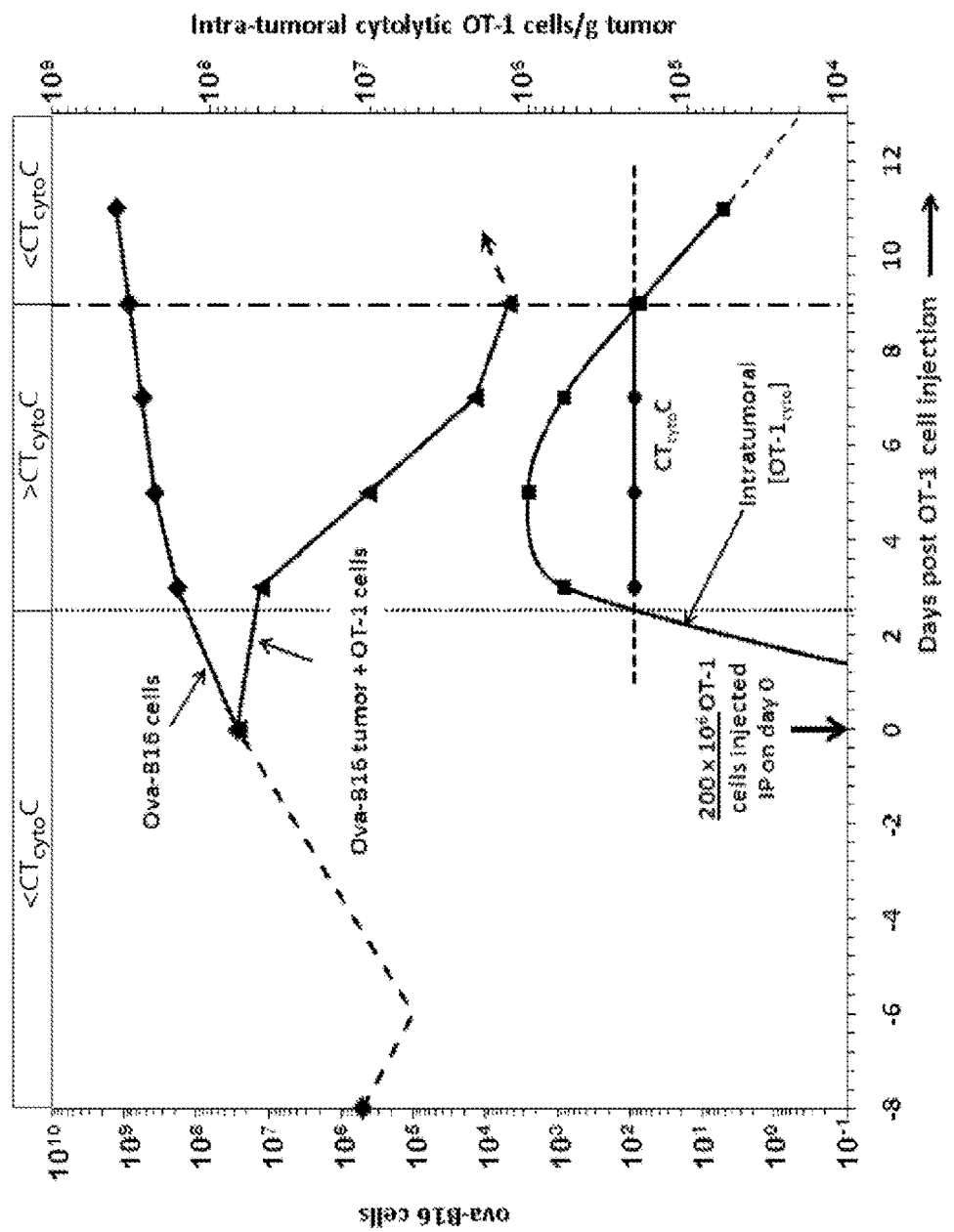
FIG. 19. Effect of a single inoculation of 200×10$^6$ OT-1 cells, 2% cytolytically active, on 8 d-established ova-B16 melanomas. Data from Petersen et al. (2006), and calculated as described in Budhu et al (2010) using Eq. 1. Intra-tumoral concentration of cytolytic OT-1 cells (■) was calculated assuming $f_c$=0.02 using data from Petersen et al. (2006) [FIG. 2]. Eq. 1, g=4.4×10$^{-4}$/min and $k_{cyto}$=2.04×10$^{-9}$ ml/OT-$1_{cyto}$/min was used to predict the number of ova-B16 cells in tumors of control mice (♦), and in tumors of mice that received 200×10$^6$ in vitro activated OT-1 cells on day 0 (▲). The $CT_{cyto}C$ (●) calculated using Eq. 2 as described in Methods. Dashed lines represent extrapolated trends based on findings reported in (Petersen, et al., 2006) and (Stephens, et al., 1978). The vertical dotted line indicates the point in time at which the intra-tumoral cytolytic OT-1 concentration exceeds the $CT_{cyto}C$. The vertical dashed-dotted indicates the estimated point in time at which the intra-tumoral cytolytic OT-1 concentration falls below the $CT_{cyto}C$, thereby permitting resumption of tumor growth (arrow).

Can a population containing 2% cytolytically active OT-1 cells produce sterilizing immunity vs. 8 d-established ova-B16 melanoma? Assuming intra-tumoral OT-1 cell concentration increases in proportion to the number of OT-1 cells adoptively transferred, and given that administration of $20 \times 10^6$ 2% cytolytically active OT-1 cells produced a maximal intra-tumoral concentration of $5 \times 10^6$ OT-$1_{tot}$ cells/g melanoma ($10^5$ OT-$1_{cyto}$ cells/g melanoma) (FIG. 17), we estimate that IP administration of $200 \times 10^6$ OT-1 cells to mice bearing 8-d established ova-B16 melanomas (90 mm$^3$ containing $2.7 \times 10^7$ ova-B16 cells total) (FIG. 19) will produce an intra-tumoral concentration of $5 \times 10^7$ OT-$1_{tot}$ cells/g melanoma in 5 d. ($200 \times 10^6$ OT-$1_{tot}$ cells is equivalent, on the basis of body weights [20 g mouse vs. 70 kg human], to $7 \times 10^{11}$ TAS CD8+T-cells to a 70 kg human.) We calculate that a single dose of $200 \times 10^6$ 2% cytolytically active OT-1 cells will kill 99.982% of $2.7 \times 10^7$ ova-B16 cells in 8 d-established ova-B16 melanomas in 9 d, but will not eradicate all of them. The tumor site will still contain $4.8 \times 10^3$ viable ova-B16 cells. Once the OT-$1_{tot}$ concentration drops below the CT$_{tot}$C ($1.1 \times 10^7$ OT-$1_{tot}$ cells/ml at this OT-$1_{tot}$ cell concentration [FIG. 19]), the remaining B16 cells will resume growth. We conclude that under the conditions Petersen et al. (2006) employed, it will not be possible to eradicate even small melanomas by adoptive transfer of OT-1 cells, only 2% of which are cytolytically active.

Curran et al. (2010) reported that immunization and treatment of mice bearing 3-d established B16 melanomas with irradiated flt-3-ligand-expressing B16 cells and anti-CTLA4, anti-PD-1, and anti-PD-1L1 IgGs to reduce/eliminate the immunosuppressive effects of the intra-tumoral environment eradicated B16 melanoma in 65% of mice. They reported the intra-tumoral concentration of CD8+T-cells in these mice averaged ~$1.3 \times 10^6$/ml tumor on d 13 post immunization. Assuming 2% of these intra-tumoral CD8+ T-cells were cytolytically active and expressed TCRs that recognized antigens on B16 cells, and that administration of anti-CTLA4, anti-PD-1, and anti-PD-1L1 IgGs enabled these CD8+T-cells to kill B16 cells in melanomas at the same efficiency as a population containing 2% cytolytically active OT-1 cells in collagen-fibrin gels ($k_{cyto} = 4$-$5 \times 10^{-8}$ ml/OT-$1_{cyto}$ cell/min), we calculate a single administration of $200 \times 10^6$ 2% cytolytically active OT-1 cells would eradicate 8-d established (90 mm$^3$) melanomas containing $2.7 \times 10^7$ cognate antigen-expressing B16 cells.

Assumptions for Curran et al.'s (2010) experiments:
1. B16 cells grow in mice at a rate of $4.4 \times 10^{-4}$/min (Pedersen et al. 2006).
2. Due to cell death following B16 cell inoculation (Budhu et al. 2010, FIG. 18), the inoculum of $10^4$ B16 cells grows to $10^5$ B16 cells on d 6.
3. B16 cell-specific CD8+T-cells elicited by immunization of mice inoculated with $10^4$ B16 cells on d=0 and immunized with irradiated flt-3-expressing-B16 cells beginning on d=3 after B16 cell inoculation begin infiltrating the growing B16 melanomas on d 6 following B16 cell inoculation.
4. 2% of anti-B16 cell-specific CD8+T-cells elicited are cytolytically active.
5. Average intra-tumoral concentration of cytolytically active B16 cell-specific CD8+T-cells between d 6 and 9=$2.6 \times 10^4$/ml tumor/2=$1.3 \times 10^4$/ml tumor (Curran et al. 2010).
6. $k_{cyto}$ for $1.3 \times 10^4$ 2% cytolytically active OT-1 cells/ml collagen-fibrin gel=$5 \times 10^{-8}$ ml/cytolytically active CD8+ T-cell/min (FIG. 14).
7. Intra-tumoral concentration on d 9 and thereafter of 2% cytolytically active B16 cell-specific CD8+T-cells=$1.3 \times 10^6$ B16 cell-specific CD8+T-cells/ml tumor ($2.6 \times 10^4$ cytolytically active anti-B16 cell-specific CD8+T-cells).
8. $k_{cyto}$ for $2.6 \times 10^4$ 2% cytolytically active OT-1 cells/ml collagen-fibrin gel=$4 \times 10^{-8}$ ml/cytolytically active CD8+ T-cell/min (FIG. 14).
9. The inoculum of $10^4$ B16 cells has grown to $10^5$ B16 cells/mouse by d=6.
10. By substituting into Eq. 1 the above values we calculated the number of B16 cells ($b_t$) remaining viable at the end of each time interval (see below).

Effect of antigen-specific CD8+T-cells produced by immunization of B16 tumor bearing mice with irradiated flt-3 B16 cells and repeated administration of anti-CTLA4, anti-PD-1, and anti-PD-L1 on B16 cell growth on d 6-9 following B16 cell inoculation.

$b_{t(d=6-9)} = 10^5$ B16 cells$\times e^{([-5 \times 10^{-8} \ ml/CD8+cytoT-cell/min \times 1.3 \times 10^{-4} \ cytolytically \ active \ CD8+T-cell/ml \times 1.44 \times 10^3 \ min/d \times 3d] + [4.4 \times 10^{-4}/min \times 1.44 \times 10^3 \ min/d \times 3d])} = 4 \times 10^4$ B16 cells/tumor Effect of antigen-specific CD8+T-cells produced by immunization of B16 tumor bearing mice with irradiated, flt-3 B16 cells and repeated administration of anti-CTLA4, anti-PD-1, and anti-PD-L1 on B16 cell growth on d 10-20 following B16 cell inoculation.

$b_{t(d=10-20)} = 4 \times 10^4$ B16 cells$\times e^{([-4 \times 10^{-8} \ ml/CD8+cytoT-cell/min \times 2.6 \times 10^{-4} \ cytolytically \ active \ CD8+T-cell/ml \times 1.44 \times 10^3 \ min/d \times 11d] + [4.4 \times 10^{-4}/min \times 1.44 \times 10^3 \ min/d \times 11d])} = 10$ B16 cells remaining.

Comment: Ten B16 cells is so close to eradication that any additional killing of B16 cells due to the presence of cytolytically active B16 cell-specific CD4+T-cells (Curran et al. 2010), or variation in the intra-tumoral concentration of cytolytically active antigen-specific CD8+T-cells will result in eradication of the B16 cells.

These calculations suggest why Curran et al. (2010) used an inoculum of only $10^4$ B16 cells and waited only 3 d to begin immunization of the inoculated mice with irradiated flt-3-B16 cells and anti-CTLA4, anti-PD-1, and anti-PD-L1 IgG administration. Had they waited until the tumor reached ~90 mm³ volume (~2.7×10⁸ B16 cells) to begin immunization and anti-CTLA4, anti-PD-1, and anti-PD-L1 IgG administration, they would have had to treat the mice for a total of 23 d, vs. the 14 d regimen described above, to eradicate the B16 cells (as shown below).

$b_{t(d=8-11)} = 2.7 \times 10^7$ B16 cells$\times e^{([-5\times10^{-8}\ ml/CD8+cytoT-cell/min\times 1.3\times 10^{-4}\ cytolytically\ active\ CD8+T-cells/ml\times 1.44\times 10^{-3}\ min/d\times 3d] + [4.4\times 10^{-4}/min\times 1.44\times 10^{-3}\ min/d\times 3d])} = 9.8 \times 10^6$ B16 cells/tumor.

$b_{t(d=11-231)} = 9.8 \times 10^6$ B16 cells$\times e^{([-4\times10^{-8}\ ml/CD8+cytoT-cell/min\times 2.6\times 10^{-4}\ cytolytically\ active\ CD8+T-cells/ml\times 1.44\times 10^{-3}\ min/d\times 20d] + [4.4\times 10^{-4}/min\times 1.44\times 10^{-3}\ min/d\times 20d])} = <1$ B16 cell remaining.

In Budhu et al. (2011B), we report that by use of adjuvants and cytokines it is possible to increase the fraction of cytolytically active, antigen-specific CD8+T-cells by 30% (from 2% to 2.6%), thereby increasing the efficiency with which these cells kill SIINFEKL-B16 cells. Under these circumstances, we estimate administration of 20×10⁶ OT-1$_{tot}$ cells, 2.6% of which are cytolytic, will kill ~99.9999% of a 1 g melanoma containing 3×10⁸ ova-B16 cells/g in 9 days (Budhu et al. 2011 B), but still will not eradicate all ova-expressing B16 cells.

Abbreviations: $b_0$=B16 cell concentration at time (t)=0; $b_t$=B16 cell concentration at any subsequent time; $CT_{tot}C$: concentration of MHC-Ik$^b$-SIINFEKL tetramer+OT-1 cells required to hold the concentration of cognate antigen-expressing target cells constant; $CT_{cyto}C$: concentration of MHC-Ik$^b$-SIINFEKL tetramer+cytolytically active OT-1 cells required to hold the concentration of cognate antigen-expressing target cells constant; g: target cell growth rate/min; $f_c$: fraction of cytolytically active CD8+T-cells; IL-2: interleukin-2; $k_{tot}$: rate constant for killing of cognate-antigen expressing target cells by all antigen-specific CD8+T-cells in a population; $k_{cyto}$: rate constant for killing of cognate-antigen expressing target cells by the cytolytically active antigen-specific CD8+T-cells in a population; OT-1$_{cyto}$: cytolytically active OT-1 cells; $p_{tot}$: concentration of all antigen-specific CD8+T-cells/ml or g; $p_{cyto}$: concentration of cytolytically active antigen-specific CD8+T-cells/ml or g; SIINFEKL: ovalbumin residues 257-264 (Ser-Ile-Ile-Asn-Phe-Glu-Lys-Leu); SIINFEKL-B16 cells: B16 melanoma cells pulsed with 1 μM SIINFEKL peptide.

In vivo Immunization and In vitro Activation Conditions Determine the Number and the Specific Cytolytic Activity of Cytolytically Active Antigen-specific CD8+T-Cells Budhu et al. (2011A) reported that only 2% of in vitro stimulated, antigen-specific CD8+T-cells are cytolytically active, that there is an inverse relationship between the rate and efficiency with which they kill cognate antigen expressing target cells and their concentration, and that the local concentration of this minor population of cytolytically active CD8+T-cells accounts for all killing of cognate antigen-expressing target cells in vitro and in vivo. These findings led us to explore whether conditions of in vivo immunization of OT-1 mice, or in vitro activation of OT-1 CD8+T-cells from spleens of these mice, affect the percentage, number and/or specific cytolytic activity of OT-1 cells. We report here methods for affecting all three parameters. In exploring the characteristics of OT-1 cells elicited by different immunization protocols we discovered that immunization of OT-1 mice with antigen alone increased the percentage and number of MHC-Ik$^b$-SIINFEKL peptide tetramer+cytolytically active OT-1 cells produced. In contrast, immunization of OT-1 mice with antigen and adjuvant (α-CD40-IgG) increased the percentage, number, and specific cytolytic activity of MHC-Ik$^b$-SIINFEKL tetramer+ cytolytically active OT-1 cells produced. Further analysis of populations of OT-1 cells, 0.86% to 2.56% of which were cytolytically active, showed a hyperbolic relationship between the percentage of cytolytically active OT-1 cells in a population and the percentage of SIINFEKL peptide-pulsed B16 cells killed by the OT-1 cells. Using these concepts and mathematical tools, we have calculated the concentration and percentage of cytolytically active OT-1 cells required to control growth and/or to eradicate cognate antigen-expressing B16 cells in vitro in collagen-fibrin gels and in B16 melanomas in vivo.

Results

Antigen presenting cell activation during CD8+T-cell activation and expansion in vivo and in vitro increases the fraction of antigen-specific cytolytically active CD8+T-cells. Bonifaz et al. (Bonifaz et al., 2002) demonstrated that OT-1 mice immunized with α-DEC205-IgG-ova in combination with α-CD40-IgG kill ovalbumin peptide SIINFEKL-expressing B16 (ova-B16) cells more efficiently than OT-1 mice immunized with α-DEC205-IgG-ova alone. These findings suggested that α-CD40-IgG activation of antigen presenting cells might increase the fraction of cytolytically active ($f_c$) OT-1 cells in the elicited population and thereby affect the rate and/or efficiency with which these cells kill SIINFEKL-B16 cells.

To investigate this possibility we immunized OT-1 mice with α-DEC205-IgG-ova alone or in combination with α-CD40-IgG and compared the number of OT-1 spleen cells elicited by the two immunization protocols by FACS analysis of MHC-Ik$^b$-SIINFEKL-PE tetramer+stained cells, and the fraction of these tetramer+OT-1 cells that were cytolytically active by limiting dilution assays (Budhu et al. 2011A). Consistent with Bonifaz et al.'s (Bonifaz et al., 2002) report, the spleens of OT-1 mice immunized with both α-DEC205-IgG-ova and α-CD40-IgG contained ~2-fold more MHC-I K$^b$-SIINFEKL tetramer+OT-1 cells than spleens of OT-1 mice immunized with α-DEC205 IgG-ova alone (Table 10, Lines 2 & 3). Limiting dilution assays using 50 and 100 MHC-Ik$^b$-SIINFEKL tetramer+OT-1 cells/well showed ~0.86% of tetramer+OT-1 cells from spleens of unimmunized OT-1 mice, 1.9% of tetramer+OT-1 cells from spleens of OT-1 mice immunized with α-DEC205-IgG-ova alone, and 2.4% of tetramer+OT-1 cells from spleens of mice immunized with α-DEC205-IgG-ova and α-CD40-IgG were cytolytically active (Table 10, Lines 1-3).

In a parallel set of assays, we co-incubated a quantity of spleen cells sufficient to yield 5×10⁶ MHC-I H2-K$^b$-SIINFEKL tetramer+OT-1 cells/ml collagen-fibrin gel from the same mice (Table 10, Lines 1-3) with 10⁶ SIINFEKL-B16 cells/ml collagen-fibrin gel at 37° C. for 24 h and measured the number of B16 cells remaining viable in these gels by clonogenic assay. Four point two million spleen cells containing 5×10⁵ tetramer+OT-1 cells from un-immunized OT-1 mice killed 21% of SIINFEKL-B16 cells in collagen-fibrin gels/d, while 4.3×10⁶ spleen cells containing 5×10⁵ tetramer+OT-1 cells from α-DEC205-IgG-ova-immunized OT-1 mice, and 3.1×10⁶ spleen cells containing 5×10⁵ OT-1 cells from α-DEC205-IgG-ova- and α-CD40-IgG-immunized OT-1 mice with killed 44% and 74% of SIINFEKL-B16 cells, respectively, in collagen-fibrin gels in 24 h (Table 10, Lines 1-3).

Additional analyses of the effects of increases in number and quality of OT-1$_{cyto}$ cells produced in response to these two immunization protocols on killing of SINFEKL-B16 cells provided further insights into the relationships between the $f_c$ OT-1 cells in a CD8+T-cell preparation and the effects of immunization with antigen alone (i.e., α-DEC205-IgG-ova) vs. antigen in combination with an antigen-independent pro-inflammatory stimulus (i.e., an adjuvant such as α-CD40-IgG). Immunization with α-DEC205-IgG-ova alone stimulated an ~18% increase in the total number of MHC-1 $k^b$ tetramer+OT-1 (OT-$1_{tot}$) cells produced/OT-1 mouse spleen, a 261% increase in the total number of cytolytically active tetramer+OT-1 cells produced/spleen (Table 10, Lines 1 & 2)($1.3 \times 10^7$ OT-$1_{tot}$ cells×0.019=2.47× $10^5$ OT-$1_{cyto}$ cells/spleen of α-DEC205-IgG-ova immunized mice vs. $1.1 \times 10^7$ OT-$1_{tot}$ cells×0.086=9.46×$10^4$ OT-$1_{cyto}$ cells unimmunized OT-1 mouse spleen); and a 221% increase in the number of cytolytically active OT-$1_{cyto}$ cells/5×$10^6$ OT-$1_{tot}$ cells/ml collagen-fibrin gel co-incubated with SIINFEKL-B16 cells/ml collagen-fibrin gel. Yet the Specific Cytolytic Activity (SCA)(number of SIINFEKL-B16 cells killed in collagen-fibrin gels/d/OT-$1_{cyto}$ cell) of the OT-$1_{cyto}$ cells from α-DEC205-IgG-ova-immunized mice was almost the same as the SCA of OT-$1_{cyto}$ cells from α-DEC205-IgG-ova-immunized mice (0.355 SIINFEKL-B16 cells killed/d/OT-$1_{cyto}$ cell vs. 0.366 SIINFEKL-B16 cells killed/d/OT-$1_{cyto}$ cell from unimmunized mice (Table 10, Lines 1 & 2 and Supplementary Text SI-1B). The total increase in killing of SIINFEKL-B16 cells observed following their co-incubation with 5×$10^6$/ml tetramer+OT-1 cells, 1.9% of which were cytolytically active vs. with 5×$10^6$/ml tetramer+OT-1 cells, 0.86% of which were cytolytically active, was 209% (44%/21% SIINFEKL-B16 cells killed [Table 10, Lines 1 & 2 and Supplementary Text SI-1]). This is in excellent agreement with the increase predicted by the product of the increase in number of OT-$1_{cyto}$ cells/5×$10^6$ OT-1 cells$_{tot}$/ml gel, and the very small decline in their SCA (2.2×0.97=214% [Supplementary Text SI-1C]).

In contrast, immunization with α-DEC205-IgG-ova plus α-CD40-IgG increased the total number of tetramer+OT-$1_{tot}$ cells/mouse spleen by 161% over the total number in spleens of OT-1 mice immunized with α-DEC205-IgG-ova alone ($2.1 \times 10^7$/$1.3 \times 10^7$ [Table 10]), a 202% increase in the number of OT-$1_{cyto}$ cells/spleen of mice immunized with α-DEC205-IgG-ova alone ($2.1 \times 10^7$ tetramer+OT-$1_{tot}$ cells/spleen×$f_c$ 0.024=5×$10^5$ vs. $1.3 \times 10^7$ tetramer+OT-$1_{tot}$ cells/spleen×$f_c$ 0.024=2.47×$10^5$ OT-$1_{cyto}$ cells/spleen (Table 10, Lines 2 & 3 and Supplementary Text SI-2A); and a 126% increase in the number of cytolytically active OT-$1_{cyto}$ cells/5×$10^6$ OT-$1_{tot}$ cells/ml collagen-fibrin gel co-incubated with SIINFEKL-B16 cells/ml collagen-fibrin gel (Table 10, Lines 1 & 2 and Supplementary text SI-2A).

The most striking difference between immunization of OT-1 mice with α-DEC205-IgG-ova plus α-CD40-IgG vs. α-DEC205-IgG-ova alone was the increase in the SCA activity of the OT-$1_{cyto}$ cells. It increased by 134% (0.47 vs. 0.35 SIINFEKL-B16 cells killed/OT-$1_{cyto}$ cell in collagen-fibrin gels/d (Table 10, Lines 2 & 3 and Supplementary text SI-2B]). A 126% increase in the number of OT-$1_{cyto}$ cells/5×$10^6$ OT-$1_{tot}$ cells/ml collagen-fibrin gel (5×$10^6$ OT-$1_{tot}$ cells×$f_c$ 0.024 per 5×$10^6$ OT-$1_{tot}$ cells vs. 5×$10^6$ OT-$1_{tot}$ cells×$f_c$ 0.019), and a 134% increase in their SCA is expected to produce a 169% increase in the percent of SIINFEKL-B16 cells killed/24 h by these cells (Supplementary Text SI-2C). The experimentally observed increase was 168% (74%/44% [Supplementary text SI-2C]), in excellent agreement with the calculated result.

Overall, immunization with α-DEC205-IgG-ova plus α-CD40-IgG increased the number of tetramer+OT-$1_{tot}$ cells/mouse spleen above the number of OT-$1_{tot}$ cells in spleens of unimmunized OT-1 mice by 190% ($2.1 \times 10^7$ vs. $1.1 \times 10^7$ [Table 10]), the number of cytolytically active OT-$1_{cyto}$ cells in spleens of α-DEC205-IgG-ova plus α-CD40-IgG immunized vs. unimmunized OT-1 mice by 528% ($2.1 \times 10^7$ tetramer+OT-$1_{tot}$ cells/spleen×$f_c$ 0.024 vs. $1.1 \times 10^7$ tetramer+OT-$1_{tot}$ cells/spleen×$f_c$ 0.0086)(Table 10); and the number of cytolytically active OT-$1_{cyto}$ cells/5×$10^6$ OT-$1_{tot}$ cells/ml collagen-fibrin gel co-incubated with SIINFEKL-B16 cells/ml collagen-fibrin gel by 126% (Table 10, Lines 1 & 3 and Supplementary text SI-3A).

These findings confirm Bonifaz et al.'s (2002) report that antigen plus α-CD40-IgG stimulates production of a larger number of cytolytically active CD8+T-cells than antigen alone. They extend Bonifaz et al.'s (2002) findings in four respects. First, they demonstrate that immunization with antigen alone (i.e., α-DEC205-IgG-ova), increases the number of cytolytically active antigen-specific CD8+T-cells but has no effect on their SCA. Second, they demonstrate that immunization with antigen in combination with an antigen-independent inflammatory stimulus (i.e., a compound with adjuvant activity such as α-CD40-IgG) increases both the total number of OT-$1_{cyto}$ cells and their SCA. Third, they show that the magnitude of the increase in killing of antigen-expressing target cells by cognate antigen-specific CD8+T-cell following in vivo immunization can be calculated precisely as the product of the percentage change in the number of cytolytically active antigen-specific CD8+T-cells produced and the percentage change in the SCA of these antigen-specific CD8+T-cells (Δ% in target cells killed=Δ% of cytolytically active antigen-specific CD8+T-cells/standard number [e.g., $10^6$/ml] of antigen-specific CD8+T-cells/ml×Δ% in the SCA of these antigen-specific CD8+T-cells. Fourth, they show that the number and the $f_c$ antigen-specific CD8+T-cells determines the extent of killing of cognate antigen-expressing target cells, thereby reinforcing our conclusion (Budhu et al. 2011A) that the cytolytically active fraction of antigen-specific CD8+T-cells accounts for all of the cytocidal activity of the antigen-specific CD8+T-cells in a population.

Effect of IL-12 or IL-21 alone or IL-21 in combination with α-CD40-IgG on the number and SCA of in vitro activated OT-1 cells. Both IL-12 and IL-21 are reported to promote formation of cytolytically active CD8+T-cells (Moroz et al., 2004; White et al., 2007). Accordingly, we compared the number and SCA of OT-1 cells activated in medium containing SIINFEKL and IL-2, IL-12, or IL-21, or in medium containing SIINFEKL, α-CD40-IgG, and IL-2 or IL-21. A significantly larger percentage of OT-1 cells activated and maintained in medium containing IL-12 or IL-21 were cytolytically active (2.2% and 2.56%, respectively), compared to OT-1 cells activated and maintained in medium containing IL-2 (2%) (Table 11, Lines 2 & 5). Addition of α-CD40-IgG to SIINFEKL peptide-stimulated OT-1 spleen cells undergoing activation in vitro increased the $f_c$ OT-1 cells from 2% to 2.2% when the medium contained 20 U IL-2, and from 2.2% to 2.5% when the medium contained 100 ng IL-21. However, in contrast to α-CD40-IgG's stimulatory effect on the SCA of OT-1 cells activated in vivo (Table 10, Line 3), α-CD40-IgG had little or no effect on the SCA of OT-1 cells activated in vitro (Table 11, Lines 3 & 4).

α-CD40-IgG in combination with IL-2 or IL-21 increased significantly the percentage of granzyme B- and Perforin-expressing OT-1 cells. To determine whether α-CD40-IgG alone or in combination with IL-2 or IL-21 affected Granzyme B and/or Perforin expression, we activated OT-1 cells in vitro in medium containing SIINFEKL and one or more of these substances, and measured the fraction of OT-1 cells produced that expressed these proteins. (Note that >90% of CD8+T-cells recovered following in vitro activation of OT-1 spleen cells under the conditions used here were MHC-Ik$^b$-SIINFEKL tetramer+[Table 11]). Forty five and 35 percent of OT-1 spleen cells activated in medium containing SIIN- FEKL and IL-21 expressed Granzyme B and Perforin, respectively, compared with 16.9% and 14.4% of CD8+ OT-1 spleen cells activated in medium containing SIINFEKL and IL-2 (Table 12). Addition of α-CD40-IgG to IL-21-treated cultures further increased Granzyme B and Perforin expression from 45% to 53% and from 35% to 40% of cells, respectively. In contrast, α-CD40-IgG had little or no effect on the percent of Granzyme B- and/or Perforin-expressing OT-1 cells activated in IL-2 containing medium (Table 12). These results demonstrate the discordance between Granzyme B/Perforin expression by OT-1 cells and their cytolytic activity (e.g., 45% and 53% and ≥35% and 41% of OT-1 cells stimulated with IL-21 alone or in combination with α-CD40-IgG expressed Granzyme B and Perforin, respectively [Table 12]), while only 2.2%-2.5% of these cells were cytolytically active) (Table 12). Thus, while Perforin is required for OT-1 cells to kill SIINFEKL-B16 cells (Snyder et al. 2003, Budhu et al. 2010), expression of this protein does not assure their cytolytic activity.

Figure 20:
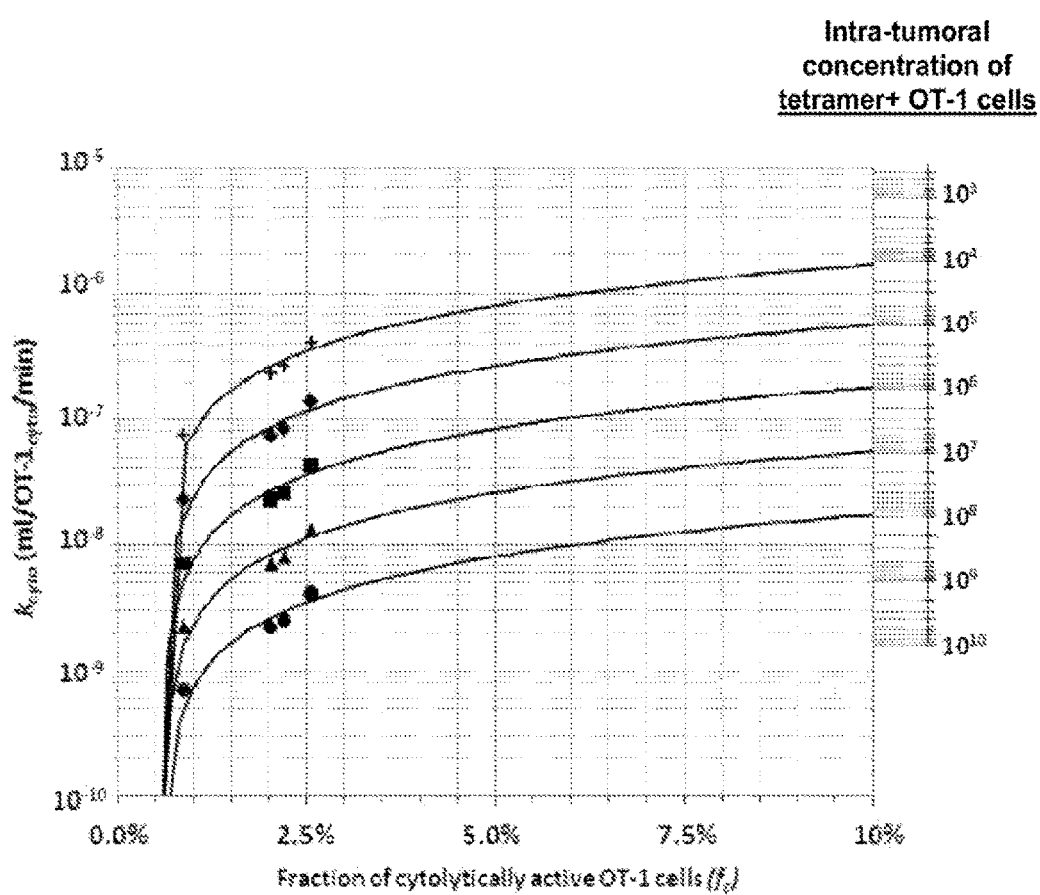
FIG. 20. The value of $k_{cytolytic}$ increases and approaches a limit as the $f_c$ OT-1 cells increases from 0.86% to 10%. Values from Tables 10 and 11 Lines plotted on a log-linear scale with trend line extrapolated to 10% represents a log-linear fit of the data with an $R^2$ value of 0.98.

Relationships between $k_{cyto}$, and $f_c$ OT-1 cells. At any OT-$1_{tot}$ cell concentration, as $f_c$ OT-$1_{tot}$ cells increases from 1.9% to 2.56%, their $k_{cyto}$, $CT_{cyto}C$, and SCA, and the percent of SIINFEKL-B16 cells killed by $10^6$ of them in collagen-fibrin gels/d increase in parallel, but in very rough proportion to the magnitude of the increase in $f_c$ (Table 14). Accordingly, the values of $k_{tot}$ and $k_{cyto}$ also decreased in rough proportion to one another. Eq. 2 ($CT_{cyto}C=g/k_{cyto}$) specifies that $k_{cyto}$ cannot be larger than g, since any value of $k_{cyto}$ larger than g yields a $CT_{cyto}C<1$ antigen-specific CD8+T-cell/ml, a physical impossibility. A plot of $k_{cyto}$ vs. $f_c$ OT-1 cells at $10^4$, $10^5$, $10^6$, $10^7$, and $10^8$ OT-$1_{tot}$ cells/ml collagen-fibrin gel shows that at all five OT-1 cell concentrations, $k_{cyto}$ increases logarithmically as the $f_c$ OT-cells increases from $f_c$=0.86% to 2.56%, and that it increases arithmetically thereafter (FIG. 20). $k_{cyto}$ reaches limiting values when $f_c$ OT-$1_{tot}$ cells=100% at concentrations of $10^4$ and $10^8$ in vitro activated OT-$1_{tot}$ cell/ml, respectively, and of $1.8\times10^{-7}$ and $1.8\times10^{-8}$ ml/OT-1 cell/min when $f_c$ OT-$1_{tot}$ cells=10% at concentrations of $10^4$ and $10^8$ in vitro activated OT-$1_{tot}$ cell/ml, respectively. Note that the limiting value of $k_{cyto}$ for $10^4$ to $10^8$ OT-$1_{cyto}$ cells/ml when $f_c$=100% always remains below the limit determined by the target cell growth rate, which for B16 cells is ~$3$-$4\times10^{-4}$/min.

The ability to calculate $k_{cyto}$ at all OT-1 cell concentrations and $f_c$ OT-1 cells from ~0.86% to 100% enables us to calculate the concentrations and $f_c$ OT-1 cells required to control growth and to achieve sterilization of antigen-expressing B16 cells in collagen-fibrin gels. These calculations show that a concentration of $10^6$ OT-$1_{tot}$ cells/ml, 1.7% of which are cytolytically active, is sufficient to control growth of SIINFEKL-B16 cells in collagen-fibrin gels (Table 13), and that $10^7$ OT-$1_{tot}$ cells/ml, 2% of which are cytolytically active, are sufficient to eradicate $3\times10^8$ SIINFEKL-B16 cells (the concentration of B16 cells in melanomas in vivo [Stephens and Peacock]) in 10 d in these gels (Table 13).

Budhu et al. (2011A) reported that in collagen-fibrin gels the value of k for killing of SIINFEKL-B16 cells by OT-1 cells, 2% of which are cytolytically active, decreases by 0.7 $\log_{10}$ for every 10-fold increase in OT-1 cell concentration. They also reported that due to immunosuppressive factors in the tumor parenchyma, the concentration of OT-$1_{tot}$ cells required to control growth of ova peptide-expressing B16 cells in melanomas in vivo is ~8-fold higher than in collagen-fibrin gels. Accordingly, the values of $k_{cyto}$ for $10^6$ and $10^7$ 2% cytolytically active OT-$1_{tot}$ cells/ml collagen-fibrin gel are ~3.4-fold larger than for the same OT-$1_{tot}$ cell concentrations ova-B16 melanomas in vivo [$k_{cyto}$=6.44 and $1.95\times10^{-9}$ ml/OT-$1_{cyto}$/min, respectively, in collagen-fibrin gels and $1.8\times10^{-9}$ and $5.5\times10^{-10}$ ml/OT-$1_{cyto}$/min, respectively, in melanomas in vivo). Thus, the critical concentrations of OT-$1_{tot}$ ($CT_{tot}C$) and of OT-$1_{cyto}$ ($CT_{cyto}C$) cells, 2% of which are cytolytically active, are ~$3.9\times10^5$ and $7.8\times10^3$/ml collagen-fibrin gel, respectively, while they are $3\times10^6$ and $6\times10^4$/ml or g melanoma in vivo (Table 13). Accordingly, while a population of 2% cytolytically active OT-$1_{tot}$ cells at a concentration of $10^7$/ml collagen-fibrin gel will eradicate $2\times10^7$ SIINFEKL-B16 cells in 7 d (Budhu et al. 2010), the same cells in the intra-tumoral environment over the same 7 day period will kill 99.974% of $2\times10^7$ ova-B16 cells. This will leave $5.2\times10^5$ viable ova-B16. If the intra-tumoral concentration of cytolytically active OT-1 cells falls below the $CT_{cyto}C$ ($6\times10^4$/ml tumor) before all remaining B16 cells have been killed, the remaining cells will resume growth. At their usual growth rate, $5.2\times10^5$ B16 cells will produce a tumor of the original size ($2\times10^7$ B16 cells) in about 16 days.

Together with previous reports (Budhu et al. 2011A), these findings provide fundamental insights into the effects of antigens, adjuvants, and cytokines on the development of cytolytically active CD8+T-cells (Tables 10 and 11), and the ways the immune system regulates the cytolytic activity of these CD8+T-cells. They also have important practical implications for cellular immunotherapy of cancer and infectious diseases.

1. Fundamental Insights into the Effects of Antigens, Adjuvants, and Cytokines on the Development of Cytolytically Active CD8+T-Cells.

A. Effects of antigen and of antigen-independent pro-inflammatory stimuli on the number and SCA of cytolytically active antigen-specific CD8+T-cells produced. The effects of immunization of OT-1 mice with α-DEC205-IgG-ova without and with α-CD40-IgG provide insights into the respective roles of antigen (i.e., α-DEC205-IgG-ova) and antigen-independent inflammatory stimuli (e.g., adjuvants such as α-CD40-IgG), in CD8+T-cell immunity. Immunization of OT-1 mice with α-DEC205-IgG-ova alone produced a 22% increase in the total number and $f_c$ MHC-$Ik^b$-SIINFEKL tetramer+OT-1 cells/spleen, but had an insignificant effect on the SCA of these cells (Table 10, Line 1 & 2, and Supplementary text SI-1 & SI-2). In contrast, immunization of OT-1 mice with α-DEC205-IgG-ova and α-CD40-IgG produced a 91% increase ([2.1-1.1]/1.1) in the number of MHC-$Ik^b$-SIINFEKL tetramer+OT-1 cells/spleen, and a 180% increase ([2.4-0.86]/0.86) in the $f_c$ OT-1 cells and in their SCA (Table 10, Lines 1 & 3, and Supplementary text SI-1 & SI-3). Similarly, pro-inflammatory cytokines (e.g., IL-12 and IL-21), increased both the $f_c$ and SCA of OT-1 cells activated in vitro in the presence of antigen (Table 11, Lines 2 and 5). Under these conditions α-CD40-IgG further increased the $f_c$ OT-1 cells produced, but, if anything, decreased their SCA (Table 11, Lines 3 & 4). Further work is required to explain this un-anticipated effect of α-CD40-IgG in vitro. Taken together with the results of in vivo immunization (Table 10), these findings suggest that immunization with antigen alone increases primarily the number of antigen-specific CD8+T-cells and has little or no effect on their SCA. In contrast, immunization with antigen in the presence of an antigen-independent activator of dendritic cells, such as α-CD40-IgG, and presumably other non-specific antigen presenting cell activators (e.g., CpG), has two effects. First, it promotes an even larger increase in the total number and $f_c$ antigen-specific CD8+ T-cells than immunization with antigen alone (Table 10, Lines 1 & 3, and Supplementary text SI-1A & 3A). Second, it significantly enhances the SCA of the CD8+T-cells produced) (Table 10, Lines 1 & 3). While in a sense this is a restatement of Janeway's hypothesis regarding the relationship between innate and acquired immunity, it expands on it in four respects. First, it distinguishes quantitatively between the number and quality of CD8+T-cells produced. Second, it identifies methods for measuring number and quality independently of one another. Third, it identifies dendritic cells as key regulators of the SCA of CD8+T-cells. Fourth, it supports the hypothesis that factors other than Granzyme and Perforin (Table 13) expression determine whether a CD8+T-cell with a TCR that demonstrably recognizes a specific antigen-MHC complex on the surface of a target cell will kill that cell.

Further work is required to identify the molecular characteristics that distinguish Granzyme- and Perforin-expressing, cytolytically active CD8+T-cells from Granzyme- and Perforin-expressing cytolytically inactive CD8+T-cells. This is a most important question to resolve since, as shown in FIG. 20, the availability of populations of tumor antigen-specific CD8+T-cells, >5% of which are cytolytically active, could produce major positive benefits for patients undergoing cellular immunotherapy of melanoma, and potentially of infectious and other neoplastic diseases.

The finding that dendritic cells have the capacity to regulate the SCA of OT-1 cells is consistent with previous studies showing that dendritic cells regulate the production of T-helper and T-regulatory cells. It extends these observations by suggesting that dendritic cells may be able to regulate the specific activity of T-helper and T-regulatory cells, thereby expanding enormously their capacities to fine tune cellular immune responses. Assays similar to the ones employed here could be used to test this hypothesis.

2. Implications for cellular immunotherapy of infectious diseases and cancer. The concepts, experimental methods and equations described in Budhu et al. (2010, 2011A) and here enable us to calculate the intra-lesional concentration of cytolytically active, antigen-specific CD8+T-cells required to control cognate antigen-expressing virally or bacterially infected normal cells and malignantly transformed cells in collagen-fibrin gels and in vivo. In the present instance, they have been employed to calculate the intra-tumoral concentration of cytolytically active OT-1 cells required to control the growth of, and to kill 100% of, $3 \times 10^8$ ova-B16 melanoma cells/ml or g melanoma in vivo.

In the aggregate, the findings reported here and in Budhu et al. (2010 and 2011A) are consistent with, and explain, many of the results achieved by cellular immunotherapists in treating animals and humans with antigen-expressing melanomas. With a few notable exceptions, these results can be summarized by the statement that administration to a mouse or human of $>5 \times 10^5$ cytolytically active CD8+T-cells/g body weight, 2% of which are cytolytically active, reproducibly leads to temporary reduction/cessation of tumor growth (Yee et al.), under specific circumstances (Dudley and Rosenberg) to regression of cognate antigen-expressing melanomas, and in a few instances to tumor eradication. This is consistent with the results Petersen et al. obtained in mice following administration of $20 \times 10^6$ (~$10^6$/g body weight) in vitro activated OT-1 cells, an estimated 2% of which were cytolytically active, to mice bearing 8 d-established ova-B16 tumors. Three, 5 and 7 d later, the tumors contained $3 \times 10^6$, $5 \times 10^6$, and $3 \times 10^6$ OT-1 cells/ml or g, respectively. Melanoma growth slowed from d 0 to 3 as the intra-tumoral OT-$1_{cyto-intra-tumoral}$ cell concentration rose from 0 to $3 \times 10^6$/g tumor (the $CT_{cyto-intra-tumoral}C$). When the OT-$1_{cyto-intra-tumoral}$ cell concentration exceeded the $CT_{cyto-intra-tumoral}C$ on d 3, tumor regression began. It continued through d 7, after which the OT-$1_{cyto-intra-tumoral}$ cell concentration fell below the $CT_{cyto-intra-tumoral}C$ and tumor growth resumed. In all, OT-1 administration produced at most 99.9% smaller tumor burden than found in animals that did not receive OT-1 cells. Nonetheless, at their nadir, tumors in OT-1 cell-treated mice were larger than on the day the OT-1 cells were administered, and the mice gained only 10 days of life.

The $CT_{tot}C$ for OT-1 cell killing ova-peptide-expressing-B16 cells in tumors in vivo ($CT_{tot-intra-tumoral}C$) is ~8-fold higher than the $CT_{tot}C$ for killing of the same ova-B16 cells in collagen-fibrin gels (Budhu et al. 2010, 2011A). This is likely a consequence of the immunosuppressive environment of tumors. Accordingly, for the purposes of this discussion we assume that the efficiency ($k_{tot}$) with which OT-1 cells kill ova-B16 cells in collagen-fibrin gels ($k_{tot-collagen-fibrin gels}$) reflects their maximal killing potential, while their killing efficiency of ova-B16 cells in melanomas in vivo ($k_{tot-intra-tumoral}$) reflects the immunosuppressive effects of the intra-tumoral environment. We calculate that in the absence of OT-1 cells the melanoma cells would have increased in number by 2,200% (i.e., from $2.7 \times 10^7$ to $6 \times 10^8$) over 7 days, while in the presence of OT-1 cells (i.e., $k_{tot-intra-tumoral}=1.3-2 \times 10^{-10}$ ml/OT-$1_{tot}$ cell/min) they would have increased in number by only 14%). This temporary reduction in B16 cell growth would have enabled the mouse to live an additional ~10 d. In contrast, had the intra-tumoral conditions been like those prevailing in collagen-fibrin gels ($k_{tot-collagen-fibrin gels}=4-7 \times 10^{-10}$ ml/OT-$1_{tot}$ cell/min), the same OT-1 cells would have reduced the number of ova-B16 cells by 99.999916%. While this would still have left $2.28 \times 10^4$ viable ova-B16 cells, and the tumor would have re-appeared, it is a significant improvement. It would have enabled the mouse to live an additional 28 d.

Allison et al. (PNAS 2010), reported eradication of 3 d-established B16 melanomas in 65% of tumor bearing mice following immunization of the mice with flt-expressing tumors and administration of a cocktail of antibodies vs. CTLA4, PD-1, and PD-L1. The reported the intra-tumoral concentration of tumor antigen-specific CD8+T-cells prior to regression of these tumors as $1.2 \times 10^6$/ml. Assuming 2% of these tumor antigen-specific CD8+T-cells were cytolytically active, values of $k_{cyto}$ equivalent to those found for OT-1 cells killing ova-B16 cells in collagen-fibrin gels and in melanomas in vivo; and that the anti-CTLA-4, anti-PD-1, anti-PD-L1 cocktail eliminates intra-tumoral suppression (i.e., converts the value of k from that found in tumors ($k_{intra-tumoral}$) to that found in collagen-fibrin gels ($k_{collagen-fibrin gel}$), we have calculated the expected outcomes of Allison et al's experiments. They indicate (Table 14) that no mice would be cured of tumors in the absence of treatment with anti-CTLA-4, anti-PD-1, and anti-PD-L1 IgG, while mice treated with anti-CTLA-4, anti-PD-1, and anti-PD-L1 IgG would have had <10 viable B16 melanoma cells remaining at the time the anti-CTLA-4, anti-PD-1, and anti-PD-L1 treatments were discontinued. These calculations demonstrate that treatments, such as those employed by Allison et al. (2010) to reduce intra-tumoral immunosuppression, are likely to be required to achieve eradication of all cognate antigen-expressing melanoma cells in established melanomas in humans.

In summary, together with equations and methods reported previously (Budhu et al. 2010 & 2011), the concepts and findings reported here provide a novel, experimentally verified, quantitative conceptual framework for understanding, exploring, and manipulating the cytocidal effector activities of antigen-specific CD8+T-cells. They provide the tools required to estimate the number and quality of CD8+T-cells that must be delivered to a cognate antigen-expressing tumor to control growth of the antigen-expressing tumor cells and to eradicate them. They have the potential to conver T cellular immunotherapy from an unpredictable and empirical method to a predictable and quantitative science. In addition to the purposes for which we have employed them here, we anticipate these concepts, equations and methods will enable investigators to calculate the concentration of other types (e.g., antigen-specific FAS ligand-expressing or IFNγ-secreting CD8+T-cells), and classes (e.g., neutrophils, monocytes, CD4+T-cells) of immune effector cells required to achieve a desired endpoint.

Supplementary Text for Table 10.

SI-1. Increase in killing of 0.86% cytolytic to 1.9% cytolytic OT-1 cells=44% (Line 2)/21% (Line 1)=2.09-fold=209%

SI-1A. Ratio of No. of 1.9% OT-1$_{cytolytic}$ cells/No. of 0.86% OT-1$_{cytolytic}$ cells/MHC-IK$^b$-SIINFEKL tetramer+ OT-1 cells=0.019×5×10$^5$/0.0086×5×10$^5$=9,500/4,300=2.21-fold=221%.

SI-1 B. Ratio of Specific Cytolytic Activities of 1.9% (Line 2) vs. 0.86% (Line 1) OT-1$_{cytolytic}$ cells=0.355/ 0.366=0.97-fold=97%.

SI-1C. Total increase in killing due to increase in number of OT-1$_{cytolytic}$ cells (1A)×increase in killing due to change in Specific Cytolytic Activity (1B)=2.21×0.97=2.14=214%.

SI-2. Increase in killing of 1.9% cytolytic to 2.4% cytolytic OT-1 cells=74% (Line 3)/44% (Line 2)=1.68-fold=168%.

SI-2A. Ratio of No. of 2.4% OT-1$_{cytolytic}$ cells/No. of 1.8% OT-1$_{cytolytic}$ cells=0.024×5×10$^5$/0.019×5×10$^5$=12,000/9,500=1.26-fold=126%.

SI-2B. Ratio of Specific Cytolytic Activities of OT-1$_{cytolytic}$ cells, 2.4% of which are cytolytically active/OT-1$_{cytolytic}$ cells 1.9% of which are cytolytically active=0.47/0.35=1.33-fold=133%.

SI-2C. Total increase in killing dues to increase in number of OT-1$_{cytolytic}$ cells (2A)×increase in killing due to change in Specific Cytolytic Activity (2B)=1.26×1.33=1.675-fold=167.5%.

SI-3. Increase in killing of 0.86% cytolytic to 2.4% cytolytic OT-1 cells=74%/21%=3.52-fold=352%.

SI-3A. Ratio of No. of 2.4% OT-1$_{cytolytic}$ cells/No. of 0.87% OT-1$_{cytolytic}$ cells=0.024×5×10$^5$/0.0086×5×10$^5$=12.0×10$^3$/4.3×10$^3$=2.79-fold=279%.

SI-3B. Ratio of Specific Cytolytic Activities of OT-1$_{cytolytic}$ cells, 2.4% of which are cytolytically active/OT-1$_{cytolytic}$ cells 0.86% of which are cytolytically active=0.472/0.366=1.29-fold=129%.

SI-3C. Total increase in killing dues to increase in number of OT-1$_{cytolytic}$ cells (2A)×increase in killing due to change in Specific Cytolytic Activity (2B)=2.79×1.29=3.59-fold=359%.

Supplementary Text for Table 11.

SII-1. Percent increase in killing of SIINFEKL-B16 cells co-incubated with OT-1 cells, 2.2% of which are cytolytically active vs. with OT-1 cells, 2% of which are cytolytically active=72.2% (Line 2)/60% (Line 1)=1.2-fold=120%.

SII-1A. Ratio of No. of 2.2% OT-1$_{cytolytic}$ cells/2% OT-1$_{cytolytic}$ cells=2.2×10$^3$/2×10$^3$=1.105-fold=110.5%.

SII-1B. Ratio of Specific Cytolytic Activities of OT-1 cells, 2.2% of which are cytolytically active/OT-1 cells, 2% of which are cytolytically active=2.4/2.19=1.095-fold=109.5%.

SII-1C. Total increase in B16 cell killing due to increase in number of OT-1$_{cytolytic}$ cells (1A)×increase in killing due to change in Specific Cytolytic Activity (1B)=1.105× 1.095=1.2-fold=120%.

SII-2. Percent increase in killing of SIINFEKL-B16 cells co-incubated with OT-1 cells, 2.5% of which are cytolytically active vs. with OT-1 cells, 2.37% of which are cytolytically active=67.5% (Line 4)/63.7% (Line 3)=1.06-fold=106%.

SII-2A. Ratio of No. of 2.5% OT-1$_{cytolytic}$ cells/2.37% OT-1$_{cytolytic}$ cells=2.5×10$^3$/2.37×10$^3$=1.055-fold=105.5%.

SII-2B. Ratio of Specific Cytolytic Activities of OT-1 cells, 2.5% of which are cytolytically active/OT-1 cells, 2.37% of which are cytolytically active=2.06/2.05=1.0048-fold=100%.

SII-2C. Total increase in killing dues to increase in number of OT-1$_{cytolytic}$ cells (2A)×increase in killing due to change in Specific Cytolytic Activity (2B)=1.055× 1.0048=1.06-fold=106%

SII-3. Percent increase in killing of SIINFEKL-B16 cells co-incubated with OT-1 cells, 2.56% of which are cytolytically active vs. with OT-1 cells, 2% of which are cytolytically active=80% (Line 5)/60 (Line 1)=1.33-fold=133%.

SII-3A. Ratio of No. of 2.56% OT-1$_{cytolytic}$ cells/2% OT-1$_{cytolytic}$ cells=2.56×10$^3$/2×10$^3$=1.25-fold=125%.

SII-3B. Ratio of Specific Cytolytic Activities of OT-1 cells, 2.56% of which are cytolytically active/OT-1 cells, 27% of which are cytolytically active=2.88/2.19%=1.31-fold=131%.

SII-3C. Total increase in killing dues to increase in number of OT-1$_{cytolytic}$ cells (3A)×increase in killing due to change in Specific Cytolytic Activity (3B)=1.25×1.31=1.63-fold=163%.

Abbreviations: $b_0$=B16 cell concentration at time (t)=0; $b_t$=B16 cell concentration at any subsequent time; $CT_{tot}C$: concentration of MHC-Ik$^b$-SIINFEKL tetramer+OT-1 cells required to hold the concentration of cognate antigen-expressing target cells constant; $CT_{cyto}C$: concentration of MHC-Ik$^b$-SIINFEKL tetramer+cytolytically active OT-1 cells required to hold the concentration of cognate antigen-expressing target cells constant; g: target cell growth rate/min; $f_c$: fraction of cytolytically active CD8+T-cells; IL-2: interleukin-2; IL-12: interleukin 12; IL-21: interleukin-21; $k_{tot}$: rate constant for killing of cognate-antigen expressing target cells by all antigen-specific CD8+T-cells in a population; $k_{cyto}$: rate constant for killing of cognate-antigen expressing target cells by the cytolytically active antigen-specific CD8+T-cells in a population; $p_{tot}$: concentration of all antigen-specific CD8+T-cells/ml or g; $p_{cyto}$: concentration of cytolytically active antigen-specific CD8+T-cells/ml or g; SIINFEKL: ovalbumin residues 257-264 (Ser-Ile-Ile-Asn-Phe-Glu-Lys-Leu); SIINFEKL-B16 cells: B16 melanoma cells pulsed with 1 μM SIINFEKL peptide; Specific Cytolytic Activity: SCA=number of antigen-expressing target cells killed/CD8+T-cell$_{cytolytic}$/24 h; TAS: tumor antigen-specific.

We have discovered co-embedment and co-incubation at 37° C. of cell culture-derived antigen-expressing mouse melanoma cells, together with cognate-antigen-specific cytolytically active mouse CD8+T-cells in gels (0.1 ml volume) composed of rat tail collagen I and thrombin clotted human fibrinogen can be used to determine the efficiency with which these CD8+T-cells kill mouse antigen-expressing melanoma cells in vitro and in vivo. This assay is described in detail in: Budhu, S., J. D. Loike, A. Pandolfi, S. Han, G. Catalano, A. Constantinescu, R. Clynes, and S. C. Silverstein. 2010. CD8+ T cell concentration determines their efficiency in killing cognate antigen-expressing syngeneic mammalian cells in vitro and in mouse tissues. J Exp Med. 207:223-35.

We have discovered co-embedment and co-incubation at 37° C. of cell culture-derived antigen-expressing human melanoma cells, together with cognate-antigen-specific cytolytically active human CD8+T-cells in gels (0.1 ml volume) composed of rat tail collagen I and thrombin clotted human fibrinogen can be used to determine the efficiency with which these CD8+T-cells kill human antigen-expressing melanoma cells in vitro and in vivo. We anticipate this assay can be used to determine the efficacy of ex-vivo expanded antigen-specific CD4+ and CD8+ Tcells to be used for cellular immunotherapy of infectious and neoplastic diseases prior to the infusion of these cells into humans afflicted with these diseases, and that assays of this type will become "standard of care" for patients receiving such therapies. Findings with human cells using this assay were presented in a seminar by Dr. Silverstein at the National Institutes of Health in July 2010, and at a symposium at the NIH Clinical Center sponsored jointly by the Clinical Center of the National Institutes of Health and by the International Society for Cellular Immunotherapy of Cancer on Sep. 29, 2009.

We have discovered that co-culture in multi-well Terasaki-type tissue culture plates of ~100 antigen-expressing mouse melanoma cells with small numbers of in vitro-activated cognate-antigen-specific mouse CD8+T-cells, in combination with use of the Poisson distribution, enables us to measure the fraction of the mouse CD8+T-cells that is cytolytically active. Using this assay we have discovered that <3% of mouse and human CD*+T-cells are cytolytically active. We also have identified ways to increase the frequency of cytolytically active mouse antigenspecific CD8+ T-cells by in vivo immunization by as much as 1.34% and in vitro by as much as 0.6% and have shown they kill cognate-antigen-expressing mouse melanoma cells with much greater efficiency than would be anticipated from these small increases in the fraction of cytolytically active CD8+T-cells. We anticipate this assay can be used to determine the efficacy of ex-vivo expanded antigen-specific CD4+ and CD8+T-cells to be used for cellular immunotherapy of infectious and neoplastic diseases prior to the infusion of these cells into humans afflicted with these diseases. This assay can be used to determine the efficacy of ex-vivo expanded antigen-specific CD4+ and CD8+T-cells to be used for cellular immunotherapy of infectious and neoplastic diseases prior to the infusion of these cells into humans afflicted with these diseases, and that assays of this type will become "standard of care" for patients receiving such therapies. Findings with human cells using this assay were presented in a seminar by Dr. Silverstein at the National Institutes of Health in July 2010, and at a symposium at the NIH Clinical Center sponsored jointly by the Clinical Center of the National Institutes of Health and by the International Society for Cellular Immunotherapy of Cancer on Sep. 29, 2009.

It is believed that the methods used to increase the frequency of cytolytically active mouse antigen-specific CD8+T-cells will also work for human CD8+T-cells and that small increases in the fraction of cytolytically active human CD8+T-cells have as large an effect on killing of cognate-antigen-expressing human melanoma cells as small increases in the fraction of cytolytically active mouse CD8+ T-cells have on killing of cognate-antigen-expressing mouse melanoma cells.

In accordance with the present invention, a method to assess quantitatively the magnitude of the suppressive effects of intra-tumoral leukocytes, stromal cells, and their secretory products, collectively and individually, on the cytolytic activity of in vitro activated OT-1 cells is further described. As described by Budhu et al., suppressor cells and substances within the tumor parenchyma reduce by ~3-fold the efficiency (k) with which in vitro activated mouse antigen-specific CD8+T-cells kill cognate-antigen expressing mouse B16 melanoma cells in melanomas in vivo vs. in collagen-fibrin gels. Budhu et al. also reported that the efficiency (k) with which OT-1 cells kill cognate antigen-expressing tumor cells in collage-fibrin gels is nearly identical to the efficiency with which Lymphocytic Choriomeningitis Virus-(LCMV) specific CD8+T-cells kill LCMV antigen-expressing splenocytes in mouse spleen in vivo. Thus, the ~3-fold difference in cytolytic efficiency of OT-1 cells in collagen-fibrinn gels and in tumors does not appear to be due to some sort of cell culture artifact. Rather, it is most likely a result of the known suppressive effects of intra-tumoral leukocytes, TSCs, and secretory products. To examine the magnitude of these effects, and to identify the cells responsible for them, we have: 1. Harvested 8-day-established ova-B16 melanomas from mice, dissociated the tumors into single cell suspensions, and documented that ova-B16 cells grow at a log-linear rate of ~2-3×$10_{-4}$/min when co-cultured in collagenfibrin gels together with tumor-infiltrating leukocytes and stromal cells. ~2-3×$10_{-4}$/min is nearly identical to the rate at which SIINFEKL-B16 cells grow in these gels and in vivo (Budhu).

In parallel, we measured the growth rate in these gels of the ova-B16 cells used to initiate these tumors. It was identical (i.e., 2-3×$10_{-4}$/min) to that observed for ova-B16 cells in the presence of tumor leukocytes and tumor stromal cells (TSCs). Thus, ova-B16 cells grow at a log-linear rate in the presence of tumor leukocytes and TSCs, and the presence of these cells neither stimulates nor retards the growth of the ova-B16 cells.

Figure 21:
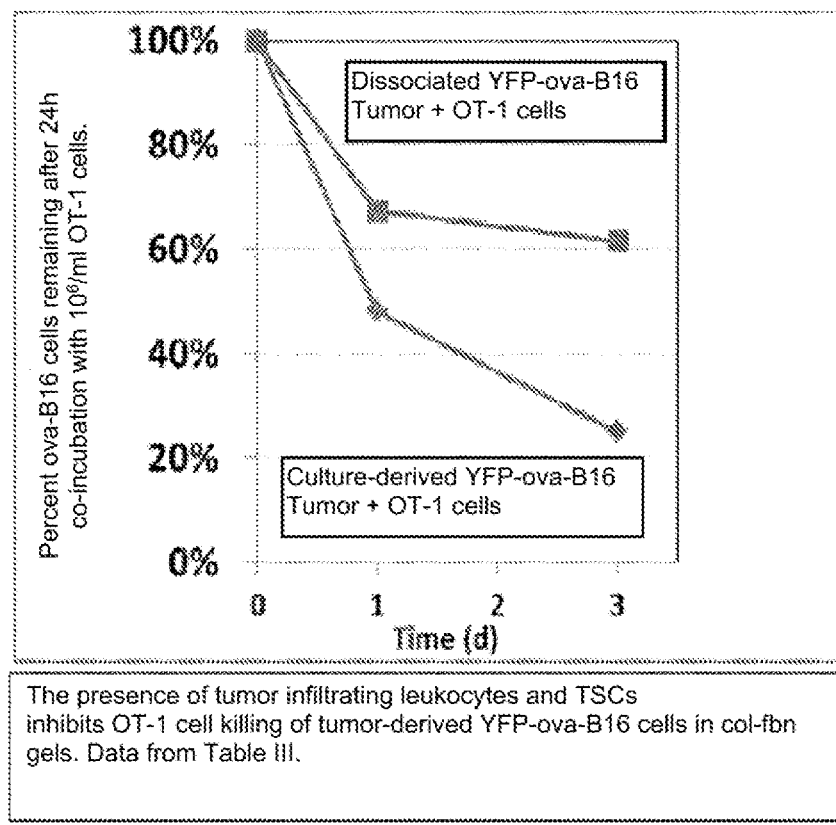
FIG. 21. The presence of tumor infiltrating leukocytes and TSCs inhibits OT-1 cell killing of tumor-derived YFP-ova-B16 cells in col-fbn gels is shown.

As a further control, we co-incubated $10_6$ ova-specific mouse CD8+T-cells/ml and $10_6$ ova-B16 cells/ml with and without $10_6$ C57Bl/6 splenocytes (T-cells, B-cells, macrophages and stromal cells)/ml collagen-fibrin gel for 1-3 d and assessed killing of the ova-B16 cells. The presence of a mixed population of normal or of mitogen-stimulated splenocytes had no effect on the percent of ova-B16 cells killed. In both instances, it was about 50% on d 1 and 75-80% on d 3. 4. We co-incubated $10_6$ total nucleated cells from these tumors/ml collagen-fibrin gel together with $10_6$ 2% cytolytically active in vitro activated mouse ova-specific CD8+T-cells/ml collagen-fibrin gel at 37° C. for 1-3 days, harvested the gels, and measured their content of clonogenic ova-B16 cells (FIG. 21 and Table 17, Lines 4-6). In parallel, we established control gels containing $10_6$/ml gel of the same cell-culture-derived ova-B16 cells used to produce these melanomas, and gels containing $10_6$ of these cell-cultured-erived ova-B16 cells plus $10_5$ of the same in vitro activated 2% cytolytically active mouse ovaspecific CD8+T-cells (FIG. 21 and Table 17, Lines 1-3). As with the tumor-derived ova-B16 cells, we harvested these "control" gels on days 0, 1 and 3, and measured their content of clonogenic ova-B16 cells.

Results

The values of ktot (Table 17) show that ova-B16 cells-derived from dissociated tumors and co-incubated with mouse ova-specific CD8+T-cells in the presence of tumor leukocytes and tumor stromal cell are killed ~3-fold less efficiently than cell culture-derived ova-B16 cells. This is precisely the difference in killing efficiency (k) noted for mouse ova-specific CD8+T-cells killing ova-B16 cells in ova-B16 cell tumors in living mice (Petersen, C. C., et al., Accumulation in tumor tissue of adoptively transferred T cells: A comparison between intravenous and intraperitoneal injection. J. Immunother., 2006. 29(3): p. 241-9). These results indicate that tumor-derived suppressor activity is reproduced in collagen-fibrin gels, and that they provide a useful system in which to measure the suppressive effects of tumor leukocytes and tumor stromal cells individually and collectively.

Inspection of FIG. 21 provides additional insight into the process. Mouse ova-specific CD8+T-cells killed tumor-derived ova-B16 cells more efficiently in the first 24 h following their placement in collagen-fibrin gels than in the next 48 h. This suggests that once dissociated, it takes tumor leukocytes and stromal cells ~24 h to re-express their suppressive activities. To test this concept we will embed a suspension of dissociated cells from 8-10 d ova-B16 tumors in collagen-fibrin gels and overlay the gels with $10_7$ ova-specific CD8+T-cells. Previous work established that it takes ~48 h for the ova-specific CD8+T-cells to crawl into the gels and distribute themselves throughout its volume. This will provide ample time for the tumor leukocytes and stromal cells to re-express their suppressive activities before the ova-specific CD8+T-cells contact them. This also will enable us to assess whether the presence of tumorderived leukocytes and stromal cells inhibits ova-specific CD8+T-cell migration into the gels. Accordingly, this in-migration configuration assay may prove to be an even more sensitive method for assessing the multiple suppressive activities of tumor-derived leukocytes and stromal cells than co-embedding ova-specific CD8+T-cells and dissociated tumor cells.

In short, this assay enables the identification of both the magnitude of overall suppression in each tumor, and the specific cells and secretory products responsible for the suppressive effects. This could open an entirely novel area of physiology and tumor immunology by demonstrating that the suppressive effects of leukocytes, TSCs, and their secretory products in one type of tumor (e.g., B-cell lymphomas) differ markedly from the suppressive effects of leukocytes, tumor stromal cells, and their secretory products in a second type of tumor (e.g., colon carcinomas). Indeed, given the heterogeneity of mutations that produce various tumors, there may be qualitative differences in the suppressive effects of leukocytes, tumor stromal cells, and their secretory products in different colon carcinomas. This is a recent discovery. It has not been described or disclosed anywhere.

Pyruvate and alanine, singly and in combination, increase the efficiency with which mouse antigen-specific CD8+T-cells kill cognate-antigen-expressing CD8+T-cells. The concentrations of puruvate (~1 mM) and alanine (~1 mM) required for this effect are markedly greater than the concentrations of these substances found in human blood or plasma. We are testing whether infusion of pyruvate and/or alanine into mice being treated with adoptive cellular immunotherapy for melanoma improves the efficiency with which the adoptively transferred tumor-antigen-specific CD8+T-cells kill cognate-antigen-expressing melanoma cells in mice with established cognate-antigen-expressing melanomas.

Cellular immunotherapy shows increasing promise as a treatment for human melanoma as well as for other human solid tumors (e.g., lung, ovary), but there is no general conceptual framework that underpins research in this area. Currently, the best cellular immunotherapy protocol for treating cancer yields an objective tumor regression in >50% of patients, yet only cures a small percentage of them. A critical determinant will be to develop a therapy that completely eradicates the tumor. The problem with conventional cancer chemotherapy is that at best it is only 99%-99.9% effective allowing the surviving tumor cells to quickly repopulate the patient. The conventional dogma prior to this discovery was that the effectiveness of the immune system in eradicating a tumor depends upon the relative numbers of tumor cells and effector immune cells (i.e. cytotoxic T-cells). This conventional way of thinking assumes that too many tumor cells are present to be destroyed by the immune system.

In accordance with the present invention, the described research completely negates this dogma. We have discovered that there is a critical concentration of immune cells that are required to eradicate the tumor cells. In our studies we have focused on a mouse model of melanoma and discovered that concentrations of greater that 10 million cells per cc of tumor have the capacity to totally eradicate mouse cancer cells, in vitro, at concentrations similar to those prevailing in tumors. To the best of our knowledge this is the first time immunotherapy has eradicated melanoma in a laboratory setting. Recently we have analyzed other scientific reports examining mouse models of immune cells killing melanoma tumor cells and discovered that these scientists have missed the critical role of immune cell concentration. By re analyzing their data, we calculate the critical concentrations required to control tumor growth. Unfortunately, that number is difficult to achieve in a clinical situation. Therefore, we have developed ways to improve the efficiency of T-cell mediated killing of melanoma cells. We have discovered that only 2% of the T cells are actually cytolytic and this is why it is difficult for the human body to recruit enough T cells to the tumor. Yet, as described in the appendix we can improve the efficiency of T cells that are cytolytic from 2% to 2.5% and demonstrate a 50% increase in the killing capacity of the system. We propose that the addition of specific biological substances to patients will also improve increase the percentage of cytolytic T cells and improve their chances to eradicate the tumor. Finally, we have re analyzed clinical data of melanoma patients undergoing transfusions of large numbers of immune cells to treat their tumors. Once again, their data matches ours in documenting that it is the critical concentration of immune cells that is required to control and eradicate the cancer. Clearly, the control and eradication of cancer is a highly complex process and there are many variables that must be addressed. However, on a simple level, a therapy protocol is provided that allows the patient to expand his or her killer immune cells to reach the critical concentration required to eradicate the tumor. In addition, critical time lines are developed for transfusing the appropriate immune cells that were obtained from the patient and expanded in the laboratory to better treat their cancer.

In these studies we have used a 3-D gel system composed of extracellular matrix proteins (e.g., collagen/fibrin/fibronectin) to assess experimentally and by mathematical modeling the bactericidal effector functions of human neutrophils (PMN), monocytes (Mo) and macrophages (Macs), the tumoricidal effector activities of Tumor Antigen-Specific human (TAS) CD8+ T-cells, and the impact of biological response modifiers, drugs, and environmental toxins on these functions. The systems to be developed have direct clinical relevance and are well suited to high throughput screening. For example, our fibrin/collagen gel system provides an important system to examine new drugs that may enhance the efficiency of tumor killing by activated T cells.

It also provides a system to examine the role of other immune cells such as NK killer cells, monocytes and macrophages in better eradicating the tumor.

An innovative model system is provided to quantitatively assess and proscribe the appropriate class of leukocytes to be elicited to fight specific cancers. In addition, a therapeutic concept in immunotherapy of cancer, the critical effector cell concentration is introduced. Our experimental evidence suggests that the critical effector cell concentration provides a clinical guideline how to administer or induce the appropriate effector cell concentration to eradicate a tumor. In addition, the time course for administration or induction may enhance the effectiveness of this immunotherapy. If effective, this intervention would virtually eliminate the need for classical high dose toxic cancer chemotherapy.

The model described provides a novel, and, extraordinarily useful, quantitative framework for analyzing the effector functions of most, if not all classes of leukocytes (e.g., PMN, monocytes, platelets, CD4+ and CD8+ lymphocytes, and dendritic cells). In addition, using the model developed will enable the identification of new therapeutic interventions, processes, and mechanisms, that would overcome key barriers to successful cellular immunotherapy of tumors and other diseases. The model utilizes an in vitro assay fibrin/collagen system to characterize immune cell effector functions in terms of cell concentrations, not as the classical effector to target ratios. It will enable the identification of suitable immune effector cells populations (CD8+, T cells, NK cells, monocytes, macrophages, neutrophils and dendritic cells) that are critical in eradicating tumors. In addition, the method can be used to identify the suitable immune effector cells that repress an overreactive immune response to alleviate and treat a variety of auto-immune diseases such as rheumatoid arthritis, lupus and multiple sclerosis.

Figure 22:
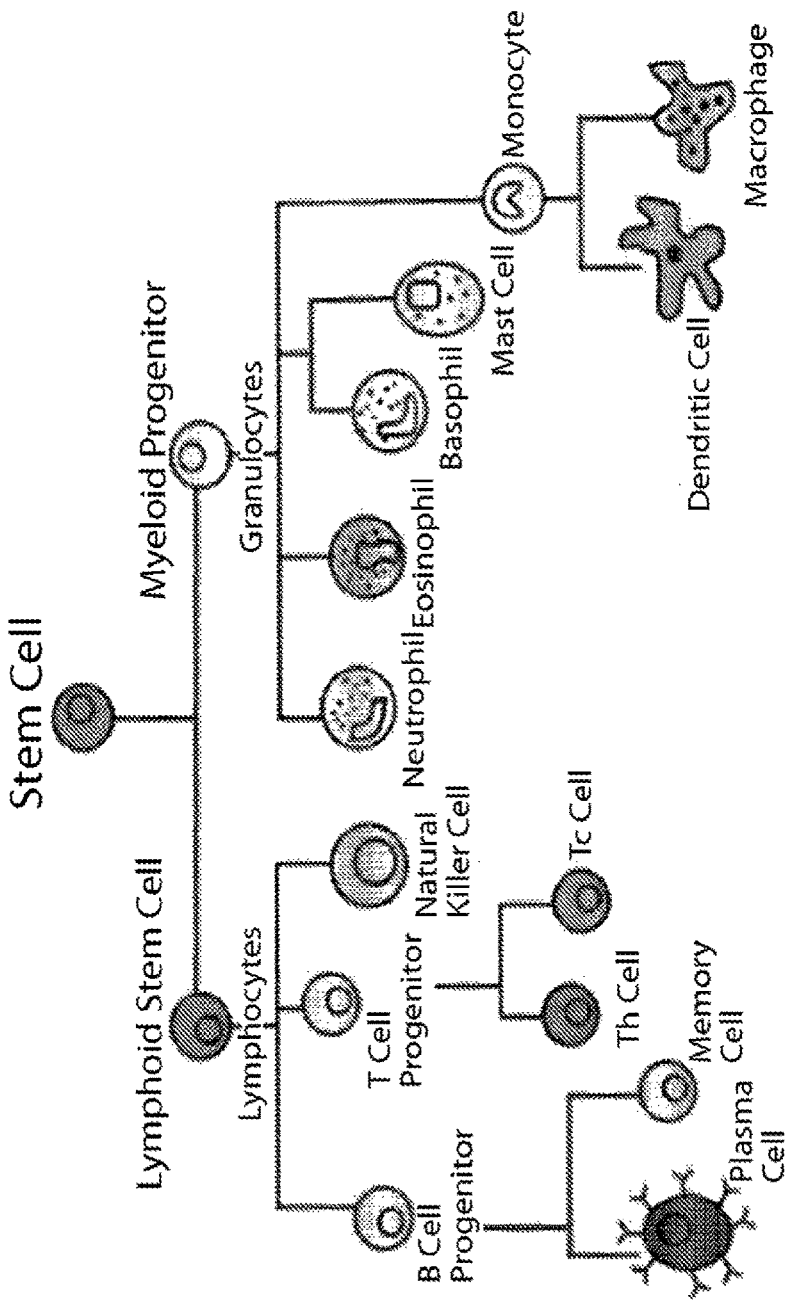
FIG. 22. A diagram of the cells that make up the immune system is shown.

The cells that make up the immune system (see FIG. 22) function in protecting the host from various pathogens and cancers. Each cell type has specific functions and operates in a coordinated fashion to ensure an appropriate immune response. Major cell types of the immune system are shown in FIG. 22.

Regarding T-cells, T lymphocytes are usually divided into two major subsets that are functionally and phenotypically different. CD8 T cells are generally cytolytic and are involved in directly killing certain tumor cells, virus-infected cells, transplant cells, and sometimes eucaryotic parasites. CD4+T cells, are involved in coordination and regulation of immunological responses. Regarding B-cells, the major function of B lymphocytes is to develop into antibody-secreting plasma cells following stimulation by foreign antigens of bacteria, viruses and tumor cells. Regarding Natural Killer (NK) cells, NK cells are similar to CTLs (CD8+T cells) and function as effector cells that directly kill certain tumors such as melanomas, lymphomas and virus-infected cells. Macrophages function in the eradication of tumors, bacteria and can serve as antigen-presenting cells (APCs) because they ingest foreign materials and present these antigens to other cells of the immune system such as T-cells and B-cells. Dendritic cells function as antigen presenting cells (APCs) and are more efficient APCs than macrophages.

In accordance with the present invention, cytolytic CD 8 T lymphocytes are immune cells that are effective in eradicating a tumor such as melanoma. An in vitro system issued to determine the critical concentration and dose of CD8 lymphocytes (or any combination of immune cells) required to eradicate a tumor cytokines such as gamma interferon increase the percent of cytolytic lymphocytes administered or naturally produced to eradicate a tumor. It is assessed which immune cells or combination of immune cells will be most effective in eradicating a tumor.

OT-1 cell concentration determines killing of SIINFEKL peptide-pulsed B16 melanoma cells in fibrin-collagen I gels. Human and mouse tumors express tumor specific-antigens that are recognized by cognate receptors on autologous CD4+ and CD8+T-cells. Infusion of very large numbers ($\geq 10^{10}$ of autologous, in vitro expanded and activated, CD8+T cells, into patients with melanoma resulted in objective tumor regression in a number of them, and cures in a few. However, more than half of the patients did not respond. There are many possible explanations for the different responses of the patients' tumors to this therapy. The one that attracted our attention was that the two patients who were cured had $\geq 10^6$ tumor antigen-specific CD8+T-cells/ml blood for more than 3 months. Active immunization rarely elicits $\geq 5 \times 10^4$ tumor antigen-specific CD8+ cells/ml blood. We reasoned that the presence of $\geq 10^6$ tumor antigen-specific CD8+T-cells/ml blood for more than 3 months allowed the intra-tumoral accumulation of a sufficient concentration of tumor antigen-specific CD8+T-cells to eradicate the tumor.

A review of the literature revealed: 1. Objective regression and even a few cures of established melanomas in mice following infusion of in vitro expanded and activated tumor antigen-specific CD8+ cells. However, there was a paucity of information on the number of infused CD8+ cells in regressing vs. progressing tumors, on the percent of infused cells with cytolytic activity, and on the intra-tumoral concentration of these cells. 2. Several studies indicate that ~10% of infused in vitro activated tumor antigen-specific CD8+ cells ultimately accumulate in experimentally induced tumors. But virtually none of these reports provides information about the types of leukocytes that accumulate in these tumors or their concentrations. 3. Approximately 85 ml blood passes through the vasculature of an established mouse or human tumor/gm tumor/24 hr. We used this value to estimate the extraction efficiency for inoculated CD8+ cells, assuming ~1% of CD8+ cells in blood emigrates into the tumor parenchyma per pass through the tumor vasculature. 4. Aside from 4 hour $^{51}$Cr-release assays, we found no studies that determined the number of antigen-specific CD8+ cells required to kill 100% of cognate antigen-bearing target cells, and none that tested whether there was a relationship between antigen-specific CD8+ cell concentration, the concentration of cognate antigen-bearing target cells, and the rate or extent of killing of the target cells by the CD8+ cells.

To examine the efficiency of T cell killing of tumor cells, we chose OT-1 CD8+ cells as cytotoxic effectors, and B16 melanoma cells (MHC I H2k$^b$) as targets. C57Bl/6 OT-1 mouse CD8+ cells express a transgene encoding a T-cell receptor that recognizes the ova peptide SIINFEKL in the context of H-2k$^b$ MHC-I. We have had substantial experience working with B16 tumor cells, and chose them because they are widely used in tumorigenesis and immunotherapy experiments, hence there is a lot of information available about them; and they are histo-compatible with the very large number of knock-out and transgenic mice constructed on the C57Bl/6 background. Most importantly, they have a high plating efficiency (~60%), enabling us to use a clonogenic assay to assess OT-1 mediated cytolytic activity. Such an assay provides 1-8 orders of magnitude of sensitivity, making it possible to detect very small differences (e.g., 99.99% vs. 99.9%) in CD8+T-cell mediated killing. and directly measures the killing efficiency of immune cells, the parameter of chief concern in cancer therapy. Finally, we have had the benefit of assistance from Dr. Rafaell Clynes, who has had many years of experience in working with OT-1 mice and cells.

Growth of B16 mouse melanoma cells in collagen/fibrin gels. B16 melanoma cells were maintained as monolayer cultures in OT-1 growth medium (RPMI 1640 medium with 10% fetal bovine serum (FBS)±50 µM β-mercaptoethanol [β-ME]) in a humidified incubator at 37° C. in 95% air/5% $CO_2$ atmosphere. For experiments, cells are detached by incubation at 37° C. for 5 min in phosphate-buffered saline (PBS) containing 5 mM EDTA, pelleted by centrifugation (400 g×10 min), and re-suspended at $1×10^6$ cells $ml^{-1}$ in OT-1 growth medium. Preliminary experiments showed that B16 cells grew efficiently in fibrin gels but lysed them after about 4 days. For this reason we formed gels with collagen I and fibrin, thereby prolonging the period ▲gels seeded with B16 cells remain intact.

Figure 23:
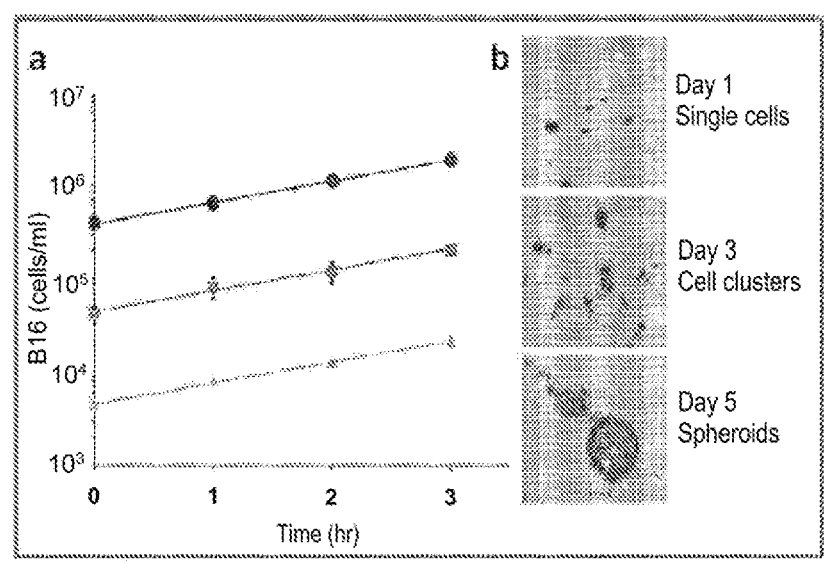
FIG. 23. B16 cells maintained in collagen-fibrin gels over time.

In FIG. 23, each well of a 48-well tissue culture plate were filled sequentially with 5 µl of PBS containing 0.1 U of thrombin and 100 µl of PBS containing 1 mg/m/human fibrinogen, 1 mg/ml rat tail collagen I, 10% FBS, and the desired number of SIINFEKL peptide-pulsed B16 cells. The plates were incubated for 15 min at 30° C. in a 95% air/5% $CO_2$ humidified atmosphere to allow the fibrin to gel. and each gel was overlaid with 0.5 ml OT-1 growth medium and incubated at 30° C. in a 95% air/5% $CO_2$ humidified atmosphere. Gels in 48 plate wells are 0.1 ml in volume and ~1500 µm in height, $4×10^4$ [▲], $4×10^5$ [■], and $4×10^6$ [●] B16 cells/ml collagen/fibrin gel containing OT-1 growth medium with BME or $4×10^5$ were incubated for 1-3 days at 37° C. Gels were harvested daily, solubilized with proteases, their content of B16 cells was assayed by clonogenic assay, and their growth rate (0.41 $day^{-1}$) and doubling time (~58 hr) calculated from the number of colonies recovered. N=3: bar=50 u.

Microscopic observation of B16 cells maintained in collagen-fibrin gels for 24 hr showed mostly single B16 cells with membranes protruding in all directions (FIG. 23b). By 72 hr, the cells began to aggregate, forming small clusters. By 96-120 hr these clusters developed into spheroids, varying from 50 to 100 µm in diameter. Each spheroid contained ~100 B16 cells, as determined by clonogenic assay. We noted considerable matrix remodeling and processing by single B16 cells and spheroids during culture. Gels containing a high concentration of B16 cells (>$10^6$ B16 cells/ml) remained intact for slightly more than 120 hrs. After ~120 hr the gels began to dissolve and the growth rate of B16 cells slowed. B16 cells, like many other mouse and human tumor cells, secrete collagenases, plasminogen activators and matrix metalloproteinases which are likely responsible for the gel dissolution observed.

The concentration of in vitro activated OT-1 cells determines the efficiency of killing of SIINFEKL peptide-pulsed B16 cells growing in collagen/fibrin gels. To determine the relationships between the concentrations of activated OT-1 cells and B16 cells, we pulsed B16 cells pulsed with $10^{-7}$ M SIINFEKL peptide (SIINFEKL-B16 cells), and measured the efficiency of killing of SIINFEKL-B16 cells by the OT-1 cells. OT-1 cells were harvested from spleens of C57Bl/6 OT-1 mice, incubated them at a concentration of $5×10^6$/ml with 0.75 ug/ml SIINFEKL peptide for 5-7 days in the presence of IL-2, added 25 ml fresh OT-1 growth medium containing mouse recombinant IL-2 (10 U/ml) on days 3 and 5, and harvested the cultures on days 5-7. OT-1 cells were purified by centrifugation at 400 g for 30 min at room temperature over a Histopaque gradient (density=1.083). Over 90% of cells isolated by this method were CD8+, Vβ5+. We co-embedded $10^4$-$10^7$ of these in vitro activated OT-1 cells with $10^4$ to $10^7$ SIINFEKL peptide-pulsed B16 cells in fibrin-collagen gels (prepared as in FIG. 23 and overlaid with OT-1 growth medium with BME), incubated the gels at 37° C. for 24 hr, lysed the gels with proteases, and measured their content of viable B16 cells by clonogenic assay. (Control experiments showed that B16 cells incubated for 2 hr in medium with $10^{-7}$ M SIINFEKL peptide were optimally sensitized for killing by OT-1 cells, and that the amount of bystander killing of un-pulsed B16 cells by activated OT-1 cells ranged from 0 to at most 12%. We used these conditions and this concentration of SIINFEKL in all subsequent experiments.

Figure 24:
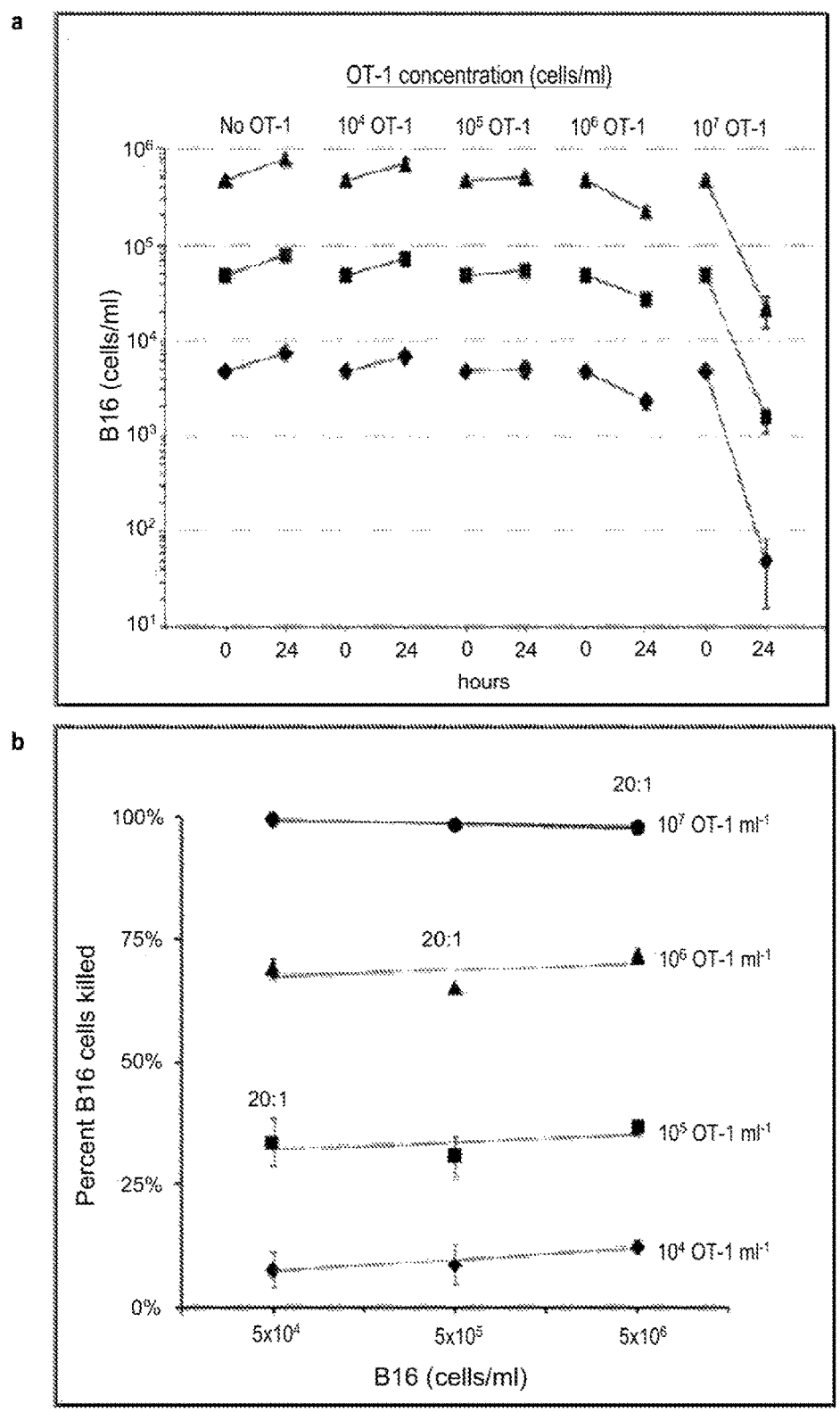
FIG. 24. The efficiency of killing of SIINFEKL-B16 cells was dependent on the concentration of OT-1 cells, and not on the ratio of OT-1 cells to B16 cells.

The efficiency of killing of SIINFEKL-B16 cells was dependent on the concentration of OT-1 cells, and not on the ratio of OT-1 cells to B16 cells (FIG. 24a). For example, $10^7$ OT-1 cells/ml gel killed ~98% of SIINFEKL-B16 cells, regardless of whether the B16 cell concentration was $5×10^5$/ml gel (▲), a 20:1 ratio of OT-1:B16 cells, $5×10^4$ B16 cells/ml gel (■), a 200:1 ratio of OT-1:B16 cells, or $5×10^3$ OT-1:B16 (♦), a 2000:1 ratio. We obtained qualitatively similar results under conditions in which the B16 cells were maintained for 24 hr in a non-proliferating state (RPMI medium without BME). That is, OT-1 cell concentration determined the efficiency with which they killed non-growing SIINFEKL-B16 cells in collagen/fibrin gels (Table 18). FIG. 24b below shows the relationship between OT-1 cell concentration and percent B16 cells killed (N=3 performed in duplicate).

To exclude the possibility that at very high cell concentrations (i.e. $10^7$ OT-1 cells/ml gel), the OT-1 cells depleted the medium of nutrients essential for B16 cell survival we incubated $10^6$ SIINFEKL-B16 cells $ml^{-1}$ gel with $10^4$-$10^6$ OT-1 cells $ml^{-1}$ gel without and with sufficient naïve or mitogen-activated C57BL/6 splenocytes to bring the total cell concentration to $10^7$ $ml^{-1}$ gel. The presence of $10^7$ naïve or mitogenactivated splenocytes had no effect on viability or growth of $10^6$ SIINFEKL-B16 cells/ml gel, and a 9-900-fold excess of naïve or mitogen-activated splenocytes had no effect on the efficiency of OT-1 cell killing of $10^6$ SIINFEKL-B16 cells/ml gel (data not shown). Thus, death of SIINFEKL-B16 cells co-cultivated with OT-1 cells is not due to nutrient depletion by the OT-1 cells.

Figure 25:
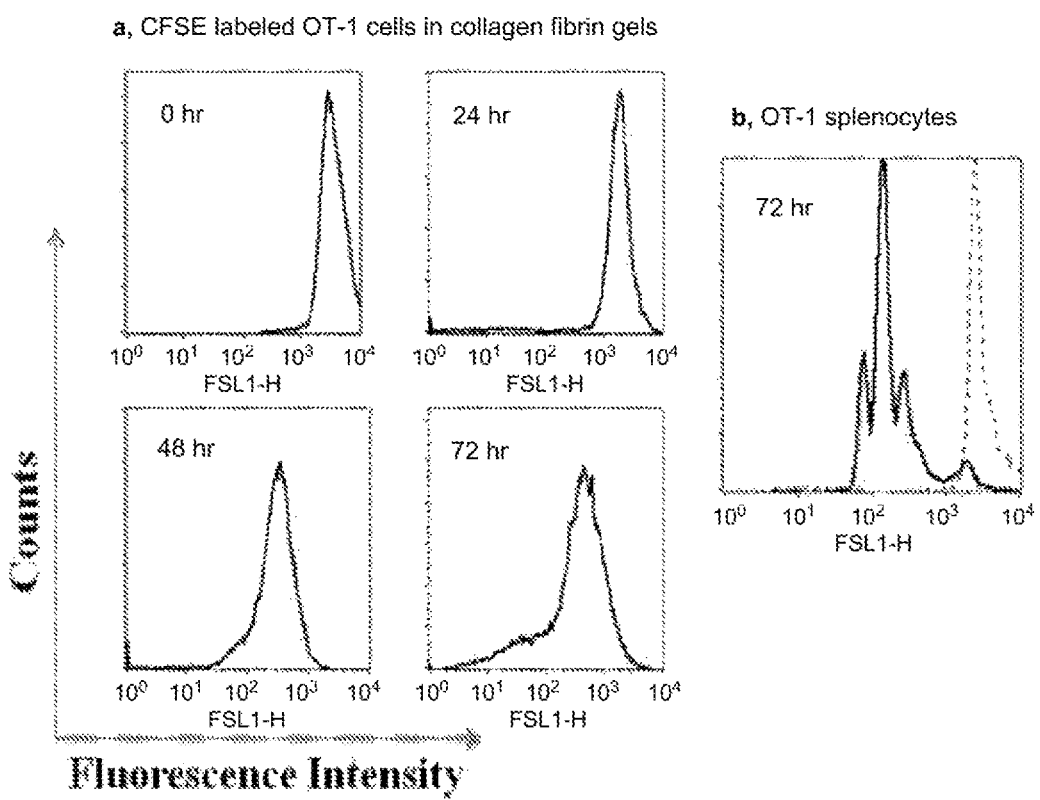
FIG. 25. Control experiments in which CFSE-labeled naïve OT-1 splenocytes were incubated with SIINFEKL peptide-pulsed tissue culture dishes.

OT-1 cells remain viable for 72 hr of co-culture with SIINFEKL peptide-pulsed B16 cells in collagen/fibrin gels. To determine whether OT-1 cell concentration changed during 1-5 days of incubation with SIINFEKL-B16 cells, we co-incubated CFSElabeled or unlabeled OT-1 cells with SIINFEKL-B16 cells in collagen/fibrin gels for 24-72 hr, lysed the gels, and assayed their content of B16 cells by clonogenic assay, and their CFSE-labeled OT-1 cells by FACS. CFSElabeled OT-1 cells killed SIINFEKL-pulsed B16 cells with the same efficiency as unlabeled OT-1 cells (data not shown). FACS analysis showed that 94% of the OT-1 cells remained viable at 24 and 48 hr, respectively, and that their exposure to SIINFEKL-B16 cells in medium containing IL-2 did not stimulate them to divide (FIG. 25). Control experiments in which CFSE-labeled naïve OT-1 splenocytes were incubated with SIINFEKL peptide-pulsed tissue culture dishes showed dilution of the CFSE label (FIG. 25), confirming that proliferation of the CFSE-labeled cells could have been detected by this method, had it occurred.

FIG. 25: (a) $10^6$ SIINFEKL-B16 cells $ml^{-1}$ were co-incubated with $10^7$ $ml^{-1}$ CFSElabeled OT-1 cells in collagen/fibrin gels in medium with or without 100 U ml$^{-1}$ IL-2. Gels were lysed at 24, 48 and 72 hr, released cells were incubated in Propidium Iodide (to identify dead cells), and analyzed by FACS. (b) CFSE-labeled naïve OT-1 splenocytes were incubated with 0.75 μg ml-1 SIINFEKL peptide at 37° C. for 72 hr after which the cells were isolated and analyzed by FACS. These are representative experiments performed in triplicate.

OT-1 cells at concentrations of $10^7$ and $10^8$/ml collagen/fibrin gel kill 100% of SIINFEKL-B16 cells. OT-1 cells at $10^7$/ml gel killed between 96% and 99% of SIINFEKL-B16 cells in 24 hr (FIG. 24a). To determine whether OT-1 cells can affect sterilizing immunity in vitro we co-incubated $10^5$/ml SIINFEKL-B16 cells and $10^6$, $10^7$, or $10^8$ OT-1 cells in collagen fibrin gels in OT-1 growth medium containing BME and 20 units/ml IL-2 at 37° C. for 2-5 days, harvested the gels daily and assayed their content of B16 cells by clonogenic assay. At concentrations of $10^7$/ml and $10^8$/ml, OT-1 cells killed 100% of 6 SIINFEKL-B16 cells at 72 and 48 hr, respectively (Table 19). Parallel gels harvested at 120 and 96 hr, respectively, also showed 100% killing, confirming that the OT-1 cells at >$10^7$/ml totally eradicated the SIINFEKL-B16 cells. The concentration of tumor cells in most mouse and human tumors is ~$10^7$-$10^8$/ml or gram tumor. Co-incubation of $10^7$ or $10^8$ OT-1 cells with ~$10^5$ SIINFEKL-B16 cells/ml collagen/fibrin gel resulted in complete eradication of the B16 cells in 72 and 48 hr respectively (Table 19). Assuming $10^7$ or $10^8$ activated OT-1 cells kill $10^7$ or $10^8$ SIINFEKL-B16 cells/ml collagen-fibrin gel at these rates, delivery of $10^7$ OT-1 cells/ml of tumor parenchyma could eradicate a tumor containing $10^7$-$10^8$ tumor cells in 108-120 hr, and delivery of $10^8$ OT-1 cells/ml tumor could eradicate a tumor containing $10^7$-$10^8$ tumor cells/ml in 60-72 hr. Co-incubation of $10^6$/ml OT-1 cells with $10^5$/ml SIINFEKL-B16 cells in collagen-fibrin gels kills ~75% of the B16 cells/24 hours. At this rate it would take 15-20 days to eradicate a tumor containing $10^7$-$10^8$ tumor cells. We will return to this topic in Aim #5. However, it is relevant and important to point out here that in all instances of which we are aware, eradication of established mouse tumors by infusion of activated tumor antigen-specific CD8+ cells required the presence of ≥$10^7$ tumor antigen-specific CD8+ cells in the tumor bed.

Figure 26:
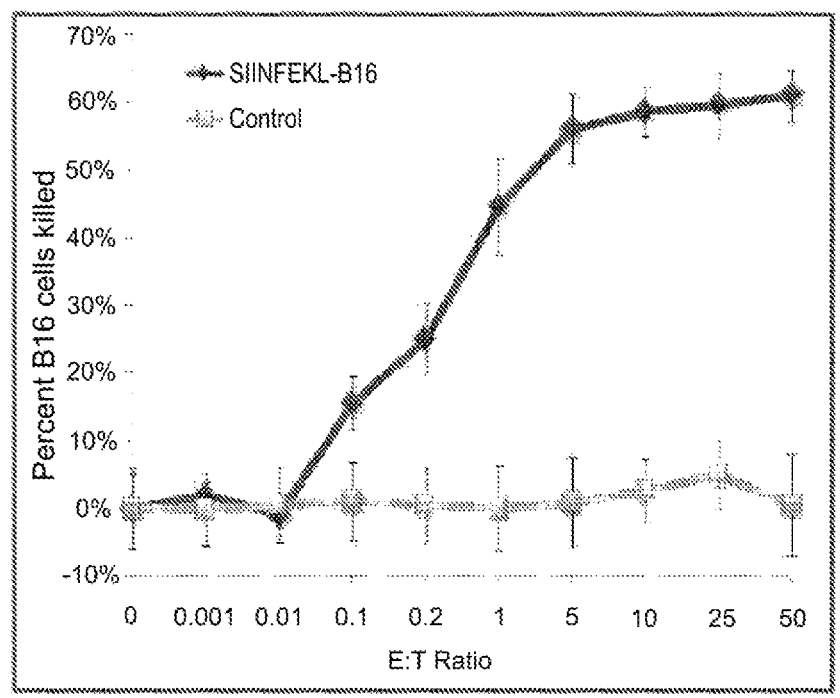
FIG. 26. SIINFEKL-pulsed and non-pulsed (control) B16 cells mixed with activated OT-1 cells and the data shown represent the average percent B16 cells killed of 3 experiments each performed in duplicate.

OT-1 cell concentration determines the efficiency of killing of SIINFEKL-peptide-pulsed B16 cells in $^{51}$Cr release-type assays. In assays of this type, the relative capacity of cytotoxic effector cells to kill a fixed number of target cells is reported as the ratio of effector to target cells. Investigators frequently observe that maximal target cell killing plateaus at less than 100% in these assays, even when the ratio of effector to target cells is very high (i.e., 100:1). This "plateau" effect is inconsistent with the concept that the extent of target cell killing is dependent on the ratio of effector to target cells. As the ratio of effector to target cells increases, the concentration of effector cells reaches a limiting value that is approximately equal to their concentration in a packed pellet containing effector cells alone, while the ratio of effector to target cells continues to increase. However, these plateaus are consistent with the concept that effector cell concentration determines target cell killing in this assay as it does in the collagen/fibrin gel assays described above. To test this hypothesis we mixed activated OT-1 cells with $10^5$ SIINFEKL-pulsed or non-pulsed B16 cells in wells of a 96 well plate, incubated these plates at 37° C., recovered the cells from each well, and assayed killing of the B16 cells (FIG. 26). Virtually no un-pulsed B16 cells were killed. In contrast, 58% and 60% of SIINFEKL-B16 cells were killed at ratios of 5:1 and 50:1 OT-1 cells:SIINFEKL-B16 cells, respectively. FIG. 24a shows an increase in OT-1 cell concentration from $10^6$/ml to $10^7$/ml produces an ~30% increase in killing of SIINFEKL-B16 cells in 24 hr. Why does a ten-fold increase in the ratio of OT-1 cells:SIINFEKL-B16 cells not result in a similar increase in SIINFEKL-B16 cell killing in a packed pellet? The answer is evident from the data in Tables 19 and 20.

FIG. 26. $10^5$ SIINFEKL-pulsed and non-pulsed (control) B16 cells were mixed with $10^2$-5×$10^6$ activated OT-1 cells in 200 μl of OT-1 medium in round-bottom wells of a 96-well plate. Plates were centrifuged at 50×g for 5 min to pellet the cells and incubated at 37° C. for 4 h. Cells in each well were dissociated with trypsin/EDTA, and their viability measured by clonogenic assay. Data shown represent the average percent B16 cells killed of 3 experiments each performed in duplicate.

To confirm that the concentration of OT-1 cells, not the ratio of OT-1 cells:SIINFEKL-B16 cells, determines the efficiency of killing of SIINFEKL-B16 cells, we co-sedimented a mixture of $10^5$ activated OT-1 cells with $10^4$ to 5×$10^5$ SIINFEKL-B16 cells and sufficient naïve wild-type C57Bl/6 splenocytes to bring the total volume of all cell pellets to ~263 nl (Table 20). Microscopic examination of these pellets showed OT-1, B16, and naïve splenocytes were randomly intermixed with one another throughout the cell pellet. Note that under these conditions the ratio of OT-1 cells varied from 1:1 to 5:1 but the OT-1 cell concentration remained constant at ~2.4×$10^9$ OT-1 cells/ml. The percent of SIINFEKL-B16 cells killed was ~18% at all three ratios, confirming that the efficiency of OT-1 cell-mediated killing of SIINFEKL-B16 cells is strictly dependent on the OT-1 cell concentration.

Figure 27:
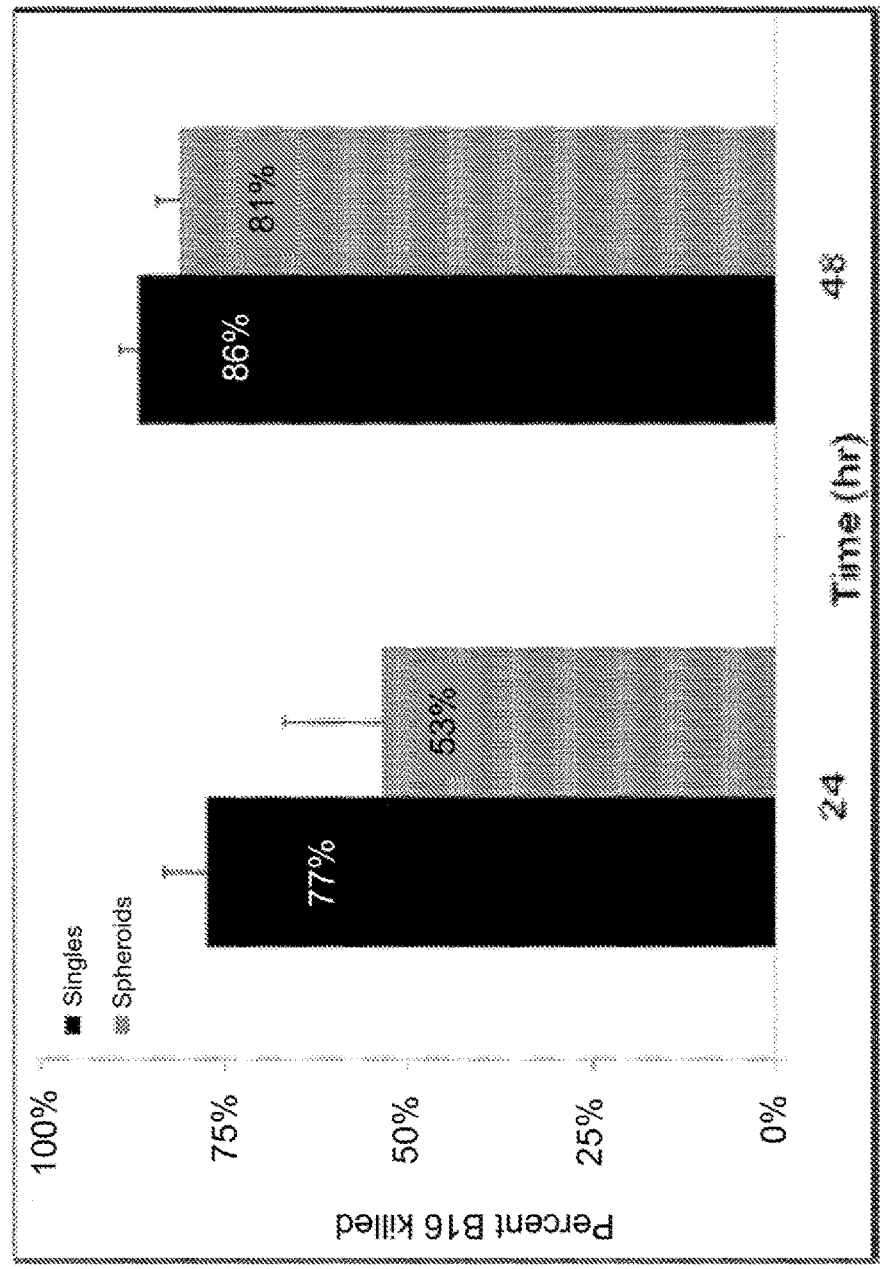
FIG. 27. The average percent of B16 cells killed for 3 experiments performed in duplicate.

FIG. 27. B16 spheroids were sedimented at 1 g through a cushion of fetal bovine serum to separate them from single B16 cells. The purified spheroids were pulsed with 1 μM SIINFEKL for 2 hr, and their concentration assessed by counting in a hemocytometer. A measured aliquot of this preparation was disaggregated by trituration in EDTA/0.05% trypsin buffer, releasing >95% of B16 cells from the spheroids. The concentration of released B16 cells was measured in a hemocytometer. The remaining spheroids, containing ~100 SIINFEKL:B16 cells/spheroid, were diluted to a concentration containing 2×$10^6$ SIINFEKL-B16 cells/ml. A measured volume of these spheroids was triturated as above to dissociate them into single cells. $10^5$ single SIINFEKL-B16 cells and $10^3$ SIINFEKLspheroids were incubated at 37° C. in collagen/fibrin gels containing OT-1 growth medium with BME. At 24 & 48 hr gels were assayed for clonogenic B16 cells as in FIG. 22. Shown is the average percent of B16 cells killed for 3 experiments performed in duplicate.

OT-1 cells kill SIINFEKL-peptide-pulsed b16 cells in spheroids as efficiently as single peptidepulsed B16 cells. In vivo, melanoma cells, like many other tumor cells, grow in nests or clusters. B16 cells spontaneously form "spheroids" (FIGS. 22 & 27) containing ~100 B16 cells when maintained in collagen/fibrin gels for more than 3 days, or when maintained in suspension cultures. To assess whether the matrix proteins produced by spheroids, or the barrier imposed by their structure, affects OT-1 killing of B16 cells, we co-incubated ~$10^3$ SIINFEKL-B16 spheroids (containing ~$10^5$ B16 cells, or $10^5$ single SIINFEKL-B16 cells dissociated from these spheroids in collagen/fibrin gels together with $10^6$ activated OT-1 cells for 24 and 48 hr. At these times we lysed the gels, dissociating any remaining spheroids into single cells and measured the number of B16 cells remaining viable by clonogenic assay. OT-1 cells killed ~24% more (not significant) spheroid-derived single SIIN-FEKL-B16 cells than SIINFEKL-B16 cells in spheroids at 24 hr. However, at 48 hr, OT-1 cells had killed nearly equal number of SIINFEKL-B16 cells dissociated from spheroids prior to placement in the gels, and SIINFEKL-B16 cells placed in the gels in spheroids. Light microscopic examination of sections of gels containing similar concentrations of OT-1 cells, and spheroidderived single SIINFEKL-B16 cells or SIINFEKL-B16 spheroids showed OT-1 cells both clustered around the spheroids and invading them. Thus, there is no evidence that the multi-layered arrangement of B16 cells in spheroids, or the matrix proteins associated with them, have any effect on the cytolytic activity of OT-1 cells.

Does (Eq. 1) $[b_t=b_0\ e^{-kpt+gt}]$, which was Derived to Describe Neutrophil Bactericidal Activity Also Describe Killing of SIINFEKL Peptide-pulsed B16 Melanoma Cells?

Figure 28:
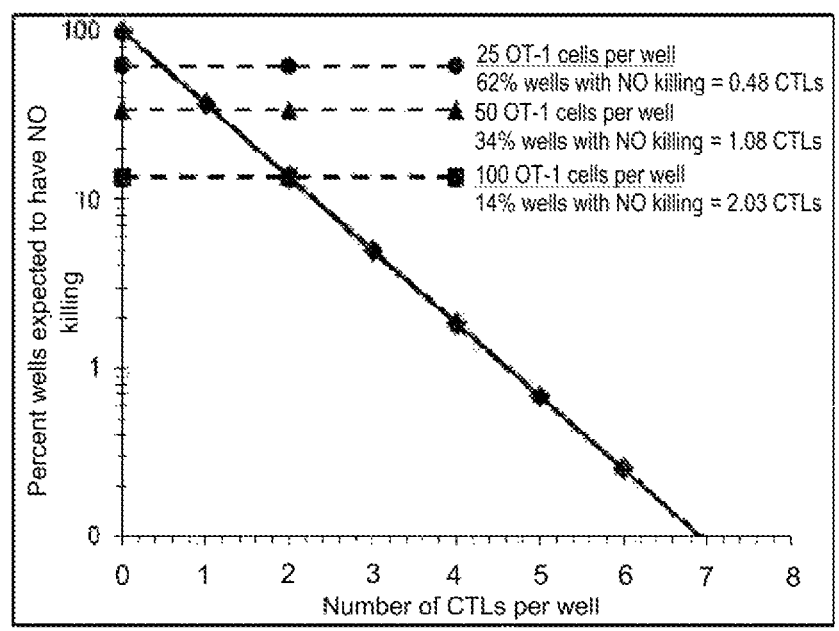
FIG. 28. The average percent of wells with no killing of eleven experiments.

FIG. 28. 100 SIINFEKL-pulsed B16 cells without or with 25, 50, or 100 in vitro activated OT-1 cells were added to each of 100 wells of Terasaki plates in 20 μl of OT-1 medium. The plates were incubated at 37° C. in a humidified incubator for 24 h. B16 cells were detached with 5 mM EDTA and assayed as described in FIG. 22. Data shown represents the average percent of wells with no killing of eleven experiments.

OT-1 cells remain viable and kill SIINFEKL pulsed B16 cells at an exponential rate for 3-5 days. We substituted values for growth of $10^4$, $10^5$, and $10^6$ SIINFEKL pulsed B16 cells/ml collagen/fibrin gel and for killing of these cells by $10^5$, $10^6$, and $10^7$ OT-1 cells/ml collagen/fibrin gel into Eq. 1 and calculated k as described by Li et al. Inspection of FIG. 24a showed the critical OT-1 cell concentration for killing SIINFEKL-B16 cells was slightly greater than $10^5$ OT-1 cells. However, using the experimentally derived values for g, and OT-1 cell concentration (p) to calculate k, we obtained a Critical OT-1 cell Concentration (g/k) of $1.2 \times 10^6$ OT-1 cells/ml, almost 10-fold higher than observed experimentally. We recognized that in calculating k we used the experimentally determined values of p, that is, the concentration of activated OT-1 cells added to the gels. While FACS analysis using antibodies vs. CD8 and Vβ5 showed the OT-1 cells used in these experiments were >90% CD8+ and expressed Vβ5 as expected for the OT-1 TCR transgene, it was possible that only a small percentage of them were cytolytically active. Indeed, Snyder et al. reported that only 2-4% of activated OT-1 cells mediate cytolysis of target cells. However, the lysis-spot assay Snyder at al. developed and used in their experiments required short incubation times (~4 hr) and had a very high background. Concerned that the high background might produce an over-estimate of the percentage of OT-1 cells that is cytolytically active, we performed limiting dilution assays and used the Poisson distribution to assess the percentage of OT-1 cells activated under our conditions that are cytolytically active. In agreement with Snyder et al., we found it is only 2% (FIG. 28). When we used the concentration of the 2% of OT-1 cells that are cytolytically active to calculate k, we obtained a value for k of $2.2 \times 10^{-4}$ ml/activated OT-1 cell/day ($\pm 0.24 \times 10^{-4}$), or $3.17 \times 10^{-7}$ ml/OT-1 cell/min. Substituting this value of k into Eq. 1, gave a Critical Concentration for cytolytic OT-1 cells of $7.7 \times 10^3$ CTLs/ml gel ($\pm 7 \times 10^2$), and a Critical Concentration for total OT-1 cells of $3.9 \times 10^5$ OT-1 cells/ml ($\pm 3 \times 10^4$). This calculated concentration of cytolytic OT-1 cells agrees closely with the value obtained from multiple experiments (e.g., FIG. 24a). We draw four important conclusions from these findings:

As found for PMN, OT-1 cytolytic activity is dependent on OT-1 cell concentration, not on the ratio of OT-I cells: target cells. 2. Using the respective values of k for PMN bactericidal activity in fibrin gels, and OT-1 cytolytic activity in collagen-fibrin gels, Eq. 1 accurately models PMN bactericidal activity in fibrin gels in vitro and in rabbit skin in vivo, and OT-1 cells killing of SIINFEKL-B16 cells in vitro (FIG. 24a). 3. The cytolytic activity of activated antigen-specific C8+ cells is attributable to the sub-population of these cells that expresses CD107a and engages in trogocytosis, following interaction with cells expressing cognate antigen. Therefore, the value of k is a function of the concentration of the effector cells that mediate the activity of interest. One hundred percent of PMN are bactericidal effector cells. Therefore the value of p used to calculate k for PMN is the concentration of all PMN. In contrast, only 2% of all OT-1 cells are cytolytic. Therefore the value of p used to calculate k for OT-1 cell-mediated cytolytic activity is the concentration of the 2% of OT-1 cells that mediate cytolysis. 4. Indirect measures (e.g., tetramer binding, interferon secretion, granzyme and perforin expression), do not accurately predict the percent of cells in an effector cell population that are responsible for the activity of interest. For example, ~90% of the activated OT-1 9 cells used in the present studies were CD8+, tetramer+, and Vβ5+, yet limiting dilution assays showed only 2% of them lysed SIINFEKL-B16 cells.

The above similarities notwithstanding, we note the following differences between the bactericidal behavior of PMN and the cytocidal behavior of OT-1 cells. 1. At all PMN concentrations tested, from $10^3$-$10^7$/ml fibrin gel, PMN bactericidal activity lasts for only ~30-45 min and then ceases. (This is also true in stirred suspensions). In contrast, in IL-2-containing medium, OT-1 cells kill SIINFEKL-B16 cells in collagen-fibrin gels at a uniform rate for 3-5 days or until they have killed all the B16 cells in the gel. 2. For PMN, both k and the critical concentration are relatively constant at bacterial concentrations $\leq 10^8$/ml fibrin gel. At bacterial concentrations $\geq 10^8$/ml fibrin gel, k decreases and the Critical PMN Concentration increases. As reported in Aim #3b, this occurs because IgG-opsonized bacteria at $\geq 10^8$/ml fibrin gel inhibit PMN H2O2 production and thereby reduce PMN bactericidal activity. In contrast, at every SIINFEKL-B16 cell concentration tested, from $10^4$ to $10^7$/ml collagen-fibrin gel, the percent SIINFEKL-B16 cells killed increased with OT-1 concentration (FIGS. 24a & b). However, a 10-fold increase in OT-1 cell concentration did not produce a commensurate increase in the number of SIINFEKL-B16 cells killed. This is because k decreased monotonically ~450-fold and the Critical OT-1 Concentration increased ~100-fold as OT-1 concentration rose from $10^4$-$10^8$/ml collagen-fibrin gel. While an increasing percentage of SIINFEKL-B16 cells were killed for every increment in OT-1 cell concentration (Table 21), the number of SIIN-FEKL-B16 cells killed per OT-1 cell decreased ~10-fold for every 10-fold increase in OT-1 cell concentration. We are unaware of previous reports of this phenomenon. We discuss possible causes for this striking phenomenon in Aim #3. However, it is of major importance for cellular immunotherapy of cancer. All available evidence suggests that the higher the concentration of CD8+ cells within a tumor, the better the prognosis for cure once the tumor is removed. The observation that CD8+ cells kill cognate antigen-expressing tumor cells with decreasing efficiency as intra-tumoral CD8+ cell concentration rises suggests that under some circumstances, high concentrations of CD8+ cells can reduce the efficiency of killing of tumor cells.

Methods to increase the percent of cytolytic cells.

IL-2 promotes killing of SIINFEKL peptide-sensitized B16 melanoma cells by SIINFEKL peptide specific CD8+ lymphocytes. Patients with metastatic melanoma who are treated by adoptive transfer of tumor antigen-specific CD8+ cells and with the cytokine, interleukin-2 (IL-2), have better clinical responses than patients treated with either agent alone. IL-2 is well known to enhance T cell function and survival in vitro. We used the previously described 3-dimensional fibrin-collagen gels containing varying concentrations of SIINFEKL peptide-sensitized B16 mouse melanoma cells (H-2 kb) and OT-1 CD8+T lymphocytes) to compare killing of SIINFEKL peptide-pulsed B16 melanoma cells maintained in gels with or without IL-2. While the addition of IL-2 (20 U/ml) had only a modest effect (71% vs 81% without or with IL-2, respectively) on killing during the first 24 hr of culture, it markedly increased the extent of killing of B16 melanoma cells during the subsequent 24-48 hr, from 80% to 98%. The effects of IL-2 is dose dependent however, higher concentrations of IL-2 (≥50 U/ml) increased killing of B16 melanoma cells by OT-1 cells to an even greater extent but also enhanced the non-specific killing of B16 cells that were not pulsed with the SIINFEKL peptide (data not shown). FACS analysis of carboxyfluorescein succinimidyl ester (CFSE) labeled OT-1 cells incubated for up to 72 hr with SIINFEKL peptide-sensitized B16 mouse melanoma cells in fibrin-collagen gels showed that the OT-1 cells did not proliferate in response to the SIINFEKL peptide-sensitized B16 cells whether or not IL-2 was present. However, addition of IL-2 increased the viability and cytotoxic effector activity of the OT-1 cells, especially after the first 24 hr of culture.

IL-21 promotes killing of SIINFEKL peptide-sensitized B16 melanoma cells by SIINFEKL peptide specific CD8+ lymphocytes. IL-21, one of the newest members to the common γ-chain cytokine family, is produced by activated CD4+T-cells and has been shown to have a very potent effect on CD8+T-cell proliferation and effector functions. Ex vivo T-cell cultures containing IL-21 increased the total number of tumor antigen-specific CD8+T-cells and sustained CD8+T cell numbers long term resulting in increased survival. We formed collagen-fibrin gels containing $10^5$/ml SIINFEKL-B16 cells and $10^6$/ml ex vivo activated OT-1 cells cultured and maintained in 100 ng/ml IL-21 or 20 units/ml IL-2. Killing was assessed at days 1, 5 and 7 by dissolving the collagen-fibrin gels using proteases and recovering the number of viable clonogenic B16 cells (as described in methods). Ex vivo OT-1 cells that were cultured and maintained with 100 ng/ml IL-21 exhibited a 24% increase in the percent of SIINFEKL-B16 cells killed in 24 h in collagen-fibrin gels in comparison to OT-1 cells culture maintained in 20 units/ml IL-2. When observing the percent of SIINFEKL-B16 cells kill at days 5 and 7, the differences between IL-2 and IL-21 do not appear significant (96.4% vs 99.8% on day 5 and 98.3% vs. 99.98% on day 7), however, there is a 1.5 log and 2 log decrease in the number of clonogenic SIINFEKL-B16 cells recovered from the gels on days 5 and 7, respectively. This highlights the sensitivity of the collagen-fibrin gels to detect several orders of magnitude differences in cell numbers. While IL-2 OT-1 cells cease to efficiently kill B16 cells after 5 days resulting in re-growth of SIINFEKL-B16 cells, IL-21 OT-1 cells continue to kill for up to 7 days nearly to the point of eradication (99.98% B16 cells killed). Thus IL-21 is a more potent cytokine to activate and maintain CD8+T-cells in vitro and in vivo.

We performed a limiting dilution assay to determine whether IL-21 the increase in the killing efficiency of OT-1 cells observed in FIG. 25 was due to an increase in the percent of cytolytically active OT-1 cells. There were 1.8% of cytolytically active OT-1 cells in cultures maintained in 100 ng/ml IL-21 compared to 2.5% cytolytically active OT-1 cells maintained in 20 units/ml IL-2. Note that data obtained in FIG. 22 reflect the percent of cytolytically active OT-1 cells maintained in 10 units/ml IL-2 which is our standard protocol for in vitro OT-1 cultures. These results suggests that IL-21 enhances OT-1 effector function activity by increasing the percentage of cytolytically active OT-1 cells or by some other mechanism. IL-21 has been shown to increase the percent of CD8+T-cells that express perforin may also account for the increase in the killing efficiency observed in the collagen-fibrin gels.

Figure 30:
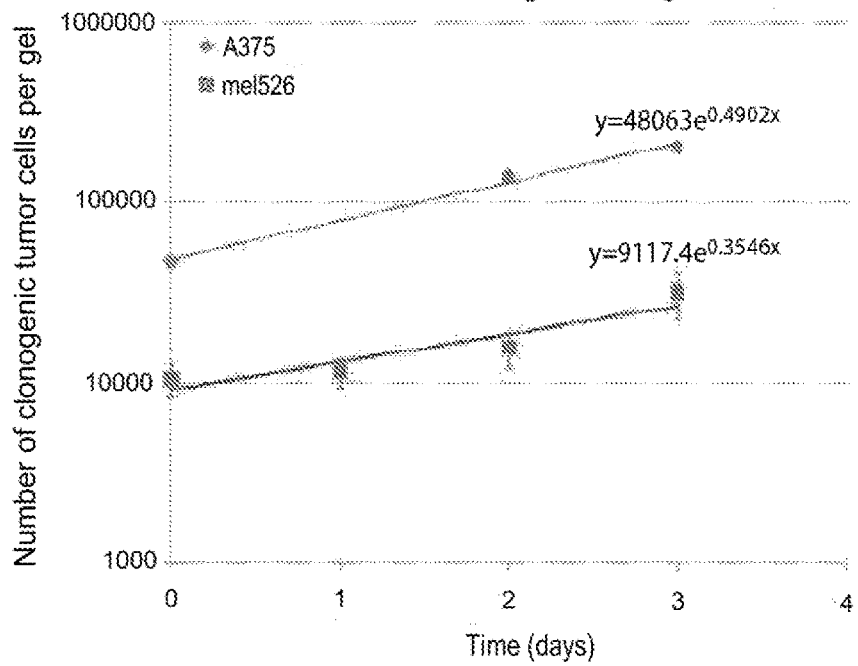
FIG. 30. The growth of human A375 and human mel526 melanoma cell lines in collagen/fibrin gels and the killing of gp100-peptide-pulsed A375 human melanoma cells by human CD8+T-cell clone 476.140 in collagen-fibrin gels.
Figure 30:
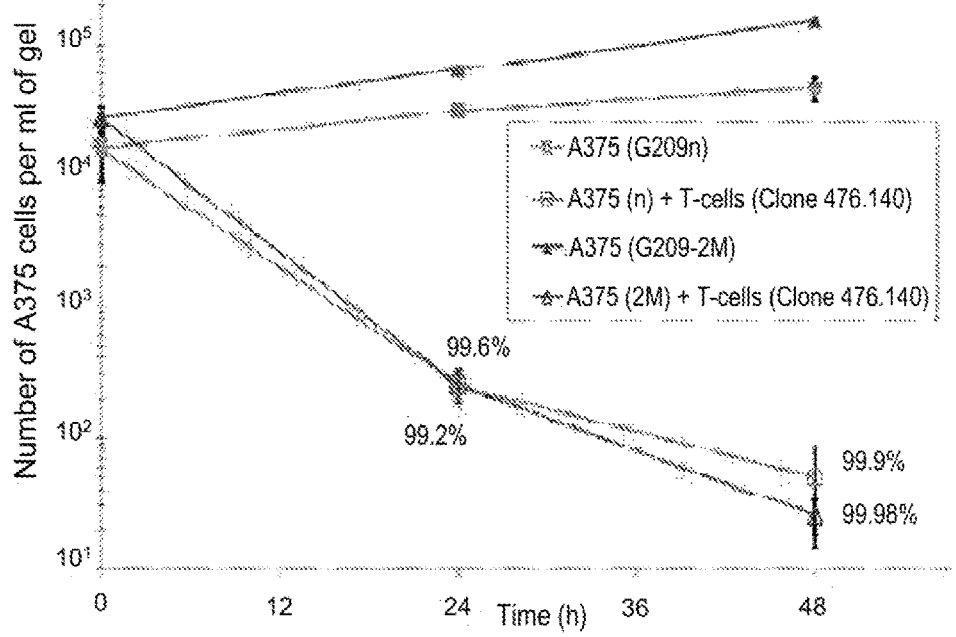

Determining the percent of these TAS human CD8+T-cells that are cytolytically active. In collaboration with Dr. Peter Lee of Stanford University we have determined that human melanoma cell lines mel526 (gp100+, Mart 1+), and A375 (gp100neg, Mart-1 neg) grow reproducibly in collagen-fibrin gels, are released from them by proteolysis, and can be assayed by clonogenic assay, all using the methods described in FIGS. 22 & 23. Clone 476.140 human CD8+ T-cells express a TCR that recognizes peptide gp100 in the context of HLA2. We prepared un-pulsed, or native (G209n) or heteroclytic (G209-2M) gp100 peptide-pulsed A375 cells and co-incubated them at $10^5$ melanoma cells/ml coil-fibrin gel with $10^7$ clone 476.140 human CD8+ cells/ml gel in medium containing 50 U/ml human IL-2 at 37° C., lysed the gels at 24 and 48 hr, and measured their content of viable A375 cells by clonogenic assay as described in FIGS. 22 & 23. See FIG. 30. As shown clone 476.140 human CD8+T-cells killed 99.9%-99.98% of human A375 melanoma cells pulsed with native or heteroclytic gp100 peptide, respectively, in coll-fibrin gels in 48 hr. See FIG. 30. This is a 1.5-2-fold higher rate of melanoma cells killing than the rate OT-1 cells kill SIINFEKL-B16 cells in these gels. See FIG. 30.

Figure 31:
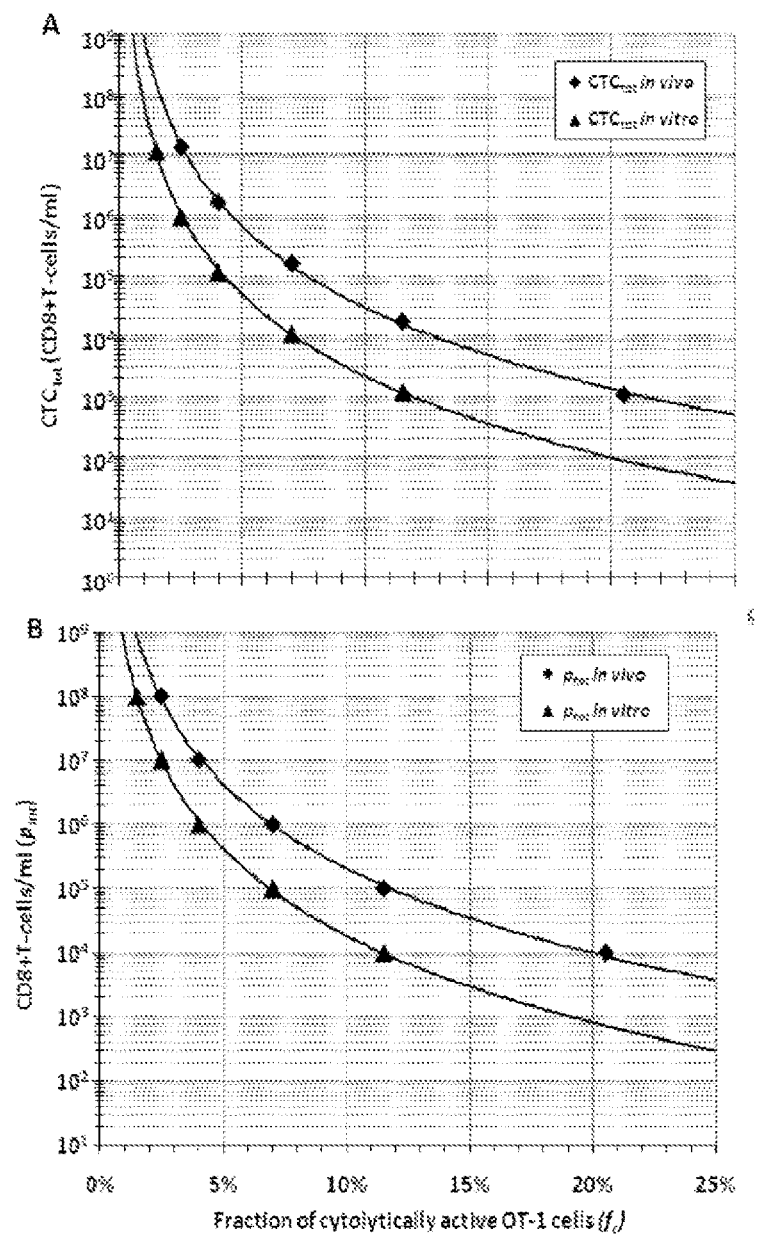
FIG. 31. Nomograms showing: (A) The relationship between $f_c$ OT-1 cells and the $CT_{tot}C$ for the indicated intra-tumoral concentrations of OT-1tot cells. (B) The relationship between $f_c$ OT-1 cells and the intra-tumoral concentration of OT-1$_{tot}$ cells ($p_{tot}$) required to kill 100% of ova-B16 cells in 8 d in melanomas containing $3 \times 10^8$ ova-B16 cells/ml or g tumor in vivo.

Nomograms showing: (A) The relationship between $f_c$ OT-1 cells and the $CT_{tot}C$ for the indicated intra-tumoral concentrations of OT-1tot cells. (B) The relationship between $f_c$ OT-1 cells and the intra-tumoral concentration of OT-$1_{tot}$ cells ($p_{tot}$) required to kill 100% of ova-B16 cells in 8 d in melanomas containing $3 \times 10^8$ ova-B16 cells/ml or g tumor in vivo. All concentrations above and all values for the $f_c$ OT-1 cells to the right of the lines=mice cured of their tumor. All below and to the left of the lines=not cured. See FIG. 31.

Impact of intra-peritoneal (IP) administration of $20 \times 10^6$ OT-1 cells on 8 d-established ova-B16 melanomas. Data from Petersen et al. (2006) as re-calculated by Budhu et al. (2010). Curve in blue=growth of $5 \times 10^5$ ova-B16 cells following their sub-cutaneous injection into C57B16/J mice. Curves in green and dark red show effect of administration of 2% cytolytically active and 5% cytolytically active preparations of OT-1 cells, respectively. Curve in orange=the $CT_{tot}C$ for a preparation containing 5% cytolytically active OT-1 cells. Curve in black=the intra-tumoral OT-$1_{tot}$ cell concentration (i.e., averages $1.5 \times 10^6$ OT-1 cells/g melanoma on d 0-3, and $4 \times 10^6$ OT-1 cells/g melanoma on d 4-7). It shows that a preparation containing 5% cytolytically active OT-1 cells will eradicate all ova-B16 cells in 8 d-established ova-B16 tumors by day 15. This calculation takes into account the changes in $k_{cyto}$ and $k_{tot}$ (i.e., the values of k for the indicated average intra-tumoral concentrations of OT-$1_{tot}$ cells [FIG. 1], and the ~3-fold decrease in $k_{cyto}$ for the decrease in efficiency with which OT-1 cells kill ova-B16 cells in tumors in vivo vs. in collagen-fibrin gels.). See FIG. 32.

Figure 29:
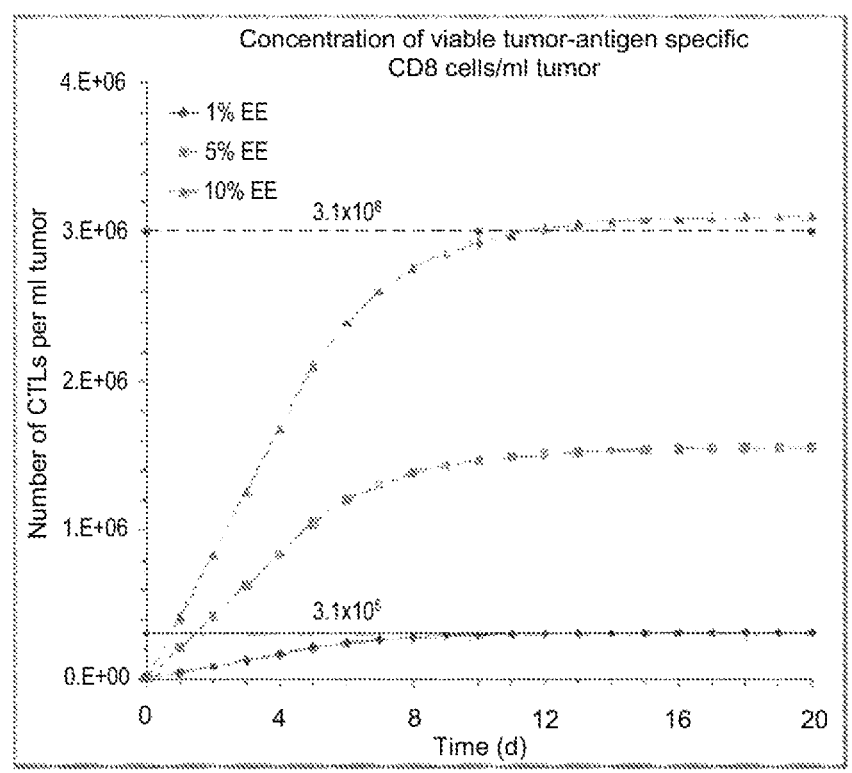
FIG. 29. The concentration of viable tumor-antigen specific CD8 cells/ml tumor.

Implications of these findings for cellular immunotherapy of cancer. The most effective immunization protocols in mice and humans elicit at a maximum $5 \times 10^4$ antigen-specific CD8+T-cells/ml blood. The percentage of these cells that is cytolytically active in vivo is unknown. For purposes of this discussion, we will assume 2% of them are cytolytically active. Tumor blood flow is ~84 ml/gm tumor/day. We estimate ~1% of CD8+ cells in the blood perfusing a tumor emigrate into the tumor parenchyma daily. At this rate, assuming $2.5 \times 10^4$ tumor-antigen specific CD8+ cells/ml blood, a perfusion rate of 84 ml blood/gm tumor/day, a CD8+ lifespan of 5 days, and a CD8+ half-life of 2 days thereafter, the maximum concentration of tumor-antigen specific CD8+ cells that can be expected to accumulate in a tumor bed at steady state will be $3.1 \times 10^5$/ml tumor (FIG. 29). $3.1 \times 10^5$ tumor-antigen-specific CD8+ cells is the COT-1C for $10^4$ SIINFEKLB16 cells/ml collagen/fibrin gel, but only about 60% of the COT-1C for $10^7$-$10^8$ SIINFEKL-B16 cells/ml gel, the average concentration of tumor cells in a tumor. Even if 10% of CD8+ cells emigrated into the tumor bed daily, the maximal CD8+ cell concentration at steady state would be $3.1 \times 10^6$/ml or gm tumor. The lowest concentration of OT-1 cells that produces sterilizing immunity for SIINFEKL-B16 cells in collagen/fibrin gels is $10^7$/ml. Literature searches show that in the small number of instances for which data are available, eradication of established tumors requires $\geq 10^7$ CD8+ cells/ml tumor.

Dudley et al. have now treated 75 melanoma patients with myelo-ablation and subsequent infusion of $\geq 10^{10}$ ex-vivo expanded autologous CD8+ cells. In over 70% of these patients, there has been objective decrease in tumor size. Two patients have experienced long term remissions/cures. These two patients had >$10^6$ of the infused CD8+ cells circulating in their blood for >3 months. Making the same assumptions used to calculate the steady-state concentration of tumor-antigen specific CD8+ cells in FIG. 29, we estimate that a blood concentration of $10^6$ tumor antigen-specific CD8+ cells would yield a steady state concentration of tumor antigen-specific CD8+ cells of $6.2 \times 10^6$/ml tumor. At a 2% extraction efficiency, the steady state intra-tumoral concentration of tumor antigen-specific CD8+ cells would be $1.2 \times 10^7$/ml tumor. As noted above, if these CD8+ cells had cytolytic activity comparable to the OT-1 cells we have used in our collagen-fibrin gel experiments, it would take between 108 and 120 hours (4.5-5 days). to eradicate a melanoma containing 107-108 melanoma cells/ml tumor.

The fibrin/collagen gel studies reported above demonstrate that concentration, not effector to target ratio, governs the cytolytic activity of antigen-specific CD8+ effector cells. The system we have designed to study these activities is simple, and applicable to studying human tumor and immune effector cell. Using it, we have obtained the first quantitative estimate of which we are aware of the concentration of tumor-antigen specific CD8+ cells that must be present in a tumor bed to effect eradication of all tumor cells in that bed. It is $\geq 10^7$ OT-1 cells/ml or per gm tumor. While this estimate is derived from in vitro studies of OT-1 cell killing of SIINFEKL-B16 cells, there are several reasons to believe it closely approximates the concentration required in vivo. First, many investigators, including ourselves, have used Winn assays to assess the number of tumoricidal effector cells required to block engraftment of $10^5$-$10^6$ B16 melanoma cells inoculated into unimmunized, immunocompetent C57Bl/6 mice. In all instances of which we are aware, prevention of tumor engraftment required $5 \times 10^6$-$10^7$ activated macrophages or cytotoxic lymphocytes/~0.5 ml volume inoculation site. This is consistent with our estimate of $\geq 10^7$ effector cells/ml or gm tumor. Second, in virtually every instance in which infused activated OT-1 cells eradicated an established B16 melanoma in immunocompetent C57Bl/6 mice, the intra-tumoral concentration of OT-1 cells exceeded $10^7$ OT-1 cells/ml tumor. In contrast, in situations in which the infused OT-1 cells failed to eradicate the tumor, and their intra-tumoral concentration was measured, it was below this threshold. We can find no comparable data on humans infused with autologous ex-vivo activated and/or expanded effector leukocytes. However, retrospective analyses by many groups of investigators have documented a direct correlation between the number of peri- and intra-tumoral CD3+ and CD8+ cells and a positive prognosis. Nedergaard, et al. reported a cancer recurrence of 62% in patients whose primary lesions had $\leq 10^6$ CD3+ and CD8+ cells/ml peri- and intra-tumoral tissue. In contrast, cancer recurred in only 12% of patients whose primary lesion had $\geq 10^7$ peri- and intra-tumoral CD3+ and CD8+ cells/ml peri- and intratumoral tissue. Similarly, Liakou et al. and Tomsova et al. noted an inverse relationship between the presence of tumor infiltrating lymphocytes and recurrence of bladder and ovarian cancers, respectively. Taken together, these studies support the hypothesis that under the most favorable circumstances, the presence within a tumor of $\geq 10^7$ autologous activated CD8+T-cells, expressing TCRs that recognize antigen(s) expressed on the tumor cells, will result in eradication of all antigen-expressing tumor cells in the tumor bed.

We believe the findings reported here provide new insights into the inconsistent results using cellular immunotherapy to treat solid tumors. The most important of these insights is the requirement for achieving an intra-tumoral concentration of cytolytic effector cells of >$10^7$/ml tumor. This is minimal requirement, not the end of the story. There are surely a very large number of steps that potentially tumoristatic/cidal effector cells must complete to eliminate a clinically recognizable tumor. We list them here under four general categories. 1. Recognition of neo-epitopes on tumor proteins and carbohydrates and generation of tumoristatic/cidal effector cells by the host's immune system. While some tumors appear more "immunogenic" than others, most tumors express antigens recognized by the host's T and B cells. 2. Production of a sufficient number of tumoristatic/cidal effector cells to achieve an intra-tumoral concentration of $\geq 10^7$/ml tumor of them. The immune system limits by unknown means the concentration of CD8+T-cells specific for a given tumor-antigen to about $5 \times 10^4$/ml blood, and only a small percentage of these tumorantigen specific cells are cytolytic (e.g., 2% of activated OT-1 cells are cytolytic [FIG. 28]. 3. These cells must emigrate from blood into the tumor. However, the tumor vasculature limits their entry into the tumor bed. 4. Ideally, the intra-tumoral environment would support the viability, growth, and effector activities of tumoristatic/cidal leukocytes. However, there is ample evidence that it generally lacks T cell survival signals, and contains many soluble suppressor substances (e.g., IL-10, TGFβ, ILT3, and regulatory cells whose receptors inhibit tumoristatic/cidal activities of effector leukocytes e.g., B7-H1, PD-1, CTLA-4, ILT3).

The central organizing principle of the research proposed here is that effector cell concentration is the critical determinant of the outcome of many immune effector functions. Simply put, absent a sufficient concentration of cells, the immune system cannot fulfill its mission. Evolution learned this lesson a long time ago. It is one of the aspects of the immune system that is clearly hard wired. By exploring the ways cell concentration affects neutrophils and CD8+ cells we have uncovered some fundamental principles, the most important of which is the critical concentration. One of the values of this approach is that it leads one to seek quantitative answers to problems in immunology and physiology. Surprisingly, many of the quantities we seek have not been measured. We first uncovered the critical concentration concept while working on neutrophils. We have now extended it to effector functions of cytotoxic lymphocytes.

Dendritic cell activation during CD8+T-cell activation and expansion in vivo and in vitro increases the fraction of antigen-specific OT-$1_{cyto}$ cells. Bonifaz et al. (2002) demonstrated that OT-1 mice immunized with α-DEC205-IgG-ova in combination with α-CD40-IgG kill ova-B16 cells more efficiently than OT-1 mice immunized with α-DEC205-IgG-ova alone. These findings suggested that α-CD40-IgG activation of dendritic cells might increase the fraction of cytolytically active ($f_c$) OT-1 cells in the elicited population and thereby affect the efficiency with which these cells kill SIINFEKL-B16 cells. Accordingly, we immunized OT-1 mice with α-DEC205-IgG-ova alone or in combination with α-CD40-IgG and compared the number of OT-1 spleen cells elicited by the two immunization protocols by FACS analysis of tetramer+stained cells, and the fraction of these tetramer+OT-1 cells that were cytolytically active by limiting dilution assays (Budhu et al. 2011A). Consistent with Bonifaz et al.'s (2002) report, the spleens of OT-1 mice immunized with both α-DEC205-IgG-ova and α-CD40-IgG contained ~2-fold more tetramer+OT-1 cells than spleens of OT-1 mice immunized with α-DEC205 IgG-ova alone (Table 22, Lines 2 & 3). Limiting dilution assays using 50 and 100 tetramer+OT-1 cells/well showed ~0.86% of tetramer+OT-1 cells from spleens of unimmunized OT-1 mice, 1.9% of tetramer+OT-1 cells from spleens of OT-1 mice immunized with α-DEC205-IgG-ova alone, and 2.4% of tetramer+OT-1 cells from spleens of mice immunized with α-DEC205-IgG-ova and α-CD40-IgG were cytolytically active (Table 22, Lines 1-3).

In parallel assays using the same preparations of OT-1 spleen cells, we co-incubated a quantity of these cells sufficient to yield $5 \times 10^6$ MHC-I H2-$K^b$-SIINFEKL tetramer+OT-1 cells/ml collagen-fibrin gel (Table 22, Lines 1-3) with $10^6$ SIINFEKL-B16 cells/ml collagen-fibrin gel at 37° C. for 24 h and measured the number of B16 cells remaining viable in these gels by clonogenic assay. Four million two hundred thousand spleen cells containing $5 \times 10^5$ tetramer+OT-1 cells from un-immunized OT-1 mice killed 21% of SIINFEKL-B16 cells in collagen-fibrin gels/24 h. Immunization increased killing such that approximately the same number of spleen cells containing $5 \times 10^5$ tetramer+ OT-1 cells from α-DEC205-IgG-ova-immunized OT-1 mice, and $3.1 \times 10^6$ spleen cells containing $5 \times 10^5$ tetramer+ OT-1 cells from α-DEC205-IgG-ova- and α-CD40-IgG-immunized OT-1 mice killed 44% and 74% of SIINFEKL-B16 cells, respectively, in collagen-fibrin gels in 24 h (Table 22, Lines 1-3). (Note that the volume of collagen-fibrin gels is 0.1 ml so the concentration of $5 \times 10^5$ OT-1 cells in these gels is $5 \times 10^6$/ml.)

We also analyzed the relationships between the $f_c$ OT-1 cells in these OT-1 cell preparations and their ability to kill SIINFEKL-B16 cells in collagen-fibrin gels. Immunization with α-DEC205-IgG-ova alone stimulated an 18% increase in the total number of tetramer+OT-1 (OT-$1_{tot}$) cells produced/OT-1 mouse spleen ($1.3 \times 10^7 \div 1.1 \times 10^7$ cells), a 261% increase in the total number of cytolytically active tetramer+ OT-1 cells produced/spleen ($1.3 \times 10^7$ OT-$1_{tot}$ cells × 0.019=$2.47 \times 10^5$ OT-$1_{cyto}$ cells/spleen of α-DEC205-IgG-ova immunized mice÷$1.1 \times 10^7$ OT-$1_{tot}$ cells × 0.0086=$9.46 \times 10^4$ OT-$1_{cyto}$ cells/spleen of unimmunized OT-1 mice); and a 221% increase in the number of cytolytically active OT-1 cells/$5 \times 10^5$ tetramer+OT-1 cells (Table 22, Lines 1 & 2 & Supplementary text SI-1A). Yet the specific cytolytic activity (SCA) of the OT-$1_{cyto}$ cells from α-DEC205-IgG-ova-immunized mice was almost the same (0.366 vs. 0.355 SIINFEKL-B16 cells killed/OT-$1_{cyto}$ cell/24 h respectively for OT-1 cells from un-immunized vs. α-DEC205-IgG-ova immunized mice) as the SCA of OT-$1_{cyto}$ cells from α-DEC205-IgG-ova-immunized mice (0.355 SIINFEKL-B16 cells killed/OT-$1_{cyto}$ cell/d vs. 0.366 SIINFEKL-B16 cells killed/OT-$1_{cyto}$ cell/d from unimmunized mice (Table 22, Lines 1 & 2 & Supplementary Text SI-1B). The total increase in the percentage of SIINFEKL-B16 cells killed following co-incubation with $5 \times 10^6$ 1.9% tetramer+OT-$1_{cyto}$ cells/ml collagen-fibrin gel/d vs. with $5 \times 10^6$ 0.86% tetramer+OT-$1_{cyto}$ cells/ml collagen-fibrin gel/d was 209% (44%/21% SIINFEKL-B16 cells killed [Table 22, Lines 1 & 2 & Supplementary Text SI-1]). This is in excellent agreement with the 215% increase predicted by the product of the increase in number of OT-$1_{cyto}$ cells/$5 \times 10^6$ OT-1 cells$_{tot}$/ml gel (220%)×the very small decline in their SCA (97%) (220%×97%=214% [Supplementary text SI-1C]). Thus, immunization with antigen alone (α-DEC205-IgG-ova), increased the number of cytolytically active antigen-specific CD8+T-cells but had an insignificant effect on their SCA.

In contrast, immunization with α-DEC205-IgG-ova plus α-CD40-IgG produced a 160% increase in the number of tetramer+OT-$1_{tot}$ cells/spleen over the number of tetramer+ OT-$1_{tot}$ cells in spleens of OT-1 mice immunized with α-DEC205-IgG-ova alone ($2.1 \times 10^7 \div 1.3 \times 10^7$ tetramer+ OT-1 cells/spleen [Table 22, Lines 2 & 3]). This is a 126% increase in the number of cytolytically active OT-1 cells/$5 \times 10^5$ tetramer+CD8+T-cells from spleens of mice immunized with α-DEC205-IgGova and α-CD40-IgG vs. with α-DEC205-IgG-ova alone ($1.2 \times 10^4$ OT-$1_{cyto}$ cells/$5 \times 10^5 \div 9.5 \times 10^4$ OT-$1_{cyto}$ cells/$5 \times 10^5$)(Table 22, Lines 2 & 3 and Supplementary Text SI-2A); and a 133% increase in the SCA of cytolytically active OT-1 cells from mice immunized with α-DEC205-IgG-ova and α-CD40-IgG vs. with α-DEC205-IgG-ova alone (0.47/0.35). The total increase in the percentage of SIINFEKL-B16 cells killed following co-incubation with $5 \times 10^6$ of 2.4% tetramer+OT-$1_{cyto}$ cells/ ml collagen-fibrin gel/d vs. with $5 \times 10^6$ of 1.9% tetramer+ OT-$1_{cyto}$ cells/ml collagen-fibrin gel/d was ~168% (44%/ 21% SIINFEKL-B16 cells killed [Table 22, Lines 2 & 3 & Supplementary Text SI-2]). This is in excellent agreement with the 167.5% increase predicted by the product of the increase in number of OT-$1_{cyto}$ cells/$5 \times 10^6$ OT-1 cells$_{tot}$/ml gel (126%), and the 133% increase in their SCA [Supplementary text SI-2C]). Thus immunization with antigen (α-DEC205-IgG-ova) in combination with an antigen-independent inflammatory stimulus (i.e., α-CD40-IgG, an adjuvant) increased both the total number of OT-$1_{cyto}$ cells and their SCA.

Overall, immunization with α-DEC205-IgG-ova plus α-CD40-IgG increased the total number and $f_c$ OT-1 cells, and their SCA over that observed for OT-1 spleen cells from un-immunized mice. Specifically, we observed a 190% ($2.1 \times 10^7$ vs. $1.1 \times 10^7$ [Table 22, Lines 3 vs. 1) increase in the number of tetramer+OT-$1_{tot}$ cells/mouse spleen, a 279% ($1.2 \times 10^4$ OT-$1_{cyto}$ cells/$5 \times 10^5 \div 4.3 \times 10^3$ OT-$1_{cyto}$ cells/$5 \times 10^5$ tetramer+OT-$1_{tot}$ spleen cells [Table 22, Lines 3 vs. 1]); and a 129% (0.472 SIINFEKL-B16 cells killed/OT-$1_{cyto}$ cell/ d÷0.366 SIINFEKL-B16 cells killed/OT-1$_{cyto}$ cell/d) (Table 22, Lines 3 vs. 1 & Supplementary text SI-3A &B) in the SCA of these cells. Again, the product of the percent increase in number of OT-1$_{cyto}$ cells/5×10$^5$ tetramer+CD8+ from spleens of mice immunized with α-DEC205-IgG-ova and α-CD40-IgG and the percent increase in these cells' SCA was 359% (279%×129%) greater than comparable percentages for OT-1$_{cyto}$ cells from spleens of un-immunized mice. Again, this is in excellent agreement with the observed 352% increase in killing of SIINFEKL-B16 cells following their co-incubation with 5×10$^6$ 2.4% OT-1$_{cyto}$ spleen cells from α-DEC205-IgG-ova plus α-CD40-IgG immunized mice/ml collagen-fibrin gel/d vs. the same number of 0.86% OT-1$_{cyto}$ spleen cells from un-immunized mice/ml collagen-fibrin gel/d (Table 22, Lines 3 vs. 1 & Supplementary text SI-3).

These findings show that while antigen alone stimulates an increase in the number of antigen-specific CD8+T-cells, antigen plus adjuvant stimulates an increase in both the number and the quality (SCA) of these cells. They show that the magnitude of the adjuvant effect is the product of the percentage change in the number of cytolytically active antigen-specific CD8+T-cells produced and the percentage change in their SCA (Δ% in target cells killed=Δ in the fraction of cytolytically active antigen-specific CD8+T-cells/standard number [e.g., 10$^6$/ml] of antigen-specific CD8+T-cells/ml×fractional Δ in the SCA of these antigen-specific CD8+T-cells×100%). Accordingly, they reinforce our conclusion (Budhu et al. 2011A) that the $f_c$ antigen-specific CD8+T-cells accounts for all of the cytocidal activity of all of the antigen-specific CD8+T-cells in a population.

Supplementary Text for Table 22.

SI-1. Experimentally observed increase in killing of SIINFEKL-B16 cells in collagen-fibrin gels/d by 5×10$^6$ 1.9% cytolytically active OT-1 cells/ml collagen fibrin gel vs. by 5×10$^6$ 0.86% cytolytically active OT-1 cells/ml collagen-fibrin gels=44% (Table 22, Line 2)/21% (Table 22, Line 1)=209%

SI-1A. Ratio of No. of 1.9% cytolytically active OT-1 cells/5×10$^5$ tetramer+CD8+T-cells÷ No. of 0.86% cytolytically active OT-1 cells/5×10$^5$ tetramer+OT-1 cells=0.019×5×10$^5$/0.0086×5×10$^5$=221%.

SI-1 B. Ratio of Specific Cytolytic Activities of 1.9% vs. 0.86% OT-1 cells=0.355/0.366=97%.

SI-1C. Total increase in killing of SIINFEKL-B16 cells in collagen-fibrin gels/d due to increase in number of cytolytically active OT-1 cells (SI-1A)×increase in their SCA (SI-1B)=2.21×0.97=214%.

SI-2. Experimentally observed increase in killing of SIINFEKL-B16 cells in collagen-fibrin gels/d by 5×10$^6$ 2.4% cytolytically active OT-1 cells/ml collagen fibrin gel vs. by 5×10$^6$ 1.9% cytolytically active OT-1 cells/ml collagen-fibrin gels=74% (Table 22, Line 3)/44% (Table 22, Line 2)=168%.

SI-2A. Ratio of No. of 2.4% cytolytically active OT-1 cells/5×10$^5$ tetramer+CD8+T-cells÷No. of 1.9% cytolytically active OT-1 cells/5×10$^5$ tetramer+OT-1 cells=0.024×5×10$^5$÷0.019×5×10$^5$=126%.

SI-2B. Ratio of Specific Cytolytic Activities of 2.4% vs. 1.9% OT-1 cells=0.47/0.35=133%.

SI-2C. Total increase in killing of SIINFEKL-B16 cells in collagen-fibrin gels/d due to increase in number of cytolytically active OT-1 cells (SI-2A)×increase in their SCA (SI-2B)=126%×133%=167.5%.

SI-3. Experimentally observed increase in killing of SIINFEKL-B16 cells in collagen-fibrin gels/d by 5×10$^6$ 2.4% cytolytically active OT-1 cells/ml collagen fibrin gel vs. by 5×10$^6$ 0.86% cytolytically active OT-1 cells/ml collagen-fibrin gels=74% (Table 22, Line 3)/21% (Table 22, Line 1)=352%.

SI-3A. Ratio of No. of 2.4% cytolytically active OT-1 cells/5×10$^5$ tetramer+CD8+T-cells÷No. of 0.86% cytolytically active OT-1 cells/5×10$^5$ tetramer+OT-1 cells=0.024×5×10$^5$÷0.0086×5×10$^5$=279%.

SI-3B. Ratio of Specific Cytolytic Activities of 2.4% vs. 0.86% OT-1 cells=0.47/0.36=129%.

SI-3C. Total increase in killing of SIINFEKL-B16 cells in collagen-fibrin gels/d due to increase in number of cytolytically active OT-1 cells (SI-3A)×increase in their SCA (SI-3B)=279%×129%=359%.

Methods. In Vivo Immunization with α-DEC205-OVA-IgG and α-CD40 IgG. OT-1 (C57BL/6) mice (2 per condition) were immunized subcutaneously in the footpad with 100 μg of anti-DEC205-IgG conjugated to ovalbumin (α-DEC205-IgG-ova) without or with 100 μg of anti-CD40-IgG (α-CD40-IgG) as described (Bonifaz et al., 2002). Six d after the last immunization the mice were sacrificed, and their splenocytes were harvested. Red blood cells were lysed using ACK buffer (0.15M NH4Cl, 1 mM KHCO3, 0.1 mM EDTA). The number of splenocytes per spleen was enumerated and an aliquot from each saline control–, α-DEC-205-IgGova–, and α-DEC-205-IgG-ova+α-CD40-IgG-immunized mouse was assayed by FACS for its content of cells that bound MHC-IKb-SIINFEKL-PE tetramers, anti-CD3, and/or anti-CD8 antibodies. In vitro activation of OT-1 cells with SIINFEKL peptide and α-CD40-IgG was performed as described in Results.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Materials. Human fibrinogen was obtained from American Diagnostica Inc., collagen I, cell culture inserts and tissue culture plates from BD, SIINFEKL peptide (OVA 257-264) from American Peptide Company, CFSE from Invitrogen, and recombinant mouse IL-2 from Millipore. All other reagents were purchased from Sigma-Aldrich. All experiments using mice were Institutional Review Board approved by Columbia University.

Cells. B16 melanoma cells (vol.=2,757 μm3 assuming spherical diameter=17.4 μm [Ochalek, et al., 1988]; H2-Kb [Hu and Lesney, 1964]), were maintained as monolayer cultures in RPMI 1640 medium supplemented with 10% FBS and 50 μM β-ME (OT-1 growth medium) at 37° C. in a 95% air/5% CO2 humidified atmosphere, detached by incubation at 37° C. for 5 min in PBS containing 5 mM EDTA, pelleted by centrifugation (400 g for 10 min), and resuspended at 10$^6$ cells/ml in OT-1 growth medium. Where indicated, B16 cells were incubated in suspension at 10$^6$ cells/ml in RPMI medium containing 1 μM SIINFEKL peptide (ovalbumin residues 257-264) for 2 h at 37° C., washed three times in PBS, and resuspended in OT-1 growth medium. B16 spheroids were sedimented at 1 g through a cushion of FBS to separate them from single B16 cells. The purified spheroids were pulsed with 1 µM SIINFEKL for 2 h and a measured aliquot of this preparation was disaggregated by trituration in EDTA/0.05% trypsin buffer, releasing >95% of cells from the spheroids. The number of released B16 cells was assessed by counting cells in a hemocytometer.

OT-1 CD8+T cells, harvested from spleens of C57BL/6 mice, express a transgene encoding a TCR that specifically recognizes SIINFEKL peptide bound to MHC-I H-2 kb (Hogquist et al., 1994). Activated OT-1 T cells were generated by incubation of $5 \times 10^6$/ml OT-1 SIINFEKL-pulsed mouse splenocytes in vitro for 5-7 d in the presence of IL-2 (Moore et al., 1988; Curtsinger et al., 1998). In brief, an OT-1 mouse spleen was homogenized, the released cells were pelleted and resuspended in 5 ml ACK buffer (0.15 M $NH_4Cl$, 1 mM $KHCO_3$, and 0.1 mM EDTA) for 1 min to lyse red blood cells, and the splenocytes were pelleted, washed, resuspended at $5 \times 10^6$ cells/ml in OT-1 growth medium containing 0.75 µg/ml SIINFEKL peptide, and incubated at 37° C. in a 95% air/5% $CO_2$ humidified atmosphere. On days 3 and 5, 25 ml of fresh OT-1 growth medium containing 10 U/ml of mouse recombinant IL-2 was added to the cultures. On day 7, the cells were harvested and OT-1 cells were purified by centrifugation at 400 g for 30 min at room temperature over a Histopaque gradient (density=1.083). Cells isolate d by this method were incubated with PE-labeled anti-CD8 or FITC-labeled anti-Vβ5 monoclonal antibodies, washed, and assayed by FACS (BD). Over 90% were CD8+ and Vβ5+.

Formation of collagen-I-fibrin gels containing B16 and OT-1 cells. Each well of a 48-well tissue culture plate was filled sequentially with 5 µl PBS containing 0.1 U thrombin, 100 µl PBS containing 1 mg/ml of human fibrinogen, 1 mg/ml of rat tail collagen I, 10% FBS, and $10^3$-$2 \times 10^6$ SIINFEKL peptide-pulsed B16 cells (SIINFEKL-B16 cells), with or without $10^3$-$10^6$ OT-1 cells. The plates were incubated for 15 min at 37° C. in a 95% air/5% $CO_2$ humidified atmosphere to allow the fibrin to gel. In some early experiments, 10 µl of 10 7 M d-phenylalanyl-1-propyl-1-arginine chloromethyl ketone (PPACK) was added to the top of each gel to inhibit thrombin and the plates were incubated at 37° C. for another 15 min to allow the collagen to gel. (Subsequent experiments indicated that this PPACK step was unnecessary and it was omitted.) Gels were overlaid with 0.5 ml OT-1 growth medium and incubated at 37° C. in a 95% air/5% $CO_2$ humidified atmosphere. These gels are 0.1 ml in volume and 1,500 µm in height. In preliminary experiments, we found that B16 cells incubated in gels composed of fibrin alone dissolved these gels in 3-4 d. Addition of collagen I maintained gel integrity for 7-10 d.

Clonogenic assay for B16 cells. SIINFEKL-B16 cells, with or without OT-1 cells, were incubated at 37° C. in collagen-fibrin gels in wells in a 48-well plate. At indicated times, medium overlying each gel was removed and gels were dissolved by overlaying each gel with 100 µl PBS containing 2.5 mg/ml collagenase type 1A for 20 min at 37° C., followed by further addition of 100 µl PBS containing 2.5 mg/ml trypsin for another 20 min at 37° C. The resulting solution containing cells and dissolved gel components was diluted 10-1,000-fold (depending on the initial B16 cell concentration in the gel) in OT-1 growth medium and 100-µl aliquots of the final dilution were plated in each of two 60×15-mm tissue culture dishes containing 2 ml OT-1 growth medium. The dishes were incubated at 37° C. for 7 d in a 95% air/5% $CO_2$ humidified atmosphere to allow B16 cells to form macroscopic colonies, washed with PBS, treated with 2 ml of 3.7% formaldehyde in PBS for 15 min to fix the B16 cells, washed again with PBS, incubated for 2 h in 2 ml of 4% wt/vol methylene blue in $H_2O$ at room temperature, washed with distilled water to remove excess methylene blue, dried, and the bluestained colonies counted manually as previously described (Freedman et al., 1984). Control experiments showed that B16 cells had a plating efficiency of ~60% regardless of whether they were released from plastic tissue culture plates with EDTA or from collagen-fibrin gels with collagenase and trypsin and/or plated in β-ME-containing medium. Thus, the number of B16 cells reported as placed into fibrin-collagen I gels is ~1.66-fold the number of cells recovered from them.

Cell sizes and volumes. Activated OT-1 cells are ~7 µm in diameter as measured by phase-contrast microcopy of unfixed cells. Packed cell volumes of B16 cells, activated OT-1 cells, and naive splenocytes from wild-type C57BL/6 spleen were determined by centrifuging 104 B16 cells, $10^4$ OT-1 cells, or 104 splenocytes in 20 µl OT-1 medium for 2 min at 200 g in 25-µl glass micropipettes (sealed at one end). The volumes of each cell type, calculated by dividing the packed cell volume by the number of cells in the pipette, were $2.5 \times 10^{-3}$ nl/B16 cell ($4 \times 10^8$ B16 cells/ml), $1.7 \times 10^{-4}$ nl/activated OT-1 cell ($5.9 \times 10^9$ OT-1 cells/ml), and $\sim 2.2 \times 10^{-4}$ nl/splenocytes ($4.5 \times 10^9$ splenocytes/ml).

Packed cell pellet-type assays. Wells of a 96-well round-bottom tissue culture plate were each filled with 0.2 ml OT-1 medium containing $10^4$ B16 cells, pulsed previously with $10^{-8}$ M SIINKFEKL peptide, and the number of activated OT-1 cells required to produce the ratios of OT-1/B16 cells indicated in the figures. The plate was centrifuged at 1,000 rpm (~200 g) for 5 min to pellet cells and then incubated at 37° C. in a humidified incubator for 4 h. The medium was removed and the pellet was disaggregated by incubation in 0.1 ml of PBS containing 5 mM EDTA for 5 min at 37° C. The solution was diluted 100-fold in OT-1 growth medium and 0.1-ml aliquots of the final dilution were plated for colony formation as described in Clonogenic assay for B16. In some experiments, naive splenocytes (filler cells) from wild-type C57BL/6 mice were added to vary the ratio of OT-1 to B16 cells while keeping total cell volume constant.

CFSE labeling of OT-1 cells. $10^6$-$10^7$ OT-1 cells were incubated in 1 ml PBS containing 0.1% glucose, 0.1% BSA (PBS-G-BSA), and 10 µM CFSE at 37° C. for 15 min, washed three times with 1 ml OT-1 medium, resuspended at a concentration of $10^6$ cells/ml in OT-1 medium, and co-embedded in collagen-fibrin gels with B16 cells at the indicated concentrations. Gels were overlaid with 1 ml OT-1 medium±100 U/ml IL-2 and incubated at 37° C. in a 95% air/5% $CO_2$ humidified atmosphere. 24, 48, and 72 h later, the gels were digested with collagenase and trypsin and the released cells were washed with PBS-G-BSA and divided into two aliquots. The cells in the first aliquot were incubated with 1.5 µM propidium iodide in PBS-G-BSA for 10 min, washed with PBS-G-BSA, and the number and fluorescence of viable CFSElabeled OT-1 cells was assessed with a FACSCalibur (BD). The second aliquot was assayed as described in Clonogenic assay for B16.

Frozen sections. Collagen-fibrin gels containing SIINFEKL-B16 cells were formed, as described in Formation of collagen-I-fibrin gels, in 8-µm pore cell culture inserts seated in wells containing 1 ml OT-1 medium in 24-well tissue culture plates (BD) and overlaid with 0.5 ml OT-1 medium, and they were incubated at 37° C. in a 95% air/5% $CO_2$ atmosphere. 24, 72 and 120 h after forming the gels, the medium overlying the gels was removed and the inserts were placed in wells containing PBS at room temperature for 15 min to wash away serum proteins, fixed with 10% neutral buffered formalin for 1 h at room temperature, washed with PBS, overlaid with 0.5 ml of 5% gelatin in PBS at 37° C., and incubated at this temperature for 20 min to allow the gelatin solution to permeate the collagen-fibrin gels. The inserts then were placed at 4° C. for 30 min to allow gelatin to gel. Gelatin impregnated gels were mechanically released from inserts using a scalpel, bisected vertically, and incubated in 30% sucrose overnight at 4° C. Each half gel was placed in a cryomold and the cryomold was filled with OCT embedding medium and placed in a bath of 2-methylbutane and dry ice. 10-µm-thick frozen sections were cut parallel to the vertically bisected face of the gels, and the sections were stained with hematoxylin/eosin and placed on glass slides for light microscopy.

Calculations. The value of k (the experimentally determined target cell killing constant) was calculated as previously described (Li et al., 2004) using Eq. 1 ($bt/b0=e-kpt+gt$). bt=experimentally determined target cell concentration per milliliter of gel or tumor at time t (in minutes) of co-incubation of antigen-expressing target cells with antigen-specific CD8+ T cells in collagen-fibrin gels or inoculation of mice with antigen-specific CD8+ T cells. b0=initial target cell concentration per ml gel or tumor. The CD8+ CTC was calculated using Eq. 2 (Li et al., 2004; CTC=g/k). g=the experimentally determined rate of B16 cell growth in vitro or in vivo or of increase in polyoma virus-infected target cells, calculated using the relationship ln $bt/b0=g \times t$ (min). We estimated mouse spleen volume and wet weight for LCMV infected mice to be 0.15 ml and 0.15 g, respectively, and 0.1 ml and 0.1 g, respectively, for polyoma virus-infected mice. B16 melanoma tumors contain $3 \times 10^8$ B16 cells/ml or /g of tumor (Stephens and Peacock, 1978).

Statistics. Unless otherwise indicated, all experiments were performed at least three times in duplicate. Data are reported as the mean±SEM for the number of experiments indicated.

FIG. 9 shows the OT-1 SIINFEKL peptide concentration required for optimal killing of B16 cells in collagen-fibrin gels. FIG. 10 shows the killing of SIINFEKL-B16 cells in spheroids versus single SIINFEKL-B16 cells by OT-1 cells. FIG. 11 shows that CMA inhibits OT-1 cell killing of SIINFEKL-B16 cells. Table 1 shows that activated OT-1 cells kill growing and nongrowing SIINFEKL-pulsed B16 cells with approximately equal efficiency. Table 2 shows that the addition of naïve spleen cells had no effect on killing efficiency of OT-1 cells in collagen-fibrin gels. Table 3 shows that OT-1 cell concentration determines the efficiency of killing of SIINFEKL-B16 cells in packed-cell-pellet type assays. Table 4 shows OT-1 cell killing of ova-B16 cells in 8-d-old tumors in vivo. Table 5 shows polyoma virus antigen-specific CD8+T cell killing of polyoma virus-infected splenocytes in mouse spleen in vivo. See also FIGS. 9 to 11 and Tables 1 to 5.

Example 2

Materials: 72-well Terasaki plates (NUNC brand) from VWR International (West Chester, Pa.); fetal bovine serum and RPMI 1640 medium were from Invitrogen Corp. (Carlsbad, Calif.); and recombinant mouse IL-21 from Chemicon (Temecula, Calif.). All other materials were obtained as described (Budhu et al., 2010).

Cells: B16 melanoma cells (H2-$K^b$) (Hu and Lesney, 1964), were maintained, harvested and pulsed with SIIN-FEKL peptide, and OT-1 CD8+T-cells were harvested, activated, purified, and used exactly as described (Budhu et al., 2010). For experiments described in FIGS. 5 and 6 only, one set of OT-1 cells was activated in Dulbecco's Minimal Essential Medium with 1 mM sodium pyruvate and non-essential amino acids. Limiting dilution assays showed 2.56% of OT-1 cells activated in this medium were cytolytically active.

Formation of collagen-I-fibrin gels containing B16 and OT-1 cells. Collagen/fibrin gels were formed, incubated, and lysed, and their contents of B16 cells assayed exactly as described (Budhu et al., 2010).

In vivo immunization with α-DEC205-OVA-IgG and α-CD40 IgG. OT-1 (C57BL/6) mice (2 per condition) were immunized subcutaneously in the footpad with 100 µg of anti-DEC205-IgG conjugated to ovalbumin (α-DEC205-IgG-ova) without or with 100 µg of anti-CD40-IgG (α-CD40-IgG) as described (Bonifaz et al., 2002). Six d after the last immunization the mice were sacrificed, and their splenocytes were harvested. Red blood cells were lysed using ACK buffer (0.15M $NH_4Cl$, 1 mM $KHCO_3$, 0.1 mM EDTA). The number of splenocytes per spleen was enumerated and an aliquot from each saline control-, α-DEC-205-IgG-ova-, and α-DEC-205-IgG-ova+α-CD40-IgG-immunized mouse was assayed by FACS for its content of cells that bound MHC-I$K^b$-SIINFEKL-PE tetramers, anti-CD3, and/or anti-CD8 antibodies. In vitro activation of OT-1 cells with SIINFEKL peptide and α-CD40-IgG was performed as described in Results.

Calculation of k and the critical T cell concentration (CTC). The value of k (the experimentally determined target cell killing constant) was calculated as described (Li et al., 2004) using Eq. 1 ($b_t=b_0 e^{-kpt \, gt}$), $b_t$=experimentally determined SIINFEKL-B16 or ova-B16 cell concentration/ml collagen-fibrin gel or per g tumor, $b_0$=experimentally determined initial concentration of SIINFEKL-B16 or ova-B16 cells per ml gel or per g tumor, and p=experimentally determined concentration of OT-1 cells. g=the experimentally determined rate of B16 cell growth per unit t (min) was calculated as ln $b_t/b_0$ divided by t (min). The Critical OT-1 cell Concentration (CTC) was calculated using Eq. 2 (Li et al., 2004) (CTC=g/k). The fraction of cytolytically active OT-1 cells ($f_c$) was determined as described below and in Results. The Critical Concentration of cytolytically active OT-1 cells ($CT_{cytolytic}C$), was calculated by substituting the product of $p_{total}$ (the concentration of tetramer+OT-1 cells/ml)$\times f_c=p_{cytolytic}$ for $p_{total}$ in Eq. 1, or the value of $k_{cytolytic}$ for $k_{total}$ in Eq. 2.

Limiting dilution assays. We determined the fraction of MHC-I$K^b$-SIINFEKL-PE tetramer+OT-1 cells in each preparation by FACS, and used this fraction as an indicator of the number of OT-1 cells contained in each preparation. To determine the fraction of cytolytically active OT-1 cells in each preparation we added 20 µl of OT-1 medium containing ~100 unpulsed or SIINFEKL peptide-pulsed B16 cells without or with a sufficient number of in vitro or in vivo activated OT-1 spleen cells to yield ~25, ~50, or ~100 tetramer+OT-1 cells in each replicate well of a 72-well Terasaki plate. The plates were incubated at 37° C. in a 95% air/5% $CO_2$ atmosphere in a humidified chamber for 24 h. Each well then was washed with 20 µl PBS. B16 cells were detached with 20 µl of PBS containing 5 mM EDTA, and the number of viable B16 cells in each well measured by clonogenic assay (Budhu et al., 2010). To determine the average number of viable B16 cells in wells without OT-1 cells, in each experiment we prepared plates with ~100 un-pulsed or SIINFEKL peptide-pulsed B16 cells in each well, incubated the plates at 37° C. for 24 h and measured the number of B16 cells in each well by clonogenic assay. We used these data to determine the fraction of wells per experimental condition that showed no B16 killing, and the Poisson distribution to calculate the fraction of cytolytically active OT-1 cells in each OT-1 cell preparation. We used Lindfors test to determine that the number of B16 cells recovered from wells containing OT-1 cells plus un-pulsed B16 cells fit a one-Gaussian distribution, and the number of B16 cells recovered from wells containing SIINFEKL-B16 cells and ~25, 50, or 100 OT-1 cells fit a two Gaussian distribution. Bootstrap analyses (i.e., repeating the analysis 100 times by re-sampling the data and using it to re-calculate the two Gaussians) showed the differences between these two Gaussian distributions were significant at p<0.05.

2. Relationships between $k_{total}$ and $k_{cytolytic}$ and OT-$1_{total}$ and OT-$1_{cytolytic}$ cell concentrations for OT-1 cells killing SIINFEKL-B16 cells in collagen-fibrin gels. The findings that the concentration of cytolytically active antigen-specific CD8+T-cells in a population ($p_{cytolytic}$)=the product of the $f_c$ antigen-specific CD8+T-cells in that population×$p_{total}$ (the concentration of all antigen-specific CD8+T-cells in the population, the critical antigen-specific CD8+T-cell concentration of all antigen-specific CD8+T-cells in a population ($CT_{total}C$)=the growth rate of the cognate antigen-expressing target cells (g) divided by $k_{total}$, and the critical antigen-specific CD8+T-cell concentration for the $f_c$ antigen-specific CD8+T-cells in the population ($CT_{cyto}C$)=g/$k_{cyto}$ enabled us to calculate $k_{total}$, $k_{cytolytic}$, $CT_{total}C$, and $CT_{cytolytic}C$ for all concentrations of OT-$1_{total}$ cells killing SIINFEKL-B16 cells in collagen-fibrin gels (Budhu et al. 2011). By substituting the experimentally determined values for $k_{total}$, $k_{cytolytic}$, and g into Eq. 2 (Budhu et al. 2011), we have calculated $CT_{total}C$ and $CT_{cytolytic}C$ for populations of OT-1 cells, 2% of which are cytolytically active, killing SIINFEKL-B16 cells in collagen-fibrin gels. As expected from the data in FIG. 20, the concentrations of OT-$1_{tot}$ and OT-$1_{cyto}$ cells required to control growth of SIINFEKL-B16 cells in collagen-fibrin gels ($CT_{tot}C$ and $CT_{cyto}C$) increased by 0.7 log 10 for every ten-fold increase in OT-1 cell concentration.

Example 3

Only 0.86% of MHC-Ik$^b$-SIINFEKL tetramer positive CD8+OT-1 T-cells from unimmunized OT-1 mouse spleen kill SIINFEKL peptide-pulsed B16 cells. Immunization of OT-1 mice with anti-DEC205-IgG-ovalbumin increased the percentage of cytolytically active tetramer positive OT-1 spleen cells to 1.9%, but had no effect on their specific cytolytic activity (number of SIINFEKL-B16 cells killed/ cytolytically active OT-1 cell/d). In contrast, immunization with anti-DEC205-IgG plus anti-CD40-IgG increased the percentage of cytolytically active OT-1 cells to 2.4%, and their specific cytolytic activity by 133%. We observed similar increases in the fraction, specific cytolytic activity, and killing efficiency (as measured by a previously described killing constant k), of SIINFEKL-B16 cells by OT-1 cells following their activation in vitro in medium containing SIINFEKL and IL-12 or IL-21 vs. in medium containing SIINFEKL and IL-2. The efficiency with which in vitro activated OT-1 cells kill SIINFEKL-B16 cells rises exponentially as the percentage of cytolytically active OT-1 cells increases from 0.86% to 2.6% and log-linearly thereafter. We calculate that while administration of 20×10$^6$ 2% cytolytically active OT-1 cells to mice bearing 8 d-established ovalbumin-expressing B16 melanomas will not eradicate these melanomas, administration of 20×10$^6$ 5% cytolytically active OT-1 cells will do so in 8 d.

Budhu et al. (2011A) reported that only 2% of in vitro activated ovalbumin-specific OT-1 cells are cytolytically active. Recognizing that this low percentage of cytolytically active OT-1 cells (OT-$1_{cyto}$) may be a barrier to success of cellular immunotherapy, we sought conditions to increase the percentage of MHC-Ik$^b$-SIINFEKL-peptide-tetramer-binding (tetramer+) OT-$1_{cyto}$ cells by immunization of OT-1 mice, or by in vitro activation of CD8+T-cells from spleens of these mice. We report that immunization of OT-1 mice with antigen alone increased the number and percentage of OT-$1_{cyto}$ cells produced, but had no effect on their specific cytolytic activity (SCA)(the number of SIINFEKL peptide-pulsed B16 [SIINFEKL-B16] cells killed in collagen-fibrin gels/OT-$1_{cyto}$ cell/d). In contrast, immunization of OT-1 mice with antigen and adjuvant (α-CD40-IgG) increased the percentage and specific cytolytic activity of tetramer+OT-$1_{cyto}$ cells produced.

In exploring the capacity of OT-1 cell preparations containing an increased percentage of OT-$1_{cyto}$ cells to kill SIINFEKL-B16 cells, we noted a hyperbolic relationship between the percentage of OT-$1_{cyto}$ cells in a preparation and the percentage of SIINFEKL-B16 cells killed by them. OT-1 cell killing of SIINFEKL-B16 cells increased at an exponential rate as the percentage of OT-$1_{cyto}$ cells increased from 0.86% of OT-1 cells harvested from spleens of un-immunized OT-1 mice to 1.9% of OT-1 cells harvested from spleens of OT-1 mice immunized with anti-DEC205-IgG-ovalbumin alone; and to 2.4% of OT-1 cells harvested from spleens of mice immunized with α-DEC205-IgG-ova and anti-CD40-IgG (α-CD40-IOgG). We observed a similar pattern of increase in number, specific cytolytic activity, and killing of SIINFEKL-B16 cells by OT-1 cells activated in vitro in medium containing SIINFEKL and IL-12 or IL-21 vs. medium containing SIINFEKL and IL-2. Our results indicate that a population containing 5% OT-$1_{cyto}$ cells will exhibit 20-fold greater efficiency in killing SIINFEKL-B16 cells, as measured by a previously reported killing constant k (ml/OT-$1_{cyto}$ cell/min [Budhu et al. 2010]), than a population containing 0.86% OT-$1_{cyto}$ cells. Using these quantitative relationships (Budhu et al. 2010, 2011A) we calculate that adoptive transfer of a quantity of OT-1 cells sufficient to produce an intra-lesional concentration of ~4×10$^6$ OT-1 cells, 5% of which are cytolytically active, will eradicate all ova-B16 cells in 8 d-established melanomas in vivo.

Results. Dendritic cell activation during immunization of OT-1 mice or in vitro activation of OT-1 cells increases the fraction and specific cytolytic activity of antigen-specific OT-$1_{cyto}$ cells. Bonifaz et al. (2002) demonstrated that OT-1 mice immunized with α-DEC205-IgG-ova in combination with α-CD40-IgG kill ova-B16 cells more efficiently than OT-1 mice immunized with α-DEC205-IgG-ova alone. These findings suggested that α-CD40-IgG activation of dendritic cells might increase the fraction of cytolytically active ($f_c$) OT-1 cells in the elicited population and thereby affect the efficiency with which these cells kill SIINFEKL-B16 cells. Accordingly, we immunized OT-1 mice with α-DEC205-IgG-ova alone or in combination with α-CD40-IgG and compared the number of OT-1 spleen cells elicited by the two immunization protocols by FACS analysis of tetramer+stained cells (Supplemental FIG. 1), and the fraction of these tetramer+OT-1 cells that were cytolytically active by limiting dilution assays (Budhu et al. 2011A). Consistent with Bonifaz et al.'s (2002) report, the spleens of OT-1 mice immunized with both α-DEC205-IgG-ova and α-CD40-IgG contained ~2-fold more tetramer+OT-1 cells than spleens of OT-1 mice immunized with α-DEC205 IgG-ova alone (Table 23, Lines 2 & 3). Limiting dilution assays (Budhu 2011a) showed ~0.86%±0.05% SEM of tetramer+OT-1 cells from spleens of unimmunized OT-1 mice, 1.9%±0.03% SEM of tetramer+OT-1 cells from spleens of OT-1 mice immunized with α-DEC205-IgG-ova alone, and 2.4%±0.04% SEM of tetramer+OT-1 cells from spleens of mice immunized with α-DEC205-IgG-ova and α-CD40-IgG were cytolytically active (Table 23, Lines 1-3).

In parallel assays using the same preparations of OT-1 spleen cells, we co-incubated a quantity of these cells sufficient to yield $5\times10^6$ tetramer+OT-1 cells/ml collagen-fibrin gel (Table 23, Lines 1-3) with $10^6$ SIINFEKL-B16 cells/ml collagen-fibrin gel at 37° C. for 24 h and measured the number of B16 cells remaining viable in these gels by clonogenic assay. Five million tetramer+spleen cells (OT-$1_{tot}$ cells) from un-immunized, α-DEC205-IgG-ova-immunized, or α-DEC205-IgG-ova- and α-CD40-IgG-immunized OT-1 mice/ml collagen-fibrin gel killed 21%, 44%, and 74%, respectively, of $10^6$ SIINFEKL-B16 cells/ml gel in 24 h (Table 23, Lines 1-3).

In parallel, we analyzed the relationships between the $f_c$ OT-1 cells in these OT-1 cell preparations and their ability to kill SIINFEKL-B16 cells in collagen-fibrin gels. Immunization with α-DEC205-IgG-ova alone stimulated a 261% increase in the total number of OT-$1_{cyto}$ cells produced/spleen ($1.3\times10^7$ OT-$1_{tot}$ cells×0.019 OT-$1_{cyto}$ cells=$2.47\times10^5$ OT-$1_{cyto}$ cells/spleen of α-DEC205-IgG-ova immunized OT-1 mice [Table 23, line 2] vs. $1.1\times10^7$ OT-$1_{tot}$ cells× 0.0086 OT-$1_{cyto}$ cells/spleen of un-immunized OT-1 mice=$9.46\times10^4$ OT-$1_{cyto}$ cells/spleen of unimmunized OT-1 mice [Table 23, line 1]); and a 221% increase in the number of OT-$1_{cyto}$ cells/$5\times10^6$ OT-$1_{tot}$ cells/ml gel ([$9.5\times10^4$ OT-$1_{cyto}$ cells/$5\times10^6$ OT-$1_{tot}$ cells from spleens of un-immunized OT-1 mice vs. $4.3\times10^4$ OT-$1_{cyto}$ cells/$5\times10^6$ OT-$1_{tot}$ cells from spleens of α-DEC205-IgG-ova immunized mice] Table 23, line 2 vs. 1 & Supplementary text SI-1A). Yet the specific cytolytic activity (SCA) of the OT-$1_{cyto}$ cells from α-DEC205-IgG-ova-immunized OT-1 mice was almost the same (0.033 SIINFEKL-B16 cells killed/OT-$1_{cyto}$ cell/d) as the SCA of OT-$1_{cyto}$ cells from unimmunized OT-1 mice (0.034 SIINFEKL-B16 cells killed/OT-$1_{cyto}$ cell/d [Table 23, Lines 2 vs. 1 & Supplementary Text SI-1B]). The total increase in the percentage of SIINFEKL-B16 cells killed following co-incubation with $5\times10^6$ 1.9% OT-$1_{cyto}$ cells/ml collagen-fibrin gel/d vs. with $5\times10^6$ 0.86% OT-$1_{cyto}$ cells/ml collagen-fibrin gel/d was 209% (44%/21% SIINFEKL-B16 cells killed [Table 23, Lines 2 vs. 1 & Supplementary Text SI-1]). This is in excellent agreement with the 215% increase predicted by the product of the increase in number of OT-$1_{cyto}$ cells/$5\times10^6$ OT-$1_{tot}$ cells/ml gel (221%) and the very small decline in their SCA (97%)(221%×97%=214% [Supplementary text SI-1C]). Thus, immunization with antigen alone (α-DEC205-IgG-ova), increased the number of cytolytically active antigen-specific CD8+T-cells but had an insignificant effect on their SCA.

In contrast, immunization with α-DEC205-IgG-ova plus α-CD40-IgG produced a 126% increase in the number of OT-$1_{cyto}$ cells/$5\times10^6$ OT-$1_{tot}$ cells/spleen of OT-1 mice immunized with α-DEC205-IgG-ova and α-CD40-IgG vs. with α-DEC205-IgG-ova alone (Table 23, line 3 vs. 2 & Supplementary Text SI-2A); and a 130% increase in the SCA of OT-$1_{cyto}$ cells from OT-1 mice immunized with α-DEC205-IgG-ova and α-CD40-IgG vs. with α-DEC205-IgG-ova alone ([0.043/0.033] Table 23, line 3 vs. 2 & Supplementary Text SI-2B). The total increase in the percentage of SIINFEKL-B16 cells killed following co-incubation with $5\times10^6$ 2.4% OT-$1_{cyto}$ cells/ml collagen-fibrin gel/d vs. with $5\times10^6$ 1.9% OT-$1_{cyto}$ cells/ml collagen-fibrin gel/d was 168% SIINFEKL-B16 cells killed ([74%/44% SIINFEKL-B16 cells killed] Table 23, Lines 3 vs. 2 & Supplementary Text SI-2). This is in excellent agreement with the 164% increase predicted by the product of the increase in number of OT-$1_{cyto}$ cells/$5\times10^6$ OT-$1_{tot}$ cells/ml gel (126%), and the 130% increase in their SCA [Supplementary text SI-2C]). Thus immunization with antigen (α-DEC205-IgG-ova) in combination with an antigen-independent inflammatory stimulus (i.e., α-CD40-IgG, an adjuvant) increases the total number of OT-1 cells, the $f_c$ OT-1 cells, and the SCA of these OT-$1_{cyto}$ cells.

Overall, immunization with α-DEC205-IgG-ova plus α-CD40-IgG increased the total number of OT-1 cells/spleen, the $f_c$ OT-1 cells/spleen, and the SCA of these OT-$1_{cyto}$ cells over that observed for OT-1 spleen cells from un-immunized mice. Specifically, we observed a 279% increase in the number of OT-$1_{cyto}$ cells/$5\times10^6$ OT-$1_{tot}$ spleen cells/ml collagen-fibrin gel/d from α-DEC205-IgG-ova-plus α-CD40-IgG-immunized OT-1 mice vs. unimmunized OT-1 mice [Table 23, Lines 3 vs. 1]; and a 129% increase in SCA of OT-$1_{cyto}$ cells/$5\times10^6$ OT-$1_{tot}$ spleen cells/ml collagen-fibrin gel/d from α-DEC205-IgG-ova-plus α-CD40-IgG-immunized OT-1 mice vs. unimmunized OT-1 mice (Table 23, Lines 3 vs. 1 & Supplementary text SI-3A &B). As above, the product of the percent increase in number of OT-$1_{cyto}$ cells/$5\times10^6$ OT-$1_{tot}$ cells from spleens of α-DEC205-IgG-ova and α-CD40-IgG-immunized OT-1 mice vs. un-immunized OT-1 mice and the percent increase in SCA of these OT-$1_{cyto}$ cells vs. OT-$1_{cyto}$ cells from un-immunized OT-1 mice was 359% (279%×129%). This is in excellent agreement with the observed 352% difference in killing of SIINFEKL-B16 cells following their co-incubation with $5\times10^6$ 2.4% OT-$1_{cyto}$ cells from α-DEC205-IgG-ova-plus α-CD40-IgG-immunized mice/ml collagen-fibrin gel/d vs. with $5\times10^6$ 0.86% OT-$1_{cyto}$ spleen cells from un-immunized mice/ml collagen-fibrin gel/d (Table 23, Lines 3 vs. 1 & Supplementary text SI-3).

These findings show that while antigen alone stimulates an increase in the number of antigen-specific CD8+T-cells, antigen plus adjuvant stimulates increases in both the number and the SCA of these cells. They show that the magnitude of the effect of adjuvant can be measured precisely, that it can be distinguished quantitatively from that of antigen, and that the combined effects of antigen and adjuvant on the cytolytic activity of antigen-specific CD8+T-cells is the product of the change in number of cytolytically active antigen-specific CD8+T-cells in a population and the change in their SCA. This is described by the equation (Eq. 3, Δ% increase in killing of antigen-expressing target cells=Δ% in number of cytolytically active antigen-specific CD8+T-cells/ml gel or per ml or gm tissue×Δ% in the SCA of these antigen-specific CD8+T-cells×100%). They are consistent with our conclusion (Budhu et al. 2011A) that the $f_c$ antigen-specific CD8+T-cells accounts for all of the cytocidal activity of all of the antigen-specific CD8+T-cells in a population.

Effect of in vitro activation of OT-1 spleen cells in medium containing SIINFEKL peptide plus IL-12 or IL-21 alone or IL-21 in combination with α-CD40-IgG on the $f_c$ and SCA of OT-1 cells. IL-12 and IL-21 are reported to promote formation of cytolytically active CD8+T-cells (Moroz et al., 2004; White et al., 2007). Therefore, we compared the $f_c$ and SCA of OT-$1_{cyto}$ cells formed in vitro in medium containing SIINFEKL and IL-2, IL-12, or IL-21, or in medium containing SIINFEKL, α-CD40-IgG, and IL-2 or IL-21. A significantly larger percentage of OT-1 cells activated and maintained in medium containing SIINFEKL and IL-12 or IL-21 were cytolytically active (2.56%±??SEM and 2.2%±??SEM, respectively), compared to OT-1 cells activated and maintained in medium containing SIINFEKL and IL-2 (2%±??SEM) (Table 24, Lines 5, 2 & 1, respectively). Addition of α-CD40-IgG to SIINFEKL peptide-stimulated OT-1 spleen cells undergoing activation in vitro increased the $f_c$ OT-1 cells from 2%±??SEM to 2.2%±??SEM when the medium contained 20 U IL-2, and from 2.2% to 2.5%±??SEM when the medium contained 100 ng IL-21. However, in contrast to α-CD40-IgG's stimulatory effect on the SCA of OT-1 cells activated in vivo (Table 24, line 3), α-CD40-IgG produced a decline in the SCA of OT-1 cells activated in vitro (Table 24, Lines 3 & 4).

α-CD40-IgG in combination with IL-2 or IL-21 increased significantly the percentage of perforin- and granzyme B-expressing OT-1 Cells. Perforin is an essential element of the cytocidal armamentarium of cytolytic T cells. Snyder et al. (2003) and Budhu et al. (2010) found perforin to be required for OT-1 killing of SIINFEKL-B16 cells. To determine whether α-CD40-IgG alone or in combination with IL-2 or IL-21 affected perforin and/or granzyme B expression, we incubated OT-1 spleen cells in medium containing SIINFEKL and IL-2 or IL-21, without or with α-CD40-IgG, and measured the fraction of OT-1$_{tot}$ cells produced that expressed these proteins. (Note that ~90% of the spleen cells recovered following in vitro activation were CD8+[Table 24]). Forty five±??SEM and 35%±??SEM of OT-1 spleen cells activated in medium containing SIINFEKL and IL-21 expressed perforin and granzyme B, respectively, compared with ~14%±??SEM and ~17%±??SEM of CD8+OT-1 spleen cells activated in medium containing SIINFEKL and IL-2 (Table 12). Addition of α-CD40-IgG to IL-21-treated cultures further increased perforin and granzyme B expression from 35% to 40% and from 45% to ~53%±??SEM, respectively. In contrast, α-CD40-IgG had little or no effect on the percent of perforin- and/or granzyme B-expressing OT-1 cells activated in IL-2 containing medium (Table 12). These results demonstrate the discordance between perforin/granzyme B expression by OT-1 cells and their cytolytic activity (e.g., only 2.2-2.5% of OT-1 cells, ≥35%-~41%, and 45-~53% of which expressed perforin and granzyme B, respectively [Table 12]), were cytolytically active [Tables 24 and 12]). Thus, while perforin is required for OT-1 cells to kill SIINFEKL-B16 cells (Snyder et al. 2003, Budhu et al. 2010), its expression does not assure their cytolytic activity.

$k_{cyto}$ increases as the $f_c$ OT-1 cells increases. Immunization of OT-1 mice with α-DEC205-ova IgG, or in vitro activation of OT-1 spleen cells in medium containing SIINFEKL plus IL-2 increases the $f_c$ OT-1 spleen cells from 0.86% to 1.9-2%, respectively. This results in a larger number of OT-1$_{cyto}$ cells/10$^6$ OT-1 spleen cells, but no change in their SCA. In contrast, immunization of OT-1 mice with α-DEC205-ova IgG plus α-CD40 IgG, or in vitro activation of OT-1 spleen cells in medium containing SIINFEKL plus IL-12 or IL-21 increases both the $f_c$ OT-1 cells from 1.9-2% to 2.4-2.6%, respectively and their SCA by 129.9%-131.5%, respectively (Tables 23 & 24).

What is the relationship between $f_c$ and $k_{cyto}$? The efficiency, as measured by k, with which 10$^6$ OT-1$_{cyto}$ cells/ml collagen-fibrin gel kill SIINFEKL-B16 cells increases in parallel and in rough proportion to the magnitude of the increase in the $f_c$ OT-1 cells (Table 12). A plot of $k_{cyto}$ vs. $f_c$ OT-1 cells at OT-1$_{tot}$ cell concentrations ranging from 10$^4$-10$^8$/ml collagen-fibrin gel shows that at each OT-1 cell concentration, $k_{cyto}$ increases exponentially as the $f_c$ OT-cells increases from 0.86% to 2%-2.2%%, and that it increases log-linearly thereafter (FIG. 20). Eq. 2 ($CT_{cyto}C=g/k_{cyto}$) specifies limiting values of $k_{cyto}$. That is, $k_{cyto}$ cannot be larger than g, since any value larger than g yields a $CT_{cyto}C<1$ antigen-specific CD8+T-cell/ml, a physical impossibility. Indeed, $k_{cyto}$ reaches limiting values between 1.82×10$^{-6}$ and 1.71×10$^{-7}$ ml/OT-1 cell/min when $f_c$ OT-1 cells=100% at concentrations of 10$^4$ and 10$^8$ in vitro activated OT-1$_{tot}$ cell/ml, respectively (not shown), and ~90% of this maximal value when the $f_c$ OT-1$_{tot}$ cells=10% (FIG. 1). Note that at a concentration of 1 OT-1 cell/ml under conditions in which the $f_c$ OT-1 cells=100%, the value of $k_{cyto}$ is below the limit predicted by Eq. 2 to be equal to the target cell growth rate. For B16 cells this is ~2-4.4×10$^{-4}$/min (data not shown).

Discussion. Together with previous reports (Budhu et al. 2010, 2011A), the findings reported here provide new and fundamental insights into two aspects of cellular immunology. First, they provide quantitative information about the effects of antigens, adjuvants, and cytokines on $f_c$ and the SCA of antigen-specific CD8+T-cells (Tables I & II). Second, they identify five new parameters ($f_c$, $p_{cyto}$, SCA, $k_{cyto}$, $CT_{cyto}C$) whose values, when inserted into Eqs. 1 and 2 (Budhu et al. 2010) enable investigators to calculate the precise concentration of cytolytically active antigen-specific CD8+T-cells required to control growth of, and to eradicate, cognate antigen-expressing tumor cells in vitro and in vivo. Accordingly, they have practical implications for cellular immunotherapy of infectious and neoplastic diseases. To facilitate their use, we have included nomograms showing the relationships between the $f_c$ OT-1 cells and the critical CD8+T-cell$_{tot}$ concentration ($CT_{tot}C$)(FIG. 31A), and between $f_c$ and the intra-tumoral OT-1$_{tot}$ cell concentration ($p_{tot}$) (FIG. 31 B) for OT-1$_{tot}$ cell killing SIINFEKL-B16 cells at the efficiencies observed in collagen-fibrin gels and in melanomas in vivo.

Effects of antigen and of antigen-independent pro-inflammatory stimuli on the $f_c$ and the SCA of antigen-specific CD8+T-cells produced. Immunization of OT-1 mice with α-DEC205-IgG-ova along produced a 221% increase in the $f_c$ OT-1 cells, but caused a reduction in their SCA (Table 23, Lines 1 & 2, & Supplementary text SI-1 & SI-2). Together, these effects produced a 209% (44%/21%) increase in killing of SIINFEKL-B16 cells in collagen-fibrin gels/24 h. In contrast, immunization of OT-1 mice with α-DEC205-IgG-ova and α-CD40-IgG produced a 279% increase in the $f_c$ OT-1 cells, and a 129% increase in their SCA (Table 23, Lines 1 & 3, & Supplementary text SI-1 & 3). This produced a 352% (74%/21%) increase in killing of SIINFEKL-B16 cells. Similarly, pro-inflammatory cytokines (e.g., IL-12 and IL-21), increased both the $f_c$ and SCA of OT-1 cells activated in vitro in the presence of antigen, and a 120%-133% increase in killing of SIINFEKL-B16 cells (72%/60% and 80%/60%) (Table 24, Lines 1, 2, & 5). Under these conditions α-CD40-IgG further increased the $f_c$ OT-1 cells produced, but for unknown reasons decreased their SCA (Table 24, Lines 3 & 4).

Ignoring for the moment the in vitro effect of α-CD40-IgG on development of OT-1$_{cyto}$ cells, the findings described in Tables 23 and 24 are consistent with the following model. 1. In the absence of adjuvants or of antigen-independent inflammatory stimuli, antigen stimulates expansion in the number of antigen-specific CD8+T-cells but has little or no effect on their SCA. 2. In the presence of adjuvants or other antigen-independent inflammatory stimuli, antigen stimulates an even larger expansion in the number of antigen-specific CD8+T-cells than in the absence of these stimuli. In addition, adjuvants and other antigen-independent inflammatory stimuli, and the cytokines they elicit (e.g., IL-12, IL-21), promote increases in CD8+T-cells' SCA.

The finding that antigen alone primarily affects the quantity of CD8+T-cells produced while antigen plus an antigen-independent inflammatory stimulus affects both the quantity and quality of CD8+T-cells is reminiscent of Janeway's hypothesis regarding the relationship between innate and acquired immunity (Janeway, Cold Spring Harbor Symposium ~1990). It expands on it in two respects. First, it identifies dendritic cells and cytokines as key regulators of CD8+T-cell SCA, and suggests that as observed for CD8+ T-cells (Table I), dendritic cells may have the capacity to similarly adjust the specific activities of T-helper and T-regulatory cells, thereby fine-tuning the quality as well as the quantity of these cells. Assays similar to the ones employed here could be used to test this idea. Second, it is consistent with our suggestion that cellular factors other than granzyme and perforin expression (Table 12) determine whether a CD8+T-cell whose TCR demonstrably recognizes a specific antigen-MHC complex on the surface of a target cell will kill that cell. Further work is required to identify the molecular characteristics that distinguish granzyme- and perforin-expressing, cytolytically active CD8+T-cells from granzyme- and perforin-expressing cytolytically inactive CD8+T-cells. This is a most important question to resolve since (FIG. 32 & FIG. 20), the availability of populations containing ≥2% antigen-specific CD8+T-cells could produce major positive benefits for patients undergoing cellular immunotherapy of melanoma, and potentially of infectious and other neoplastic diseases.

Differences in $k_{cyto}$ and SCA of OT-$1_{cyto}$ cells elicited by immunization in vivo vs. in vitro. OT-$1_{cyto}$ cells elicited by immunization in vivo with α-DEC205-IgG-ova alone or in combination with α-CD40-IgG, exhibit values of $k_{cyto}$ and SCA, respectively that are ~3.5- and 2.1-fold and ~1.6-2.1-fold smaller, respectively, than the corresponding values for OT-$1_{cyto}$ cells elicited by in vitro activation of OT-1 spleen cells in medium containing SIINFEKL peptide plus IL-2 (Table II Line 1 vs. Table IB, Line 1) or SIINFEKL plus IL-21 (Table II, Line 4 vs. Table IB, Line 3). These differences in $k_{cyto}$ and SCA cannot be ascribed to differences in T-cell antigen receptors because the activities measured are mediated by the same transgenic receptor. They are unlikely to reflect differences in the immunogenic potency of α-DEC205-IgG-ova vs. SIINFEKL since ovalbumin is processed to SIINFEKL by dendritic cells for presentation to OT-1 cells. And they are larger than can be accounted for by the 0.1% difference in the fraction of cytolytically active OT-1 cells in these preparations (FIG. 1). We think it likely that in vivo immunization with α-DEC205-IgG-ova, without or with α-CD40-IgG, induces formation of suppressive cells and/or substances and that these cells/substances blunt OT-1 cell cytolytic activity at the high concentrations of OT-1 spleen cells used to measure OT-1 cell killing of SIINFEKL-B16 cells collagen-fibrin gels. Similarly, we suspect these suppressive cells and substances have little or no effect at the very low concentration of OT-1 cells used in limiting dilution assays (~100 tetramer+OT-1 cells/20 μL=6×10³-4.2×10⁴ OT-$1_{tot}$ spleen cells/ml. While further work is required to identify the cellular mechanism(s) responsible for these differences in cytocidal activity of in vivo vs. in vitro activated OT-1 cells, these findings suggest that for purposes of cellular immunotherapy, in vitro activated antigen-specific CD8+T-cells may be more effective than their in vivo activated counterparts.

The finding that the values of $k_{tot}$ and $k_{cyto}$ decline in parallel 0.7 $\log_{10}$ for every $\log_{10}$ increase in CD8+T-cell concentration (Budhu et al. 2011A, FIG. 3), indicates that for the most part, it will not be possible to kill all tumor antigen-expressing cells in a tumor simply by delivering a higher number of TAS CD8+T-cells to the tumor parenchyma. For example, Buckanovitch et al. showed that blockade of endothelin B receptors on endothelial cells of vessels of a murine ovarian tumor increased the entry of adoptively transferred TAS CD8+T-cells into the parenchyma of these tumors by ≥10-fold. The increased intra-tumoral concentration of TAS CD8+T-cells produced a larger decline in tumor volume than in untreated mice. It did not, however, eradicate the tumor. We believe its failure to do so is a consequence of the limited lifespan of CD8+T-cells, of the immunosuppressive effects of intra-tumoral leukocytes, stromal cells and their secretory products, and of the 0.7 $\log_{10}$ decrease in efficiency (k) of killing of cognate antigen-expressing tumor cells with each $\log_{10}$ increase in the intra-tumoral concentration of TAS CD8+T-cells. The findings described in FIG. 1 provide, in principle, a strategy for overcoming this last barrier. It is to increase the $f_c$ antigen-specific CD8+T-cells. Significant increases in the $f_c$ (~280%) and SCA (~130%) of antigen-specific CD8+T-cells can be achieved by use of adjuvants and cytokines, and these increases produce ~130%-170% increases in killing of SIINFEKL-B16 cells in collagen-fibrin gels (Table 23, Line 3 vs. 2 & Table 24, Line 5 vs. 1). This increase in killing occurs primarily because a 5-fold increase in $f_c$ OT-1 cells (from 1% to 5%) holding OT-$1_{tot}$ cell concentration constant at $10^6$/ml raises both the SCA of these cells (Tables 23 & 24) the value of $k_{cyto}$ 11.3-fold (FIG. 20).

Figure 32:
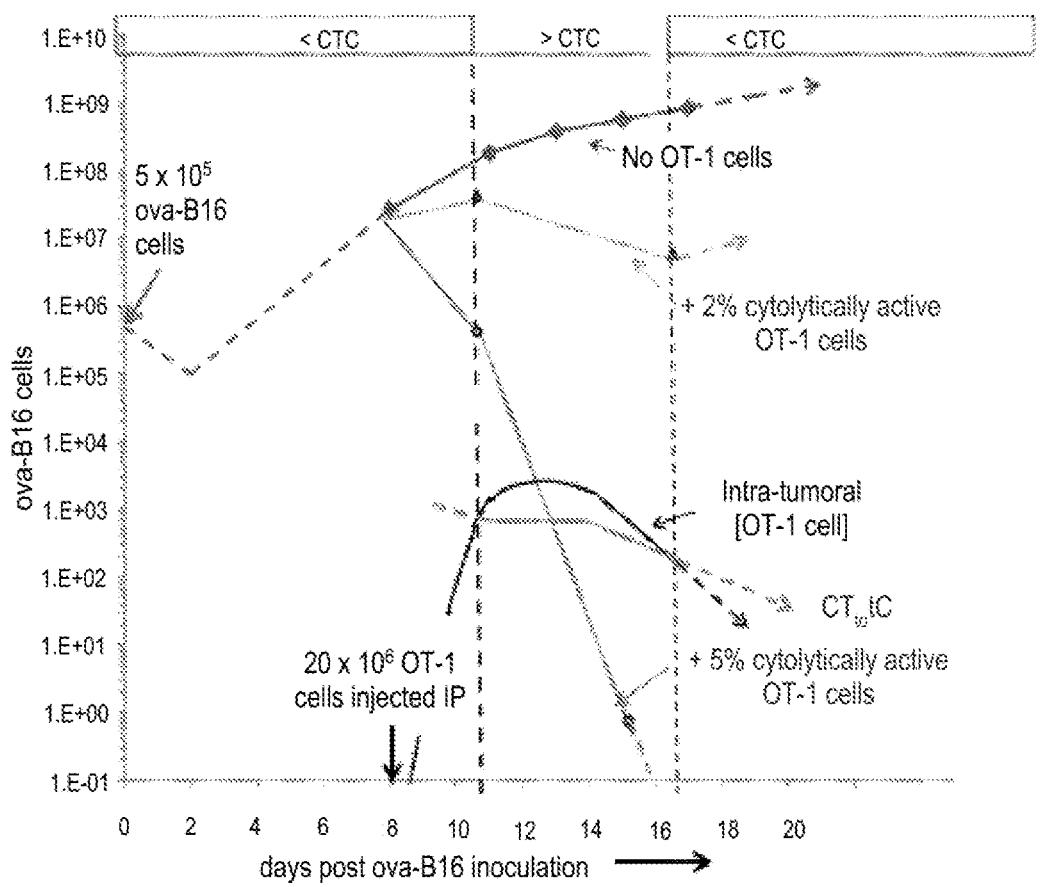
FIG. 32. Impact of intra-peritoneal (IP) administration of $20 \times 10^6$ OT-1 cells on 8 d-established ova-B16 melanomas.

To illustrate the impact of an increase in the $f_c$ OT-1 cells employed in cellular immunotherapy we return to Petersen et al.'s (2006) experiment in which adoptive transfer of 20×10⁶ of 2% cytolytically active OT-$1_{tot}$ cells reduced growth of ova-B16 tumors from 2,200% to 14% in 7 d, but did not eliminate them. At their nadir, tumors of OT-1 cell-treated mice were 14% larger than on the day the OT-1 cells were administered (Budhu et al 2010, FIG. 7). We calculate that Petersen et al. (2006) would have had to administer 20×10⁶ OT-1 cells, 8% of which were cytolytically active, to kill all ova-expressing B16 cells in 8 d-established ova-B16 tumors in 7 d (FIG. 32 & Supplementary text SIII).

Implications for cellular immunotherapy of cancer. There are at least four recognized barriers to the success of immunotherapy of antigen-expressing tumors by immunization or by adoptive transfer of cognate-antigen receptor expressing CD8+T-cells. They are: 1. Lack of methods to calculate the intra-tumoral concentration of cytolytically active tumor antigen-specific (TAS) CD8+T-cells required to control growth of, and to eradicate, cognate antigen-expressing tumor cells in a tumor. 2. Lack of expression of tumor-specific antigen(s) by many cancer cells (Weissman Nature paper, July 2010), and/or loss by mutation or selection of antigen expression by previously antigen-expressing cancer cells (Cassian Yee paper). 3. The very low efficiency with which immune effector cells emigrate from the blood into the tumor parenchyma (Buckanovitch et al.). 4. The high level of immuno-suppressive cells, and their soluble (e.g., TGFβ, IL-10), and matrix-bound (e.g., tenascin) secretory products within the tumor parenchyma.

These barriers notwithstanding, there has been substantial progress in tumor antigen-specific (TAS) cellular immunotherapy in of cancer (Weiner, L. M. 2008). Presently, administration of ≥10⁶ TAS CD8+T-cells/g body weight, an unknown percentage of which is cytolytically active, often leads to temporary reduction/cessation of tumor growth, and to significant (25%-75%) regression of cognate antigen-expressing melanomas (Dutton et al.). In a few instances, it eradicates the tumor (Curren et al. 2010, Dudley and Rosenberg). These findings are consistent with Petersen et al.'s (2006) findings cited above.

The findings reported here and in Budhu et al. (2010 and 2011A), further advance the field of cellular immunotherapy in four important respects. First, they show that only a small percentage (1.9-2.6% [Tables 23 and 24]) of antigen-specific CD8+T-cells produced in response to in vivo immunization or in vitro activation is cytolytically active, and that this percentage can be increased by 279%-302% (2.4%/0.86% and 2.6%/0.86% [Tables 23 and 24]) by in vivo immunization with antigen plus a dendritic cell activator or by in vitro activation with medium containing antigen and IL-12. Second, they demonstrate that specific in vivo and in vitro CD8+T-cell activation protocols increase both the $f_c$ and the SCA of CD8+T-cells. Third, they identify an inverse relationship between antigen-specific CD8+T-cell concentration and the efficiency ($k_{cyto}$) with which cytolytically active antigen-specific CD8+T-cells kill cognate antigen-expressing tumor cells (Budhu et al. 2011A, FIG. 3). Finally, they describe an experimentally verified method for calculating the intra-tumoral concentration of cytolytically active tumor antigen-specific CD8+T-cells required for eradicating cognate antigen-expressing tumor cells in collagen gels in vitro and in tumors in vivo. This alone is a substantial achievement. It is far easier to reach a summit of known altitude than to wander about in a fog hoping to identify it by chance.

Neutralizing the immuno-suppressive effects of the intra-tumoral environment. Curren et al. (2010) reported eradication of 65% of 3 d-established B16 tumors by immunization of these mice with irradiated flt-3-ligand-expressing B16 (flt-B16) cells and administration of anti-CTLA-4, anti-PD-1, and anti-PD-L1 IgGs. They showed administration of anti-CTLA-4, anti-PD-1, and anti-PD-L1 IgGs increased the intra-tumoral concentration of effector CD4+ and CD8+T-cells from ~1.3×10$^5$/ml tumor in 16-d-old melanomas in flt-B16 cell-immunized mice to ~1.8×10$^6$/ml in 16-d-old melanomas of flt-B16 cell-immunized, anti-CTLA-4, anti-PD-1, and anti-PD-L1 IgG-treated mice. To test further the utility of the methods described here and previously (Budhu et al. 2010) in predicting the outcome of cellular immunotherapy, we calculated the effect of anti-CTLA-4–, anti-PD-1–, and anti-PD-L1-IgG-administration on B16 melanomas in flt-B16 cell immunized mice. In making these calculations we made two assumptions. 1. 2.5% of the CD4+ and CD8+T-cells elicited by flt-B16 cell immunization were TAS and cytolytically active. 2. Administration of anti-CTLA-4–, anti-PD-1–, and anti-PD-L1-IgG produced an intra-tumoral environment in which TAS CD4+ and CD8+ T-cells killed B16 cells at the same efficiency (measured by $k_{cyto}$) as observed for comparable concentrations of OT-1$_{cyto}$ cells killing SIINFEKL-B16 cells in collagen-fibrin gels (FIG. 1). Accordingly, we substituted previously determined values for B16 cell concentration and growth rate in melanomas in vivo (Budhu et al. 2010), and values for $k_{cyto}$ (FIG. 20) at the intra-tumoral concentration of CD4+ and CD8+ T-cells reported by Curren et al. (2010) (Supplementary text SIV), into Eq. 1 and calculated the outcome (Supplementary text SIV). These calculations indicate that under the conditions stipulated, immunized, anti-CTLA-4–, anti-PD-1–, anti-PD-L1-IgG-treated mice would have had had ~5.2 viable B16 melanoma cells remaining by the end of d 20 following inoculation of 1.5×10$^5$ B16 cells (Supplementary text SIV). In contrast, even if flt-B16 cell immunization had produced 5% cytolytically active TAS CD4+ and CD8+T-cells, in the absence of anti-CTLA-4–, anti-PD-1–, and anti-PD-L1-IgG treatment, no mice would have been cured of their melanomas (data not shown). These results are consistent with Curren et al.'s (2010) findings. We draw two important conclusions from these calculations. First, the methods and equations we have derived enable us to model the impacts and outcomes of various immuno-therapeutic interventions in mice bearing B16 melanomas and perhaps other tumors. At a minimum, such modeling will facilitate identification of more and less promising interventions. Second, treatments such as those employed by Curran et al. (2010) to reduce the immuno-suppressive effects of the intra-tumoral environment combined with CD8+T-cell activation protocols that produce ≥2.5% cytolytically active TAS CD8+T-cells (Table II), are likely to be required to reproducibly eradicate all cognate antigen-expressing melanoma cells in established melanomas. While these are stringent requirements, they are not beyond the bounds of the possible. Two point six percent of OT-1 cells activated in vitro in medium containing SIINFEKL and IL-12 are cytolytically active vs. SIINFEKL-B16 cells, and 2.8% of human clone 476.140 CD8+T-cells (Stuge et al.) are cytolytically active vs. gp100 peptide pulsed A375 human melanoma cells (Budhu et al., manuscript in preparation).

In summary, the concepts, equations, and methods reported here and in Budhu et al. (2010 and 2011A) are provide an experimentally verified, quantitative framework for understanding, exploring, and manipulating cytocidal effector activities of antigen-specific CD8+T-cells. They have the potential to place cellular immunotherapy on the same quantitative and predictable basis as has been established for pharmaceuticals.

Supplementary Text I.

SI-1. Experimentally observed increase in killing of SIINFEKL-B16 cells in collagen-fibrin gels/d by 5×10$^6$ 1.9% cytolytically active OT-1 cells/ml collagen fibrin gel vs. by 5×10$^6$ 0.86% cytolytically active OT-1 cells/ml collagen-fibrin gels=44% (Table IA, Line 2)/21% (Table IA, Line 1)=209%

SI-1A. Ratio of No. of 1.9% cytolytically active OT-1 cells/5×10$^5$ tetramer+CD8+T-cells÷No. of 0.86% cytolytically active OT-1 cells/5×10$^5$ tetramer+OT-1 cells=0.019× 5×10$^5$/0.0086×5×10$^5$=221%.

SI-1 B. Ratio of Specific Cytolytic Activities of 1.9% vs. 0.86% OT-1 cells=0.355/0.366=97%.

SI-1C. Total increase in killing of SIINFEKL-B16 cells in collagen-fibrin gels/d due to increase in number of cytolytically active OT-1 cells (SI-1A)×increase in their SCA (SI-1 B)=2.21×0.97=214%.

SI-2. Experimentally observed increase in killing of SIINFEKL-B16 cells in collagen-fibrin gels/d by 5×10$^6$ 2.4% cytolytically active OT-1 cells/ml collagen fibrin gel vs. by 5×10$^6$ 1.9% cytolytically active OT-1 cells/ml collagen-fibrin gels=74% (Table 1A, Line 3)/44% (Table 1A, Line 2)=168%.

SI-2A. Ratio of No. of 2.4% cytolytically active OT-1 cells/5×10$^5$ tetramer+CD8+T-cells÷No. of 1.9% cytolytically active OT-1 cells/5×10$^5$ tetramer+OT-1 cells=0.024× 5×10$^5$÷0.019×5×10$^5$=126%.

SI-2B. Ratio of Specific Cytolytic Activities of 2.4% vs. 1.9% OT-1 cells=0.47/0.35=133%.

SI-2C. Total increase in killing of SIINFEKL-B16 cells in collagen-fibrin gels/d due to increase in number of cytolytically active OT-1 cells (SI-2A)×increase in their SCA (SI-2B)=126%×133%=167.5%.

SI-3. Experimentally observed increase in killing of SIINFEKL-B16 cells in collagen-fibrin gels/d by 5×10$^6$ 2.4% cytolytically active OT-1 cells/ml collagen fibrin gel vs. by 5×10$^6$ 0.86% cytolytically active OT-1 cells/ml collagen-fibrin gels=74% (Table 1A, Line 3)/21% (Table 1A, Line 1)=352%.

SI-3A. Ratio of No. of 2.4% cytolytically active OT-1 cells/$5 \times 10^5$ tetramer+CD8+T-cells÷No. of 0.86% cytolytically active OT-1 cells/$5 \times 10^5$ tetramer+OT-1 cells=0.024×$5 \times 10^5$+0.0086×$5 \times 10^5$=279%.

SI-2B. Ratio of Specific Cytolytic Activities of 2.4% vs. 0.86% OT-1 cells=0.47/0.36=129%.

SI-2C. Total increase in killing of SIINFEKL-B16 cells in collagen-fibrin gels/d due to increase in number of cytolytically active OT-1 cells (SI-3A)×increase in their SCA (SI-3B)=279%×129%=359%.

Supplementary Text II.

SII-1. Experimentally observed increase in killing of SIINFEKL-B16 cells co-incubated with 2.2% cytolytically active OT-1 cells vs. with 2% cytolytically active OT-1 cells=72.2% (Table II, Line 2)/60% (Table II, Line 1)=120%.

SII-1A. Ratio of No. of 2.2% cytolytically active OT-1 cells/2% cytolytically active OT-1 cells=$2.2 \times 10^3/2 \times 10^3$ OT-1 cells=110.5%.

SII-1B. Ratio of Specific Cytolytic Activities of 2.2% cytolytically active OT-1 cells/2% cytolytically active OT-1 cells=2.4/2.2=109%.

SII-1C. Total increase in killing of SIINFEKL-B16 cells in collagen-fibrin gels/d due to increase in number of cytolytically active OT-1 cells (511-1A)×increase in killing due to change in Specific Cytolytic Activity (511-1 B)=110.5%×109%=120%.

SII-2. Experimentally observed increase in killing of SIINFEKL-B16 cells co-incubated with 2.5% cytolytically active OT-1 cells vs. with 2.37% cytolytically active OT-1 cells=67.5% (Table II, Line 4)/63.7% (Table II, Line 3)=106%.

SII-2A. Ratio of No. of 2.5% cytolytically active OT-1 cells/2.37% cytolytically active OT-1 cells=$2.5 \times 10^3/2.37 \times 10^3$ OT-1 cells=105.5%.

SII-2B. Ratio of Specific Cytolytic Activities of 2.5% cytolytically active OT-1 cells/2.37% cytolytically active OT-1 cells=2.06/2.05=100.5%.

SII-2C. Total increase in killing of SIINFEKL-B16 cells in collagen-fibrin gels/d due to increase in number of cytolytically active OT-1 cells (SII-2A)×increase in killing due to change in Specific Cytolytic Activity (SII-2B)=105.5%×100.5%=106%.

SII-3. Experimentally observed increase in killing of SIINFEKL-B16 cells co-incubated with 2.56% cytolytically active OT-1 cells vs. with 2% cytolytically active OT-1 cells=80% (Table II, Line 5)/60% (Table II, Line 1)=133%.

SII-3A. Ratio of No. of 2.56% cytolytically active OT-1 cells/$10^6$ tetramer+OT-1 cells/ml collagen-fibrin gels÷No. of 2% cytolytically active OT-1 cells/$10^6$ tetramer+OT-1 cells/ml collagen-fibrin gel=$2.56 \times 10^4/2 \times 10^4$ OT-1 cells=128%.

SII-3B. Ratio of Specific Cytolytic Activities of 2.56% cytolytically active OT-1 cells÷2% cytolytically active OT-1 cells=2.88/2.19=132%.

SII-3C. Total increase in killing of SIINFEKL-B16 cells in collagen-fibrin gels/d due to increase in number of cytolytically active OT-1 cells (SII-3A)×increase in killing due to change in Specific Cytolytic Activity (SII-3B)=128%×132%=169%.

Supplementary Text III.

Re-analysis of Budhu et al.'s (2010) analysis of Petersen et al.'s (2006) study of the effect of intra-peritoneal administration of $20 \times 10^6$ in vitro activated OT-1 spleen cells to mice bearing 8 d-established ova-B16 cell melanomas assuming 8% of the in vitro activated OT-1 cells administered were cytolytically active.

Data from Budhu et al.'s (2010) re-analysis of Petersen et al.'s (2006) data:

1. Intra-tumoral OT-1 concentration averaged $1.5 \times 10^6$ OT-$1_{tot}$ cells/ml or g tumor for the period 0-3 d, and $4 \times 10^6$ OT-$1_{tot}$ cells/ml or g tumor for the period 3-7 d following IP administration of $20 \times 10^6$ OT-1 cells.

2. $k_{cyto}$=$1.2 \times 10^{-7}$ ml/OT-$1_{cyto}$ cell/min and $7 \times 10^{-8}$ ml/OT-$1_{cyto}$ cell/min for $1.5 \times 10^6$ and $4 \times 10^6$ respectively, 8% cytolytically active OT-$1_{cyto}$ cells killing SIINFEKL-B16 cells in collagen-fibrin gels (FIG. 1).

3. $k_{cyto}$ for $1.5 \times 10^6$/ml 8% cytolytically active OT-$1_{cyto}$ cells killing ova-B16 cells in melanomas in vivo is 10.98% of the value of $k_{cyto}$ for the same OT-$1_{cyto}$ cells killing SIINFEKL-B16 cells in collagen-fibrin gels (Budhu et al. 2010). Therefore, $k_{cyto}$ for an intra-tumoral concentration of $1.5 \times 10^6$/ml or g ova-B16 melanoma killing ova-B16 cells in vivo on d 0-3=$1.2 \times 10^{-7}$ ml/OT-$1_{cyto}$ cell/min in collagen-fibrin gels×0.1098=$1.3 \times 10^{-8}$ ml/OT-$11_{cyto}$ cell/min, and for an intra-tumoral concentration of $4 \times 10^6$/ml or g ova-B16 melanoma killing ova-B16 cells in vivo on d 4-7=$7 \times 10^{-8}$ ml/OT-$1_{cyto}$ cell/min in collagen-fibrin gels×0.1098=$1.3 \times 10^{-8}$ ml/OT-$11_{cyto}$ cell/min.

4. The growth rate (g) of ova-B16 cells in vivo is $4.4 \times 10^{-4}$/min (Budhu et al. 2010).

5. 8 d-established ova-B16 melanomas 90.5 mm3 contain $2.7 \times 10^7$ ova-B16 cells (Budhu et al. 2010).

Substitution of these values into Eq. 1 for d 0-3 and d 4-7 for 8% cytolytically active OT-1 cells gives the following values for $b_t$ at the end of d 0-3, and of d 4-7.

End of d 3: $b_t$=$2.7 \times 10^7$ ova-B16 cells×$e^{-1.3 \times 10-8 \ ml/OT-1cyto \ cell/min \times 1.2 \times 10+5 \ OT-1cyto \ cells/ml \times 1.44 \times 10+3 \ min/d \times 3 \ d+4.4 \times 10-4/min \times 1.44 \times 10+3 \ min/d \times 3 \ d}$=$2.025 \times 10^5$ ova-B16 cells remaining.

End of d 7: $b_t$=$2.025 \times 10^5$ ova-B16 cells×$e^{-7.69 \times 10-8 \ ml/OT-1cyto \ cell/min \times 3.2 \times 10+5 \ OT-1cyto \ cells/ml \times 1.44 \times 10+3 \ min/d \times 4 \ d+4.4 \times 10-4/min \times 1.44 \times 10+3 \ min/d \times 4 \ d}$=1.8 ova-B16 cells remaining.

Supplementary Text IV: Analysis of Data from Curren et al. (2010): Sources of Data:

1. Inoculation of mice with $1.5 \times 10^5$ B16 melanoma cells produces melanomas containing $1.33 \times 10^7$ and $10^9$ B16 cells on d 12 and 20, respectively (Supplementary FIG. 1).

2. B16 cells grow at $4.4 \times 10^{-4}$/min (Budhu et al. 2010, FIG. 7).

3. TAS CD4+ and CD8+T-cells begin entering melanomas on d 12 and reach a steady state intra-tumoral concentration of $1.8 \times 10^6$ TAS CD4+ and CD8+T-cells/ml or g tumor on d 16 (Curren et al 2010).

4. 2.5% of CD4+ and CD8+T-cells elicited by immunization with irradiated flt-B16 cells in mice repeatedly treated with anti-CTLA-4, anti-PD-1, and anti-PD-L1 IgGs as described by Curren (2010) are cytolytically active.

5. Average intra-tumoral concentration of total TAS CD4+ and CD8+T-cells between d 12 and 16=$1.8 \times 10^6$ TAS CD4+ and CD8+T-cells/2=$9 \times 10^5$. Accordingly, the intra-tumoral concentration of cytolytically active CD4+ and CD8+T-cells between d12 and 16=$2.5 \times 10^{-2} \times 9 \times 10^5$=$2.25 \times 10^4$ cytolytically active CD4+ and CD8+T-cells, and $k_{cyto}$=$4 \times 10^{-8}$ ml/cytolytically active CD4+ and CD8+T-cell/min (FIG. 1).

6. Average intra-tumoral concentration of total TAS CD4+ and CD8+T-cells between d 16 and 20=$1.8 \times 10^6$ TAS CD4+ and CD8+T-cells. Accordingly, the intra-tumoral concentration of cytolytically active CD4+ and CD8+T-cells between d16 and 20=$2.5 \times 10^{-2} \times 1.8 \times 10^6$=$2.7 \times 10^5$ cytolytically active CD4+ and CD8+T-cells, and $k_{cyto}$=$1.3 \times 10^{-8}$ ml/cytolytically active CD4+ and CD8+T-cell/min (FIG. 1). 1)=$8 \times 10^{-8}$ ml/OT-$1_{cyto}$ cell/min, and $k_{cyto}$ for intra-tumoral concentration of $1.2 \times 10^6$ TAS CD8+T-cells from d 4-7 (FIG. 1)=$5 \times 10^{-8}$ ml/OT-$1_{cyto}$ cell/min.

Substituting the above values into Eq. 1:

$b_t$, d 12-16=$1.3 \times 10^7 e^{-8 \times 10-8 \times 2.28 \times 10+4 \times 1.44 \times 10+3 \times 3+4.4 \times 10-4 \times 1.44 \times 10+3 \times 3}$=$1.3 \times 10^8 \ e^{-2}$=$7.1 \times 10^6$ B16 cells remain viable.

$b_t$, d 16-20=$7.1 \times 10^6 e^{-1.1 \times 10-8 \times 2.7 \times 10+5 \times 1.44 \times 10+3 \times 4+4.4 \times 10-4 \times 1.44 \times 10+3 \times 4}$=$7.1 \times 10^6 \ e^{-14.573}$=5.2 B16 cells remain viable.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

TABLE 1

Activated OT-1 cells kill growing and nongrowing SIINFEKL-pulsed B16 cells with approximately equal efficiency

| OT-1 cells | $10^4$ B16 cells/ml | | $10^5$ B16 cells/ml | | $10^4$ B16 cells/ml | | |
|---|---|---|---|---|---|---|---|
| | Growing % | Nongrowing % | Growing % | Nongrowing % | Growing % | Nongrowing % | Mean % |
| $10^4$ | 9 ± 3 | 11 ± 3 | 14 ± 4 | 10 ± 4 | 14 ± 1 | 14 ± 1 | 12 ± 2 |
| $10^5$ | 27 ± 7 | 26 ± 4 | 31 ± 5 | 30 ± 3 | 34 ± 4 | 31 ± 4 | 30 ± 3 |
| $10^6$ | 65 ± 6 | 64 ± 6 | 65 ± 1 | 61 ± 7 | 66 ± 6 | 61 ± 6 | 62 ± 2 |
| $10^7$ | 98 ± 2 | 97 ± 1 | 99 ± 1 | 98 ± 1 | 98 ± 1 | 97 ± 1 | 98 ± 1 |

Killing efficiencies from FIG. 2 and unpublished data. Values represent the mean percentage of B16 killed ± SEM at t = 24 for these experiments performed in duplicate.

TABLE 2

Addition of naive spleen cells had no effect on killing efficiency of OT-1 cells in collagen-fibrin gels

| OT-1 cells/ml⁻ | Naive spleen cells/ml | Total lymphocytes/ml | B16 killed (±SEM) % |
|---|---|---|---|
| 0 | 0 | 0 | 0 |
| 0 | $10^7$ | $10^7$ | 0 |
| $10^4$ | 0 | $10^4$ | 18 ± 5 |
| $10^4$ | $9.99 \times 10^6$ | $10^7$ | 19 ± 3 |
| $10^5$ | 0 | $10^5$ | 35 ± 6 |
| $10^5$ | $9.9 \times 10^6$ | $10^7$ | 33 ± 2 |
| $10^6$ | 0 | $10^6$ | 75 ± 6 |
| $10^6$ | $9 \times 10^6$ | $10^7$ | 71 ± 3 |
| $10^7$ | 0 | $10^7$ | 97 ± 2 |

Collagen-fibrin gels contained $10^6$/ml of gel SIINFEKL-B16 cells, $10^4$, $10^5$, $10^6$, or $10^7$/ml of gel in vitro-activated OT-1 cells, and, where indicated, a sufficient concentration of naive splenocytes from wild-type C576L/6 mice to produce a final concentration of $10^7$ lymphocytes/ml of gel.
Gels were incubated at 37° C. for 24 h, digested, and the number of clonogenic B16 cells remaining was assessed as described in Materials and methods.
Data shown represent the mean percentage of B16 cells killed ±SEM at 24 h for three experiments, each performed in duplicate.

TABLE 3

OT-1 cell concentration determines the efficiency of killing of SIINFEKL-B16 cells

| B16 cells added | Packed volume B16 cells nl | OT-1 cells added | Packed volume OT-1 cells nl | Splenocytes added | Packed volume splenocytes nl | Packed volume all cells | OT-1/B16 cell ratio | OT-1 cells concentration | B16 cells killed % |
|---|---|---|---|---|---|---|---|---|---|
| $2 \times 10^4$ | 49 | $10^5$ | 16 | $8.9 \times 10^5$ | 198 | 263 nl | 5:1 | $2.4 \times 10^9$ | ~18 |
| $4 \times 10^4$ | 99 | $10^5$ | 16 | $6.7 \times 10^5$ | 148 | 263 nl | 2.5:1 | $2.4 \times 10^9$ | ~18 |
| $10^5$ | 247 | $10^5$ | 16 | 0 | 0 | 263 nl | 1:1 | $2.4 \times 10^9$ | ~18 |

B16 cells were pulsed with 1 μM SIINFEKL as described in Materials and methods.

TABLE 4

OT-1 cell killing of ova-B16 cells in 8-d-old tumors in vivo

| Days after inoculation[a] | ova-B16 tumor volume (control mice)[b] mm³ | ova-B16 cells per tumor (control mice)[b,c] | Intratumoral OT-1 cells/g of tumor[b] | ova-B16 tumor volume (OT-1 cell-inoculated mice)[b] mm³ | ova-B16 cells per tumor (OT-1-inoculated mice)[b,c] | ova-B16 cells in tumors of OT-1 cell-inoculated mice on the day indicated/ova-B16 cells in tumors on day 0 | g/min[d] | k ml/OT-1 cell/min[e] | CTC (OT-1 cells/ml) = g/k |
|---|---|---|---|---|---|---|---|---|---|
| 0 | 90.5 | $2.71 \times 10^8$ | 0 | 90.5 | $2.71 \times 10^7$ | day 0 = 1 | | | |
| 3 | 615.4 | $1.84 \times 10^8$ | days 0-3 = $3 \times 10^6$, mean days 0-3 = $1.5 \times 10^6$ | 299.6 | $8.99 \times 10^7$ | day 3 = 3.32 | days 0-3 = $4.4 \times 10^{-4}$ | days 0-3 = $1.1 \times 10^{-10}$ | days 0-3 = $4 \times 10^6$ |

TABLE 4-continued

OT-1 cell killing of ova-B16 cells in 8-d-old tumors in vivo

| Days after inoculation[a] | ova-B16 tumor volume (control mice)[b] mm$^3$ | ova-B16 cells per tumor (control mice)[b,c] | Intratumoral OT-1 cells/g of tumor[b] | ova-B16 tumor volume (OT-1 cell-inoculated mice)[b] mm$^3$ | ova-B16 cells per tumor (OT-1-inoculated mice)[b,c] | ova-B16 cells in tumors of OT-1 cell-inoculated mice on the day indicated/ova-B16 cells in tumors on day 0 | g/min[d] | k ml/OT-1 cell/min[e] | CTC (OT-1 cells/ml) = g/k |
|---|---|---|---|---|---|---|---|---|---|
| 5 | 1,267 | $3.8 \times 10^8$ | day 5 = $5 \times 10^6$, mean days 3-5 = $4 \times 10^6$ | 212.7 | $6.38 \times 10^7$ | day 5 = 2.35 | days 3-5 = $2.5 \times 10^{-4}$ | days 3-5 = $0.92 \times 10^{-10}$ | days 3-5 = $2.7 \times 10^6$ |
| 7 | ~1,900 | $5.7 \times 10^8$ | day 7 = $3 \times 10^6$, mean days 5-7 = $4 \times 10^6$ | 149.5 | $4.48 \times 10^7$ | day 7 = 1.65 | days 6-7 = $1.4 \times 10^{-4}$ | days 6-7 = $0.66 \times 10^{-10}$ | days 6-7 = $2.1 \times 10^6$ |

[a]Days after i.p. inoculation of in vitro-activated OT-1 cells into mice beaning 8-d-old ova-B16 tumors.
[b]Data from Petersen et al. (2006. *J. Immunother*.dio: 10.1097/01.cji.0000203078.97493.e3). See also Agger et al. (2007. *J. Immunother.* dol: 10.1097/01.cji.0003211326.38149.7e).
[c]B16 cell/mm$^3$ or Img of wet weight of tumor = $3 \times 10^6$(Stephens, T. C., and J. H. Peacock. 1978. *St. J. Cancer.* 38: 591-598).
[d]g = growth rate of ova-B16 cells calculated as in Li et al. (2004. *J. Exp. Med.* dol: 10.1064/jem.20040725) and in Materials and methods for days 0-3, 3-5, and 5-7, assuming $3 \times 10^5$ ova-B16 cells/mm$^3$ tumor and tumor volume as reported in FIG. 4 of Petersen et al. (2006. *J. Immunother*.dol: 10.1097/01.cji.0000003078.97493.c3).
[e]Killing constant (k) calculated using Eq. 1 from Li et al. (2004. *J. Exp.Med.* dol: 10.1084/jem.20040725) as described in Materials and methods.

TABLE 5

Polyoma virus antigen-specific CD8$^+$ T-cell killing of polyoma virus-infected splenocytes in mouse spleen in vivo.

| Days after polyoma virus infection | Plaque forming units polyoma virus per mg spleen[a] | Number of polyoma antigen-specific CD8$^+$ T cells per spleen[a] | Intrasplenic concentration of polyoma antigen-specific CD8$^+$ T cells[b] | PFU polyoma virus/ mg spleen on the day Indicated/PFU on day 3[c] | k (ml/polyoma virus antigen-specific CD8$^+$ T cell/min)[d] | CTC/ml[e] |
|---|---|---|---|---|---|---|
| 3 | $4.2 \times 10^2$ | $1.7 \times 10^4$ | $1.7 \times 10^5$ | 1 | | |
| 4 | $5.5 \times 10^3$ | Mean days 3-5 = $2.8 \times 10^5$ | Mean days 3-5 = $2.8 \times 10^5$ | 1.31 | | |
| 5 | $6.1 \times 10^3$ | $5.4 \times 10^5$ | $5.4 \times 10^6$ | 1.45 | days 4-5 = $2.13 \times 10^{-11}$ | $8.63 \times 10^6$ |
| 6 | $1.2 \times 10^2$ | Mean days 5-7 = $1.46 \times 10^8$ | Mean days 5-7 = $1.46 \times 10^7$ | 0.29 | days 5-6 = $6.98 \times 10^{-11}$ | $2.05 \times 10^6$ |
| 7 | $4.5 \times 10^2$ | $2.39 \times 10^5$ | $2.39 \times 10^7$ | 0.11 | days 6-7 = $3.63 \times 10^{-11}$ | $5.07 \times 10^6$ |
| 8 | $1.2 \times 10^1$ | Mean days 7-9 = $2.46 \times 10^8$ | Mean days 7-3 = $2.46 \times 10^7$ | 0.003 | days 7-8 = $1.11 \times 10^{-11}$ | $1.66 \times 10^6$ |
| 9 | 5.8 | $2.49 \times 10^5$ | $2.49 \times 10^7$ | 0.001 | days 8-9 = $2.78 \times 10^{-11}$ | $6.62 \times 10^6$ |

For all calculations, $b_0$ is $4.2 \times 10^3$, the number of polyoma virus PFU/mg of spleen on day 3.
[a]Data in this table is from Lukacher et. al. (1999. *J. Immunol.* 163: 3369-3378). g = ln $b_1/b_0(5,500/4,200)$ divided by $1.44 \times 10^3$ min/d = $1.87 \times 10^{-4}$/min.
[b]Calculated assuming spleen vol = 0.1 ml.
[c]Calculated from FIG. 2. in Lukacher et al. (1999. *J. Immunol.* 163: 3369-3378).
[d]Calculated as in Li et al. (2002. *Proc. Natl. Acad. Sci.* USA. dol: 10.1073/pnas.122244799) and Li et al. (2004. *J. Exp. Med.* dol: 10.1084/jem.20040725), k = ln $b_1/b_0$ divided by the sum of the intrasplenic concentration of polyoma virus antigen-specific CD8$^+$ T cells/ml × time in minutes + g × time in minutes. k (mean) = $3.7 \times 10^{-11}$ ml/polyoma virus antigen-specific CD8$^+$ T cell/min.
[e]CTC = g/k as in Li et al. (2002. *Proc. Natl. Acad.* Sci. USA. dol: 10.1073/pnas.l22244799) and Li et al. (2004. *J. Exp. Med.* dol: 10.1084/jem.20040725), CTC (mean) = $4.8 \times 10^6$ polyoma antigen-specific CD8$^+$ T cells/ml.

TABLE 6

Killing of $10^5$ SIINFEKL-B16 cells/ml[1] by $10^6$ OT-1 cells/ml[1], activated and maintained in vitro in medium containing IL-2 for 24 h in collagen-fibrin gels.

| Activation & expansion stimuli | % tetramer+ cells/ culture[2] | % OT-1$_{cyto}$ cells[3] | $b_t/b_o \times$ 100/ D[4] | $k_{tot}$ (ml/ OT-1 cell/ min)[5] | $k_{cyto}$ (ml/ OT-1 cell/ min)[5] | $CT_{tot}C$ (OT-1 cells/ ml)[6] | $CT_{cyto}C$ (OT-1 cells/ ml)[6] |
|---|---|---|---|---|---|---|---|
| SIINFEKL + IL-2[2] | >90% | 2% | 60% | $6 \times 10^{-10}$ | $3 \times 10^{-8}$ | $5.2 \times 10^5$ | $1.0 \times 10^4$ |

[1]Assessed using a hemocytometer;
[2]Assayed by FACS using MHC-Ik$^b$-SIINFEKL tetramers;
[3]Limiting dilution assay (see Methods);
[4]Incubated in collagen-fibrin gels for 24 h and measured by clonogenic assay (see Methods);
[5]Calculated using Eq. 1 and data reported in this table;
[6]$k_{tot}$ and $k_{cyto}$ calculated by substitution of experimentally-derived values of $b_0$, $b_t$, $p_{tot}$, and $p_{cyto}$, and g into Eq. 1.

TABLE 7

Specific Cytolytic Activity of OT-1$_{cyto}$ cells killing SIINFEKL-B16 cells in collagen-fibrin gels.[1,2]

| [OT-1$_{tot}$ cells] | [OT-1$_{cyto}$ cells] | [SIINFEKL-B16 cells] at t = 0 | % SIINFEKL-B16 cells killed/24 h | [SIINFEKL-B16 cells] after 24 h co-incubation with OT-1$_{cyto}$ cells | No. SIINFEKL-B16 cells killed/24 h | SCA (SIINFEKL-B16 cells/OT-1$_{cyto}$ cell/ml collagen-fibrin gel/24 h) |
|---|---|---|---|---|---|---|
| $10^5$ | $2 \times 10^3$ | $5 \times 10^5$ | 34% | $4.65 \times 10^5$ | $2.39 \times 10^5$ | 119 |
| $10^5$ | $2 \times 10^3$ | $5 \times 10^4$ | 31% | $4.85 \times 10^4$ | $2.19 \times 10^4$ | 10.9 |
| $10^6$ | $2 \times 10^4$ | $5 \times 10^5$ | 66% | $2.39 \times 10^5$ | $4.65 \times 10^5$ | 23.2 |
| $10^6$ | $2 \times 10^4$ | $5 \times 10^4$ | 65% | $2.46 \times 10^4$ | $4.58 \times 10^4$ | 2.29 |
| $10^7$ | $2 \times 10^5$ | $5 \times 10^5$ | 98% | $7.04 \times 10^3$ | $6.97 \times 10^5$ | 3.48 |
| $10^7$ | $2 \times 10^5$ | $5 \times 10^4$ | 99% | $1.4 \times 10^3$ | $6.9 \times 10^4$ | 0.344 |
| $10^8$ | $2 \times 10^6$ | $5 \times 10^4$ | 99.96% | 28 | $7.037 \times 10^4$ | 0.035 |

[1]Data from Budhu et al. [2010] FIG. 2 & Table S1.
[2]$b_t = 7.04 \times 10^5$ when $b_0 = 5 \times 10^5$, and $7.04 \times 10^4$ when $b_0 = 5 \times 10^4$. $g = 2.84 \times 10^{-4}$/min, $t = 1.44 \times 10^3$ min.

TABLE 8

OT-1 cell killing of established ova-B16 cells in tumors in vivo.

| | Days post OT-1 administration | | | |
|---|---|---|---|---|
| | 0 | 3 | 5 | 7 |
| Number of ova-B16 cells/tumor (control mice)[1] | $2.71 \times 10^7$ | $1.84 \times 10^8$ | $3.8 \times 10^8$ | $5.7 \times 10^8$ |
| Number of ova-B16 cells/tumor (OT-1 inoculated mice)[1] | $2.71 \times 10^7$ | $8.99 \times 10^7$ | $6.38 \times 10^7$ | $4.48 \times 10^7$ |
| Intra-tumoral cytolytic OT-1 cell concentration/gm[1,2] | 0 | $6 \times 10^4$ | $1 \times 10^5$ | $6 \times 10^4$ |

| Days | 0-3 | 3-5 | 5-7 | Average |
|---|---|---|---|---|
| g (per min)[1] | $4.4 \times 10^{-4}$ | $4.4 \times 10^{-4}$ | $4.4 \times 10^{-4}$ | $4.4 \times 10^{-4}$ |
| $k_{tot}$ (ml/OT-1$_{tot}$ cell/min)[3] | $1.11 \times 10^{-10}$ | $1.41 \times 10^{-10}$ | $1.42 \times 10^{-10}$ | $1.31 \times 10^{-10}$ |
| $k_{cyto}$ (ml/OT-1$_{cyto}$ cell/min)[3] | $5.54 \times 10^{-9}$ | $7.03 \times 10^{-9}$ | $7.07 \times 10^{-9}$ | $6.55 \times 10^{-9}$ |
| $CT_{tot}C$ (OT-1$_{tot}$ cells/ml)[4] | $4.01 \times 10^6$ | $3.15 \times 10^6$ | $3.13 \times 10^6$ | $3.43 \times 10^6$ |
| $CT_{cyto}C$ (OT-1$_{cyto}$ cells/ml)[4] | $8.0 \times 10^4$ | $6.31 \times 10^4$ | $6.27 \times 10^4$ | $6.86 \times 10^4$ |

[1]Values were obtained from Petersen et al (2006) and Budhu et al. (2010).
[2]Calculated using $p_{cyto} = p_{tot} \times f_c$ ($f_c = 0.02$)
[3]Killing constant ($k_{tot}$ and $k_{cyto}$) calculated using Eq. 1 (Li et al., 2004, Budhu et al., 2010) as described in Materials and methods.
[4]$CT_{tot}C$ and $CT_{cyto}C$ calculated using Eq. 2 CTC = g/k (Li et al., 2004, Budhu et al., 2010)

TABLE 9

Percent of ova-B16 cells killed. Comparing experimental data vs. the values calculated using Eq. 1.

| | Days post OT-1 administration | | |
|---|---|---|---|
| | 3 | 5 | 7 |
| Experimental data[1] | 51% | 83% | 92% |
| Equation Predicted[2] | 57% | 84% | 91% |

[1]Experiment values were calculated using data from Budhu et al. (2010) [FIG. 6]. The percent of ova-B16 cells killed was calculated as described in methods.
[2]Eq. 1 ($b_t = b_0 e^{-kpt+gt}$) was used to predict the number of ova-B16 cells killed at the indicated time points using $k_{cyto} = 6.54 \times 10^{-9}$ ml/OT-1$_{cyto}$ cell/min and $g = 4.4 \times 10^{-4}$/min.
The Pearson correlation coefficient for these two data sets was 0.997 ($R^2 = 0.994$).

TABLE 10

| OT-1 mice immunized with: | Total number of splenocytes/spleen[1] | Number of MHC-Ik$^b$-SIINFEKL tetramer+ cells/spleen[2] | % OT-1$_{cyto}$ cells[3] | $b_t/b_o$ × 100/d[4] | $k_{tot}$ (ml/ OT-1 cell/ min)[5] | $k_{cyto}$ (ml/ OT-1 cell/ min)[5] | $CT_{tot}C$ (OT-1 cells/ ml)[6] | $CT_{cyto}C$ (OT-1 cells/ ml)[6] | No. SIINFEKL-B16 cells killed/ OT-1$_{tot}$ cell/d | No. SIINFEKL-B16 cells killed/ OT-1$_{cyto}$ cell/d |
|---|---|---|---|---|---|---|---|---|---|---|
| A. Effect of co-incubation of 5 × 10$^6$ MHC-Ik$^b$-SIINFEKL tetramer+ OT-1 cells/ml[1], activated by immunization of OT-1 mice with aDEC-205-Ig-ova with or without áCD40-IgG, and 10$^4$ SIINFEKL-B16 cells/ml[1] in collagen-fibrin gels in 1 d. | | | | | | | | | | |
| 1. Saline[7] | 9.1 × 10$^7$ ± SEM | 1.1 × 10$^7$ ± SEM | 0.86% ± SEM | 21% | 2.8 × 10$^{-11}$ | 3.1 × 10$^{-9}$ | 1.3 × 10$^7$ | 1.2 × 10$^5$ | 0.00315 ± SEM | 0.366 ± SEM |
| 2. α-DEC205-IgG-ova[7] | 1.1 × 10$^8$ ± SEM | 1.3 × 10$^7$ ± SEM | 1.9% ± SEM | 44% | 7.3 × 10$^{-11}$ | 3.8 × 10$^{-9}$ | 4.8 × 10$^6$ | 9.1 × 10$^4$ | 0.00366 ± SEM | 0.355 ± SEM |
| 3. α-DEC205-IgG-ova + α-CD40-IgG[7] | 1.3 × 10$^8$ ± SEM | 2.1 × 10$^7$ ± SEM | 2.4% ± SEM | 74% | 1.6 × 10$^{-10}$ | 6.7 × 10$^{-9}$ | 2.2 × 10$^6$ | 5.2 × 10$^4$ | 0.011 ± SEM | 0.472 ± SEM |
| B. Calculated values for lines 1-3 above for 10$^6$ OT-1 cells/ml[1] co-incubated with 10$^4$ SIINFEKL-B16 cells/ml[1] in collagen-fibrin gels for 24 h.[7] | | | | | | | | | | |
| 1. Saline[8] | 9.1 × 10$^7$ | 1.1 × 10$^7$ | 0.86% | 9% | 6.2 × 10$^{-11}$ | 7.2 × 10$^{-9}$ | 5.6 × 10$^6$ | 4.8 × 10$^4$ | 0.0074 | 0.868 |
| 2. α-DEC205-IgG-ova[8] | 9.1 × 10$^7$ | 1.1 × 10$^7$ | 0.86% | 21% | 1.6 × 10$^{-10}$ | 8.6 × 10$^{-9}$ | 2.1 × 10$^6$ | 4.1 × 10$^4$ | 0.017 | 0.917 |
| 3. α-DEC205-IgG-ova + α-CD40-IgG[8] | 1.1 × 10$^8$ | 1.3 × 10$^7$ | 1.9% | 40% | 3.6 × 10$^{-10}$ | 1.5 × 10$^{-8}$ | 9.7 × 10$^5$ | 2.3 × 10$^4$ | 0.055 | 1.38 |

[1] Assessed using a hemocytometer;
[2] Assayed by FACS using MHC-Ik$^b$-SIINFEKL;
[3] Limiting dilution assay (see Methods);
[4] Incubated in collagen-fibrin gels and measured by clonogenic assay (see Methods);
[5] Values of $k_{total}$ and $k_{cytolytic}$ calculated by substitution of experimentally-derived values of $p_{total}$, $p_{cytolytic}$, $b_0$, $b_t$ and g into Eq. 1;
[6] Calculated using Eq. 2, CTC = g/k
[7] k for 10$^6$ OT-1 ml at the $f_c$ OT-1 cells indiciated in Fig. ??
[8] N = 3.

TABLE 11

Killing of 10$^5$ SIINFEKL-B16 cells/ml[1] by 10$^6$ OT-1 cells/ml[1], activated and maintained in medium containing IL-2, IL21, or IL12, with or without áCD40-IgG, for 24 h in collagen-fibrin gels.

| Activation & expansion stimuli | No. tetramer+ cells/ culture[4] | % OT-1$_{cyto}$ cells[5] | $b_t/b_o$ × 100/d[6] | $k_{tot}$ (ml/ OT-1 cell/ min)[7] | $k_{cyto}$ (ml/ OT-1 cell/ min)[7] | $CT_{tot}C$ (OT-1 cells/ ml)[8] | $CT_{cyto}C$ (OT-1 cells/ ml)[8] | Total No. SIINFEKL-B16 cells killed per 24 h | No. SIINFEKL-B16 cells killed/ OT-1$_{tot}$ cell/d | No. SIINFEKL-B16 cells killed/ OT-1$_{cyto}$ cell/d |
|---|---|---|---|---|---|---|---|---|---|---|
| 1. SIINFEKL + IL-2[2] | >90% | 2% | 60% | 6 × 10$^{-10}$ | 3 × 10$^{-8}$ | 5.2 × 10$^5$ | 1.0 × 10$^4$ | 4,399 | 0.044 | 2.19 |
| 2. SIINFEKL + IL-21[2] | >90% | 2.2% | 72.2% | 7.9 × 10$^{-10}$ | 3.6 × 10$^{-8}$ | 3.9 × 10$^5$ | 8.6 × 10$^3$ | 5,591 | 0.053 | 2.4 |
| 3. SIINFEKL + IL-2 + α-CD40-IgG[2] | >90% | 2.37% | 63.7% | 7.9 × 10$^{-10}$ | 3.0 × 10$^{-8}$ | 6.7 × 10$^5$ | 1.0 × 10$^4$ | 4,863 | 0.048 | 2.05 |
| 4. SIINFEKL + IL-21 + α-CD40-IgG[2] | >90% | 2.5% | 67.5% | 7.9 × 10$^{-10}$ | 3.1 × 10$^{-8}$ | 6.7 × 10$^5$ | 9.7 × 10$^3$ | 5,157 | 0.051 | 2.06 |
| 5. SIINFEKL + IL-12[3] | >90% | 2.56 | 80% | 1.1 × 10$^{-9}$ | 4.4 × 10$^{-8}$ | 2.8 × 10$^5$ | 7.2 × 10$^3$ | 7,400 | 0.074 | 2.88 |

[1] Assessed using a hemocytometer;
[2] N = 3;
[3] N = 1;
[4] Assayed by FACS using MHC-Ik$^b$-SIINFEKL tetramers;
[5] Limiting dilution assay (see Methods);
[6] Incubated in collage-fibrin gels for 24 h and measured by clonogenic assay (see Methods);
[7] Calculated using Eq. 1 and data reported in this table;
[8] $k_{tot}$ calculated by substitution of experimentally-derived values of $b_0$, $b_t$, $p_{tot}$, and g from Petersen et al. (2006) into Eq. 1. $k_{cyto} = k_{tot}/2 × 10^{-2}$. $p_{cyto} = p_{tot} × 2 × 10^{-2}$ SUPPLEMENT TO TABLE 11
Effect of co-incubation of $5 \times 10^6$ MHC-Ik$^b$-SIINFEKL tetramer+ OT-1 cells/ml[1], activated by immunization of OT-1 mice with áDEC-205-Ig-ova with or without áCD40-IgG, with $10^4$ SIINFEKL-B16 cells/ml[1] in collagen-fibrin gels at 37° C. for 1 d.

| OT-1 mice immunized with: | % cytolytically active OT-1 cells[3] | $b_t$ (without OT-1 cells) | $b_t$ (with OT-1 cells) | % B16 cells killed ([$b_t$-$b_0$) | No. B16 cells killed ($b_t$ × % killed) | No. OT-$1_{total}$ cells | No. OT-$1_{cytolytic}$ cells | No B16 cells killed/OT-$1_{total}$ cells | No B16 cells killed/OT-$1_{cytolytic}$ cells |
|---|---|---|---|---|---|---|---|---|---|
| 1. Saline[7] | 0.86% | $7.5 \times 10^3$ | $5.925 \times 10^3$ | 21% | 1,575 | $5 \times 10^5$ | 4,300 | 0.00315 | 0.366 |
| 2. α-DEC205-IgG-ova[7] | 1.9% | $7.5 \times 10^3$ | $4.196 \times 10^3$ | 44% | 3,304 | $5 \times 10^5$ | 9,500 | 0.0066 | 0.355 |
| 3. α-DEC205-IgG-ova + α-CD40-IgG[7] | 2.4% | $7.5 \times 10^3$ | $1.95 \times 10^3$ | 74% | 5,550 | $5 \times 10^5$ | 12,000 | 0.011 | 0.472 |

TABLE 12

CD8, Granzyme B and Perforin expression by OT-1 spleen cells cultured in IL-2 vs. IL-21 +/− α-CD40-IgG.

| | % CD8+ | % Granzyme B+ | % Perforin+ |
|---|---|---|---|
| SIINFEKL + IL-2[1] | 96% | 16.9% | 14.4% |
| SIINFEKL + IL-2 + α-CD40-IgG[1] | 89% | 18.5% | 12.3% |
| SIINFEKL + IL-21[1] | 91% | 45.4% | 35.3% |
| SIINFEKL + IL-21 + α-CD40-IgG[1] | 87.5% | 53.2% | 40.8% |

[1]=90% of CD8+ T-cells were MHC-Ik$^b$-SIINFEKL tetramer+.

SUPPLEMENT TO TABLE 12
Effect of co-incubation of $10^6$ OT-1 cells/ml1, activated and maintained in vitro in medium containing IL-2, IL-21, or IL-12, with or without αCD40-IgG, with $10^5$ SIINFEKL-B16 cells/ml1 at 37° C. for 1 d in collagen-fibrin gels.

| OT-1 mice immunized with: | % cyt-active OT-1 cells[3] | $b_t$ (without OT-1 cells) | $b_t$ (with OT-1 cells) | % B16 cells killed ($b_t$-$b_0$) | No. B16 cells killed ($b_t$ × % killed) | No. OT-$1_{total}$ cells | No. OT-$1_{cytolytic}$ cells | No B16 cells killed/OT-$1_{total}$ cells | No SIINFEKL-B16 cells killed/OT-$1_{cytolytic}$ cell |
|---|---|---|---|---|---|---|---|---|---|
| 4. SIINFEKL + IL-2[7] | 2% | $7.331 \times 10^3$ | $2.932 \times 10^3$ | 60% | $4.399 \times 10^3$ | $10^5$ | $2 \times 10^3$ | 0.0219 | 2.19 |
| 5. SIINFEKL + IL-21[7] | 2.2% | $7.331 \times 10^3$ | $2.04 \times 10^3$ | 72.2% | $5.291 \times 10^3$ | $10^5$ | $2.2 \times 10^3$ | 0.024 | 2.4 |
| 7. SIINFEKL + IL-2 + α-CD40-IgG[7] | 2.37% | $7.638 \times 10^3$ | $2.775 \times 10^3$ | 63.7% | $4.863 \times 10^3$ | $10^5$ | $2.37 \times 10^3$ | 0.0205 | 2.05 |
| 8. SIINFEKL + IL-21 + α-CD40-IgG[7] | 2.5% | $7.638 \times 10^3$ | $2.481 \times 10^3$ | 67.5% | $5.157 \times 10^3$ | $10^5$ | $2.5 \times 10^3$ | 0.0206 | 2.06 |

TABLE 13

Concentrations and $f_c$ OT-1 cells to control growth of, and to eradicate, ova-peptide expressing B16 cells in collagen-fibrin gels and in melanomas in vivo.

| | Collagen-fibrin gels | | | Melanomas in vivo | | |
|---|---|---|---|---|---|---|
| | OT-$1_{tot}$ cells/ml | $f_c$ | $k_{cyto}$ | OT-$1_{tot}$ cells/ml | $f_c$ | $k_{cyto}$ |
| CT$_{tot}$C OT-1 cells @ $f_c$ shown | $10^6$ | 1.7% | $2 \times 10^{-8}$ | $10^6$ | 5% | $6.44 \times 10^{-9}$ |

TABLE 13-continued

Concentrations and $f_c$ OT-1 cells to control growth of, and to eradicate, ova-peptide expressing B16 cells in collagen-fibrin gels and in melanomas in vivo.

| | Collagen-fibrin gels | | | Melanomas in vivo | | |
|---|---|---|---|---|---|---|
| | OT-1$_{tot}$ cells/ml | $f_c$ | $k_{cyto}$ | OT-1$_{tot}$ cells/ml | $f_c$ | $k_{cyto}$ |
| [OT-1$_{tot}$ cell] required to yield sterilizing immunity vs. $3 \times 10^8$ antigen-expressing B16 cells | $10^7$ | 2% | $8.5 \times 10^{-9}$ | $10^7$ | 2.6% | $1.95 \times 10^{-9}$ |

TABLE 14

Values of $k_{cyto}$ and $CT_{cyto}C$ for in vitro-activated OT-1$_{tot}$ cells killing SIINFEKL-B16 cells in collagen-fibrin gels and ova-B16 cells in 8 d established tumors.

| | $CT_{tot}C$ (OT-1$_{tot}$ cells/ml) | $CT_{cyto}C$ (OT-1$_{cyto}$ cells/ml) | Ratio of $CT_{tot}C/CT_{cyto}C$ | $k_{tot}$ (ml/OT-1 cell/min) | $k_{cyto}$ (ml/OT-1 cell/min) | Ratio of $k_{cyto}/k_{tot}$ |
|---|---|---|---|---|---|---|
| 1. In vitro activated OT-1 cells killing SIINFEKL-B16 cells in collagen-fibrin gels[1] | $3.5 \times 10^5$ | $7.0 \times 10^3$ | 50.6 | $8.1 \times 10^{-10}$ | $4.1 \times 10^{-8}$ | 50 |
| 2. In vitro activated OT-1 killing ova-B16 cells in tumors in vivo[2] | $2.9 \times 10^6$ | $5.9 \times 10^4$ | 51.6 | $8.9 \times 10^{-11}$ | $4.6 \times 10^{-9}$ | 49.1 |
| 3. Ratio $CTC_{in\ vivo}/CTC_{in\ vitro}$ | 8.2 | 8.4 | N.A.[3] | N.A. | N.A. | N.A. |
| 4. Ratio $k_{in\ vitro}/k_{in\ vivo}$ | N.A.[3] | N.A. | N.A. | 9.1 | 8.9 | N.A. |

[1]Calculated using values of $CT_{tot}C$ and $k_{tot}$ from Budhu et al. (2010), FIG. 2 and $g = 2.84 \times 10^{-4}$/min.
[2]Calculated as described in the text using average values of $CT_{tot}C$ and $k_{tot}$, from Budhu et al. (2010), Table S4 and $g = 2.7 \times 10^{-4}$/min.
[3]N.A. = not applicable

TABLE 15

Number of spleen cells from unimmunized, α-DEC205-IgG-ova immunized, and α-DEC205-IgG-ova and α-CD40-IgG immunized OT-1 mice required to yield $5 \times 10^5$ MHC-Ik$^b$ tetramer+ OT-1 cells

| Immunization protocol | Ratio of tetramer+ OT-1 spleen cells per spleen/total number of OT-1 splenocytes per spleen[1] | Number of OT-1 mouse spleen cells required to yield $5 \times 10^5$ tetramer+ OT-1 cells |
|---|---|---|
| Control = Saline | 0.12 | $4.165 \times 10^6$ |
| α-DEC205-IgG-ova | 0.118 | $4.235 \times 10^6$ |
| α-DEC205-IgG-ova + α-CD40-IgG | 0.16 | $3.1 \times 10^6$ |

[1]Data from Table I.

TABLE 16

Number of spleen cells from unimmunized, α-DEC205-IgG-ova immunized, and α-DEC205-IgG-ova and α-CD40-IgG immunized OT-1 mice required to yield $5 \times 10^5$ MHC-Ik$^b$ tetramer+ OT-1 cells

| Immunization protocol | Ratio of tetramer+ OT-1 spleen cells per spleen/total number of OT-1 splenocytes per spleen[1] | Number of OT-1 mouse spleen cells required to yield $5 \times 10^5$ tetramer+ OT-1 cells |
|---|---|---|
| Control = Saline | 0.12 | $4.165 \times 10^6$ |
| α-DEC205-IgG-ova | 0.118 | $4.235 \times 10^6$ |
| α-DEC205-IgG-ova + α-CD40-IgG | 0.16 | $3.1 \times 10^6$ |

[1]Data from Table I.

TABLE 17

Tumor leukocytes and stromal cells inhibit OT-1 cell mediated killing of YFP-ova-B16 cells from dissociated tumors in col-fbn gels.

| | cfu/ml of YFP-ova-B16 cells recovered on: | | |
|---|---|---|---|
| Contents of col-fbn gels | day = 0 | day = 1 | day = 3 |
| 1. $10^6$/ml gel cell culture-derived YFP-ova-B16 cells | $3 \times 10^5$ | $5.5 \times 10^5$ | $1.7 \times 10^6$ |

TABLE 17-continued

Tumor leukocytes and stromal cells inhibit OT-1 cell mediated killing of YFP-ova-B16 cells from dissociated tumors in col-fbn gels.

| Contents of col-fbn gels | cfu/ml of YFP-ova-B16 cells recovered on: | | |
|---|---|---|---|
| | day = 0 | day = 1 | day = 3 |
| 2. $10^6$/ml gel cell culture-derived YFP-ova-B16 cells + $10^6$/ml OT-1 cells | $3 \times 10^5$ | $2.64 \times 10^5$ | $3 \times 10^6$ |
| % cell culture-derived YFP-ova B16 cells killed (Line 2/Line1) | 0% | 52% | 75% |
| Values of g, $k_{tot}$ & $CT_{tot}C$ = $3.84 \times 10^{-4}$/min, $3.17 \times 10^{-10}$ ml/OT-1 cell/min & $1.2 \times 10^6$ OT-1 cells/ml, respectively. | | | |
| 3. $10^6$/ml gel tumor-derived cells | $4.3 \times 10^4$ | $9.5 \times 10^4$ | $1.9 \times 10^5$ |
| 4. $10^5$/ml gel tumor-derived cells + $10^5$/ml OT-1 cells | $4.3 \times 10^4$ | $6.4 \times 10^4$ | $1.18 \times 10^5$ |
| % YFP-ova B16 cells killed (Line 4/Line3) | 0% | 33% | 38% |
| Values of g, $k_{tot}$ & $CT_{tot}C$ = $3.26 \times 10^{-4}$/min, $9.78 \times 10^{-11}$ ml/OT-1 cell/min & $3.3 \times 10^6$ OT-1 cells/ml, respectively. | | | |

TABLE 18

Activated OT-1 cells kill growing and non-growing SIINFEKL-pulsed B16 cells with approximately equal efficiency.

| | $10^4$ B16 cells ml$^{-1}$ | | $10^5$ B16 cells ml$^{-1}$ | | $10^5$ B16 cells ml$^{-1}$ | | |
|---|---|---|---|---|---|---|---|
| | Growing | Non-growing | Growing | Non-growing | Growing | Non-growing | Average |
| $10^4$ OT-1 | 9 ± 3 | 11 ± 3 | 14 ± 4 | 10 ± 4 | 14 ± 1 | 14 ± 1 | 12 ± 2 |
| $10^5$ OT-1 | 27 ± 7 | 26 ± 4 | 31 ± 5 | 30 ± 3 | 34 ± 4 | 31 ± 4 | 30 ± 3 |
| $10^6$ OT-1 | 65 ± 6 | 64 ± 6 | 65 ± 1 | 61 ± 7 | 66 ± 6 | 61 ± 6 | 62 ± 2 |
| $10^7$ OT-1 | 98 ± 2 | 97 ± 1 | 99 ± 1 | 98 ± 1 | 98 ± 1 | 97 ± 1 | 98 ± 1 |

Killing efficiencies from FIG. 2 and data not shown at the indicated OT-1 and B16 concentrations.
Values represent the average percent B16 killed ± SEM at t = 24 from three experiments performed in duplicates.

TABLE 19

| Percent $10^5$/ml SIINFEKL-B16 cells killed by: | | | |
|---|---|---|---|
| Hours incubated with SIINFEKL-B16 | $10^6$/ml OT-1 cells | $10^7$/ml OT-1 cells | $10^8$/ml OT-1 cells |
| 24 hr | 74% | 95% | 99.96% |
| 48 hr | 94% | ND | 100% |
| 72 hr | 98.4% | 100% | ND |
| 96 hr | 99.4% | ND | 100% |
| 120 hr | 99.84% | 100% | ND |

TABLE 20

OT-1 cell concentration determines efficiency of killing of SIINFEKL-B16 cells

| *No. B16 cells added | Packed volume B16 cells | No. OT-1 cells added | Packed volume OT-1 cells | No. splenocytes added | Packed volume splenocytes | Packed volume all cells | OT-1:B16 cell ratio | OT-1 cell concentration | % B16 cells killed |
|---|---|---|---|---|---|---|---|---|---|
| $2 \times 10^4$ | 49.4 nl | $10^5$ | 16.4 nl | $8.9 \times 10^5$ | 197.6 nl | 263.4 nl | 5:1 | $2.4 \times 10^9$ | ~18% |
| $4 \times 10^4$ | 98.8 nl | $10^5$ | 16.4 nl | $6.7 \times 10^5$ | 148.2 nl | 263.4 nl | 2.5:1 | $2.4 \times 10^9$ | ~18% |
| $10^5$ | 247 nl | $10^5$ | 16.4 nl | 0 | 0 | 263.4 nl | 1:1 | $2.4 \times 10^9$ | ~18% |

*All B16 cells used in this experiment were pulsed with SIINFEKL peptide.

TABLE 21

Inverse relationship between OT-1 cell concentration and the efficiency with which OT-1 cells kill SIINFEKL-B16 cells.

| | | | |
|---|---|---|---|
| SIINFEKL-B16 concentration | $10^7$ | $10^7$ | $10^7$ |
| OT-1 concentration | $10^6$ | $10^7$ | $10^8$ |
| % SIINFEKL-B16 killed/24 hr | 70% | 95% | 99.9% |
| Number of SIINFEKL-B16 killed/OT-1 cell | 7 | 0.95 | 0.099 |
| Critical OT-1 Concentration | $1.1 \times 10^5$ | $4.2 \times 10^5$ | $4.2 \times 10^6$ |

TABLE 22

| OT-1 mice immunized with: | Total number of splenocytes/ spleen[1] | Number of MHC-IK$^b$- SIINFEKL tetra- mer+ cells/ spleen[2] | % OT-1$_{cyto}$ cells[3] | $b_f/b_o \times$ 100/ d[4] | $k_{tol}$ (ml/ OT-1 cell/ min)[5] | $k_{cyto}$ (ml/ OT-1 cell/ min)[5] | $CT_{tot}C$ (OT-1 cells/ ml)[6] | $CT_{cyto}C$ (OT-1 cells/ ml)[6] | No. SIINFEKL- B16 cells killed/ OT-1$_{tot}$ cell/d | No. SIINFEKL- B16 cells killed/ OT-1$_{cyto}$ cell/d |
|---|---|---|---|---|---|---|---|---|---|---|
| A. Effect of co-incubation of $5 \times 10^6$ MHC-Ikb-SIINFEKL tetramer+ OT-1 cells/ml, activated by immunization of OT-1 mice with αDEC-205-Ig-ova with or without αCD40-IgG, and $10^4$ SIINFEKL-B16 cells/ml in collagen-fibrin gels in 1 day. | | | | | | | | | | |
| 1. Saline[7] | $9.1 \times 10^7 \pm$ SEM | $1.1 \times 10^7 \pm$ SEM | 0.86% ± SEM | 21% | $2.8 \times 10^{-11}$ | $3.1 \times 10^{-4}$ | $1.3 \times 10^7$ | $1.2 \times 10^5$ | 0.00315 ± SEM | 0.366 ± SEM |
| 2. α-DEC205- IgG-ova[7] | $1.1 \times 10^8 \pm$ SEM | $1.3 \times 10^7 \pm$ SEM | 1.9% ± SEM | 44% | $7.3 \times 10^{-11}$ | $3.8 \times 10^{-3}$ | $4.8 \times 10^6$ | $9.1 \times 10^4$ | 0.00366 ± SEM | 0.355 ± SEM |
| 3. α-DEC205- IgG-ova + α-CD40-IgG[7] | $1.3 \times 10^8 \pm$ SEM | $2.1 \times 10^7 \pm$ SEM | 2.4% ± SEM | 74% | $1.6 \times 10^{-10}$ | $6.7 \times 10^{-3}$ | $2.2 \times 10^6$ | $5.2 \times 10^4$ | 0.011 ± SEM | 0.472 ± SEM |
| B. Calculated values for lines 1-3 above for $10^6$ OT-1 cells/ml[1] co-incubated with $10^4$ SIINFEKL-B16 cells/ml[1] in collagen-fibrin gels for 24 h.[7] | | | | | | | | | | |
| 1. Saline[8] | $9.1 \times 10^7$ | $1.1 \times 10^7$ | 0.86% | 9% | $6.2 \times 10^{-11}$ | $7.2 \times 10^{-5}$ | $5.6 \times 10^6$ | $4.8 \times 10^4$ | 0.0074 | 0.868 |
| 2. α-DEC205- IgG-ova[8] | $9.1 \times 10^7$ | $1.1 \times 10^7$ | 1.9% | 21% | $1.6 \times 10^{-10}$ | $8.6 \times 10^{-4}$ | $2.1 \times 10^6$ | $4.1 \times 10^4$ | 0.017 | 0.917 |
| 3. α-DEC205- IgG-ova + α-CD40-IgG[8] | $1.1 \times 10^8$ | $1.3 \times 10^7$ | 2.4% | 40% | $3.6 \times 10^{-10}$ | $1.5 \times 10^{-8}$ | $9.7 \times 10^5$ | $2.3 \times 10^4$ | 0.055 | 1.38 |

[1]Assessed using a hemocytometer;
[2]Assayed by FACS using MHC-Ik$^b$-SIINFEKL;
[3]Limiting dilution assay (see Methods);
[4]Incubated in collagen-fibrin gels and measured by clonogenic assay (see Methods;
[5]Values of $k_{total}$ and $k_{cytolytic}$ calculated by substitution of experimentally-derived values of $p_{total}$, $p_{cytolytic}$, $b_o$, $b_c$ and g into Eq. 1.
[6]Calculated using Eq. 2, CTC = g/k
[7]k for $10^6$ OT-1/ml at the $f_e$ OT-1 cells
[8]N = 3.

TABLE 23

| OT-1 mice immunized with: | Total number of splenocytes/ spleen[1] | Number of MHC-IK$^b$- SIINFEKL tetra- mer+ cells/ spleen[2] | % OT-1$_{cyto}$ cells[3] | $b_f/b_o \times$ 100/ d[4] | $k_{tol}$ (ml/ OT-1 cell/ min)[5] | $k_{cyto}$ (ml/ OT-1 cell/ min)[5] | $CT_{tot}C$ (OT-1 cells/ ml)[6] | $CT_{cyto}C$ (OT-1 cells/ ml)[6] | No. SIINFEKL- B16 cells killed/ OT-1$_{tot}$ cell/d[8] | No. SIINFEKL- B16 cells killed/ OT-1$_{cyto}$ cell/d[8] |
|---|---|---|---|---|---|---|---|---|---|---|
| A. Effect of co-incubation of $5 \times 10^6$ MHC-Ik$^b$-SIINFEKL tetramer+ OT-1 cells/ml[1], activated by immunization of OT-1 mice with αDEC-205-Ig-ova with or without αCD40-IgG, and $10^4$ SIINFEKL-B16 cells/ml[1] in collagen-fibrin gels in 1 d. | | | | | | | | | | |
| 1. Saline[8] | $9.1 \pm 2.2 \times 10^7$ | $1.1 \pm 0.47 \times 10^7$ | 0.86% ± 0.05% | 21% | $2.8 \times 10^{-11}$ | $3.1 \times 10^{-9}$ | $1.3 \times 10^7$ | $1.2 \times 10^5$ | $2.96 \times 10^{-3} \pm$ 0.0011 | 0.034 ± 0.141 |
| 2. α-DEC205- IgG-ova[8] | $1.1 \pm 0.14 \times 10^8$ | $1.3 \pm 0.3 \times 10^7$ | 1.9% ± 0.03% | 44% | $7.3 \times 10^{-11}$ | $3.8 \times 10^{-9}$ | $4.8 \times 10^6$ | $9.1 \times 10^4$ | $6.2 \times 10^{-3} \pm$ 0.0019 | 0.033 ± 0.091 |
| 3. α-DEC205- IgG-ova + α-CD40-IgG[8] | $1.3 \pm 0.1 \times 10^8$ | $2.1 \pm 0.56 \times 10^7$ | 2.4% ± 0.04% | 74% | $1.6 \times 10^{-10}$ | $6.7 \times 10^{-9}$ | $2.2 \times 10^6$ | $5.2 \times 10^4$ | $1.04 \times 10^{-3} \pm$ 0.0027 | 0.043 ± 0.096 |

TABLE 23-continued

| OT-1 mice immunized with: | Total number of splenocytes/ spleen[1] | Number of MHC-IK$^b$-SIINFEKL tetra-mer+ cells/ spleen[2] | % OT-1$_{cyto}$ cells[3] | $b_t/b_o$ × 100/ d[4] | $k_{tot}$ (ml/ OT-1 cell/ min)[5] | $k_{cyto}$ (ml/ OT-1 cell/ min)[5] | $CT_{tot}C$ (OT-1 cells/ ml)[6] | $CT_{cyto}C$ (OT-1 cells/ ml)[6] | No. SIINFEKL-B16 cells killed/ OT-1$_{tot}$ cell/d[8] | No. SIINFEKL-B16 cells killed/ OT-1$_{cyto}$ cell/d[8] |
|---|---|---|---|---|---|---|---|---|---|---|
| B. Calculated values for lines 1-3 above for 10$^6$ OT-1 cells/ml[1] co-incubated with 10$^5$ SIINFEKL-B16 cells/ml[1] in collagen-fibrin gels for 24 h.[7] | | | | | | | | | | |
| 1. Saline[8] | 9.1 × 10$^7$ | 1.1 × 10$^7$ | 0.86% | 9% | 6.2 × 10$^{-11}$ | 7.2 × 10$^{-9}$ | 5.6 × 10$^6$ | 4.8 × 10$^4$ | 6.3 × 10$^{-3}$ | 0.73 |
| 2. α-DEC205-IgG-ova[8] | 1.1 ± 0.14 × 10$^8$ | 1.3 ± 0.3 × 10$^7$ | 1.9% ± 0.03% | 21% | 1.6 × 10$^{-10}$ | 8.6 × 10$^{-9}$ | 2.1 × 10$^6$ | 4.1 × 10$^4$ | 1.5 × 10$^{-4}$ | 0.78 |
| 3. α-DEC205-IgG-ova + α-CD40-IgG[8] | 1.3 ± 0.1 × 10$^8$ | 2.1 ± 0.56 × 10$^7$ | 2.4% ± 0.04% | 40% | 3.6 × 10$^{-10}$ | 1.5 × 10$^{-8}$ | 9.7 × 10$^5$ | 2.3 × 10$^4$ | 2.8 × 10$^{-4}$ | 1.17 |

[1]Assessed using a hemocytometer;
[2]Assayed by FACS using MHC-Ik$^b$-SIINFEKL;
[3]Limiting dilution assay (see Methods);
[4]Incubated in collagen-fibrin gels and measured by clonogenic assay (see Methods);
[5]Values of $k_{total}$ and $k_{cytolytic}$ calculated by substitution of experimentally-derived values of $p_{total}$, $p_{cytolytic}$, $b_0$, $b_t$ and g into Eq. 1;
[6]Calculated using Eq. 2, CTC = g/k
[7]k for 10$^6$ OT-1/ml at the $f_c$ OT-1 cells.
[8]Data represent the average value ± SEM for N = 3 experiments performed in duplicate.

TABLE 24

Killing of 10$^5$ SIINFEKL-B16 cells/ml[1] by 10$^6$ OT-1 cells/ml[1], activated and maintained in medium containing IL-2, IL21, or IL12, with or without αCD40-IgG, for 24 h in collagen-fibrin gels.

| Activation & expansion stimuli | No. tetra-mer+ cells/ culture[4] | % OT-1$_{cyto}$ cells[5] | $b_t/b_o$ × 100/ d[6] | $k_{tot}$ (ml/ OT-1 cell/ min)[7] | $k_{cyto}$ (ml/ OT-1 cell/ min)[7] | $CT_{tot}C$ (OT-1 cells/ ml)[8] | $CT_{cyto}C$ (OT-1 cells/ ml)[8] | Total No. SIINFEKL-B16 cells killed/ml gel/24 h | SCA = No. SIINFEKL-B16 cells killed/ OT-1$_{tot}$ cell/d | SCA = No. SIINFEKL-B16 cells killed/ OT-1$_{cyto}$ cell/d |
|---|---|---|---|---|---|---|---|---|---|---|
| 1. SIINFEKL + IL-2[2] | >90% | 2% | 60% | 6 × 10$^{-10}$ | 3 × 10$^{-8}$ | 5.2 × 10$^5$ | 1.0 × 10$^4$ | 42,200 | 0.042 | 2.11 |
| 2. SIINFEKL + IL-21[2] | >90% | 2.2% | 72.2% | 7.9 × 10$^{-10}$ | 3.6 × 10$^{-8}$ | 3.9 × 10$^5$ | 8.6 × 10$^3$ | 50,800 | 0.050 | 2.3 |
| 3. SIINFEKL + IL-2 + α-CD40-IgG[2] | >90% | 2.37% | 63.7% | 7.9 × 10$^{-10}$ | 3.0 × 10$^{-8}$ | 6.7 × 10$^5$ | 1.0 × 10$^4$ | 44,900 | 0.045 | 1.89 |
| 4. SIINFEKL + IL-21 + α-CD40-IgG[2] | >90% | 2.5% | 67.5% | 7.9 × 10$^{-10}$ | 3.1 × 10$^{-8}$ | 6.7 × 10$^5$ | 9.7 × 10$^3$ | 47,500 | 0.047 | 1.9 |
| 5. SIINFEKL + IL-12[3] | >90% | 2.56 | 80% | 1.1 × 10$^{-9}$ | 4.4 × 10$^{-8}$ | 2.8 × 10$^5$ | 7.2 × 10$^3$ | 56,320 | 0.056 | 2.2 |

[1]Assessed using a hemocytometer;
[2]N = 3;
[3]N = 1;
[4]Assayed by FACS using MHC-Ik$^b$-SIINFEKL tetramers;
[5]Limiting dilution assay (see Methods);
[6]Incubated in collage-fibrin gels for 24 h and measured by clonogenic assay (see Methods);
[7]Calculated using Eq. 1 and data reported in this table;
[8]$k_{tot}$ and $k_{cyto}$ calculated by substitution of experimentally-derived values of $b_0$, $b_t$, $p_{tot}$, and $p_{cyto}$, and g into Eq. 1.

TABLE 25

Estimated concentration of OT-1 cells required to eradicate $3 \times 10^8$ SIINFEKL-B16 cells/ml collagen-fibrin gel in 24 h.

| | $k_{cytolytic} = 2 \times 10^{-8}$ | | | | $k_{cytolytic} = 2 \times 10^{-7}$ | | | |
|---|---|---|---|---|---|---|---|---|
| | $f_c = 2\%$ | | $f_c = 10\%$ | | $f_c = 2\%$ | | $f_c = 10\%$ | |
| [OT-$1_{total}$] per ml | [OT-$1_{cytolytic}$] per ml | % of $3 \times 10^8$/ml B16 cells killed/d | [OT-$1_{cytolytic}$] per ml | % of $3 \times 10^8$/ml B16 cells killed/d | [OT-$1_{cytolytic}$] per ml | % of $3 \times 10^8$/ml B16 cells killed/d | [OT-$1_{cytolytic}$] per ml | % of $3 \times 10^8$/ml B16 cells killed/d |
| $10^6$ | $2 \times 10^4$ | 13.7% | $10^5$ | 91.4% | $2 \times 10^4$ | 99.5% | $10^5$ | 100% |
| $2 \times 10^6$ | $4 \times 10^4$ | 51.3% | $10^5$ | 99.5% | $4 \times 10^4$ | 99.998% | $2 \times 10^5$ | 100% |
| $4 \times 10^6$ | $8 \times 10^4$ | 84.6% | $10^5$ | 99.998% | $8 \times 10^4$ | 100% | $4 \times 10^5$ | 100% |
| $6 \times 10^6$ | $1.2 \times 10^5$ | 95.1% | $10^5$ | 99.999995% | $1.2 \times 10^5$ | 100% | $6 \times 10^5$ | 100% |
| $7 \times 10^6$ | $1.4 \times 10^5$ | 97.3% | $10^5$ | 100% | $1.4 \times 10^5$ | 100% | $7 \times 10^5$ | 100% |

Calculated using Eq. 1 and $g = 3 \times 10^{-4}$ min$^{-1}$; $b_t$ @ 24 h in the absence of OT-1 cells = $4.6 \times 10^8$ B16 cells/ml

TABLE 26

Ratio of $k_{total}$, $k_{cytolytic}$, $CT_{total}C$, $CT_{cytolytic}C$, and Specific Cytotoxic Activities of OT-$1_{cytolytic}$ cells elicited by immunization in vitro vs. in vivo.

| | $k_{total}$ (ml/ OT-1 cell/ min)$^5$ | $k_{cytolytic}$ (ml/ OT-1 cell/ min)$^5$ | $CT_{total}C$ (OT-1 cells/ ml)$^6$ | $CT_{cytolytic}C$ (OT-1 cells/ ml)$^6$ | No. SIINFEKL-B16 cells killed/ OT-$1_{total}$ cell/d | No. SIINFEKL-B16 cells killed/ OT-$1_{cytolytic}$ cell/d |
|---|---|---|---|---|---|---|
| 1. In vitro (antigen alone) | $6 \times 10^{-10}$ | $3 \times 10^{-8}$ | $5.2 \times 10^5$ | $1.0 \times 10^4$ | 0.044 | 2.19 |
| 2. In vivo (antigen alone) | $7.3 \times 10^{-11}$ | $3.8 \times 10^{-9}$ | $4.8 \times 10^6$ | $9.1 \times 10^4$ | 0.0066 | 0.355 |
| In vitro (1)/in vivo (2) | 8.2 | 7.9 | 0.1 | 0.1 | 6.7 | 6.2 |
| 3. In vitro (antigen + αCD40-IgG) | $7.9 \times 10^{-10}$ | $3.0 \times 10^{-8}$ | $6.7 \times 10^5$ | $1.0 \times 10^4$ | 0.048 | 2.05 |
| 4. In vivo (antigen + α-CD4-IgG) | $1.6 \times 10^{-10}$ | $6.7 \times 10^{-9}$ | $2.2 \times 10^6$ | $5.2 \times 10^4$ | 0.011 | 0.472 |
| In vitro (3)/In vivo (4) | 4.9 | 4.5 | 0.3 | 0.19 | 4.36 | 4.34 |

Documents:

1. Agger, R., M. S. Petersen, C. C. Petersen, S. B. Hansen, H. Stødkilde-Jorgensen, U. Skands, T. Blankenstein, T. E. Andersen, E. F. Hulgaard, J. T. Jorgensen, et al. 2007. T cell homing to tumors detected by 3D-coordinated positron emission tomography and magnetic resonance imaging. *J. Immunother.* 30:29-39. doi:10.1097/01.cji.0000211326.38149.7e 2. Baramova, E. N., P. Coucke, P. Leprince, M. G. De Pauw-Gillet, R. Bassleer, and J. M. Foidart. 1994. Evaluation of matrix metalloproteinases and serine proteases activities in three B16 melanoma cell lines with distinct tumorigenic potential. Anticancer Res. 14:841-846.

3. Blattman, J. N., and P. D. Greenberg. 2006. PD-1 blockade: rescue from a near-death experience. Nat. Immunol. 7:227-228. doi:10.1038/ni0306-227

4. Bronte, V., and S. Mocellin. 2009. Suppressive influences in the immune response to cancer. *J. Immunother.* 32:1-11. doi:10.1097/CJI.0b013e3181837276

5. Brunner, K. T., J. Mauel, J. C. Cerottini, and B. Chapuis. 1968. Quantitative assay of the lytic action of immune lymphoid cells on 51-Cr-labelledallogeneic target cells in vitro; inhibition by isoantibody and by drugs. *Immunology.* 14:181-196.

6. Buckanovich, R. J., A. Facciabene, S. Kim, F. Benencia, D. Sasaroli, K. Balint, D. Katsaros, A. O'Brien-Jenkins, P. A. Gimotty, and G. Coukos. 2008. Endothelin B receptor mediates the endothelial barrier to T cell homing to tumors and disables immune therapy. Nat. Med. 14:28-36. doi: 10.1038/nm1699

7. Cerottini, J. C., H. D. Engers, H. R. Macdonald, and T. Brunner. 1974. Generation of cytotoxic T lymphocytes in vitro. I. Response of normal and immune mouse spleen cells in mixed leukocyte cultures. J. Exp. Med. 140:703-717. doi:10.1084/jem.140.3.703

8. Curtsinger, J. M., D. C. Lins, and M. F. Mescher. 1998. CD8+ memory T cells (CD44high, Ly-6C+) are more sensitive than naive cells to (CD44low, Ly-6C-) to TCR/CD8 signaling in response to antigen. J. Immunol. 160:3236-3243.

9. Daugherty, D. F., T. P. Pretlow, L. M. Peacock, A. M. Pitts, C. E. Mitchell, and T. G. Pretlow II. 1981. Separation and characterization of the neoplastic and stromal elements of the R3230AC mammary adenocarcinoma. Cancer Res. 41:5064-5069.

10. Dewever, J., F. Frérart, C. Bouzin, C. Baudelet, R. Ansiaux, P. Sonveaux, B. Gallez, C. Dessy, and O. Feron. 2007. Caveolin-1 is critical for the maturation of tumor blood vessels through the regulation of both endothelial tube 11. Dobrzanski, M. J., J. B. Reome, and R. W. Dutton. 2001. Immunopotentiating role of IFN-gamma in early and late stages of type 1 CD8 effector cell mediated tumor rejection. *Clin. Immunol.* 98:70-84. doi:10.1006/clim.2000.4945

12. Dudley, M. E., and S. A. Rosenberg. 2003. Adoptive-cell-transfer therapy for the treatment of patients with cancer. *Nat. Rev. Cancer.* 3:666-675. doi:10.1038/nrc1167

13. Dudley, M. E., J. R. Wunderlich, P. F. Robbins, J. C. Yang, P. Hwu, D. J. Schwartzentruber, S. L. Topalian, R. Sherry, N. P. Restifo, A. M. Hubicki, et al. 2002. Cancer regression and autoimmunity in patients after clonal repopulation with antitumor lymphocytes. *Science.* 298:850-854. doi:10.1126/science.1076514

14. Dvorak, H. F., J. A. Nagy, B. Berse, L. F. Brown, K. T. Yeo, T. K. Yeo, A. M. Dvorak, L. van de Water, T. M. Sioussat, and D. R. Senger. 1992. Vascular permeability factor, fibrin, and the pathogenesis of tumor stroma formation. *Ann. N.Y. Acad. Sci.* 667:101-111. doi:10.1111/j.1749-6632.1992.tb51603.x 15. Freedman, V. H., T. E. Gorrell, C. F. Nathan, C. S. Copeland, and S. C. Silverstein. 1984. *Bacillus* Calmette-Guérin-activated murine macrophages kill syngeneic melanoma cells under strict anaerobic conditions. *J. Exp. Med.* 160:94-107. doi:10.1084/jem.160.1.94

16. Grabowska, M. 1959. Collagen content of normal connective tissue, of tissue surrounding a tumour and of growing rat sarcoma. *Nature.* 183:1186-1187. doi:10.1038/1831186a0

17. Hemstreet, G. P. III, P. G. Enoch, and T. G. Pretlow II. 1980. Tissue disaggregation of human renal cell carcinoma with further isopyknic and isokinetic gradient purification. *Cancer Res.* 40:1043-1049.

18. Hofmann, U. B., R. Houben, E.-B. Bröcker, and J. C. Becker. 2005. Role of matrix metalloproteinases in melanoma cell invasion. *Biochimie.* 87:307-314. doi:10.1016/j.biochi.2005.01.013

19. Hogquist, K. A., S. C. Jameson, W. R. Heath, J. L. Howard, M. J. Bevan, and F. R. Carbone. 1994. T cell receptor antagonist peptides induce positive selection. *Cell.* 76:17-27. doi: 10.1016/0092-8674(94)90169-4

20. Hu, F., and P. F. Lesney. 1964. The isolation and cytology of two pigment cell strains from B-16 mouse melanomas. *Cancer Res.* 24:1634-1643.

21. Huang, S.-C., C.-T. Ho, S.-Y. Lin-Shiau, and J.-K. Lin. 2005. Carnosol inhibits the invasion of B16/F10 mouse melanoma cells by suppressing metalloproteinase-9 through down-regulating nuclear factorkappa B and c-Jun. *Biochem. Pharmacol.* 69:221-232. doi:10.1016/j.bcp 0.2004.09.019

22. Joseph-Pietras, D., A. Carlier, C. Madoulet, and P. Albert. 2006. Antitumoural activity of peripheral blood mononuclear cells against melanoma cells: discrepant in-vitro and in-vivo effects. *Melanoma Res.* 16:325-333. doi: 10.1097/01.cmr.0000205016.31235.a9

23. Kataoka, T., N. Shinohara, H. Takayama, K. Takaku, S. Kondo, S. Yonehara, and K. Nagai. 1996. Concanamycin A, a powerful tool for characterization and estimation of contribution of perforin- and Fas-based lytic pathways in cell-mediated cytotoxicity. *J. Immunol.* 156:3678-3686.

24. Kuwashima, Y., T. Yamada, M. Saio, and T. Takami. 1993. Growth characteristics of murine B16 melanoma multicellular spheroids: a model for invasion and effects of doxorubicin treatments. *Anticancer Res.* 13:1215-1217.

25. Le, D. T., P. Borgs, T. W. Toneff, M. H. Witte, and S. I. Rapaport. 1998. Hemostatic factors in rabbit limb lymph: relationship to mechanisms regulating extravascular coagulation. *Am. J. Physiol.* 274:H769-H776.

26. Li, X. H., G. Paulus, G. Atassi, and N. Buyssens. 1984. Growth response of B16 melanoma to in vivo treatment with 1-(2-chloroethyl)-3-cyclohexyl-1-nitrosourea (CCNU) at the initial stage after tumor transplantation. *Am. J. Pathol.* 115:403-411.

27. Li, Y., A. Karlin, J. D. Loike, and S. C. Silverstein. 2002. A critical concentration of neutrophils is required for effective bacterial killing in suspension. *Proc. Natl. Acad. Sci. USA.* 99:8289-8294. doi:10.1073/pnas.122244799

28. Li, Y., A. Karlin, J. D. Loike, and S. C. Silverstein. 2004. Determination of the critical concentration of neutrophils required to block bacterial growth in tissues. *J. Exp. Med.* 200:613-622. doi:10.1084/jem.20040725

29. Lukacher, A. E., J. M. Moser, A. Hadley, and J. D. Altman. 1999. Visualization of polyoma virus-specific CD8+T cells in vivo during infection and tumor rejection. *J. Immunol.* 163:3369-3378.

30. Martz, E. 1975. Early steps in specific tumor cell lysis by sensitized mouse T lymphocytes. I. Resolution and characterization. *J. Immunol.* 115: 261-267.

31. Moore, M. W., F. R. Carbone, and M. J. Bevan. 1988. Introduction of soluble protein into the class I pathway of antigen processing and presentation. *Cell.* 54:777-785. doi: 10.1016/S0092-8674(88) 91043-4

32. Ochalek, T., F. J. Nordt, K. Tullberg, and M. M. Burger. 1988. Correlation between cell deformability and metastatic potential in B16-F1 melanoma cell variants. *Cancer Res.* 48:5124-5128.

33. Petersen, C. C., M. S. Petersen, R. Agger, and M. E. Hokland. 2006. Accumulation in tumor tissue of adoptively transferred T cells: A comparison between intravenous and intraperitoneal injection. *J. Immunother.* 29:241-249. doi: 10.1097/01.cji.0000203078.97493.c3

34. Regoes, R. R., D. L. Barber, R. Ahmed, and R. Antia. 2007. Estimation of the rate of killing by cytotoxic T lymphocytes in vivo. *Proc. Natl. Acad. Sci. USA.* 104:1599-1603. doi:10.1073/pnas.0508830104

35. Snyder, J. E., W. J. Bowers, A. M. Livingstone, F. E. Lee, H. J. Federoff, and T. R. Mosmann. 2003. Measuring the frequency of mouse and human cytotoxic T cells by the Lysispot assay: independent regulation of cytokine secretion and short-term killing. *Nat. Med.* 9:231-235. doi:10.1038/nm821

36. Stephens, T. C., and J. H. Peacock. 1978. Cell yield and cell survival following chemotherapy of the B16 melanoma. *Br. J. Cancer.* 38:591-598.

37. Stuge, T. B., S. P. Holmes, S. Saharan, A. Tuettenberg, M. Roederer, J. S. Weber, and P. P. Lee. 2004. Diversity and recognition efficiency of T cell responses to cancer. *PLoS Med.* 1:e28. doi:10.1371/journal.pmed.0010028

38. Sutherland, R. M. 1988. Cell and environment interactions in tumor microregions: the multicell spheroid model. *Science.* 240:177-184. doi:10.1126/science.2451290

39. Svedman, C., B. B. Yu, T. J. Ryan, and H. Svensson. 2002. Plasma proteins in a standardised skin mini-erosion (I): permeability changes as a function of time. *BMC Dermatol.* 2:3. doi:10.1186/1471-5945-2-3

40. Takeda, Y., and A. Y. Chen. 1967. Studies of the metabolism and distribution of fibrinogen in patients with hemophilia A. *J. Clin. Invest.* 46:1979-1985.

41. Virgin, H. W., E. J. Wherry, and R. Ahmed. 2009. *Redefining chronic viral infection. Cell.* 138:30-50. doi: 10.1016/j.cell.2009.06.036

42. Whiteside, T. L., S. Miescher, H. R. MacDonald, and V. Von Fliedner. 1986. Separation of tumor-infiltrating lymphocytes from tumor cells in human solid tumors. A comparison between velocity sedimentation and discontinuous density gradients. *J. Immunol. Methods.* 90:221-233. doi: 10.1016/0022-1759(86)90079-7

43. Bonifaz, L., D. Bonnyay, K. Mahnke, M. Rivera, M. G. Nussenzweig, and R. M. Steinman. 2002. Efficient targeting of protein antigen to the dendritic cell receptor DEC-205 in the steady state leads to antigen presentation on major histocompatibility complex class I products and peripheral CD8+T cell tolerance. *J Exp Med.* 196:1627-38.

44. Budhu, S., J. D. Loike, A. Pandolfi, S. Han, G. Catalano, A. Constantinescu, R. Clynes, and S. C. Silverstein. 2010. CD8+T cell concentration determines their efficiency in killing cognate antigen-expressing syngeneic mammalian cells in vitro and in mouse tissues. *J Exp Med.* 207:223-35.

45. Budhu, S., Loike, J. D., Rabadan, R., Clynes, R., Silverstein, S. C. A Critical intra-tumoral concentration of cytolytically active CD8+T-cells is required to control tumor cell growth. 2011A. Manuscript in preparation for submission to the *J Exp Med.*

46. Budhu, S., Wang, B., Rabadan, R., Loike, J. D., Clynes, R., Steinman, R., and Silverstein, S. C. The percent and specific activity of cytolytically active antigen-specific CD8+T-cells determines the outcome of cellular immunotherapy of cancer. 2011 B. Manuscript in preparation for submission to the *J Exp Med.*

47. Boon, T. and P. van der Bruggen, Human tumor antigens recognized by T lymphocytes. J Exp Med, 1996. 183(3): p. 725-9.

48. Dudley, M. E., et al., Cancer regression and autoimmunity in patients after clonal repopulation with antitumor lymphocytes. *Science,* 2002. 298(5594): p. 850-4.

49. Dudley, M. E., et al., Adoptive cell transfer therapy following non-myeloablative but lymphodepleting chemotherapy for the treatment of patients with refractory metastatic melanoma. *J Clin Oncol,* 2005. 23(10): p. 2346-57.

50. Morgan, R. A., et al., Cancer regression in patients after transfer of genetically engineered lymphocytes. Science, 2006. 314(5796): p. 126-9.

51. Helmich, B. K. and R. W. Dutton, The role of adoptively transferred CD8 T cells and host cells in the control of the growth of the EG7 thymoma: factors that determine the relative effectiveness and homing properties of Tc1 and Tc2 effectors. J Immunol, 2001. 166(11): p. 6500-8.

52. Petersen, C. C., et al., Accumulation in tumor tissue of adoptively transferred T cells: A comparison between intravenous and intraperitoneal injection. J Immunother, 2006. 29(3): p. 241-9.

53. Moore, M. W., F. R. Carbone, and M. J. Bevan, Introduction of soluble protein into the class I pathway of antigen processing and presentation. Cell, 1988. 54(6): p. 777-85.

54. Hu, F. and P. F. Lesney, The Isolation and Cytology of Two Pigment Cell Strains from B-16 Mouse Melanomas. Cancer Res, 1964. 24: p. 1634-43.

55. Hogquist, K. A., et al., T cell receptor antagonist peptides induce positive selection. Cell, 1994. 76(1): p. 17-27.

56. Kyner, D., et al., Co-cultivation of tumorigenic mouse melanoma cells with cells of a non-tumorigenic subclone inhibits plasminogen activator expression by the melanoma cells. J Cell Physiol, 1978. 95(2): p. 159-67.

57. Newcomb, E. W., S. C. Silverstein, and S. Silagi, Malignant mouse melanoma cells do not form tumors when mixed with cells of a non-malignant subclone: relationships between plasminogen activator expression by the tumor cells and the host's immune response. J Cell Physiol, 1978. 95(2): p. 169-77.

58. Freedman, V. H., et al., Macrophages elicited with heat-killed *bacillus* Calomette-Guerin protect C57BL/6J mice against a syngeneic melanoma. J Exp Med, 1980. 152(3): p. 657-73.

59. Calvelli, T. A., et al., Leukocyte subpopulations elicited by a nontumorigenic variant of B16 melanoma: their role in direct rejection of the melanoma and in prevention of tumorigenesis in Winn assays. J Exp Med, 1982. 156(6): p. 1723-38.

60. Freedman, V. H., et al., *Bacillus* Calmette-Guerin-activated murine macrophages kill syngeneic melanoma cells under strict anaerobic conditions. J Exp Med, 1984. 160(1): p. 94-107.

61. Sutherland, R. M., Cell and environment interactions in tumor microregions: the multicell spheroid model. Science, 1988. 240(4849): p. 177-84.

62. Hofmann, U. B., et al., Role of matrix metalloproteinases in melanoma cell invasion. Biochimie, 2005. 87(3-4): p. 307-314.

63. Huang, S.-C., et al., Carnosol inhibits the invasion of B16/F10 mouse melanoma cells by suppressing metalloproteinase-9 through down-regulating nuclear factor-kappaB and c-Jun. Biochemical Pharmacology, 2005. 69(2): p. 221-232.

64. Baramova, E. N., et al., Evaluation of matrix metalloproteinases and serine proteases activities in three B16 melanoma cell lines with distinct tumorigenic potential. Anticancer Res, 1994. 14(3A): p. 841-6.

65. Curtsinger, J. M., D. C. Lins, and M. F. Mescher, CD8+ memory T cells (CD44high, Ly-6C+) are more sensitive than naive cells to (CD44low, Ly-6C−) to TCR/CD8 signaling in response to antigen. J Immunol, 1998. 160(7): p. 3236-43.

66. Hersh, E. M., et al., Mononuclear cell content of human solid tumors. Med Pediatr Oncol, 1976. 2(1): p. 1-9.

67. Kuwashima, Y., et al., Growth characteristics of murine B16 melanoma multicellular spheroids: a model for invasion and effects of doxorubicin treatments. Anticancer Res, 1993. 13(4): p. 1215-7.

68. Bonnefoix, T., et al., Quantitating effector and regulatory T lymphocytes in immune responses by limiting dilution analysis modeling. J Immunol, 2005. 174(6): p. 3421-31.

69. Koehne, G., et al., Quantitation, selection, and functional characterization of Epstein-Barr virus specific and alloreactive T cells detected by intracellular interferon-gamma production and growth of cytotoxic precursors. Blood, 2002. 99(5): p. 1730-40.

70. Rubio, V., et al., Ex vivo identification, isolation and analysis of tumor-cytolytic T cells. Nat Med, 2003. 9(11): p. 1377-82. 15

71. Machlenkin, A., et al., Capture of tumor cell membranes by trogocytosis facilitates detection and isolation of tumor-specific functional CTLs. Cancer Res, 2008. 68(6): p. 2006-13.

72. Li, Y., M. Bleakley, and C. Yee, IL-21 influences the frequency, phenotype, and affinity of the antigen-specific CD8 T cell response. J Immunol, 2005. 175(4): p. 2261-9.

73. Moroz, A., et al., IL-21 enhances and sustains CD8+T cell responses to achieve durable tumor immunity: comparative evaluation of IL-2, IL-15, and IL-21. J Immunol, 2004. 173(2): p. 900-9.

74. White, L., et al., Differential effects of IL-21 and IL-15 on perforin expression, lysosomal degranulation, and proliferation in CD8 T cells of patients with human immunodeficiency virus-1 (HIV). Blood, 2007. 109(9): p. 3873-80.

75. Stuge, T. B., et al., Diversity and recognition efficiency of T cell responses to cancer. PLoS Med, 2004. 1(2): p. e28.

76. Dudley, M. E., et al., Adoptive cell therapy for patients with metastatic melanoma: evaluation of intensive myeloablative chemoradiation preparative regimens. J Clin Oncol, 2008. 26(32): p. 5233-9.

77. Bathe, O. F., N. Dalyot-Herman, and T. R. Malek, Therapeutic limitations in tumor-specific CD8+ memory T cell engraftment. BMC Cancer, 2003. 3: p. 21.

78. Wallace, A., et al., Transforming growth factor-beta receptor blockade augments the effectiveness of adoptive T-cell therapy of established solid cancers. Clin Cancer Res, 2008. 14(12): p. 3966-74.

79. Agger, R., et al., T cell homing to tumors detected by 3D-coordinated positron emission tomography and magnetic resonance imaging. J Immunother, 2007. 30(1): p. 29-39.

80. Nedergaard, B. S., et al., Low density of CD3+, CD4+ and CD8+ cells is associated with increased risk of relapse in squamous cell cervical cancer. Br J Cancer, 2007. 97(8): p. 1135-8.

81. Liakou, C I, et al., Focus on TILs: Prognostic significance of tumor infiltrating lymphocytes in human bladder cancer. Cancer Immun, 2007. 7: p. 10.

82. Tomsova, M., et al., Prognostic significance of CD3+ tumor-infiltrating lymphocytes in ovarian carcinoma. Gynecol Oncol, 2008. 108(2): p. 415-20.

83. Martz, E., Early steps in specific tumor cell lysis by sensitized mouse T lymphocytes. I. Resolution and characterization. J Immunol, 1975. 115(1): p. 261-7.

84. Snyder, C. A. and A. B. Bowers, A new inhalation exposure system for the determination of inhaled doses in laboratory rats. Arch Toxicol, 1987. 61(1): p. 3-6.

85. Buckanovich, R. J., et al., Endothelin B receptor mediates the endothelial barrier to T cell homing to tumors and disables immune therapy. Nat Med, 2008. 14(1): p. 28-36.

86. Askenasy, N., A. Kaminitz, and S. Yarkoni, Mechanisms of T regulatory cell function. Autoimmun Rev, 2008. 7(5): p. 370-5.

87. Curiel, T. J., Tregs and rethinking cancer immunotherapy. J Clin Invest, 2007. 117(5): p. 1167-74.

88. Suciu-Foca, N. and R. Cortesini, Central role of ILT3 in the T suppressor cell cascade. Cell Immunol, 2007. 248(1): p. 59-67.

What is claimed is:

1. A method of treating a subject suffering from an infectious or neoplastic disease with immunotherapy comprising:
    (a) providing a gel comprising:
        (i) collagen and fibrin, which gel is sufficient to support viability of an immune cell and growth of a cell from an infectious or neoplastic disease obtained from the subject; and
        ii an immune cell and a cell from an infectious or neoplastic disease obtained from the subject disposed within the gel;
    (b) incubating the gel under conditions that support viability of the immune cell and growth of the cell from the infectious or neoplastic disease obtained from the subject for a period of time sufficient to determine whether the immune cell has an effect on the cell from the infectious or neoplastic disease obtained from the subject;
    (c) determining the number of viable cells from the infectious or neoplastic disease, if any, that are present after step (b), wherein the determining step comprises carrying out a clonogenic assay to determine how many, if any, infectious or neoplastic disease cells are present;
    (d) determining a critical concentration of immune cells required to treat or eradicate the infectious or neoplastic disease in the subject; and
    (e) administering to the subject the critical concentration of immune cells determined in step (d).

2. The method according to claim 1, wherein the subject is a human.

3. The method according to claim 2, wherein the neoplastic disease is a melanoma.

4. The method according to claim 3, wherein the immune cell is a tumor antigen-specific $CD4^+$ or $CD8^+$ T-cell.

5. The method according to claim 4, wherein the critical concentration is at least $10^7$ tumor antigen-specific $CD4^+$ or $CD8^+$ T-cells/ml tumor.

6. The method according to claim 1 further comprising in step (e) co-administering a cytokine with the immune cells.

7. The method according to claim 6, wherein the cytokine is an interleukin.

8. The method according to claim 7, wherein the interleukin is selected from the group consisting of IL-2, IL-12, IL-21, and combinations thereof.

* * * * *

UNITED STATES PATENT AND TRADEMARK OFFICE
CERTIFICATE OF CORRECTION

PATENT NO. : 10,137,153 B2
APPLICATION NO. : 15/345144
DATED : November 27, 2018
INVENTOR(S) : Samuel C. Silverstein et al.

It is certified that error appears in the above-identified patent and that said Letters Patent is hereby corrected as shown below:

In the Specification

In Column 1, please replace the paragraph immediately after the heading "GOVERNMENT RIGHTS IN THE INVENTION" and immediately before the heading "FIELD OF THE INVENTION" with the following:
This invention was made with government support under grant no. AI020516 awarded by the National Institutes of Health. The government has certain rights in the invention.

Signed and Sealed this
Twenty-third Day of January, 2024

Katherine Kelly Vidal
*Director of the United States Patent and Trademark Office*